(12) United States Patent
Bansal-Mutalik et al.

(10) Patent No.: US 11,659,850 B2
(45) Date of Patent: May 30, 2023

(54) FUNCTIONAL MUNG BEAN-DERIVED COMPOSITIONS

(71) Applicant: Eat JUST, Inc., San Francisco, CA (US)

(72) Inventors: Ritu Bansal-Mutalik, Albany, CA (US); Siddharth Bhide, San Francisco, CA (US); Brenna Gibson, San Francisco, CA (US); Camilla Hall, San Jose, CA (US); Malgorzata Jakubasch, Laguna Nigel, CA (US); Jake Kleiner, Mill Valley, CA (US); Viviane Lanquar, Redwood City, CA (US); Swetha Mahadevan, Oakland, CA (US); Trevor Niekowal, Oakland, CA (US); Jade Proulx, Redwood City, CA (US); Ben Roche, San Francisco, CA (US); Meng Xu, Cupertino, CA (US); James Flatt, San Francisco, CA (US); Nathaniel Park, San Francisco, CA (US)

(73) Assignee: EAT JUST, INC., San Francisco, CA (US)

( * ) Notice: Subject to any disclaimer, the term of this patent is extended or adjusted under 35 U.S.C. 154(b) by 0 days.

(21) Appl. No.: 16/428,835

(22) Filed: May 31, 2019

(65) Prior Publication Data

US 2020/0352195 A1 Nov. 12, 2020

Related U.S. Application Data

(63) Continuation of application No. 15/436,711, filed on Feb. 17, 2017, now Pat. No. 10,321,705.
(Continued)

(51) Int. Cl.
| | | |
|---|---|---|
| *A23J 1/14* | (2006.01) | |
| *A23G 9/38* | (2006.01) | |
| *A23J 3/22* | (2006.01) | |
| *A23L 11/40* | (2021.01) | |
| *A23L 13/40* | (2023.01) | |
| *A23L 15/00* | (2016.01) | |
| *A23L 7/109* | (2016.01) | |
| *A21D 13/40* | (2017.01) | |
| *A23C 9/152* | (2006.01) | |
| *A23C 13/12* | (2006.01) | |
| *A23C 15/12* | (2006.01) | |
| *A23L 2/66* | (2006.01) | |
| *C07K 1/36* | (2006.01) | |
| *C07K 14/415* | (2006.01) | |

(Continued)

(52) U.S. Cl.
CPC .............. *A23J 1/14* (2013.01); *A21D 2/266* (2013.01); *A21D 13/40* (2017.01); *A23C 9/1526* (2013.01); *A23C 11/06* (2013.01); *A23C 13/12* (2013.01); *A23C 15/12* (2013.01); *A23C 20/005* (2013.01); *A23G 9/38* (2013.01); *A23J 1/148* (2013.01); *A23J 3/14* (2013.01); *A23J 3/227* (2013.01); *A23L 2/66* (2013.01); *A23L 7/109* (2016.08); *A23L 11/40* (2021.01); *A23L 13/426* (2016.08); *A23L 15/35* (2016.08); *C07K 1/145* (2013.01); *C07K 1/30* (2013.01); *C07K 1/34* (2013.01); *C07K 1/36* (2013.01); *C07K 14/415* (2013.01); *A23V 2002/00* (2013.01)

(58) Field of Classification Search
CPC ...... A23J 1/14; A23J 1/148; A23J 3/14; A23J 3/227; A23L 15/35; A23L 13/426; A23L 7/109; A23L 2/66; A21D 2/266; A21D 13/40; A23C 9/1526; A23C 11/06; A23C 13/12; A23C 15/12; A23C 20/005; A23G 9/38; C07K 1/145; C07K 1/30; C07K 1/34; C07K 1/36; C07K 14/415; A23V 2002/00; A23V 2200/12
USPC ........................................................ 426/549
See application file for complete search history.

(56) References Cited

U.S. PATENT DOCUMENTS

| | | | |
|---|---|---|---|
| 3,966,702 A | 6/1976 | Carey | |
| 4,514,432 A * | 4/1985 | Grzinia | .................... A23J 3/08 |
| | | | 426/564 |

(Continued)

FOREIGN PATENT DOCUMENTS

| | | |
|---|---|---|
| CN | 101703147 A | 5/2010 |
| CN | 102934731 A | 2/2013 |

(Continued)

OTHER PUBLICATIONS

Hoang—Ph. D. Dissertation—Abstract (Year: 2012).*
(Continued)

*Primary Examiner* — Hamid R Badr
(74) *Attorney, Agent, or Firm* — Squire Patton Boggs (US) LLP

(57) ABSTRACT

Provided herein are methods for producing a mung bean protein isolate having high functionality for a broad range of food applications. In some embodiments, the methods for producing the isolate comprise one or more steps selected from: (a) extracting one or more mung bean proteins from a mung bean protein source in an aqueous solution, for example, at a pH between about 6.5-10.0; (b) purifying protein from the extract using at least one of two methods: (i) precipitating protein from the extract at a pH near the isoelectric point of a globulin-rich fraction, for example a pH between about 5.0-6.0; and/or (ii) fractionating and concentrating protein from the extract using filtration such as microfiltration, ultrafiltration or ion-exchange chromatography; and (c) recovering purified protein isolate.

27 Claims, 67 Drawing Sheets

Specification includes a Sequence Listing.

Related U.S. Application Data

(60) Provisional application No. 62/297,788, filed on Feb. 19, 2016.

(51) Int. Cl.

| | |
|---|---|
| *A21D 2/26* | (2006.01) |
| *A23C 11/06* | (2006.01) |
| *A23C 20/00* | (2006.01) |
| *A23J 3/14* | (2006.01) |
| *C07K 1/14* | (2006.01) |
| *C07K 1/30* | (2006.01) |
| *C07K 1/34* | (2006.01) |

(56) References Cited

U.S. PATENT DOCUMENTS

| | | | |
|---|---|---|---|
| 6,391,361 B1 | 5/2002 | Peters et al. | |
| 2007/0054031 A1 | 3/2007 | Liu | |
| 2012/0270810 A1 | 10/2012 | Preiss-Bloom et al. | |
| 2013/0052304 A1* | 2/2013 | Li | A23L 15/35 426/74 |
| 2014/0356507 A1* | 12/2014 | Tetrick | A23L 29/10 426/550 |
| 2015/0313269 A1* | 11/2015 | Rodriguez | A23P 30/20 426/602 |
| 2016/0050951 A1* | 2/2016 | Motoyama | A23C 20/025 426/573 |

FOREIGN PATENT DOCUMENTS

| | | |
|---|---|---|
| CN | 103743869 A | 4/2014 |
| CN | 105077033 A | 11/2015 |
| EP | 2 982 248 A1 | 2/2016 |
| EP | 2 984 938 A1 | 2/2016 |
| WO | WO 03/017777 A1 | 3/2003 |
| WO | WO 2013/010037 A1 | 1/2013 |
| WO | WO 2013/010042 A1 | 1/2013 |
| WO | WO 2013/067453 | 5/2013 |

OTHER PUBLICATIONS

Coffmann, C. W. et al. J. Fd. Technol. 12: 473-484 (Year: 1977).*
Barac et al., "Comparative study of the functional properties of three legume seed isolates: adzuki, pea and soy bean", Journal of Food Science and Technology, Springer (India) Private Ltd, India, Mar. 5, 2014, vol. 52, No. 5, pp. 2779-2787.
Burgess, Richard R. "Chapter 20: Protein Precipitation Techniques", *In Guide to Protein Purification, vol. 463, Second Edition (Methods in Enzymology)*, edited by Richard R. Burgess and Murray P. Deutscher. San Diego, California: Academic Press / Elsevier Inc., 2009.
Butt et al., "Nutritional and Functional Properties of Some Promising Legumes Protein Isolates", *Pakistan Journal of Nutrition*, 2010, vol. 9, No. 4, pp. 373-379.
Coffmann et al., "Functional properties and amino acid content of a protein isolate from mung bean flour", *J. Fd Technol.*, 1977, vol. 12, pp. 473-484.
El-Adawy, T.A. "Functional properties and nutritional quality of acetylated and succinylated mung bean protein isolate", Food Chemistry, 2000, vol. 70, pp. 83-91.
Ferreira et al., "Hypocholesterolaemic effect of rat-administered oral doses of the isolated 7S globulins from cowpeas and adzuki beans", *Journal of Nutritional Science*, (2015), vol. 4, e7, p. 1 of 9.
Fukuda, T. et al., "Physicochemical Properties of Native Adzuki Bean (*Vigna angularis*) 7S Globulin and the Molecular Cloning of Its cDNA Isoforms", J. Agric. Food Chem., 2007, vol. 55, pp. 3667-3674.
Kagawa et al., "Soybean basic 7 S globulin represents a protein widely distributed in legume species", *FEBS Letters*, Dec. 1987, vol. 226, No. 1, pp. 145-149.
Li et al., "Characteristics of sixteen mung bean cultivars and their protein isolates", International Journal of Food Science and Technology, 2010, vol. 45, pp. 1205-1211.
Liu et al., "Functional properties of 8S globulin fractions from 15 mung bean (*Vigna radiata* (L.) Wilczek) cultivars", International Journal of Food Science and Technology, 2015, vol. 50, pp. 1206-1214.
Meng et al., "Thermal properties of *Phaseolus angularis* (red bean) globulin", Food Chemistry, 2001, vol. 73, pp. 453-460.
Mohamed et al., "Differences in Functional Properties of Mungbean Protein Concentrate and the Effect of Incorporation into Fish Sausages", *Pertanika J. Trop. Agric. Sci.*, 1996, vol. 19, No. 1, pp. 69-75.
Tang et al., "Properties of cast films of vicilin-rich protein isolates from Phaseolus legumes: Influence of heat curing", LWT—Food Science and Technology, Academic Press, United Kingdom, Dec. 1, 2009, vol. 42, No. 10, pp. 1659-1666.
Tang et al., Agric. Food Chem. 58, 2010, pp. 6395-6402.
Tjamjadi et al., "Isolation and Characterization of Adzuki Bean (*Vigna angularis* cv Takara) Proteins", Journal of Food Science, 1988, vol. 53, No. 5, pp. 1438-1443.
Wang et al., "Optimization of Extraction Process of Protein Isolate from Mung Bean", *Procedia Engineering*, 2011, vol. 15, pp. 5250-5258.
Antonets et al., "Accumulation of storage proteins in plant seeds is mediated by amyloid formation", PLOS Biology, Jul. 23, 2020, https://doi.org/10.1371/journal.pblo.3000564; 32 pages.
Bernardo et al., "8S Globulin of Mungbean [*Vigna radiata* (L.) Wilczek]: Cloning and Characterization of Its cDNA Isoforms, Expression in *Escherichia coli*, Purification, and Crystallization of the Major Recombinant 8S Isoform", J. Agric. Food Chem. 2004, vol. 52, pp. 2552-2560.
Mendoza et al., "Mungbean [*Vigna radiata* (L.) Wilczek] Globulins: Purification and Characterization", J. Agric. Food Chem. 2001, vol. 49, pp. 1552-1558.
Molins, Ricardo; "Phosphates in Food", Taylor & Francis Group, Boca Raton London New York, 1991, ISBN 0-8493-4588-X; pp. 2-3 and pp. 54-55.

* cited by examiner

Global Protein alignment. Reference molecule: SEQ ID 1, Region 1 to 453
Sequences: 12. Scoring matrix: BLOSUM 62

| Sequence | Start | End | #Match | NonMatch | %Match |
|---|---|---|---|---|---|
| SEQ ID 1 | 1 | 453 | 452 | 2 | 99 |
| SEQ ID 2 | 1 | 453 | 441 | 13 | 97 |
| SEQ ID 3 | 1 | 454 | 408 | 46 | 89 |
| SEQ ID 4 | 1 | 454 | 383 | 76 | 83 |
| SEQ ID 5 | 1 | 453 | 351 | 109 | 76 |
| SEQ ID 6 | 1 | 379 | 381 | 72 | 84 |
| SEQ ID 7 | 1 | 431 | 366 | 87 | 80 |
| SEQ ID 8 | 1 | 431 | 254 | 200 | 55 |
| SEQ ID 9 | 1 | 338 | 190 | 269 | 41 |
| SEQ ID 10 | 1 | 246 | 108 | 550 | 16 |
| SEQ ID 11 | 1 | 613 | 307 | 233 | 56 |
| SEQ ID 12 | 1 | 532 | | | |

Global Protein alignment. Reference molecule: SEQ ID 1, Region 1 to 453
Sequences: 12. Scoring matrix: BLOSUM 62

▫ Areas of significant similarity (window length 10 bases)

Egg　　　　　　　　　　　　　　HC208N

Egg White          HC208a

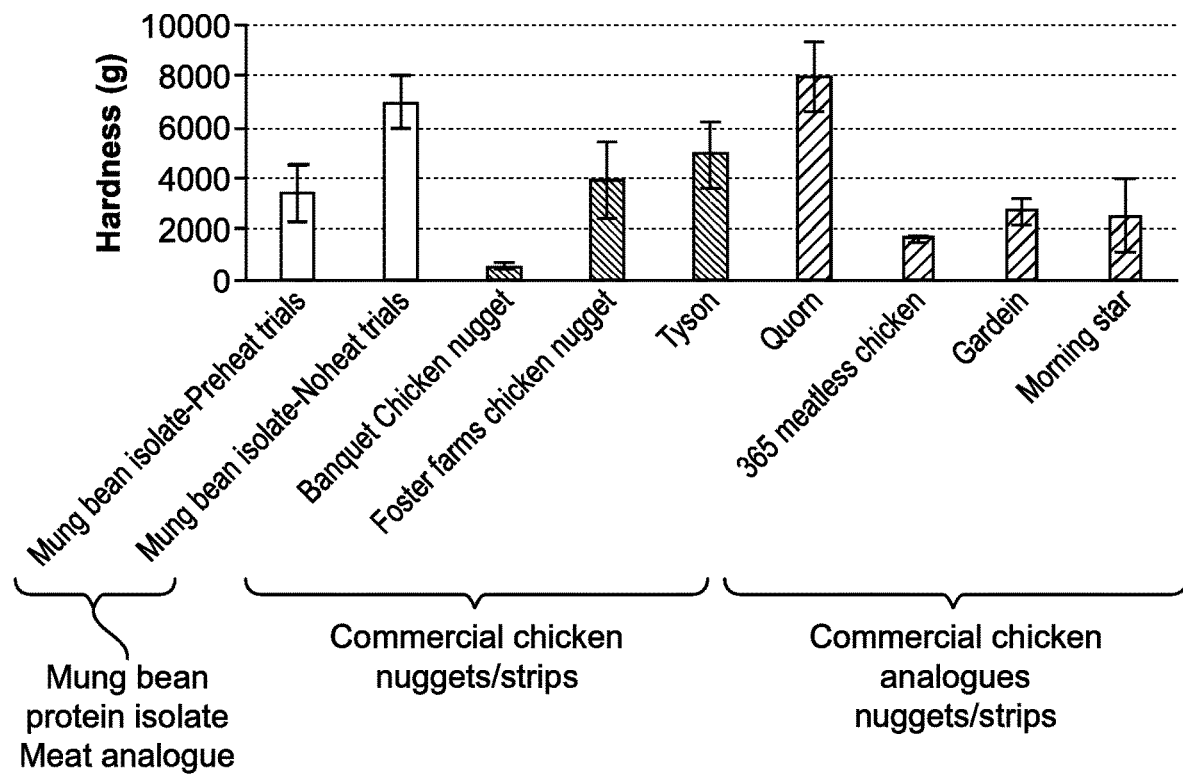
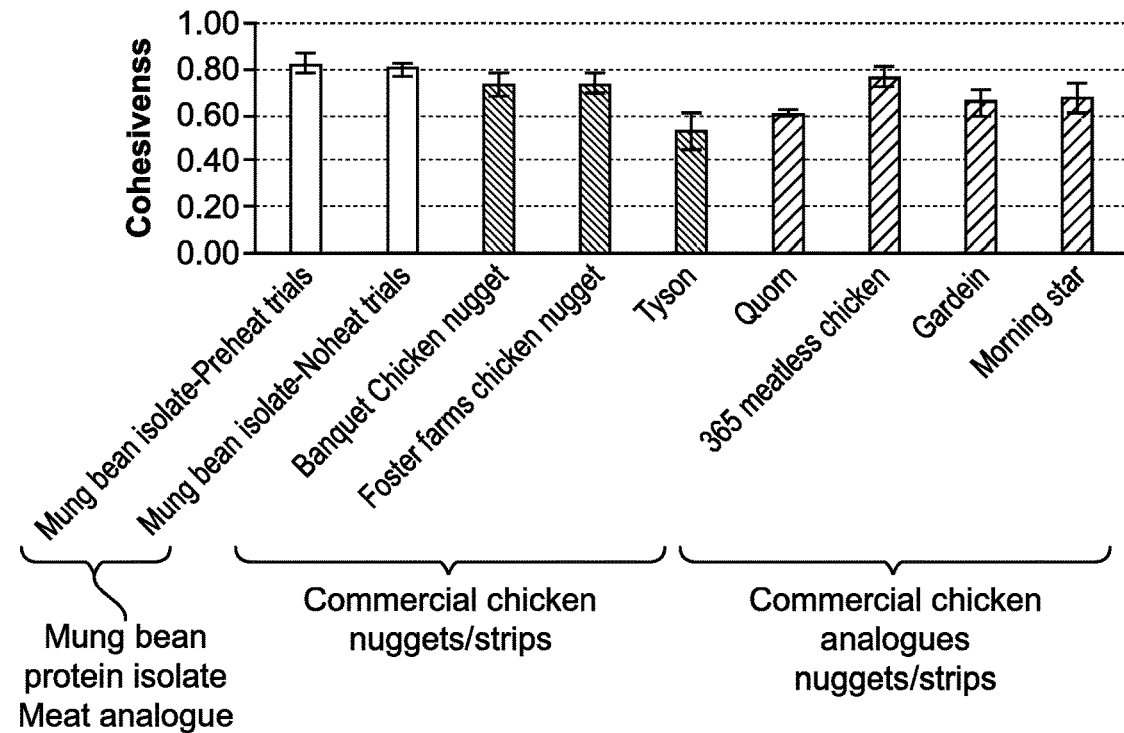
FIG. 55

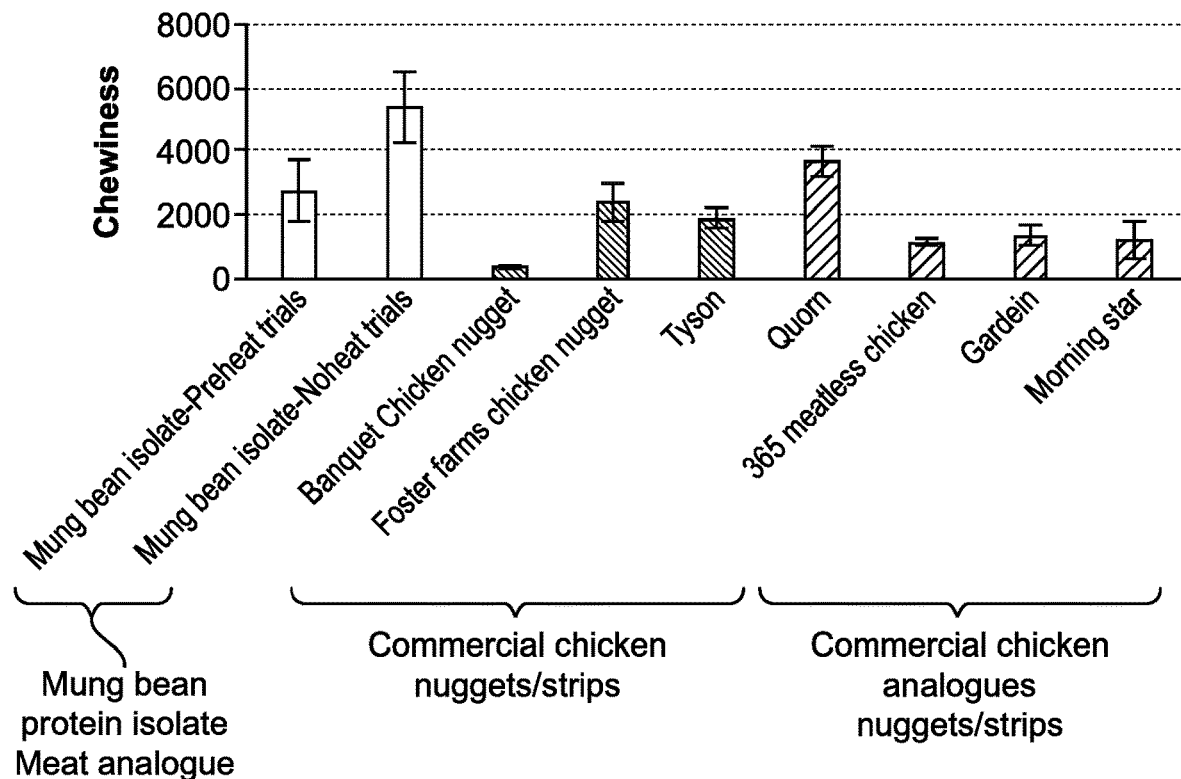
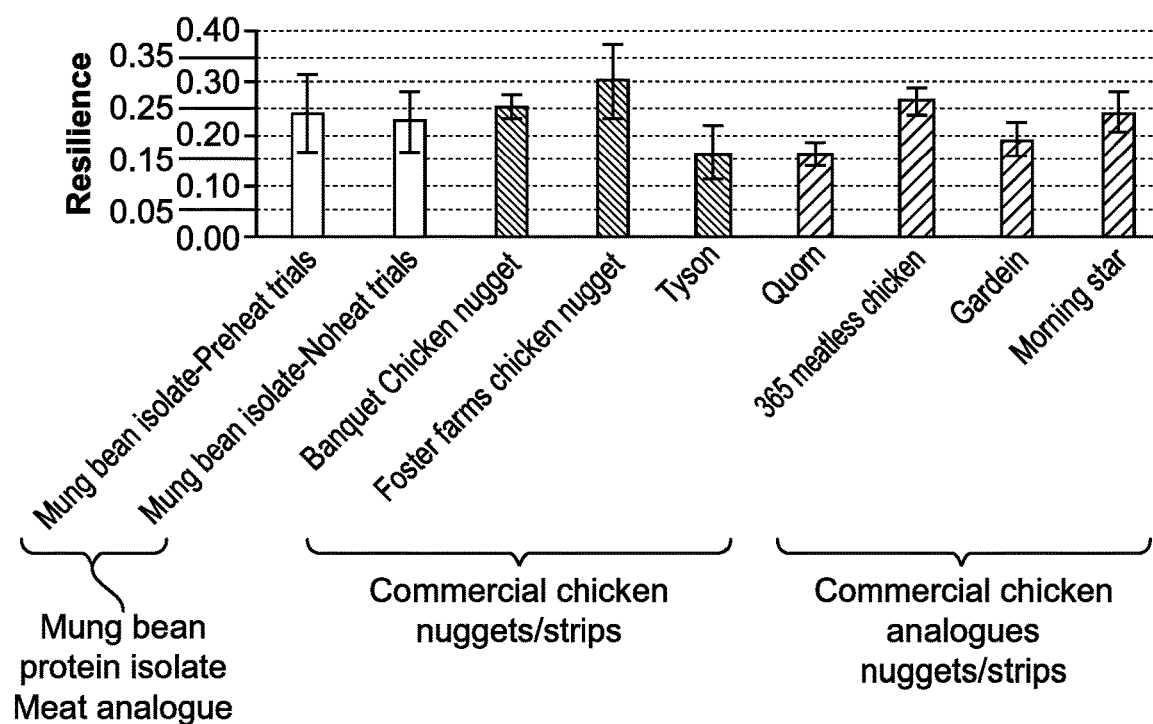
FIG. 55 (Cont.)

A                               B

SEQUENCE LISTING

<160> NUMBER OF SEQ ID NOS: 15

<210> SEQ ID NO 1
<211> LENGTH: 453
<212> TYPE: PRT
<213> ORGANISM: Vigna radiata var. radiata

<400> SEQUENCE: 1

```
Met Met Ser Ala Arg Val Pro Leu Leu Leu Leu Gly Ile Leu Phe
1               5                   10                  15

Leu Ala Ser Leu Ser Val Ser Phe Gly Ile Val His Arg Glu Asn His
            20                  25                  30

Asp Ala Ala Glu Val Ser Val Ser Arg Gly Lys Asn Asn Pro Phe Tyr
            35                  40                  45

Phe Asn Ser Asp Arg Trp Phe Arg Thr Leu Phe Arg Asn Glu Phe Gly
50                  55                  60

His Leu Arg Val Leu Gln Arg Phe Asp Gln Arg Ser Lys Gln Met Gln
65                  70                  75                  80

Asn Leu Glu Asn Tyr Arg Val Val Glu Phe Gln Ser Lys Pro Asn Thr
                85                  90                  95

Leu Leu Leu Pro His His Ala Asp Ala Asp Phe Leu Leu Val Val Leu
            100                 105                 110

Asn Gly Arg Ala Val Leu Thr Leu Val Asn Pro Asp Gly Arg Asp Ser
            115                 120                 125

His Ile Leu Glu Gln Gly His Ala Gln Lys Ile Pro Ala Gly Thr Ile
        130                 135                 140

Phe Phe Leu Val Asn Pro Asp Asp Asn Glu Asn Leu Arg Ile Ile Lys
145                 150                 155                 160

Leu Ala Val Pro Val Asn Asn Pro His Arg Phe Gln Asp Phe Phe Leu
                165                 170                 175

Ser Ser Thr Glu Ala Gln Gln Ser Tyr Leu Gln Gly Phe Ser Lys Asn
            180                 185                 190

Ile Leu Glu Ala Ser Phe Asp Ser Asp Ile Lys Glu Ile Asn Arg Val
        195                 200                 205

Leu Phe Gly Glu Glu Gly Gln Gln Gln Gln Gly Gln Glu Ser Gln
    210                 215                 220

Gln Glu Gly Val Ile Val Glu Leu Lys Arg Glu Gln Ile Arg Glu Leu
225                 230                 235                 240

Thr Lys His Ala Lys Ser Ser Ser Lys Lys Ser Leu Ser Ser Glu Asp
                245                 250                 255

Gln Pro Phe Asn Leu Arg Asn Gln Lys Pro Ile Tyr Ser Asn Lys Phe
            260                 265                 270

Gly Glu Phe Tyr Glu Ile Thr Pro Lys Lys Asn Pro Gln Leu Lys Asp
        275                 280                 285

Leu Asp Val Phe Ile Ser Ser Val Asp Met Lys Glu Gly Ser Leu Leu
    290                 295                 300

Leu Pro His Tyr Asn Ser Lys Ala Ile Val Ile Leu Val Ile Asn Glu
305                 310                 315                 320

Gly Glu Ala Asn Ile Glu Leu Val Gly Leu Arg Glu Glu Gln Gln Gln
                325                 330                 335

Gln Gln Gln Asp Glu Arg Leu Glu Val Gln Arg Tyr Arg Ala Glu Val
            340                 345                 350

Ser Glu Asp Asp Val Phe Val Ile Pro Ala Ala Tyr Pro Val Ala Ile
        355                 360                 365
```

```
Asn Ala Thr Ser Asn Leu Asn Phe Ala Phe Gly Ile Asn Ala Glu
    370                 375                 380

Asn Asn Gln Arg Asn Phe Leu Ala Gly Glu Lys Asp Asn Val Ile Ser
385                 390                 395                 400

Glu Ile Pro Thr Glu Val Leu Asp Leu Ala Phe Pro Ala Pro Gly Glu
                405                 410                 415

Lys Val Glu Lys Leu Val Gln Lys Gln Ser Thr Ser His Phe Val Asp
            420                 425                 430

Ala Gln Pro Glu Glu Gln Arg Glu Glu Gly Pro Lys Gly Arg Lys
        435                 440                 445

Gly His Phe Val Tyr
    450

<210> SEQ ID NO 2
<211> LENGTH: 453
<212> TYPE: PRT
<213> ORGANISM: Vigna radiata

<400> SEQUENCE: 2

Met Ser Ala Arg Val Pro Leu Leu Leu Leu Gly Ile Leu Phe Leu
1               5                   10                  15

Ala Ser Leu Ser Val Ser Phe Gly Ile Val His Arg Glu Asn His Asp
            20                  25                  30

Ala Ala Glu Val Ser Val Ser Arg Gly Lys Asn Asn Pro Phe Tyr Phe
        35                  40                  45

Asn Ser Asp Arg Trp Phe Arg Thr Leu Phe Arg Asn Glu Phe Gly His
    50                  55                  60

Leu Arg Val Leu Gln Arg Phe Asp Gln Arg Ser Lys Gln Met Gln Asn
65                  70                  75                  80

Leu Glu Asn Tyr Arg Val Val Glu Phe Gln Ser Lys Pro Asn Thr Leu
                85                  90                  95

Leu Leu Pro His His Ala Asp Ala Asp Phe Leu Leu Val Val Leu Asn
            100                 105                 110

Gly Arg Ala Val Leu Thr Leu Val Asn Pro Asp Gly Gly Arg Asp Ser
        115                 120                 125

His Ile Leu Glu Gln Gly His Ala Gln Lys Ile Pro Ala Gly Thr Ile
    130                 135                 140

Phe Phe Leu Val Asn Pro Asp Asp Asn Glu Asn Leu Arg Ile Ile Lys
145                 150                 155                 160

Leu Ala Val Pro Val Asn Asn Pro His Arg Phe Gln Asp Phe Phe Leu
                165                 170                 175

Ser Ser Thr Glu Ala Gln Gln Ser Tyr Leu Gln Gly Phe Ser Lys Asn
            180                 185                 190

Ile Leu Glu Ala Ser Phe Asp Ser Asp Ile Lys Glu Ile Asn Arg Val
        195                 200                 205

Leu Phe Gly Glu Glu Gly Gln Gln Gln Gln Gly Gln Glu Ser Gln
    210                 215                 220

Gln Glu Gly Val Ile Val Glu Leu Lys Arg Glu Gln Ile Arg Glu Leu
225                 230                 235                 240

Thr Lys His Ala Lys Ser Ser Lys Lys Ser Leu Ser Ser Glu Asp
                245                 250                 255

Gln Pro Phe Asn Leu Arg Asn Gln Lys Pro Ile Tyr Ser Asn Lys Phe
            260                 265                 270

Gly Glu Phe Tyr Glu Ile Thr Pro Lys Lys Asn Pro Gln Leu Lys Asp
        275                 280                 285
```

Leu Asp Val Phe Ile Ser Ser Val Asp Met Lys Glu Gly Ser Leu Leu
            290                 295                 300

Leu Pro His Tyr Asn Ser Lys Ala Ile Val Ile Leu Val Ile Asn Glu
305                 310                 315                 320

Gly Glu Ala Asn Ile Glu Leu Val Gly Leu Arg Glu Glu Gln Gln Gln
                325                 330                 335

Gln Gln Gln Asp Glu Arg Leu Glu Val Gln Arg Tyr Arg Ala Glu Val
            340                 345                 350

Ser Glu Asp Asp Val Phe Val Ile Pro Ala Ala Tyr Pro Val Ala Ile
            355                 360                 365

Asn Ala Thr Ser Asn Leu Asn Phe Phe Ala Phe Gly Ile Asn Ala Glu
            370                 375                 380

Asn Asn Gln Arg Asn Phe Leu Ala Gly Glu Lys Asp Asn Val Ile Ser
385                 390                 395                 400

Glu Ile Pro Thr Glu Val Leu Asp Leu Ala Phe Pro Ala Pro Gly Glu
                405                 410                 415

Lys Val Glu Lys Leu Val Gln Lys Gln Ser Thr Ser His Phe Val Asp
            420                 425                 430

Ala Gln Pro Glu Glu Gln Gln Arg Glu Glu Gly Pro Lys Gly Arg Lys
            435                 440                 445

Gly His Phe Val Tyr
    450

<210> SEQ ID NO 3
<211> LENGTH: 454
<212> TYPE: PRT
<213> ORGANISM: Vigna radiata var. radiata
<220> FEATURE:
<221> NAME/KEY: misc_feature
<222> LOCATION: (56)..(57)
<223> OTHER INFORMATION: Xaa can be any naturally occurring amino acid

<400> SEQUENCE: 3

Met Val Arg Ala Arg Ile Pro Leu Leu Leu Leu Gly Ile Leu Phe
1               5                   10                  15

Leu Ala Ser Leu Ser Val Ser Phe Gly Ile Val His Arg Glu Asn Ile
                20                  25                  30

Asp Gly Ala Glu Val Ser Val Ser Arg Gly Lys Asn Asn Pro Phe Tyr
            35                  40                  45

Phe Asn Ser Asp Arg Trp Phe Xaa Xaa Leu Phe Arg Asn Gln Phe Gly
    50                  55                  60

His Leu Arg Val Leu Gln Arg Phe Asp Gln Arg Ser Lys Gln Met Gln
65                  70                  75                  80

Asn Leu Glu Asn Tyr Arg Val Val Glu Phe Met Ser Lys Pro Asn Thr
                85                  90                  95

Leu Leu Leu Pro His His Ala Asp Ala Asp Phe Leu Leu Val Val Leu
                100                 105                 110

Asn Gly Arg Ala Val Leu Thr Leu Val Asn Pro Asp Gly Arg Asp Ser
            115                 120                 125

Asn Ile Leu Glu Gln Gly His Ala Gln Lys Ile Pro Ala Gly Thr Thr
        130                 135                 140

Phe Phe Leu Val Asn Pro Asp Asp Asn Glu Asn Leu Arg Ile Ile Lys
145                 150                 155                 160

Leu Ala Val Pro Val Asn Asn Pro His Arg Phe Gln Asp Phe Phe Leu
                165                 170                 175

```
Ser Ser Thr Glu Ala Gln Gln Ser Tyr Leu Gln Gly Phe Ser Lys Asn
            180                 185                 190

Ile Leu Glu Ala Ser Phe Asp Ser Asp Ile Lys Glu Ile Ser Arg Val
            195                 200                 205

Leu Phe Gly Glu Glu Gly Gln Gln Gln Gln Gly Gln Glu Ser Gln
210                 215                 220

Gln Glu Gly Val Ile Val Glu Leu Lys Arg Glu Gln Ile Arg Glu Leu
225                 230                 235                 240

Thr Lys His Ala Lys Ser Ser Lys Lys Ser Leu Ser Glu Asp
            245                 250                 255

Gln Pro Phe Asn Leu Arg Asn Gln Lys Pro Ile Tyr Ser Asn Lys Phe
            260                 265                 270

Gly Glu Phe Tyr Glu Ile Thr Pro Lys Lys Asn Pro Gln Leu Lys Asp
            275                 280                 285

Leu Asp Val Phe Ile Ser Ser Val Asp Met Lys Glu Gly Ser Leu Leu
            290                 295                 300

Leu Pro His Tyr Asn Ser Lys Ala Ile Val Ile Leu Val Ile Asn Glu
305                 310                 315                 320

Gly Glu Ala Asn Ile Glu Leu Val Gly Leu Arg Glu Glu Gln Gln Gln
            325                 330                 335

Gln Gln Gln Gln Asp Glu Arg Leu Glu Val Gln Arg Tyr Arg Ala Glu
            340                 345                 350

Val Ser Glu Asp Asp Val Phe Val Ile Pro Ala Ala Tyr Pro Val Ala
            355                 360                 365

Ile Asn Ala Thr Ser Asn Leu Asn Phe Phe Ala Phe Gly Ile Asn Ala
            370                 375                 380

Glu Asn Asn Gln Arg Asn Phe Leu Ala Gly Glu Lys Asp Asn Val Ile
385                 390                 395                 400

Ser Glu Ile Pro Thr Glu Val Leu Asp Leu Ala Phe Pro Ala Pro Gly
            405                 410                 415

Glu Lys Val Glu Lys Leu Val Gln Lys Gln Ser Thr Ser His Phe Val
            420                 425                 430

Asp Ala Gln Pro Glu Glu Gln Gln Arg Glu Glu Gly Pro Lys Gly Arg
            435                 440                 445

Lys Gly His Phe Val Tyr
450

<210> SEQ ID NO 4
<211> LENGTH: 454
<212> TYPE: PRT
<213> ORGANISM: Vigna radiata

<400> SEQUENCE: 4

Met Val Arg Ala Arg Ile Pro Leu Leu Leu Leu Gly Ile Leu Phe
1               5                   10                  15

Leu Ala Ser Leu Ser Val Ser Phe Gly Ile Val His Arg Glu Asn Ile
            20                  25                  30

Asp Gly Ala Glu Val Ser Val Ser Arg Gly Lys Asn Asn Pro Phe Tyr
            35                  40                  45

Phe Asn Ser Asp Arg Trp Phe His Thr Leu Phe Arg Asn Gln Phe Gly
            50                  55                  60

His Leu Arg Val Leu Gln Arg Phe Asp Gln Arg Ser Lys Gln Met Gln
65                  70                  75                  80

Asn Leu Glu Asn Tyr Arg Val Val Glu Leu Met Ser Lys Pro Asn Thr
            85                  90                  95
```

```
Leu Leu Leu Pro His His Ala Asp Ala Asp Phe Leu Val Val Leu
            100                 105                 110

Asn Gly Arg Ala Val Leu Thr Leu Val Asn Pro Asp Gly Arg Asp Ser
            115                 120                 125

Asn Ile Leu Glu Gln Gly His Ala Gln Lys Ile Pro Ala Gly Thr Thr
130             135                 140

Phe Phe Leu Val Asn Pro Asp Asp Asn Glu Asn Leu Arg Ile Ile Lys
145             150                 155                 160

Leu Ala Val Pro Val Asn Asn Pro His Arg Phe Gln Asp Phe Phe Leu
                165                 170                 175

Ser Ser Thr Glu Ala Gln Gln Ser Tyr Leu Gln Gly Phe Ser Lys Asn
            180                 185                 190

Ile Leu Glu Ala Ser Phe Asp Ser Asp Ile Lys Glu Ile Ser Arg Val
            195                 200                 205

Leu Phe Gly Glu Glu Gly Gln Gln Gln Gln Gly Gln Glu Ser Gln
            210                 215                 220

Gln Glu Gly Val Ile Val Glu Leu Lys Arg Glu Gln Ile Arg Glu Leu
225             230                 235                 240

Thr Lys His Ala Lys Ser Ser Lys Lys Ser Leu Ser Ser Glu Asp
                245                 250                 255

Gln Pro Phe Asn Leu Arg Asn Gln Lys Pro Ile Tyr Ser Asn Lys Leu
            260                 265                 270

Gly Arg Trp Phe Glu Ile Thr Pro Glu Lys Asn Pro Gln Leu Arg Asp
            275                 280                 285

Leu Asp Met Phe Ile Arg Ser Val Asp Met Lys Glu Gly Ser Leu Leu
290             295                 300

Leu Pro His Tyr Asn Ser Lys Ala Ile Val Ile Leu Val Ile Asn Glu
305             310                 315                 320

Gly Lys Ala Asn Ile Glu Leu Val Gly Gln Arg Glu Gln Gln Lys Gln
            325                 330                 335

Gln Glu Glu Gln Glu Glu Ser Trp Glu Val Gln Arg Tyr Arg Ala Glu
            340                 345                 350

Leu Ser Glu Asp Asp Val Phe Ile Ile Pro Ala Thr Tyr Pro Val Ala
            355                 360                 365

Ile Asn Ala Thr Ser Asn Leu Asn Phe Phe Ala Phe Gly Ile Asn Ala
370             375                 380

Glu Asn Asn Gln Arg Asn Phe Leu Ala Gly Glu Lys Asp Asn Val Ile
385             390                 395                 400

Ser Glu Ile Pro Thr Glu Val Leu Asp Val Thr Phe Pro Ala Ser Gly
            405                 410                 415

Glu Lys Val Lys Lys Leu Ile Lys Lys Gln Ser Glu Ser Gln Phe Val
            420                 425                 430

Asp Ala Gln Pro Glu Gln Gln Glu Arg Glu Glu Ala Arg Lys Gly Gly
            435                 440                 445

Lys Gly Pro Phe Val Tyr
            450

<210> SEQ ID NO 5
<211> LENGTH: 453
<212> TYPE: PRT
<213> ORGANISM: Vigna radiata

<400> SEQUENCE: 5

Met Val Arg Ala Arg Val Gln Leu Leu Leu Gly Ile Leu Phe Leu Ala
```

```
1               5                   10                  15
Ser Leu Ser Val Ser Phe Gly Ile Val His Arg Glu His Gln Glu Ser
                20                  25                  30

Gln Glu Glu Ser Asp Ser Arg Gly Gln Asn Asn Pro Phe Tyr Phe Asn
            35                  40                  45

Ser Asp Arg Arg Phe His Thr Leu Phe Lys Asn Gln Tyr Gly His Leu
    50                  55                  60

Arg Val Ile His Arg Phe Asp Gln Arg Ser Lys Gln Ile Gln Asn Leu
65                  70                  75                  80

Glu Asn Tyr Arg Val Val Glu Phe Lys Ser Lys Pro Asn Thr Leu Leu
                85                  90                  95

Leu Pro His His Ala Asp Ala Asp Phe Leu Leu Val Val Leu Asn Gly
            100                 105                 110

Arg Ala Ile Leu Thr Leu Val Asn Pro Asp Gly Arg Asp Ser Tyr Ile
            115                 120                 125

Leu Glu Gln Gly His Ala Gln Lys Ile Pro Ala Gly Thr Thr Phe Phe
    130                 135                 140

Leu Val Asn Pro Asn Asp Asn Asp Asn Leu Arg Ile Ile Lys Leu Ala
145                 150                 155                 160

Ile Pro Val Asn Asn Pro His Arg Phe Gln Asn Phe Phe Leu Ser Ser
                165                 170                 175

Thr Glu Ala Gln Gln Ser Tyr Leu Arg Gly Phe Ser Lys Asn Ile Leu
            180                 185                 190

Glu Ala Ser Phe Asp Ser Asp Phe Lys Glu Ile Asp Arg Val Leu Phe
            195                 200                 205

Gly Glu Glu Arg Gln Gln Gln His Gly Glu Glu Ser Gln Glu Glu Gly
    210                 215                 220

Val Ile Val Glu Leu Lys Arg Glu Gln Ile Arg Glu Leu Ile Lys His
225                 230                 235                 240

Ala Lys Ser Ser Arg Lys Glu Leu Ser Ser Gln Asp Glu Pro Phe
                245                 250                 255

Asn Leu Arg Asn Ser Asn Pro Ile Tyr Ser Asn Lys Phe Gly Arg Trp
            260                 265                 270

Tyr Glu Ile Thr Pro Glu Lys Asn Pro Gln Leu Lys Asp Leu Asp Val
    275                 280                 285

Phe Ile Ser Ser Val Asp Met Lys Glu Gly Leu Leu Leu Pro His
            290                 295                 300

Tyr Asn Ser Lys Ala Ile Val Ile Leu Val Ile Asn Glu Gly Glu Ala
305                 310                 315                 320

Lys Ile Glu Leu Val Gly Pro Ser Asp Gln Gln Gln Asp Glu Ser
                325                 330                 335

Leu Glu Val Gln Arg Tyr Arg Ala Glu Leu Ser Glu Asp Val Phe
            340                 345                 350

Val Ile Pro Ala Ala Tyr Pro Val Ala Ile Asn Ala Thr Ser Asn Leu
            355                 360                 365

Asn Phe Phe Ala Phe Gly Ile Asn Ala Glu Asn Asn Gln Arg Asn Phe
    370                 375                 380

Leu Ala Gly Glu Lys Asp Asn Val Met Ser Glu Ile Pro Thr Glu Val
385                 390                 395                 400

Leu Asp Val Ser Phe Pro Ala Ser Gly Asn Lys Val Glu Lys Leu Ile
                405                 410                 415

Lys Lys Gln Ser Glu Ser His Phe Val Asp Ala Gln Pro Glu Gln Gln
            420                 425                 430
```

-continued

```
Gln Arg Glu Glu Gly His Lys Gly Arg Lys Gly Ser Leu Ser Ser Ile
        435                 440                 445

Leu Gly Ser Leu Tyr
    450

<210> SEQ ID NO 6
<211> LENGTH: 379
<212> TYPE: PRT
<213> ORGANISM: Vigna radiata var. radiata
<220> FEATURE:
<221> NAME/KEY: misc_feature
<222> LOCATION: (56)..(57)
<223> OTHER INFORMATION: Xaa can be any naturally occurring amino acid

<400> SEQUENCE: 6

Met Met Arg Ala Arg Ile Pro Leu Leu Leu Leu Gly Ile Leu Phe
1               5                   10                  15

Leu Ala Ser Leu Ser Val Ser Phe Gly Ile Val His Arg Glu Asn Ile
            20                  25                  30

Asp Gly Ala Glu Val Ser Val Ser Arg Gly Lys Asn Asn Pro Phe Tyr
        35                  40                  45

Phe Asn Ser Asp Arg Trp Phe Xaa Xaa Leu Phe Arg Asn Gln Phe Gly
    50                  55                  60

His Leu Arg Val Leu Gln Arg Phe Asp Gln Arg Ser Lys Gln Met Gln
65                  70                  75                  80

Asn Leu Glu Asn Tyr Arg Val Val Glu Phe Met Ser Lys Pro Asn Thr
                85                  90                  95

Leu Leu Leu Pro His His Ala Asp Ala Asp Phe Leu Leu Val Val Leu
            100                 105                 110

Asn Gly Arg Ala Val Leu Thr Leu Val Asn Pro Asp Gly Arg Asp Ser
        115                 120                 125

Asn Ile Leu Glu Gln Gly His Ala Gln Lys Ile Pro Ala Gly Thr Thr
    130                 135                 140

Phe Phe Leu Val Asn Pro Asp Asp Asn Glu Asn Leu Arg Ile Ile Lys
145                 150                 155                 160

Leu Ala Val Pro Val Asn Asn Pro His Arg Phe Gln Asp Phe Phe Leu
                165                 170                 175

Ser Ser Thr Glu Ala Gln Gln Ser Tyr Leu Gln Gly Phe Ser Lys Asn
            180                 185                 190

Ile Leu Glu Ala Ser Phe Asp Ser Asp Ile Lys Glu Ile Asn Arg Val
        195                 200                 205

Leu Phe Gly Glu Asp Ser Val Asp Met Lys Glu Gly Ser Leu Leu Leu
    210                 215                 220

Pro His Tyr Asn Ser Lys Ala Ile Val Ile Leu Val Ile Asn Glu Gly
225                 230                 235                 240

Glu Ala Asn Ile Glu Leu Val Gly Leu Arg Glu Glu Gln Gln Gln Gln
                245                 250                 255

Gln Gln Gln Asp Glu Arg Leu Glu Val Gln Arg Tyr Arg Ala Glu Val
            260                 265                 270

Ser Glu Asp Asp Val Phe Val Ile Pro Ala Ala Tyr Pro Val Ala Ile
        275                 280                 285

Asn Ala Thr Ser Asn Leu Asn Phe Phe Ala Phe Gly Ile Asn Ala Glu
    290                 295                 300

Asn Asn Gln Arg Asn Phe Leu Ala Gly Glu Lys Asp Asn Val Ile Ser
305                 310                 315                 320
```

```
Glu Ile Pro Thr Glu Val Leu Asp Leu Ala Phe Pro Ala Pro Gly Glu
            325                 330                 335

Lys Val Glu Lys Leu Ile Glu Lys Gln Ser Thr Ser His Phe Val Asp
        340                 345                 350

Ala Gln Pro Glu Glu Gln Lys Glu Asp Arg Asn Gly Lys Lys
        355                 360                 365

Gly Pro Leu Ser Ser Ile Leu Asp Thr Leu Tyr
    370                 375

<210> SEQ ID NO 7
<211> LENGTH: 431
<212> TYPE: PRT
<213> ORGANISM: Vigna radiata var. radiata
<220> FEATURE:
<221> NAME/KEY: misc_feature
<222> LOCATION: (56)..(57)
<223> OTHER INFORMATION: Xaa can be any naturally occurring amino acid

<400> SEQUENCE: 7

Met Val Arg Ala Arg Ile Pro Leu Val Leu Leu Gly Ile Leu Phe
1               5                   10                  15

Leu Ala Ser Leu Ser Val Ser Phe Gly Ile Val His Arg Glu Asn Ile
            20                  25                  30

Asp Gly Ala Glu Val Ser Val Ser Arg Gly Lys Asn Asn Pro Phe Tyr
        35                  40                  45

Phe Asn Ser Asp Arg Trp Phe Xaa Xaa Leu Phe Arg Asn Gln Phe Gly
    50                  55                  60

His Leu Arg Val Leu Gln Arg Phe Asp Gln Arg Ser Lys Gln Met Gln
65                  70                  75                  80

Asn Leu Glu Asn Tyr Arg Val Val Glu Phe Met Ser Lys Pro Asn Thr
                85                  90                  95

Leu Leu Leu Pro His His Ala Asp Ala Asp Phe Leu Leu Val Val Leu
            100                 105                 110

Asn Gly Arg Ala Val Leu Thr Leu Val Asn Pro Asp Gly Arg Asp Ser
        115                 120                 125

Asn Ile Leu Glu Gln Gly His Ala Gln Lys Ile Pro Ala Gly Thr Thr
    130                 135                 140

Phe Phe Leu Val Asn Pro Asp Asp Asn Glu Asn Leu Arg Ile Ile Lys
145                 150                 155                 160

Leu Ala Val Pro Val Asn Asn Pro His Arg Phe Gln Asp Phe Phe Leu
                165                 170                 175

Ser Ser Thr Glu Ala Gln Gln Ser Tyr Leu Gln Gly Phe Ser Lys Asn
            180                 185                 190

Ile Leu Glu Ala Ser Phe Asp Ser Asp Ile Lys Glu Ile Ser Arg Ile
        195                 200                 205

Leu Phe Gly Glu Glu Gly Gln Gln Gln Gln Gly Gln Glu Ser Gln
    210                 215                 220

Gln Glu Gly Val Ile Val Glu Leu Lys Arg Glu Gln Ile Arg Lys Leu
225                 230                 235                 240

Thr Lys His Ala Lys Ser Ser Lys Lys Ser Leu Ser Ser Glu Asp
                245                 250                 255

Glu Pro Phe Asn Leu Arg Asn Gln Lys Pro Ile Tyr Ser Asn Lys Leu
            260                 265                 270

Gly Arg Trp Phe Glu Ile Thr Pro Glu Arg Asn Pro Gln Leu Arg Asp
        275                 280                 285

Leu Asp Met Phe Ile Arg Ser Val Asp Ile Asn Glu Gly Ser Leu Leu
```

```
              290                 295                 300
Leu Pro His Tyr Asn Ser Arg Ala Thr Ala Ile Leu Val Ile Asn Glu
305                 310                 315                 320

Gly Asn Ala Asn Ile Glu Leu Val Gly Gln Arg Glu Gln Glu Glu Ser
                325                 330                 335

Leu Glu Val Gln Arg Tyr Ile Ala Glu Leu Ser Glu Gly Asp Val Phe
                340                 345                 350

Ile Ile Pro Ala Thr Tyr Pro Val Val Ile Asn Ala Thr Ser Asn Leu
                355                 360                 365

Asn Phe Phe Ala Phe Gly Ile Asn Ala Glu Asn Asn Gln Arg Asn Phe
                370                 375                 380

Leu Ala Gly Glu Lys Asp Asn Val Ile Ser Glu Ile Pro Thr Glu Val
385                 390                 395                 400

Leu Asp Val Thr Phe Pro Ala Ser Gly Glu Lys Val Lys Lys Leu Ile
                405                 410                 415

Lys Lys Gln Ser Glu Ser Gln Phe Val Asp Ala Gln Pro Glu Gln
                420                 425                 430

<210> SEQ ID NO 8
<211> LENGTH: 431
<212> TYPE: PRT
<213> ORGANISM: Vigna radiata var. radiata

<400> SEQUENCE: 8

Met Met Arg Ala Arg Val Pro Leu Leu Leu Leu Gly Ile Leu Phe
1               5                   10                  15

Leu Ala Ser Leu Ser Val Thr Phe Gly Ile Val His Arg Glu His Gln
                20                  25                  30

Gln Ser Gln Glu Glu Ser Asp Ser Arg Gly Arg Asn Asn Pro Phe Tyr
                35                  40                  45

Phe Asn Ser Asp Arg Phe His Thr Leu Tyr Arg Asn Glu Tyr Gly His
                50                  55                  60

Leu Arg Val Leu Gln Arg Phe Asp Gln Arg Ser Lys Gln Ile Gln Asn
65                  70                  75                  80

Leu Glu Asn Tyr Arg Leu Val Glu Phe Lys Ser Lys Pro Asn Thr Leu
                85                  90                  95

Leu Leu Pro His His Ala Asp Ala Asp Phe Leu Leu Val Val Leu Asn
                100                 105                 110

Gly Arg Ala Val Leu Thr Leu Val Asn Ala Asp Gly Arg Asp Ser Tyr
                115                 120                 125

Ile Leu Glu Gln Gly His Ala Gln Arg Ile Pro Ala Gly Thr Ile Phe
                130                 135                 140

Phe Val Val Asn Pro Asn Asp Asn Glu Asn Leu Arg Ile Ile Lys Met
145                 150                 155                 160

Ala Val Pro Val Asn Asn Pro His Arg Phe Gln Asp Phe Phe Leu Ser
                165                 170                 175

Ser Thr Glu Ala Gln Gln Ser Tyr Leu Gln Gly Phe Ser Lys Asn Val
                180                 185                 190

Leu Glu Ala Ser Phe Asp Ser Glu Phe Lys Glu Ile Asn Arg Val Leu
                195                 200                 205

Phe Gly Gly Glu Gly Gln Gln Gln Gln Gly Gln Glu Ser Gln Gln Glu
                210                 215                 220

Gly Val Ile Val Glu Leu Glu Arg Glu Gln Ile Arg Glu Leu Ile Lys
225                 230                 235                 240
```

```
His Ala Lys Ser Ser Ser Arg Arg Ala Leu Ser Ser Gln Asp Glu Pro
                245                 250                 255

Ile Asn Leu Arg Asn Arg Lys Pro Ile Tyr Ser Asn Lys Phe Gly Arg
            260                 265                 270

Trp Tyr Glu Ile Thr Pro Glu Lys Asn Pro Gln Leu Arg Asp Met Asp
        275                 280                 285

Met Phe Ile Ser Ser Val Asn Met Lys Glu Gly Leu Leu Leu Pro
    290                 295                 300

His Tyr Asn Ser Lys Ala Ile Val Ile Leu Val Ile Asn Lys Gly Glu
305                 310                 315                 320

Ala Asn Leu Glu Leu Val Gly Gln Arg Glu Gln Glu Gln Glu Ser
                325                 330                 335

Trp Glu Val Gln Arg Tyr Arg Ala Glu Leu Ser Glu Asp Asp Val Phe
                340                 345                 350

Ile Ile Pro Ala Thr Tyr Pro Val Ala Ile Asn Ala Thr Ser Asn Leu
            355                 360                 365

Asn Phe Phe Ala Phe Gly Ile Asn Ala Glu Asn Asn Gln Arg Asn Phe
        370                 375                 380

Leu Ala Gly Glu Arg Asp Asn Val Ile Ser Glu Ile Pro Thr Glu Val
385                 390                 395                 400

Leu Asp Val Thr Phe Pro Ala Ser Gly Glu Lys Val Val Lys Leu Val
                405                 410                 415

Lys Lys Gln Ser Glu Ser Tyr Phe Val Asp Ala Gln Ser Glu Gln
                420                 425                 430

<210> SEQ ID NO 9
<211> LENGTH: 338
<212> TYPE: PRT
<213> ORGANISM: Vigna radiata var. radiata

<400> SEQUENCE: 9

Met Leu Arg Ala Arg Val Gln Phe Leu Leu Gly Ile Leu Leu Leu Ala
1               5                   10                  15

Ser Leu Ser Ile Ser Phe Gly Ile Leu His Trp Glu His Gln Glu Ser
                20                  25                  30

Gln Glu Glu Ser Asp Ser Arg Gly Gln Asn Asn Pro Phe Tyr Phe Ser
            35                  40                  45

Ser His Lys Arg Phe His Thr Leu Phe Lys Asn Gln Tyr Gly His Leu
        50                  55                  60

Arg Val Leu His Arg Phe Asp Gln Arg Phe Gly Gln Ile Leu Asn Leu
65                  70                  75                  80

Glu Asn Tyr Arg Val Val Gln Phe Lys Ser Lys Pro Asn Thr Leu Leu
                85                  90                  95

Leu Pro His His Ala Asp Ala Asp Phe Leu Leu Val Val Leu Asn Gly
            100                 105                 110

Arg Ala Ile Leu Thr Leu Val Asn Pro Asp Gly Arg Asp Ser Tyr Ile
        115                 120                 125

Leu Glu Gln Gly His Ala Gln Lys Ile Pro Ala Gly Thr Thr Phe Phe
    130                 135                 140

Leu Val Asn Pro Asn Asp Asn Asp Asn Leu Arg Ile Ile Lys Leu Ala
145                 150                 155                 160

Ile Pro Val Asn Asn Pro His Arg Phe Gln Asn Phe Leu Ser Ser
                165                 170                 175

Thr Glu Ala Gln Gln Ser Tyr Leu Arg Gly Phe Ser Lys Asn Ile Leu
            180                 185                 190
```

-continued

```
Glu Ala Ser Phe Asp Ser Asp Phe Lys Glu Ile Asp Arg Val Leu Phe
            195                 200                 205

Gly Glu Arg Gln Gln Gln His Gly Glu Ser Gln Glu Glu Gly
    210                 215                 220

Val Ile Val Glu Leu Lys Arg Glu Gln Ile Arg Glu Leu Ile Lys His
225                 230                 235                 240

Ala Lys Ser Ser Arg Lys Glu Leu Ser Ser Gln Asp Glu Pro Phe
            245                 250                 255

Asn Leu Arg Asn Asn Pro Ile Tyr Ser Asn Lys Phe Gly Arg Trp
            260                 265                 270

Tyr Glu Ile Thr Pro Glu Arg Asn Pro Gln Leu Lys Asp Leu Asp Val
            275                 280                 285

Phe Ile Ser Ser Val Asp Met Glu Glu Pro Glu Ile Phe His Phe Phe
            290                 295                 300

Ser Ser Leu Met Leu Leu Pro Ser Val Leu Phe Pro Leu Thr Leu Ser
305                 310                 315                 320

Asp Arg Ile Tyr Phe Cys Ala Gly Phe Leu Ala Leu Glu His Asp Phe
                    325                 330                 335

Cys Ala

<210> SEQ ID NO 10
<211> LENGTH: 246
<212> TYPE: PRT
<213> ORGANISM: Vigna radiata var. radiata

<400> SEQUENCE: 10

Phe Gly Glu Glu Gly Gln Gln Gln Gln Gly Gln Glu Ser Gln Gln
1               5                   10                  15

Glu Gly Val Ile Val Glu Leu Lys Arg Glu Gln Ile Arg Glu Leu Ile
                20                  25                  30

Arg His Ala Lys Ser Asn Ser Lys Thr Leu Ser Ser Gln Asn Glu Pro
            35                  40                  45

Phe Asn Leu Arg Asn Gln Lys Pro Val Tyr Ser Asn Arg Phe Gly Arg
    50                  55                  60

Met His Glu Ile Thr Pro Glu Lys Asn Pro Gln Leu Arg Asp Leu Asp
65                  70                  75                  80

Val Phe Leu Ser Tyr Val Asp Met Lys Glu Gly Gly Leu Leu Met Pro
                85                  90                  95

Asn Tyr Asn Ser Lys Ala Ile Val Ile Leu Val Leu Asn Lys Gly Glu
            100                 105                 110

Ala Asn Ile Glu Leu Val Gly Leu Lys Glu Pro Gln Gln Gln Gln Gln
        115                 120                 125

Glu Glu Ser Trp Asp Val Gln Arg Tyr Ser Ala Glu Leu Thr Glu Asp
    130                 135                 140

Asp Val Phe Val Ile Pro Ala Ala Tyr Pro Val Ala Ile Asn Ala Thr
145                 150                 155                 160

Ser Asn Met Asn Phe Leu Ala Phe Gly Ile Asn Ala Glu Asn Asn Gln
                165                 170                 175

Arg Asn Phe Leu Ala Gly Glu Lys Asp Asn Val Ile Ser Glu Ile Pro
            180                 185                 190

Ser Gln Val Leu Glu Val Ala Phe Pro Gly Ser Gly Glu Lys Val Val
        195                 200                 205

Lys Leu Ile Asn Lys Gln Ser Leu Ser Tyr Phe Val Asp Ala Gln Ser
    210                 215                 220
```

```
Gln Gln Lys Glu Glu Gln Ser Lys Gly Arg Lys Gly Pro Leu Ser Ser
225                 230                 235                 240

Ile Leu Asp Thr Leu Tyr
                245

<210> SEQ ID NO 11
<211> LENGTH: 613
<212> TYPE: PRT
<213> ORGANISM: Vigna radiata var. radiata

<400> SEQUENCE: 11

Met Ala Arg Pro Phe Thr Leu Ser Leu Leu Ser Leu Cys Val Leu Leu
1               5                   10                  15

Ser Ala Arg Ser Cys Phe Gly Ser Ser Ser Thr Asn Arg Phe Asn
            20                  25                  30

Arg Cys Gln Phe Asn Ser Leu Asn Ala Leu Lys Pro Asp His Arg Val
            35                  40                  45

Glu Thr Asp Gly Gly Leu Val Glu Thr Trp Ser Arg His Pro Glu
    50                  55                  60

Leu Glu Cys Ala Gly Val Thr Ala Thr Arg Arg Thr Leu Tyr Arg Asn
65                  70                  75                  80

Gly Leu Gln Met Pro Ser Tyr Ser Pro Tyr Ser Gln Met Ile Ile Val
                85                  90                  95

Ile Gln Gly Lys Gly Ala Phe Gly Leu Ala Leu Ser Gly Cys Ala Glu
            100                 105                 110

Thr Tyr Glu Glu Pro Ala Lys Glu Ser Ser Ser Ser His Lys Pro
            115                 120                 125

Ser Asp Ser His Gln Lys Ile His Gln Ser Gly Pro Gly His Val Ile
130                 135                 140

Leu Ile Pro Arg Gly Val Pro Phe Trp Ile Phe Asn Thr Gly Asp Glu
145                 150                 155                 160

Pro Leu Ile Thr Val Thr Leu Leu Asp Thr Val Ser Glu Asp Asn Gln
                165                 170                 175

Leu Asp Gln Ser Pro Arg Glu Phe Tyr Leu Ala Gly Asn Pro Asp Ile
            180                 185                 190

Glu His Pro Glu Ala Met Lys Glu Lys Gln Gln Gln Ala Glu Glu
    195                 200                 205

Glu Gly Gly Asn Val Leu Ser Gly Phe Gly Lys Arg Phe Leu Ala Arg
210                 215                 220

Ala Leu Asn Ile Asp Gln Asp Ile Ala Asn Lys Leu Ile Ser Pro Asp
225                 230                 235                 240

Asp Glu Met Lys Gln Ile Val Lys Leu Lys Glu Gly Leu Ser Val Ile
                245                 250                 255

Ser Pro Lys Trp Gln Gly Gln Gln Glu Asp Glu Asp Glu Asp Asp
            260                 265                 270

Asp Glu Asp Glu Asp Glu Asp Glu Ser Val Ser Arg Pro Ser Arg Arg
            275                 280                 285

Pro Ser His Gly Lys Arg Val Arg Lys Glu Glu Lys Glu Val Glu
    290                 295                 300

Pro Tyr Gly Lys His Val His Lys Glu Val Lys Glu Val Glu Pro
305                 310                 315                 320

Leu Pro Pro Arg Lys His Val His Lys Glu Glu Lys Glu Ile Glu
                325                 330                 335

Pro Leu Pro Pro Arg Arg Ser Arg His His His Asp Glu Asp Glu Asp
```

```
            340                 345                 350
Glu Asp Glu Asp Glu Glu Lys Pro Arg Arg Thr Arg Gly Pro Thr
            355                 360                 365

Pro Ser Pro Lys Gly Glu Gly His Arg Gly Val Glu Val Glu Glu Asp
        370                 375                 380

Glu Ser Asp Glu Ser Val Arg His Lys Thr Arg His Glu Lys Ser Trp
385                 390                 395                 400

Lys Glu His Arg Pro Ala Gln Glu Asp Val Glu Arg Gly Glu Ala His
                405                 410                 415

Glu Glu Trp Glu Thr Arg Pro Ser Lys Asp Lys Arg His Gly Ser Asn
            420                 425                 430

Gly Leu Glu Glu Thr Ile Cys Ser Ser Lys Leu Gln Phe Asn Ile Ala
        435                 440                 445

Arg Pro Lys Ser Ala Asp Phe Tyr Asn Pro Lys Ala Gly Arg Ile Lys
    450                 455                 460

Asn Leu Asn Ser Gln Ser Leu Pro Ala Leu Arg Asn Phe Gly Leu Ser
465                 470                 475                 480

Ala Gln Tyr Val Val Leu Tyr Lys Asn Gly Ile Tyr Ser Pro His Trp
                485                 490                 495

Asn Met Asp Ala Asn Ser Val Ile Tyr Val Ile Arg Gly Gln Gly Gln
            500                 505                 510

Val Arg Val Val Asn Asn Glu Gly Ile Met Val Phe Asp Asp Glu Leu
        515                 520                 525

Ser Lys Gly Gln Leu Leu Val Val Pro Gln Asn Phe Met Val Ala Glu
    530                 535                 540

Glu Ala Gly Asp Gln Gly Phe Glu Tyr Val Val Phe Lys Thr Asn Asp
545                 550                 555                 560

Asn Ala Val Thr Ser Tyr Leu Lys Glu Thr Phe Arg Ala Phe Pro Ala
                565                 570                 575

Glu Val Leu Ala Asn Ile Tyr Lys Leu Lys Gln Ser Gln Val Tyr Asp
            580                 585                 590

Leu Lys Tyr Asn Gly Asn Trp Gly Pro Leu Ala Asn Pro Val Gln Ser
        595                 600                 605

Gln Asp Gln Ser Ser
    610
```

<210> SEQ ID NO 12
<211> LENGTH: 532
<212> TYPE: PRT
<213> ORGANISM: Vigna radiata var. radiata

<400> SEQUENCE: 12

```
Met Met Arg Ser Arg Phe Pro Leu Leu Leu Leu Gly Val Val Phe
1               5                   10                  15

Leu Ala Ser Val Ser Val Ser Phe Gly Ile Ala Tyr Trp Glu Lys Glu
                20                  25                  30

Asn Leu Ser His Asn Lys Cys Leu Arg Ser Cys Ser Ser Glu Lys Ser
            35                  40                  45

Thr Tyr Arg Ile Gln Ala Cys His Ala Arg Cys Asn Leu Leu Lys Glu
        50                  55                  60

Asp Lys Glu His Gln Glu Gly Glu His Ser Leu Pro Thr His His Glu
65                  70                  75                  80

Glu Glu Asp Glu Asp Glu Ser Arg Gln Pro Arg Pro Phe Pro Phe Pro
                85                  90                  95
```

```
Phe Pro Ile Pro Leu Arg Pro Arg Glu Arg Gln Ser Glu Gly Ser Glu
                100                 105                 110

Ser Ser Arg Lys Gln Asn Asn Pro Phe His Phe Ser Ser Asn Arg Phe
            115                 120                 125

His Ser Leu Phe Lys Asn Pro Asn Gly His Ile Arg Leu Leu Gln Arg
        130                 135                 140

Phe Asp Gln Gln Ser Lys Gln Leu Gln Asn Leu Gln Asp Tyr Arg Leu
145                 150                 155                 160

Leu Glu Val Gln Leu Arg Pro Arg Thr Leu Leu Pro His His Val
                165                 170                 175

Asp Ala Asp Tyr Ile Ile Ile Ile Leu Ser Gly Arg Ala Ile Leu Thr
                180                 185                 190

Leu Gln Asn Pro Asp Asp Arg Asp Ser Tyr Asn Leu Gln Asn Gly Asp
            195                 200                 205

Val Gln Asn Ile Pro Ala Gly Thr Thr Leu Tyr Leu Ile Asn Pro Asp
            210                 215                 220

Asn Glu Glu Thr Leu Lys Val Met Val Leu Ala Arg Pro Ile Asn Asn
225                 230                 235                 240

Pro Gly Arg Leu Glu Ser Phe Phe Leu Ser Ser Thr Glu Ala Gln Gln
                245                 250                 255

Ser Tyr Leu Gln Gly Phe Ser Lys Lys Thr Leu Glu Ala Ser Phe Asp
            260                 265                 270

Thr Gln Phe Lys Glu Ile Asn Arg Val Leu Phe Gly Glu Glu Gly Gln
            275                 280                 285

Gln Gln Asp Glu Glu Lys Gln Glu Gly Val Ile Val Lys Leu Ser Lys
        290                 295                 300

Glu Gln Ile Arg Glu Leu Ser Lys His Ala Lys Ser Ser Lys Lys
305                 310                 315                 320

Thr Ile Ser Ser Lys Asp Lys Pro Phe Asn Leu Arg Ser Ser Ser Pro
                325                 330                 335

Val Tyr Ser Asn Thr Leu Gly Lys Phe Tyr Glu Ile Thr Pro Glu Lys
            340                 345                 350

Asn Pro Gln Leu Arg Asp Met Asp Val Phe Val Ser Phe Val Asn Met
            355                 360                 365

Lys Glu Gly Ala Leu Leu Pro His Tyr Asn Ser Lys Ser Ile Val
        370                 375                 380

Ile Leu Val Val Asn Lys Gly Glu Ala Asn Ala Glu Leu Val Gly Glu
385                 390                 395                 400

Arg Glu Gln Gln Gln Glu Glu Ser Gly Glu Val Gln Arg Tyr Arg Ala
                405                 410                 415

Glu Leu Ser Glu Glu Asp Val Leu Val Ile Pro Ala Thr Tyr Pro Val
            420                 425                 430

Ala Ile Asn Ala Thr Ser Asn Leu Asn Phe Phe Ala Phe Gly Ile Asn
        435                 440                 445

Ala Glu Asn Asn Gln Arg Asn Phe Leu Ala Gly Glu Lys Asp Asn Val
        450                 455                 460

Met Ser Asp Ile Pro Arg Pro Val Leu Glu Val Ala Phe Pro Gly Ser
465                 470                 475                 480

Gly Glu Glu Thr Glu Lys Leu Ile Lys Lys Gln Thr Glu Ser Tyr Phe
                485                 490                 495

Val Asp Ala Gln Pro Gln Gln Lys Gln Ser Gln Glu Lys Glu Lys Glu
            500                 505                 510

Glu Lys Glu Glu Gly Ser Lys Gly Arg Asn Pro Leu Tyr Ser Ile Leu
```

```
                515                 520                 525

Asn Ala Phe Tyr
    530

<210> SEQ ID NO 13
<211> LENGTH: 155
<212> TYPE: PRT
<213> ORGANISM: Vigna radiata

<400> SEQUENCE: 13

Met Ala Val Phe Thr Phe Asp Asp Gln Ala Thr Ser Pro Val Ala Pro
1               5                   10                  15

Ala Thr Leu Tyr Asn Ala Leu Ala Lys Asp Ala Asp Asn Ile Ile Pro
            20                  25                  30

Lys Ala Val Gly Ser Phe Gln Ser Val Glu Ile Val Glu Gly Asn Gly
        35                  40                  45

Gly Pro Gly Thr Ile Lys Lys Ile Ser Phe Val Glu Asp Gly Glu Thr
    50                  55                  60

Lys Phe Val Leu His Lys Ile Glu Ser Val Asp Glu Ala Asn Leu Gly
65                  70                  75                  80

Tyr Ser Tyr Ser Ile Val Gly Gly Val Ala Leu Pro Asp Thr Ala Glu
                85                  90                  95

Lys Ile Thr Ile Asp Thr Lys Ile Ser Asp Gly Ala Asp Gly Gly Ser
            100                 105                 110

Leu Ile Lys Leu Thr Ile Ser Tyr His Gly Lys Gly Asp Ala Pro Pro
        115                 120                 125

Asn Glu Asp Glu Leu Lys Ala Gly Lys Ala Lys Ser Asp Ala Leu Phe
    130                 135                 140

Lys Ala Val Glu Ala Tyr Leu Leu Ala Asn Pro
145                 150                 155

<210> SEQ ID NO 14
<211> LENGTH: 297
<212> TYPE: PRT
<213> ORGANISM: Vigna radiata var. radiata

<400> SEQUENCE: 14

Met Ala Val Ser Ser Thr Asn Tyr Ser Phe Leu Ile Ala Val Phe Ala
1               5                   10                  15

Phe Val Thr Met Leu Leu Met Phe Pro Asn Lys Val Lys Ser Ala Gln
            20                  25                  30

Ser Leu Ser Phe Ser Phe Ser Arg Phe Gly Pro Asp His Lys Asp Leu
        35                  40                  45

Ile Phe Gln Gly Asp Ala Ile Ser Thr Asn Asn Val Leu Gln Leu Thr
    50                  55                  60

Lys Leu Asp Ser Ala Gly Asn Pro Leu Ser Gly Ser Val Gly Arg Val
65                  70                  75                  80

Leu Tyr Ser Ala Pro Leu His Leu Trp Glu Asn Ser Ala Val Val Ser
                85                  90                  95

Ser Phe Glu Thr Ser Phe Thr Phe Gln Ile Ser Thr Pro Tyr Thr Ser
            100                 105                 110

Pro Pro Ala Asp Gly Val Ala Phe Phe Leu Ala Pro Tyr Asp Thr Val
        115                 120                 125

Ile Pro Ser Asn Ser Gly Gly Ser Leu Leu Gly Leu Phe Ser Asn Leu
    130                 135                 140

Asn Ala Leu Arg Asn Ser Ser Thr Ser Gln Asn Gln Thr Ile Leu Asp
```

```
                145                 150                 155                 160
        Phe Lys Ala Val Ser Asn Lys Val Ala Val Glu Phe Asp Thr Tyr
                        165                 170                 175
        Pro Asn Glu Asn Ile Gly Asp Pro Ala Tyr Lys His Ile Gly Ile Asp
                        180                 185                 190
        Val Asn Ser Ile Arg Ser Lys Thr Thr Ala Arg Trp Asn Trp Gln Asn
                        195                 200                 205
        Gly Lys Thr Ala Thr Ala His Ile Ser Tyr Asn Ser Ala Ser Lys Arg
        210                 215                 220
        Leu Thr Val Ser Thr Phe Tyr Pro Gly Ser Asn Pro Val Thr Leu Ser
        225                 230                 235                 240
        Tyr Asp Val Glu Leu His Thr Val Leu Ser Glu Trp Val Arg Val Gly
                        245                 250                 255
        Phe Ser Ala Ser Ser Gly Glu Gln Lys Glu Arg Asn Thr Ile Leu Ser
                        260                 265                 270
        Trp Ser Phe Thr Ser Ser Leu Lys Asn Asn Glu Val Lys Asp Glu Lys
                        275                 280                 285
        Gln Asp Met Phe Ile Lys Thr Val Val
                        290                 295

<210> SEQ ID NO 15
<211> LENGTH: 246
<212> TYPE: PRT
<213> ORGANISM: Vigna radiata var. radiata

<400> SEQUENCE: 15

Met Arg Ala Ser Thr Ser Ser Ile Pro Ile Pro Ser Ser Ser Ser Arg
1               5                   10                  15
Phe Ser Ile Phe Phe Phe Leu Leu Phe Ala Leu Leu Ala Leu Arg Ser
                20                  25                  30
Ser Ser Ser Asp Cys Ser His Phe Gln His Arg Ala Pro Met Ala Thr
            35                  40                  45
Val Gly Gly Val Arg Asp Ser Pro Val Ser Gln Asn Ser Leu Glu Thr
        50                  55                  60
Glu Ser Leu Ala Arg Phe Ala Val Asp Glu His Asn Lys Lys Gln Asn
65                  70                  75                  80
Ser Leu Leu Glu Phe Ala Arg Val Val Lys Ala Gln Glu Gln Val Val
                85                  90                  95
Ala Gly Thr Leu His His Leu Thr Leu Glu Ala Ile Glu Ala Gly Glu
            100                 105                 110
Lys Lys Leu Tyr Glu Ala Lys Val Trp Val Lys Pro Trp Leu Asn Ser
        115                 120                 125
Lys Glu Leu Gln Glu Phe Lys Pro Ala Gly Val Ala Ser Pro Phe Thr
    130                 135                 140
Ser Ala Asp Leu Gly Val Lys Lys Asp Gly His Lys Ser Gly Trp Gln
145                 150                 155                 160
Ser Val Pro Thr His Asp Pro Gln Val Gln Asp Ala Ala Asn His Ala
                165                 170                 175
Ile Arg Thr Ile Gln Gln Arg Ser Asn Ser Leu Val Pro Tyr Val Leu
            180                 185                 190
His Glu Val Ala Asp Ala Lys Ala Glu Val Ile Asp Asp Phe Ala Lys
        195                 200                 205
Phe Asn Leu Leu Leu Lys Val Lys Arg Gly Glu Lys Glu Glu Lys Phe
    210                 215                 220
```

-continued

```
Lys Val Glu Val His Lys Asn Asn Glu Gly Ala Leu His Leu Asn Gln
225                 230                 235                 240

Met Glu Gln Asp His Ser
                245
```

FUNCTIONAL MUNG BEAN-DERIVED COMPOSITIONS

1. CROSS REFERENCE TO RELATED APPLICATIONS

This application is a continuation of U.S. application Ser. No. 15/535,020, filed on Jun. 9, 2017, now patented as U.S. Pat. No. 10,321,705 B2, which in turn claims priority to U.S. Provisional Application No. 62/297,788, entitled "Plant Protein Isolates, Methods and Compositions," filed Feb. 19, 2016, and U.S. Provisional Application No. 62/433,182, entitled "Mung Bean Protein Isolates," filed Dec. 12, 2016, each of which is hereby incorporated by reference.

SEQUENCE LISTING

This application incorporates the Sequence Listing filed concurrently herewith, the contents of which is incorporated by reference in its entirety.

2. FIELD OF THE INVENTION

The present disclosure relates to mung bean-derived compositions, methods for producing such compositions, and food products derivable from such compositions.

3. BACKGROUND

Conventional methods and processes used for extracting legume protein isolates and concentrates include alkaline extraction and acid precipitation or ultrafiltration (wet process) and air classification (dry process). The quality of the legume protein compositions produced by these methods is directly dependent on the operating conditions used to prepare them. Application of an acidic, alkaline or neutral extraction process directly influences functional properties, e.g., the gelling, foaming or emulsifying properties of the protein compositions obtained, which makes the resulting protein compositions unsuitable for certain applications. It may therefore be necessary to modify the protein compositions so as to confer desired properties in the context of food applications.

Use of plant-based proteins such as soy and pea as animal protein substitutes have garnered increasing attention largely as consumers seek alternatives to conventional animal-based products, however, replicating functional properties while removing off-flavors are still challenges that need to be addressed.

What is needed, therefore, is a method and composition for producing purified plant protein isolates that exhibit one or more desired functional properties including replicating one or more desired organoleptic properties suitable for various applications. Disclosed herein are methods addressing the limitations of the current art.

4. SUMMARY OF THE INVENTION

Described herein are methods and compositions for producing a purified mung bean protein isolate. In some embodiments, the mung bean protein isolate comprises mung bean protein content of at least 60% by weight. In some embodiments, a globulin-type protein content represents at least 50% by weight of the mung bean protein in the isolate. In some embodiments, the globulin-type protein is a protein having at least 50% identity to 8S globulin/beta-conglycinin of *Vigna radiata*.

In some embodiments, the mung bean protein isolate comprises a reduced oxidative enzyme activity relative to an otherwise unmodified source of the mung bean protein. In some embodiments, mung bean protein isolate comprises one or more modulated organoleptic properties that differ from the otherwise unmodified source of the mung bean protein.

Also provided herein are methods for producing a mung bean protein isolate having high functionality for a broad range of food applications. In some embodiments, the methods for producing the isolate comprise one or more steps selected from:

(a) Extracting one or more mung bean proteins from a mung bean protein source in an aqueous solution. In some embodiments, the extraction is performed at a pH between about 6.5-10.0.

(b) Purifying protein from the extract using at least one of two methods:

(i) precipitating protein from the extract at a pH near the isoelectric point of a globulin-rich fraction, for example a pH between about 5.0-6.0; and/or (ii) fractionating and concentrating protein from the extract using filtration such as microfiltration, ultrafiltration or ion-exchange chromatography.

(c) Recovering purified protein isolate.

In particular embodiments, the extraction is performed at a pH of about 7.0+/−0.2. In particular embodiments, the isoelectric precipitation of mung bean protein is performed at pH 5.6+/−0.2. In other particular embodiments, the isoelectric precipitation of mung bean protein is performed at pH 6.0+/−0.2.

Also disclosed is a process to produce an edible mung bean protein isolate from a source of a mung bean protein, the process comprising: subjecting the source of the mung bean protein to a fractionation process to obtain a protein-rich fraction, wherein at least 50% by weight of the protein-rich fraction comprises or consists of one or more globulin-type proteins; reducing at least one impurity, the at least one impurity associated with an off-odor or an off-flavor in the edible mung bean protein isolate; and purifying the protein-rich fraction to obtain the edible mung bean protein isolate, wherein: at least 60% by weight of the edible protein isolate is mung bean protein, an oxidative enzymatic activity of the edible protein isolate is lower than a corresponding oxidative enzymatic activity of the source of the mung bean protein, and an organoleptic property of the edible protein isolate differs from a corresponding organoleptic property of the source of the mung bean protein.

In accordance with preferred aspects of the present invention, methods and compositions for egg replacement are provided, said composition comprising a plant-based protein isolate modified by transglutaminase; wherein said composition is essentially egg-free and, wherein said composition comprises one or more functional properties of a natural egg. Preferably, composition comprises emulsifying properties of a natural egg. More preferably, the composition provides mung bean protein isolate modified by 0.0001% to 0.0125% transglutaminase and exhibits significantly reduced activity of lipoxygenase or other enzymes that can oxidize lipids.

In certain aspects, the methods and compositions described herein provide purified protein isolates having modulated organoleptic properties of one or more of the following characteristics: astringent, beany, bitter, burnt, buttery, nutty, sweet, sour, fruity, floral, woody, earthy, beany, spicy, metallic, sweet, musty, grassy, green, oily, vinegary, neutral and bland flavor or aromas. Preferably, the purified protein isolates exhibit modulated organoleptic properties such as a reduction or absence in one or more of the following: astringent, beany, bitter, burnt, buttery, nutty, sweet, sour, fruity, floral, woody, earthy, beany, spicy, metallic, sweet, musty, grassy, green, oily, vinegary neutral and bland flavor or aromas.

The purified protein isolates are suitable for various food applications and have been incorporated into, e.g., edible egg-free emulsion, egg analog, egg-free scrambled eggs, egg-free patty, egg-free pound cake, egg-free angel food cake, egg-free yellow cake, egg- and dairy-free cream cheese, egg-free pasta dough, egg-free custard, egg-free ice cream, and dairy-free milk. The purified protein isolates are also suitable for use as plant-based analogs for cream cheese, pasta dough, pasta, milk or milk-like beverage, a food product comprising said milk or milk-like beverage, custard, ice cream, frozen desert, meat replicas (e.g., deli meat replicas; emulsified extruded meats (e.g., sausages, fish cake replicas); dips, fillings and spreads, chips, and crackers. Other applications are also suitable for the functional mung bean protein isolates described herein, and the foregoing list is non-limiting.

5. BRIEF DESCRIPTION OF THE FIGURES

Figure 2:
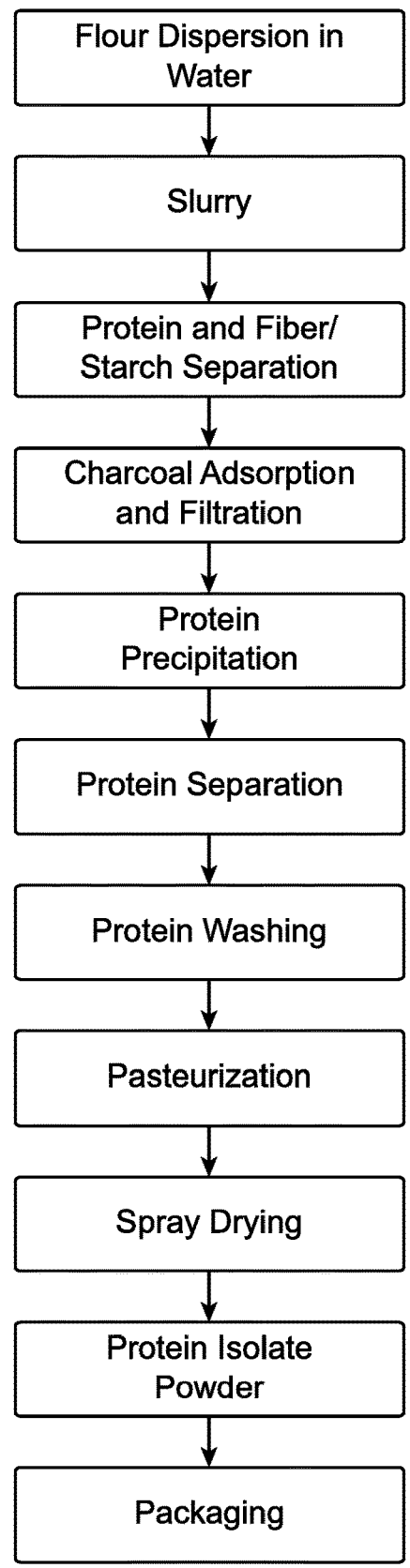

FIG. 2 provides one embodiment of a process for preparation of protein isolate in accordance with the methods provided herein.

Figure 3:
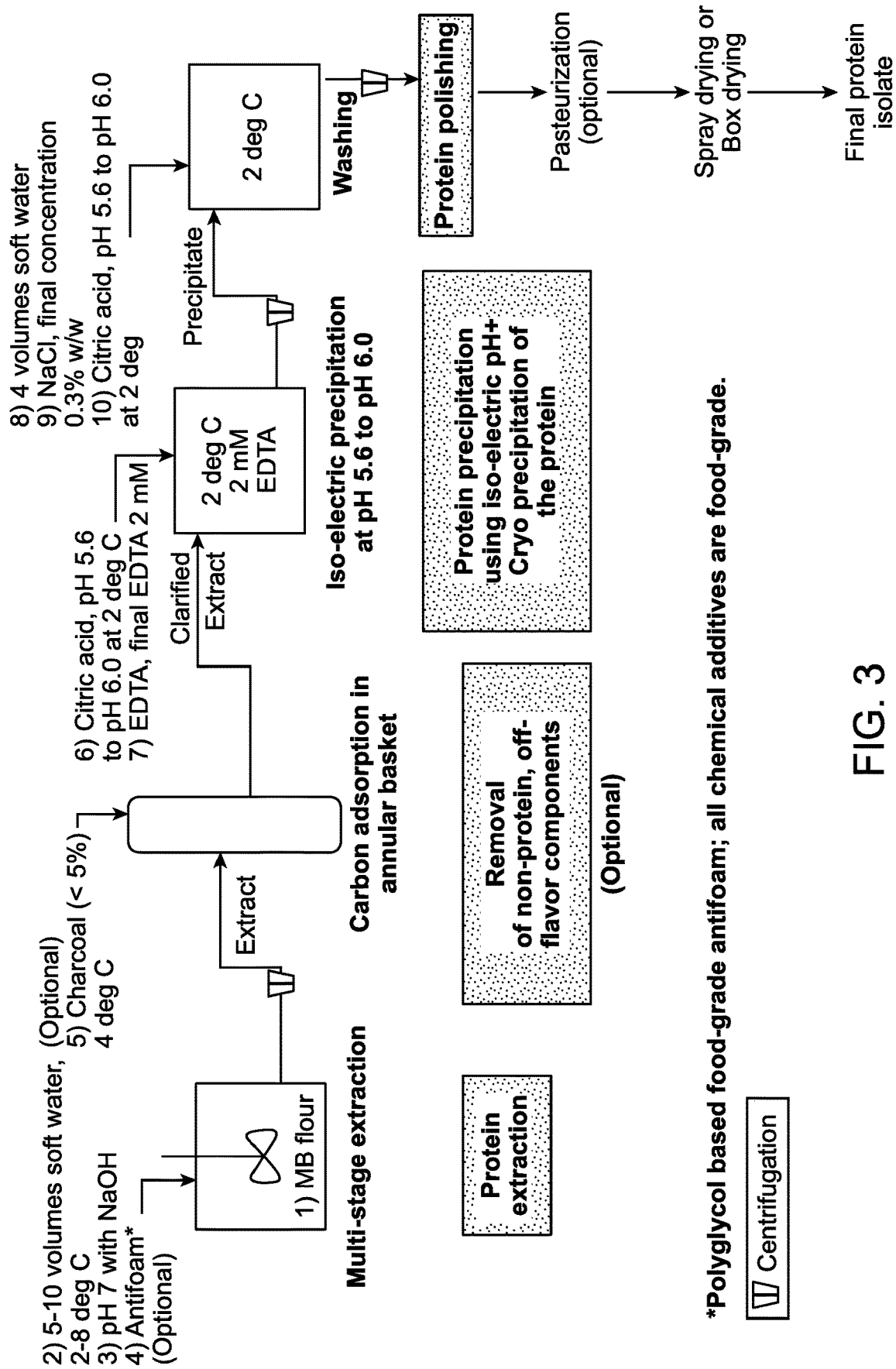

FIG. 3 depicts a general process block flow diagram for pilot scale protein isolation.

Figure 4:
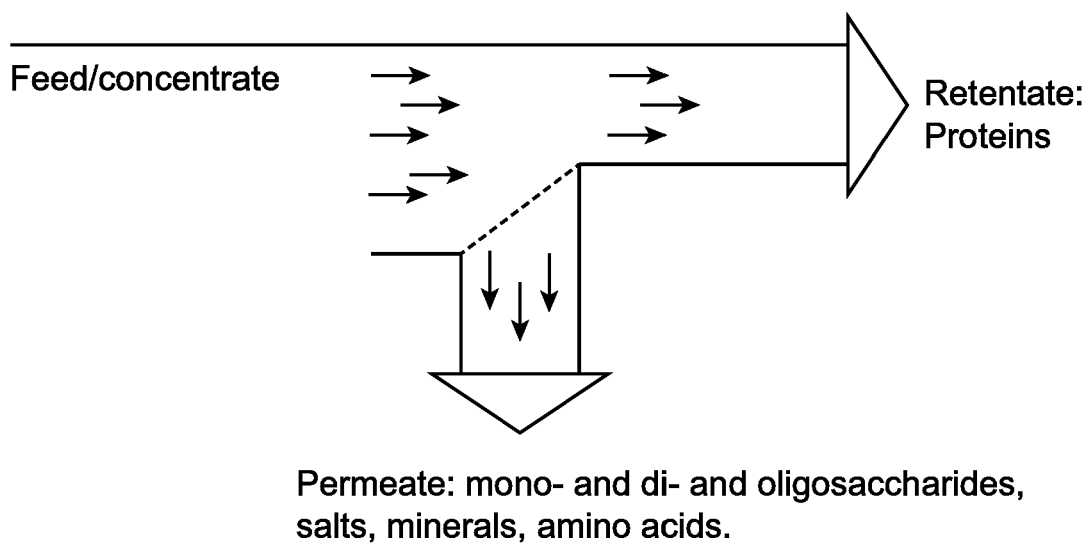

FIG. 4 graphically depicts the principal of ultrafiltration. The diagonal line represents a semipermeable membrane in which water and lower molecular weight solutes pass through into the permeate, while higher molecular weight solutes are retained in the retentate.

Figures 5A, 5B:
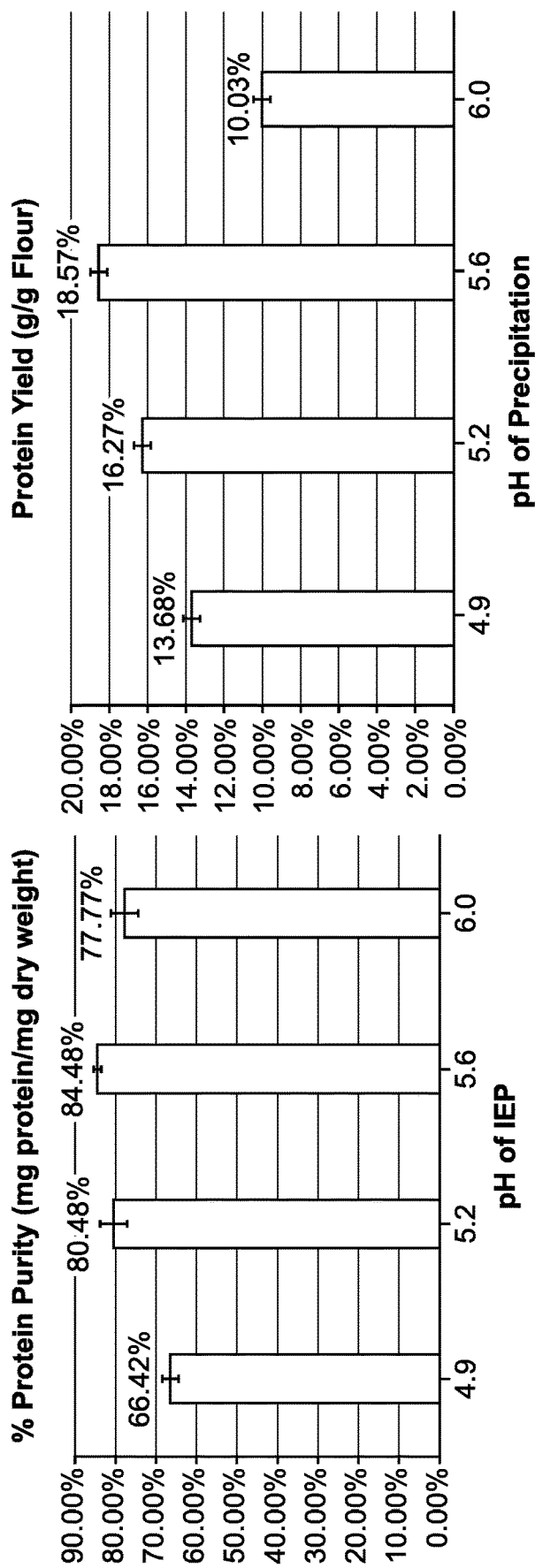

FIG. 5A graphically depicts the protein purity of mung bean isolates having undergone acid precipitations at pH 4.9, 5.2, 5.6 and 6, respectively.

FIG. 5B graphically depicts the protein yield of mung bean isolates having undergone acid precipitations at pH 4.9, 5.2, 5.6 and 6, respectively.

Figure 6A:
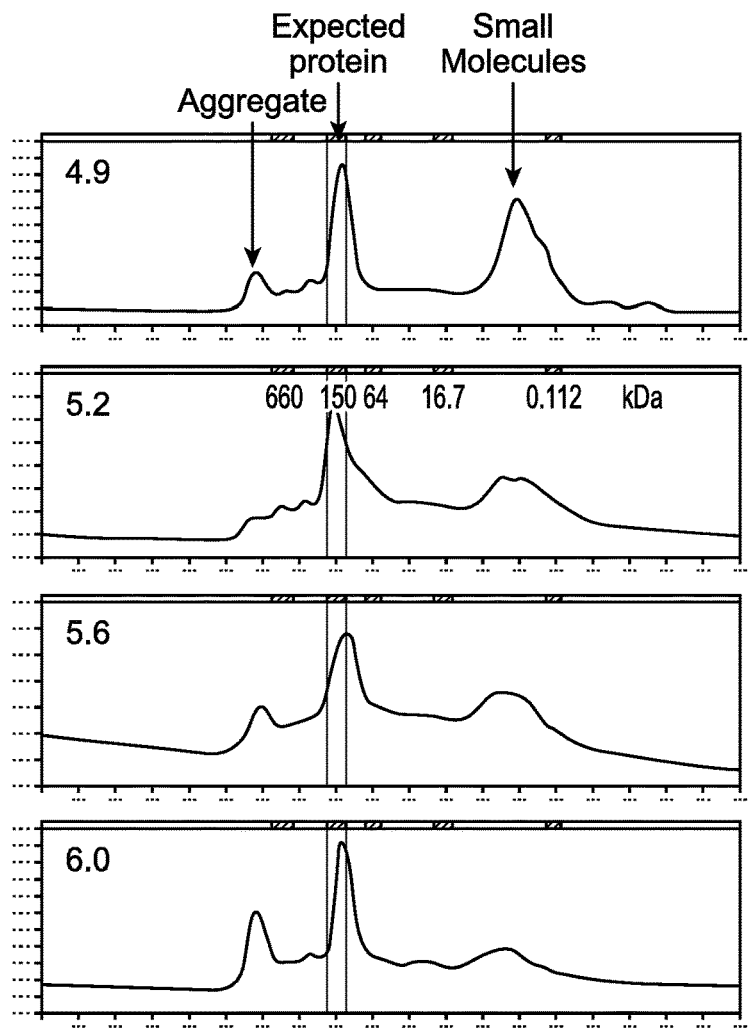

FIG. 6A depicts size exclusion chromatographs of mung bean isolates having undergone acid precipitations at pH 4.9, 5.2, 5.6 and 6, respectively.

Figure 6B:
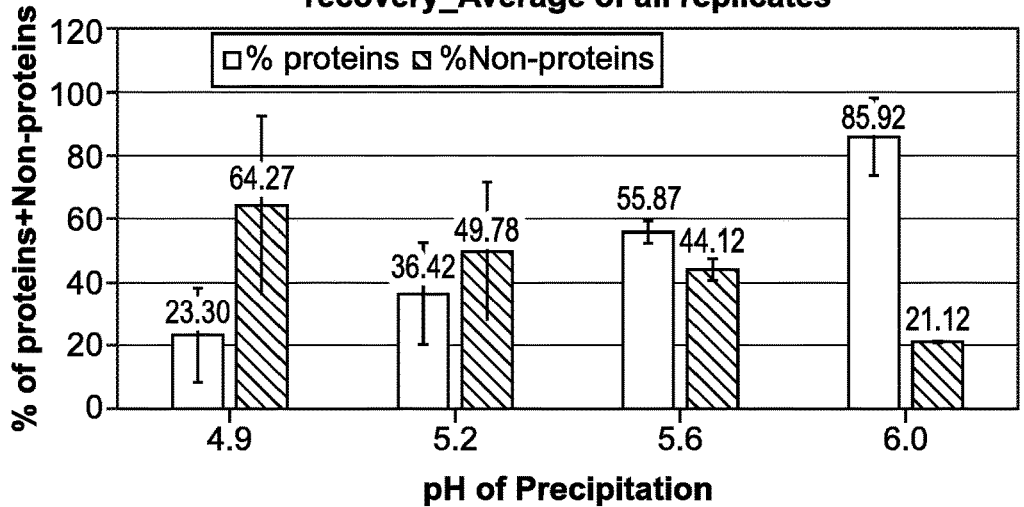

FIG. 6B graphically depicts the amounts of protein and non-protein species of mung bean isolates having undergone acid precipitations at pH 4.9, 5.2, 5.6 and 6, respectively.

Figure 7:
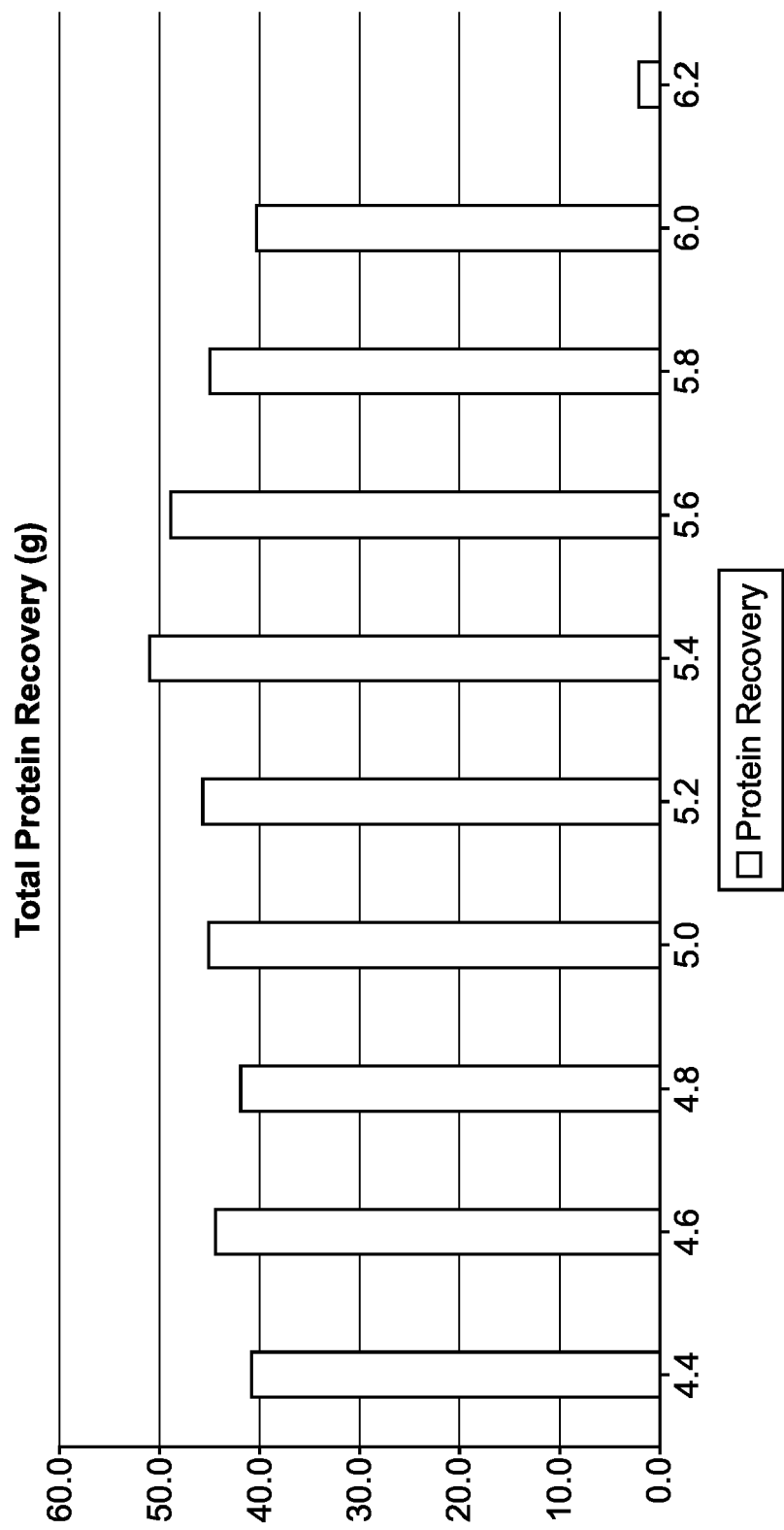

FIG. 7 graphically depicts total protein recovery in mung bean isolates that have undergone acid precipitations at pH 4.4, 4.6, 4.8, 5.0, 5.2, 5.4, 5.6, 5.8, 6.0 and 6.2, respectively. The y-axis represents grams of protein recovered from 100.7 grams of extract comprising the protein.

Figure 8B:
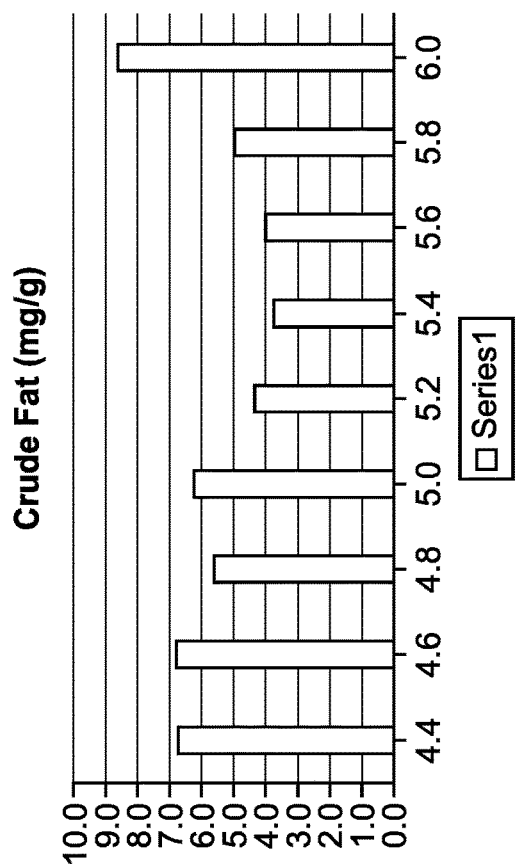
Figure 8A:
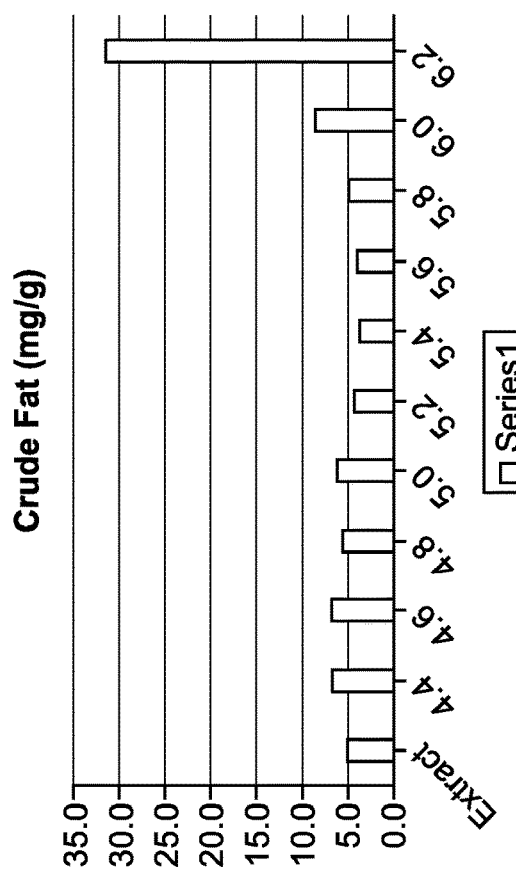

FIGS. 8A and 8B graphically depicts total oils recovered in mung bean protein isolates that have undergone acid precipitations at pH 4.4, 4.6, 4.8, 5.0, 5.2, 5.4, 5.6, 5.8, 6.0 and 6.2, respectively. The y-axis represents milligrams of crude fat recovered per gram of sample (extract or isolate).

FIG. 8A provides a view of the amounts of crude fat recovered for isolates precipitated each of the above pH values and also including a mung bean protein extract prior to precipitation (far left). FIG. 8B provides a closer view of the amounts of crude fat recovered for isolates precipitated at pH 4.4, 4.6, 4.8, 5, 5.2, 5.4, 5.6, 5.8 and 6.0.

Figure 9A:
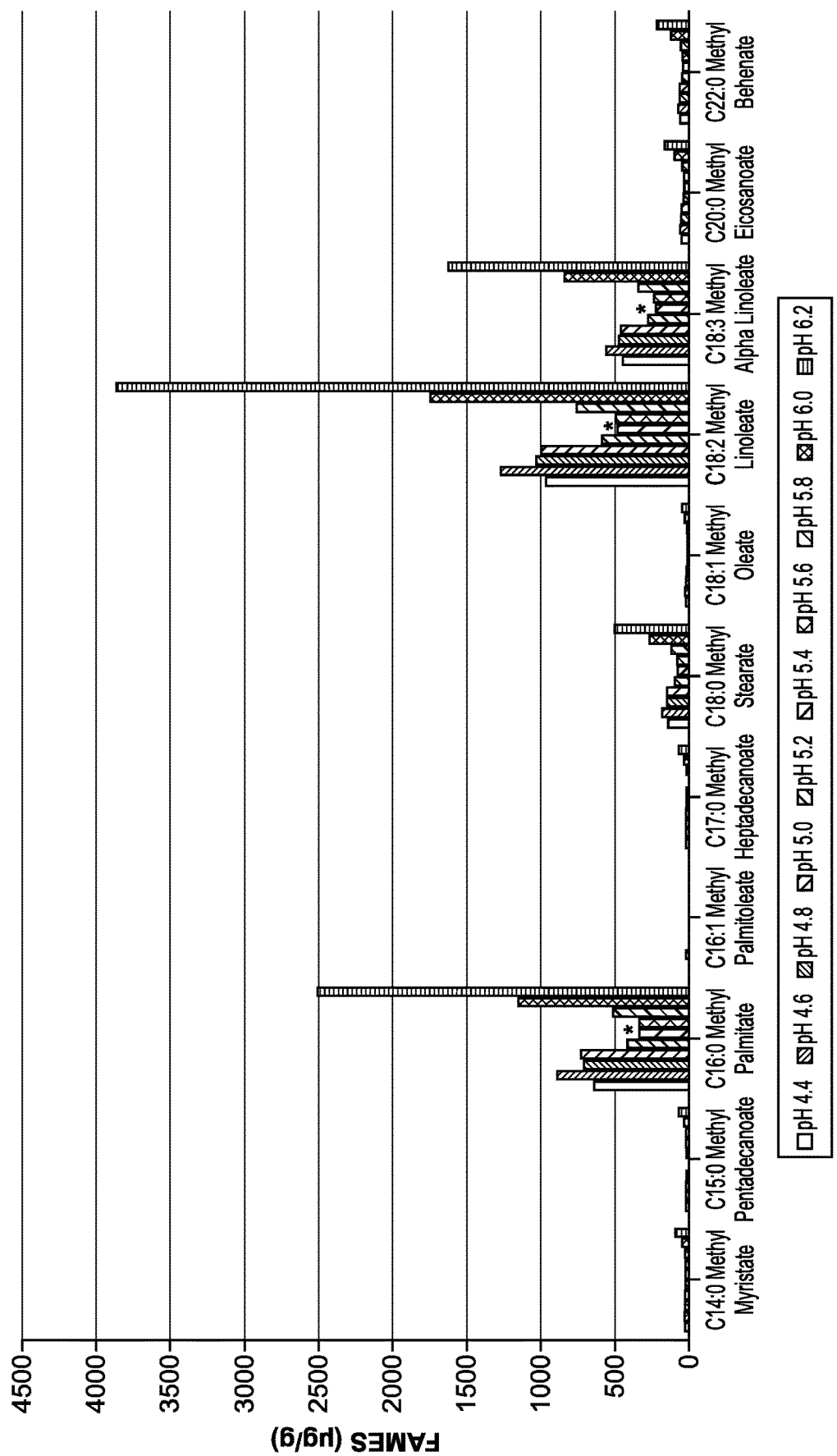
Figure 9B:
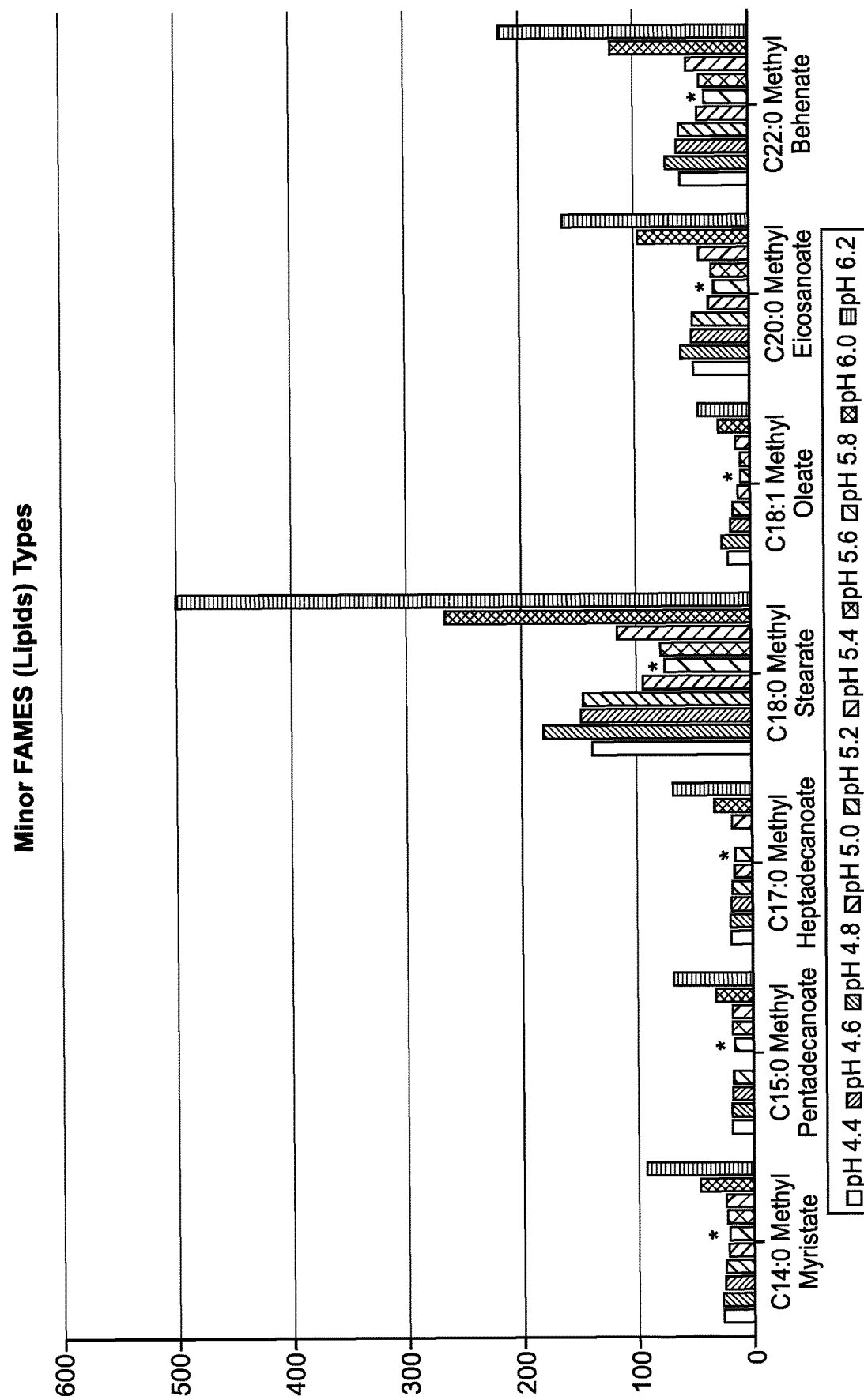

FIGS. 9A and 9B graphically depicts amounts of fatty acids (measured as fatty acid methyl esters) recovered in mung bean protein isolates that have undergone acid precipitations at pH 4.4, 4.6, 4.8, 5.0, 5.2, 5.4, 5.6, 5.8, 6.0 and 6.2, respectively. The specific fatty acids measured are (from left to right): C14:0 (methyl myristate); C15:0 (methyl pentadecanoate); C16:0 (methyl palmitate; C16:1 methyl palmitoleate; C17:0 methyl heptadecanoate; C18:0 methyl stearate; C18:1 methyl oleate; C18:2 methyl linoleate; C18:3 methyl alpha linoleate; C20:0 methyl eicosanoate; and C22:0 methyl behenate. FIG. 9A provides a view of the amounts of each of these fatty acids recovered for isolates precipitated at each of the above pH values, while FIG. 9B provides a closer view of the amounts of the minor lipid types.

Figure 10:
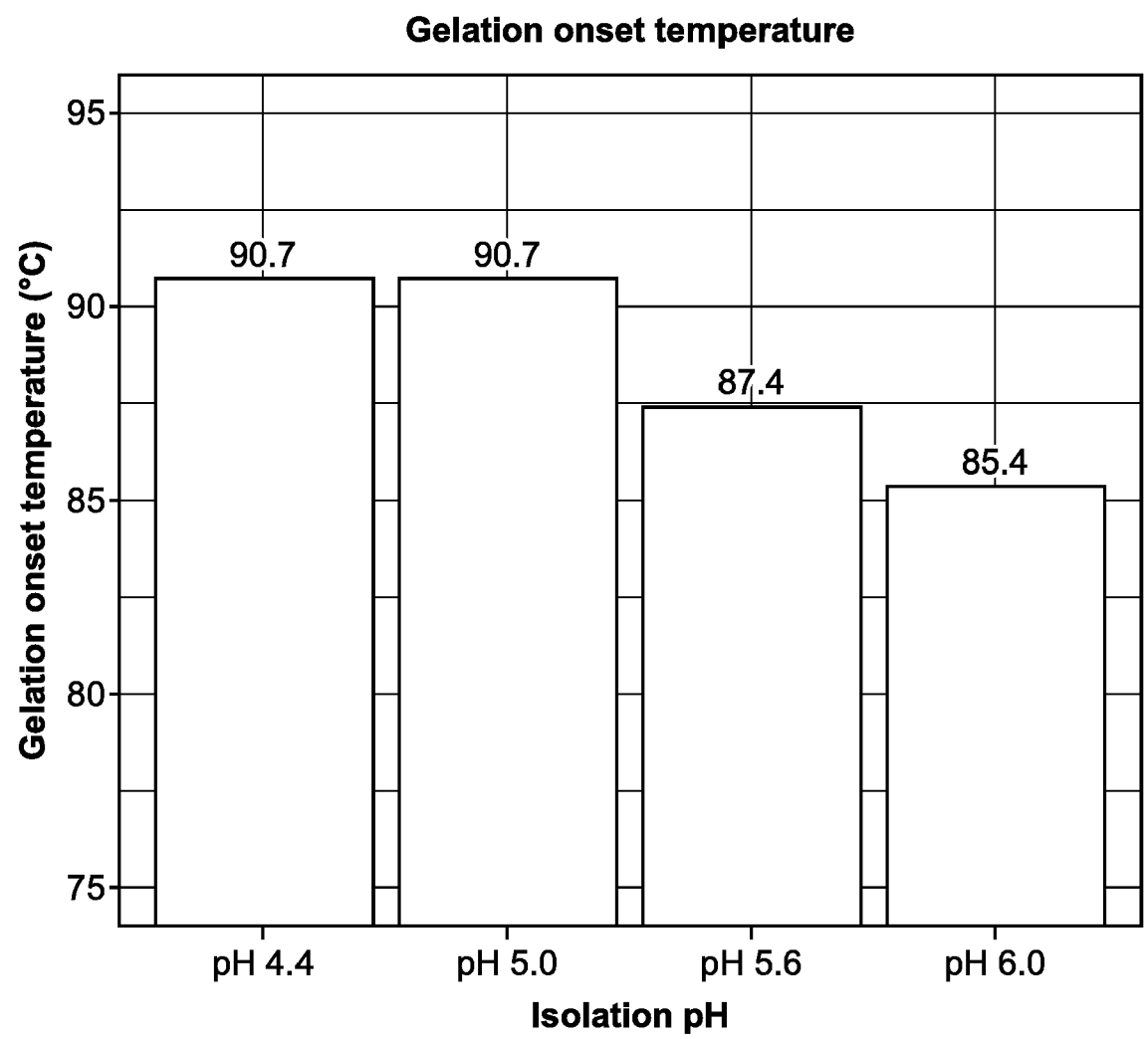

FIG. 10 graphically depicts the gelation onset temperature for mung bean protein isolates that have undergone acid precipitations at pH 4.4, 5.0, 5.6 and 6.0, respectively.

Figure 11:
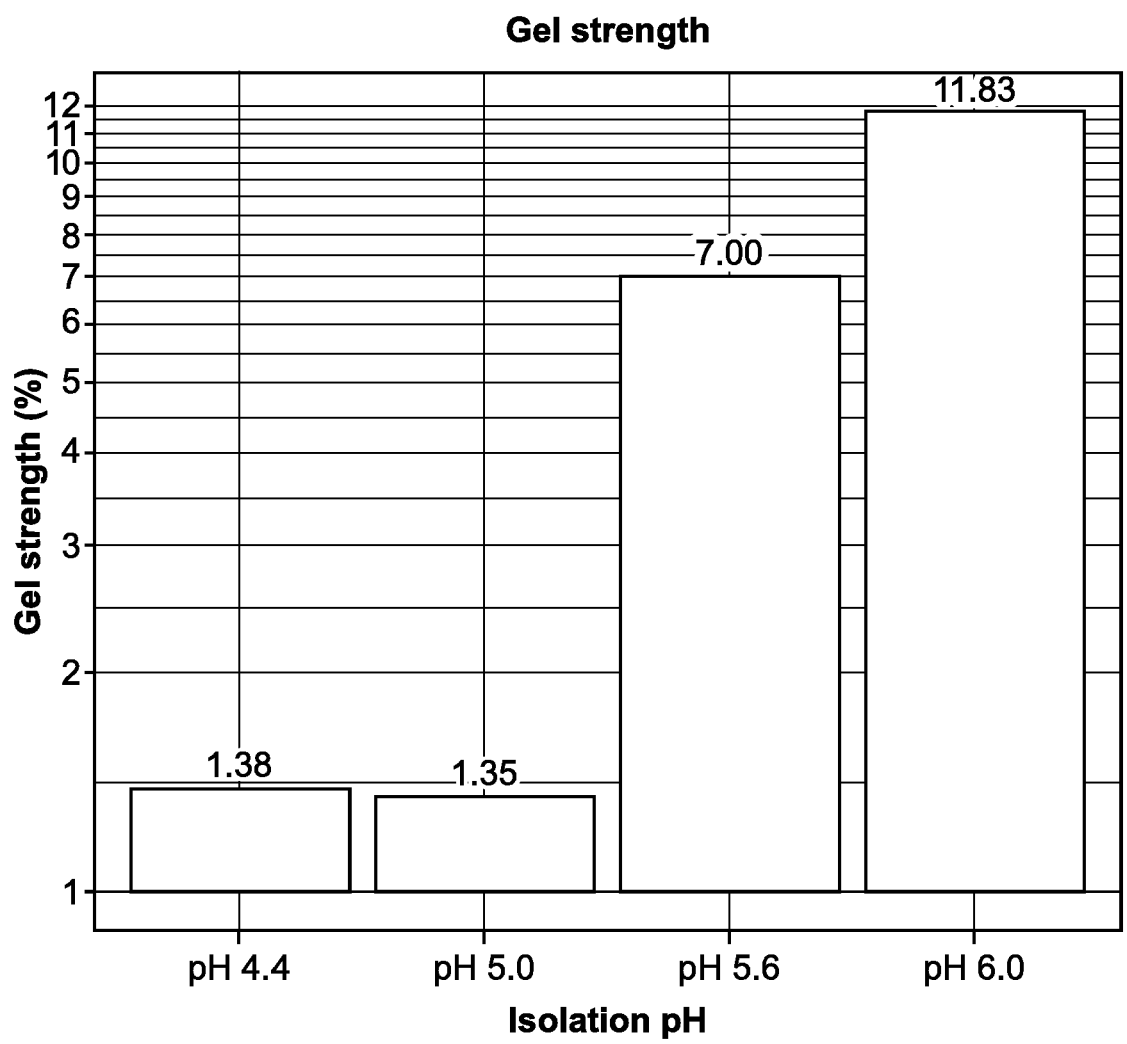

FIG. 11 graphically depicts the gel strength for mung bean protein isolates that have undergone acid precipitations at pH 4.4, 5.0, 5.6 and 6.0, respectively.

Figure 12:
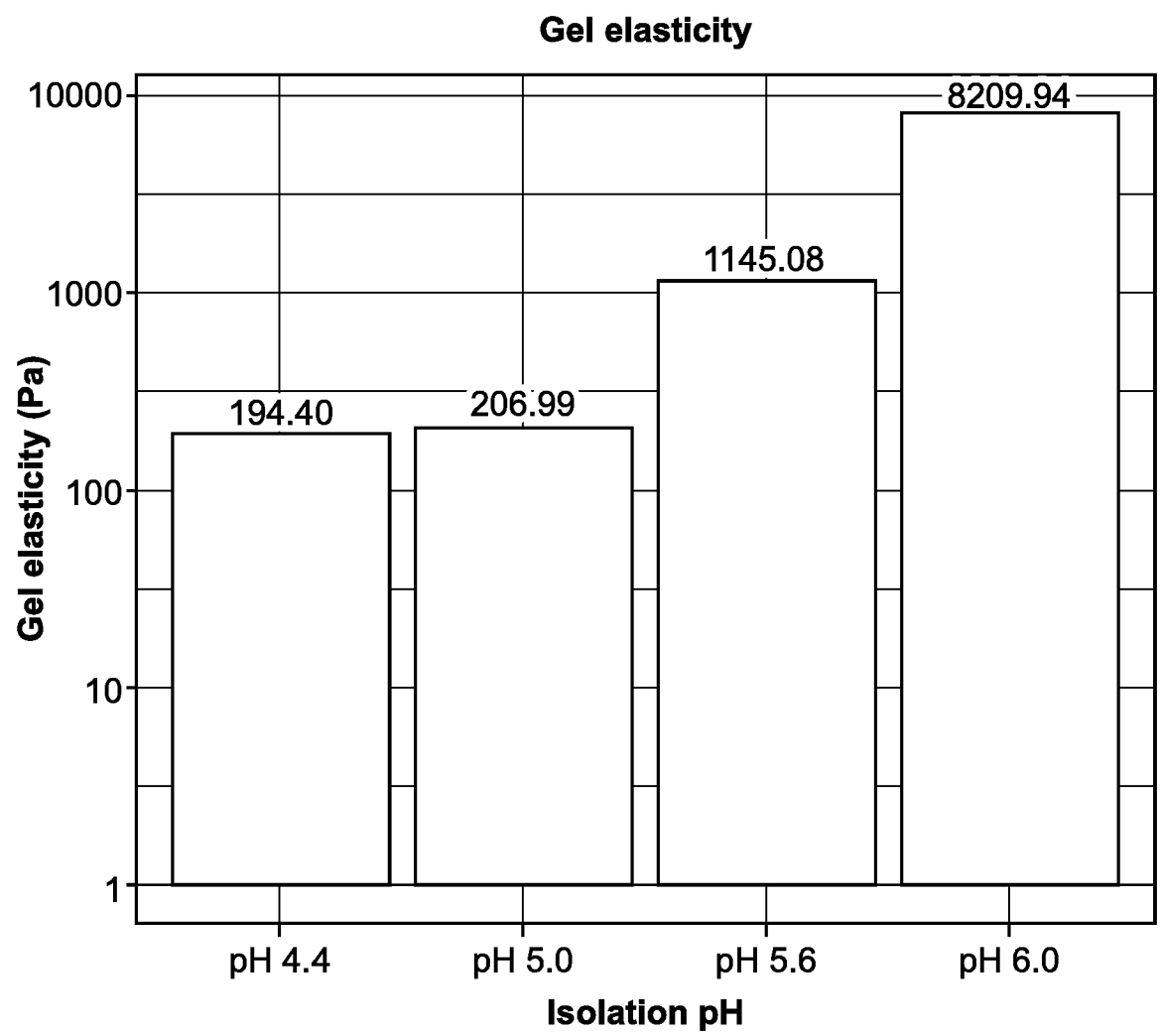

FIG. 12 graphically depicts the gel elasticity for mung bean protein isolates that have undergone acid precipitations at pH 4.4, 5.0, 5.6 and 6.0, respectively.

Figure 13:
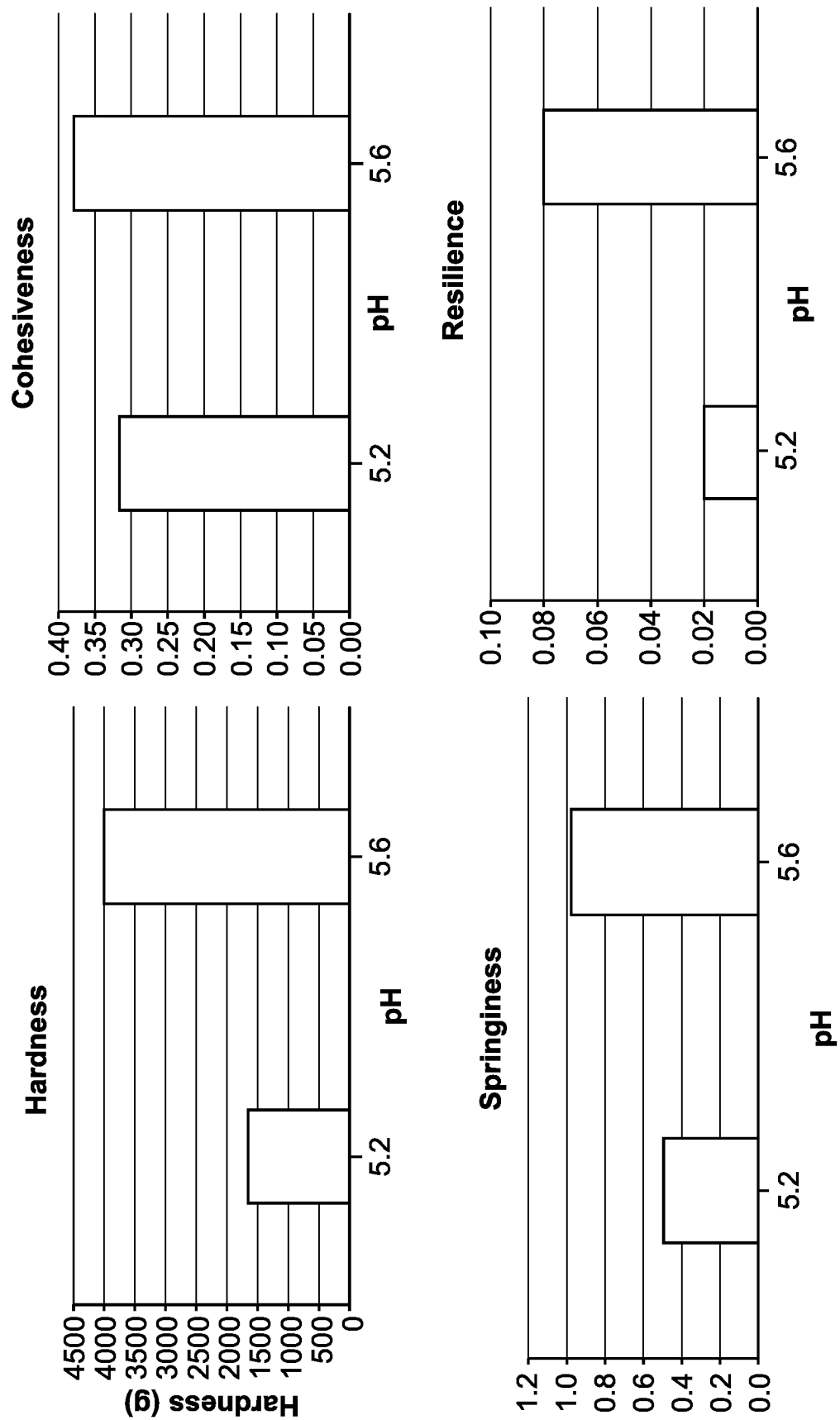

FIG. 13 graphically depicts the hardness, cohesiveness, springiness and resilience of egg analog pattys made from mung bean protein isolates that have undergone acid precipitations at pH 5.2 and 5.6, respectively.

Figure 14A:
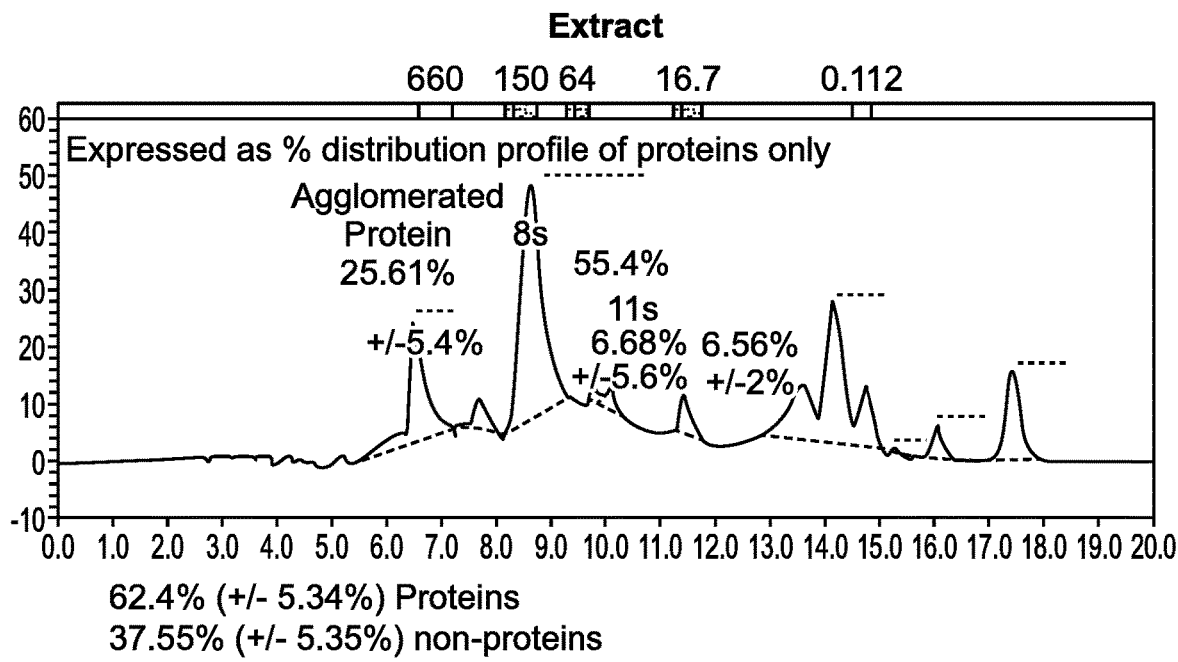

FIG. 14A depicts a size exclusion chromatograph of a mung bean protein extract. Relative percentages of proteins (including 8S globulin and 11S globulin) and non-proteins are as indicated.

Figure 14B:
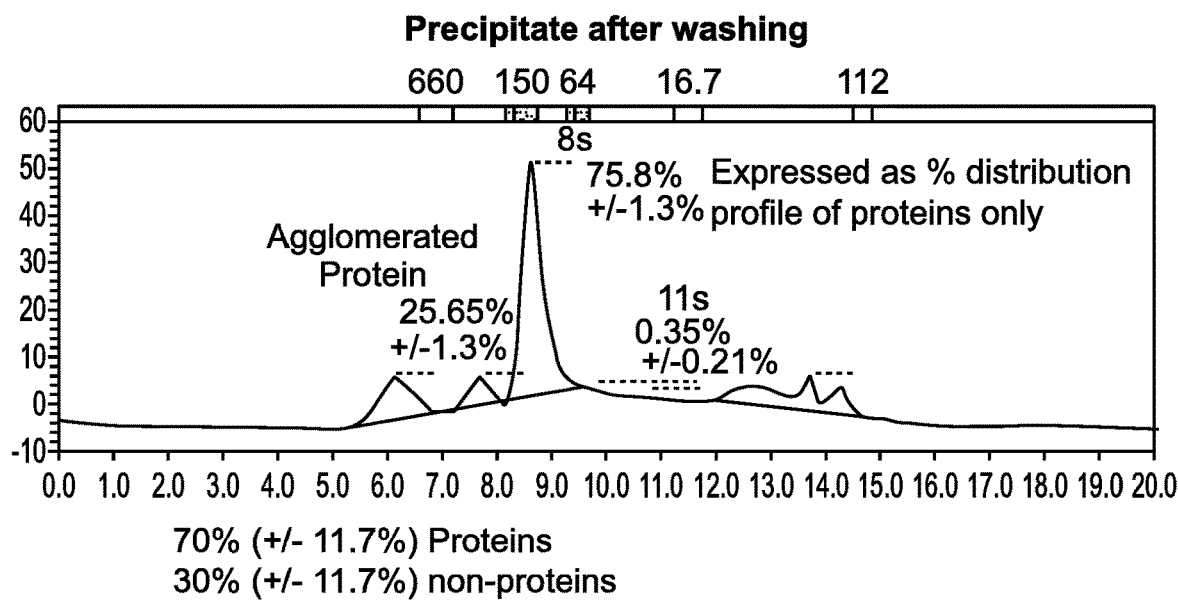

FIG. 14B depicts a size exclusion chromatograph of a mung bean protein precipitate taken through extraction, isoelectric precipitation and washing steps. Relative percentages of proteins (including 8S globulin and 11S globulin) and non-proteins are as indicated.

Figure 14C:
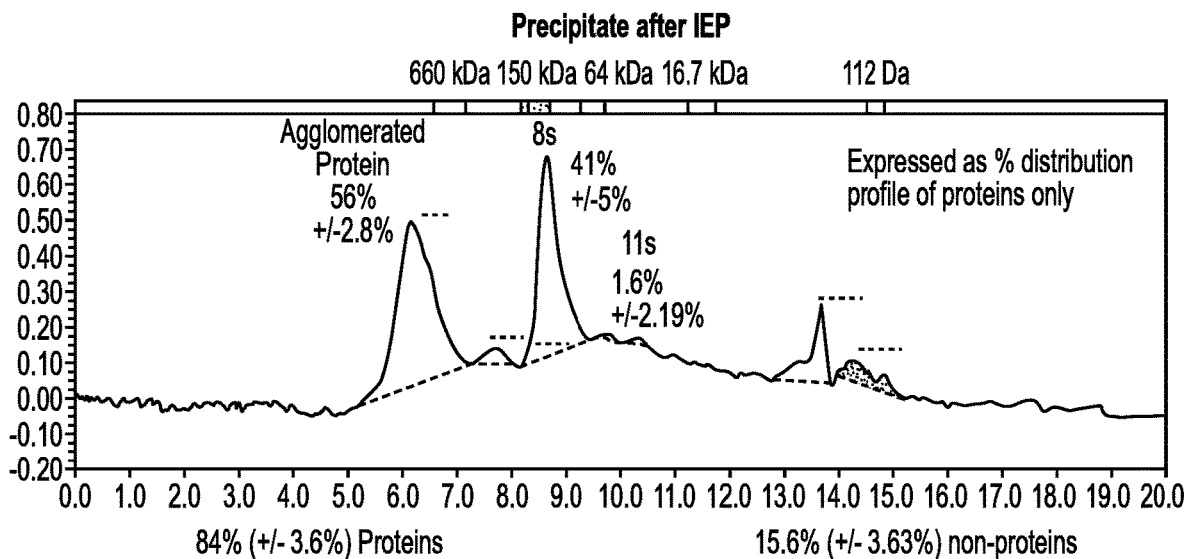

FIG. 14C depicts a size exclusion chromatograph of a mung bean protein precipitate taken through extraction and isoelectric precipitation. Relative percentages of proteins (including 8S globulin and 11S globulin) and non-proteins are as indicated.

Figure 14D:
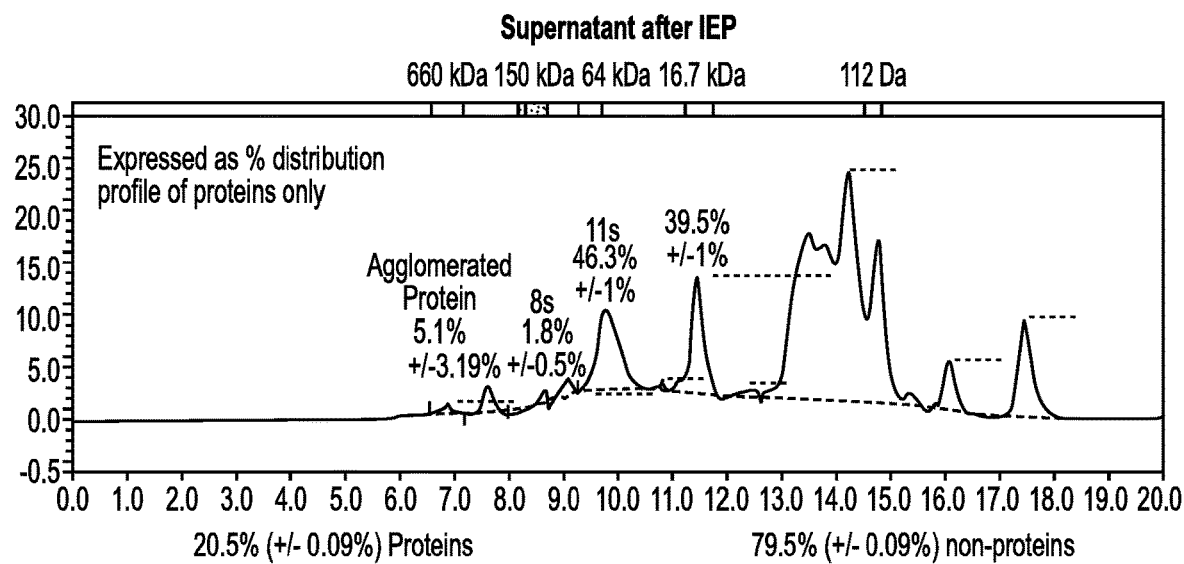

FIG. 14D depicts a size exclusion chromatograph of the supernatant of a mung bean protein precipitate taken through extraction and isoelectric precipitation. Relative percentages of proteins (including 8S globulin and 11S globulin) and non-proteins are as indicated.

Figure 14E:
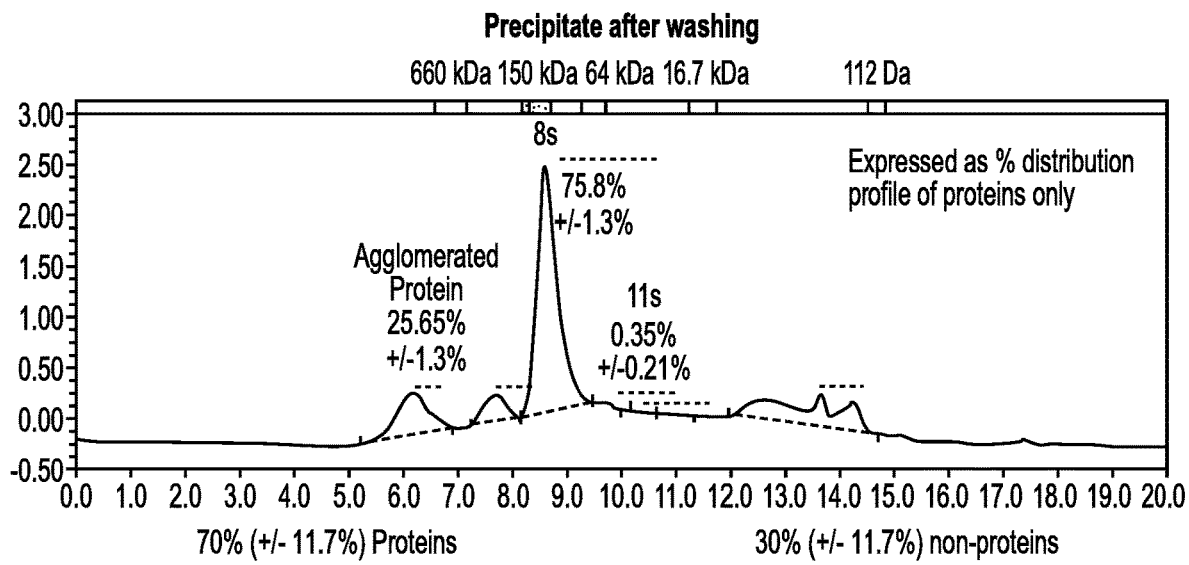

FIG. 14E depicts a size exclusion chromatograph of a mung bean protein precipitate taken through extraction, isoelectric precipitation and washing steps. Relative percentages of proteins (including 8S globulin and 11S globulin) and non-proteins are as indicated.

Figure 14F:
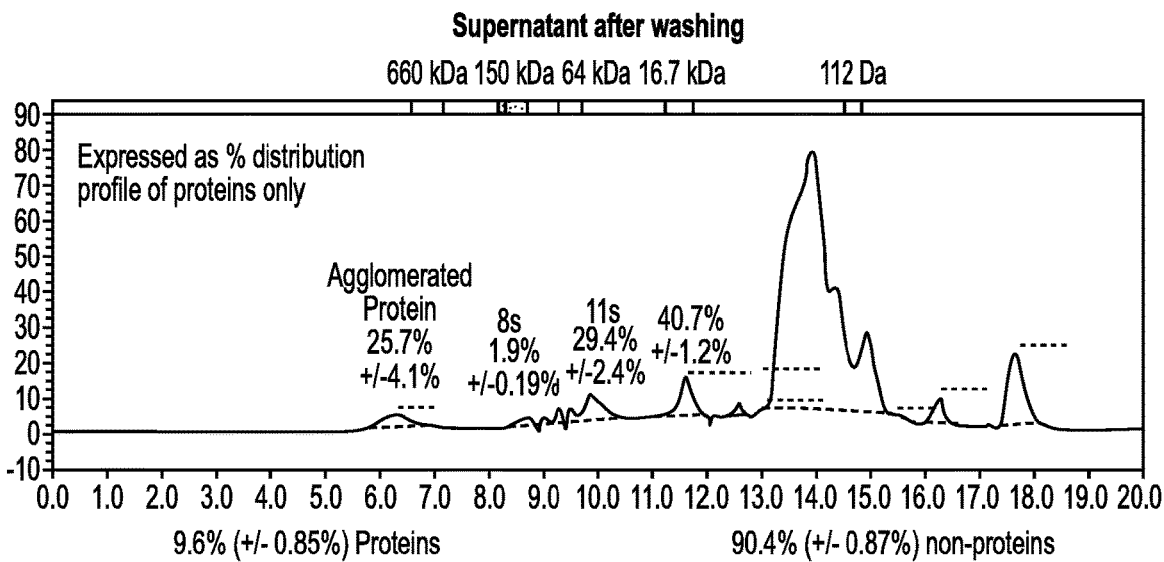

FIG. 14F depicts a size exclusion chromatograph of the supernatant of a mung bean protein precipitate taken through extraction, isoelectric precipitation and washing steps. Relative percentages of proteins (including 8S globulin and 11S globulin) and non-proteins are as indicated.

FIG. 15 provides an amino acid sequence alignment of SEQ ID NOs:1-12 in both tabular and graphical form.

Figure 16:
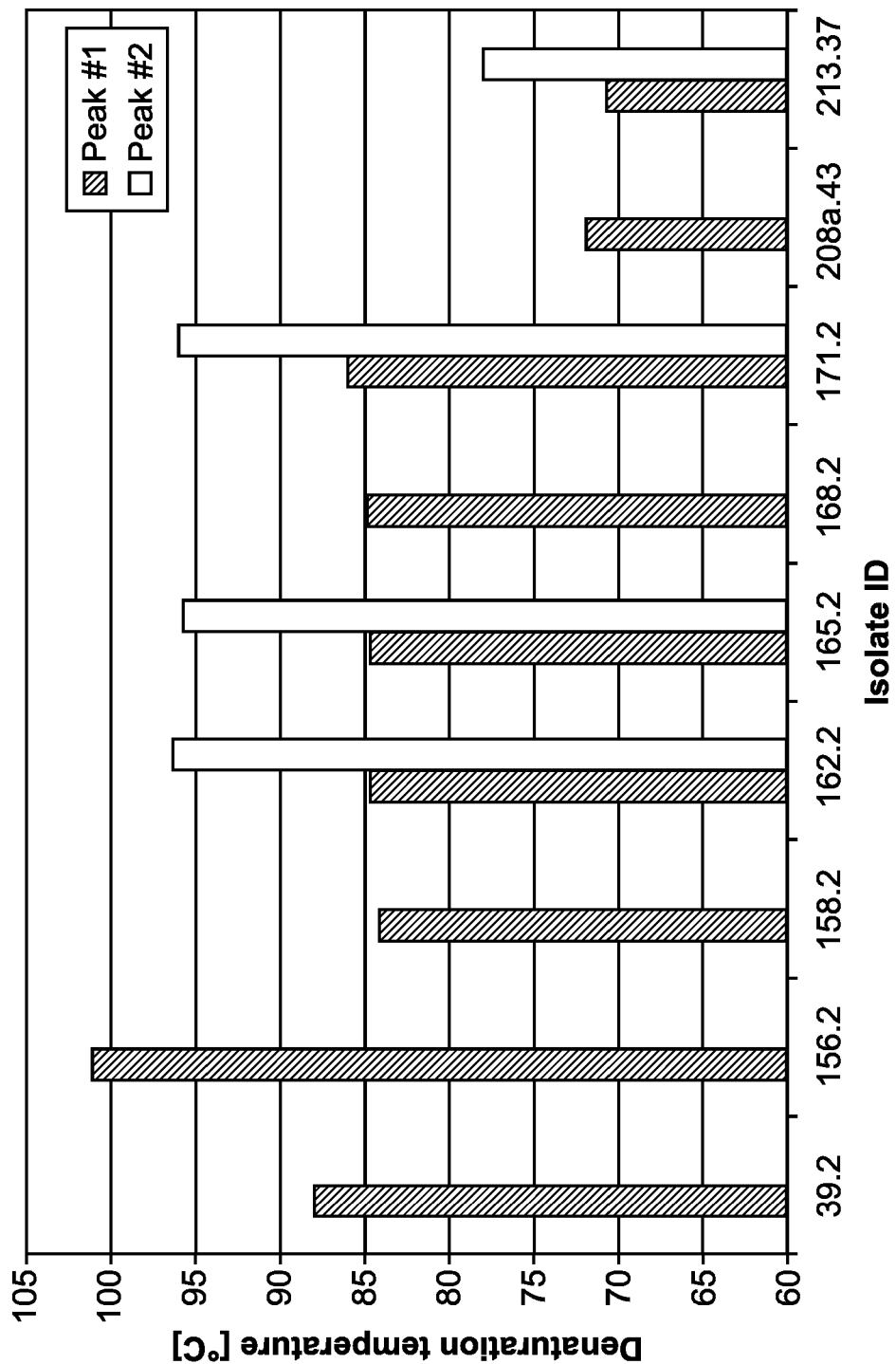

FIG. 16 graphically depicts denaturation temperature profiles of different purified protein isolates.

Figure 17:
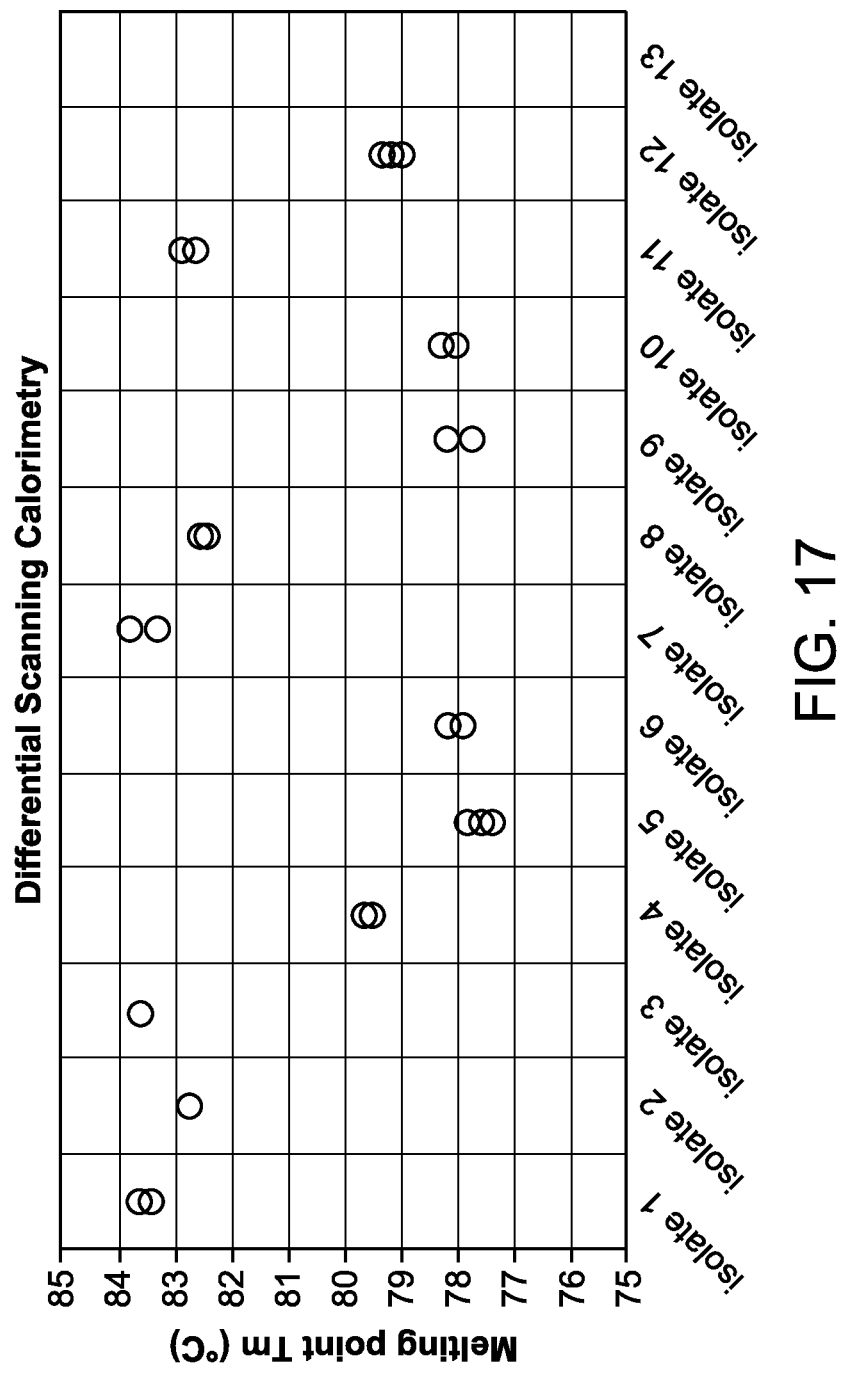

FIG. 17 represents a plot from a solid-state differential scanning calorimetry used to study the unfolding thermodynamics of protein isolate purified from different sources.

Figure 18:
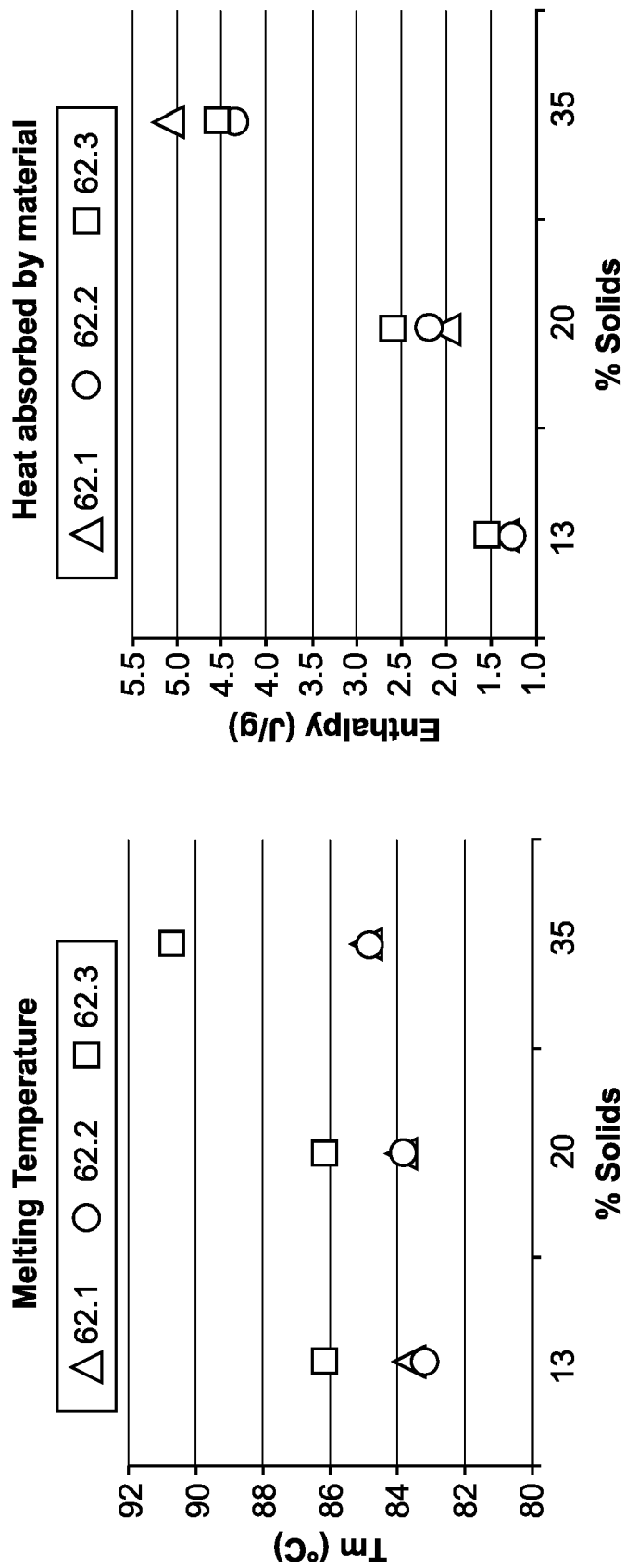

FIG. 18 graphically represents (A) melting temperatures and (B) heat absorbed by the material of various purified protein isolates.

Figure 19:
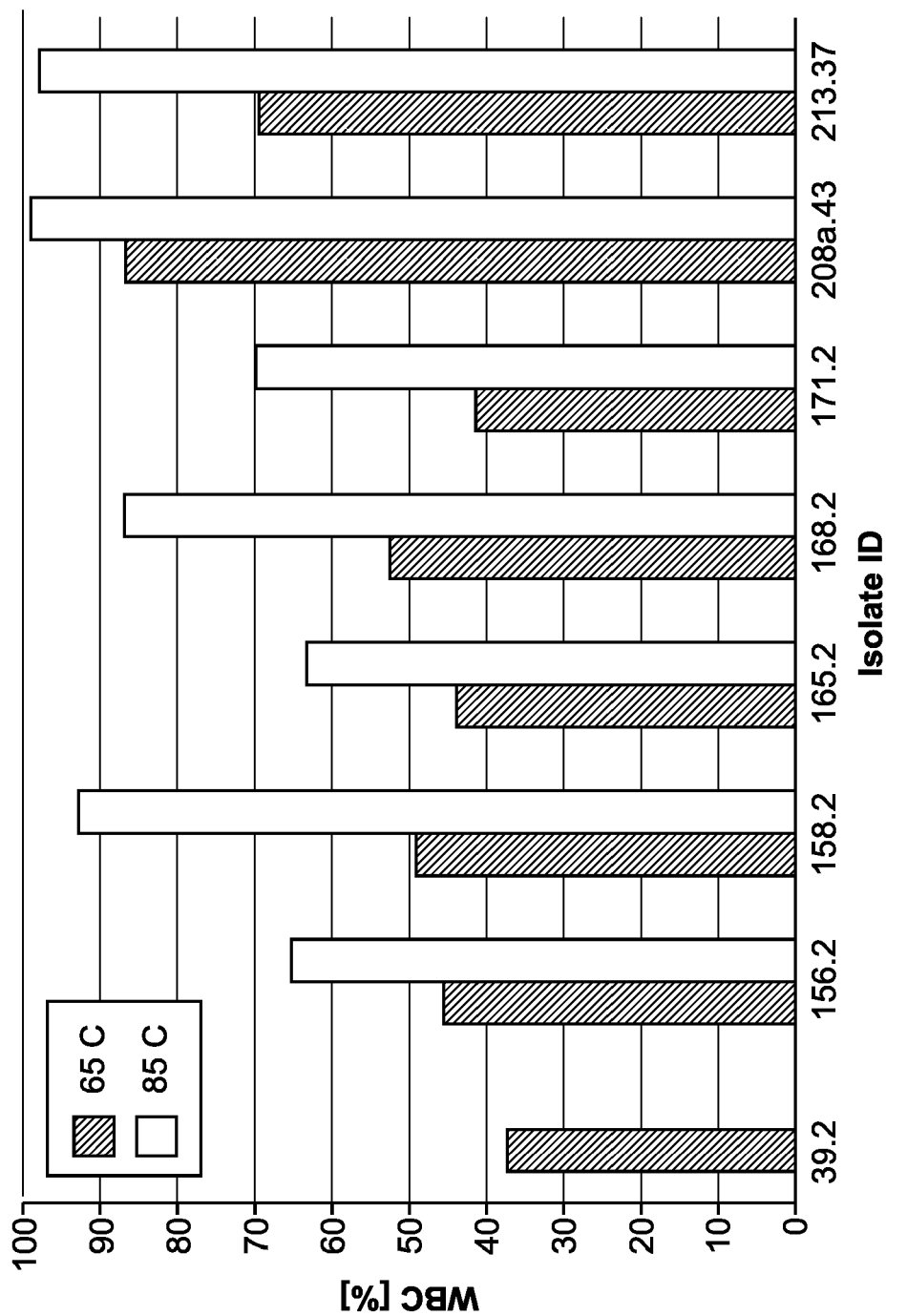

FIG. 19 depicts results from a water binding capacity test used to assess the ability of a sample to retain liquid (water) after heat-induced gelation, following disruption via centrifugation.

Figure 20:
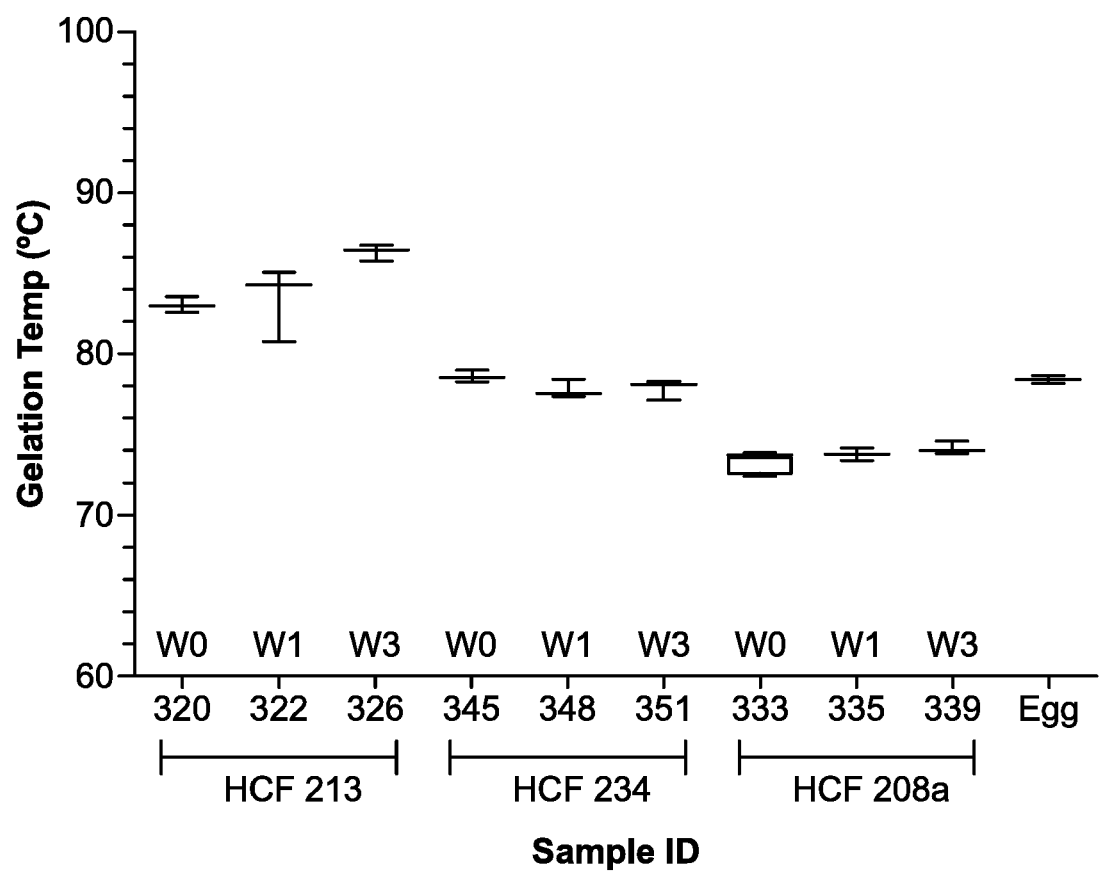

FIG. 20 shows gelation temperature of purified protein isolates from various sources.

Figure 21:

FIG. 21 visually depicts a cross section of an egg patty substitute made using (A) eggs; purified mung bean protein isolates obtained from (B) salt precipitation; and (C) isoelectric precipitation.

Figure 22:
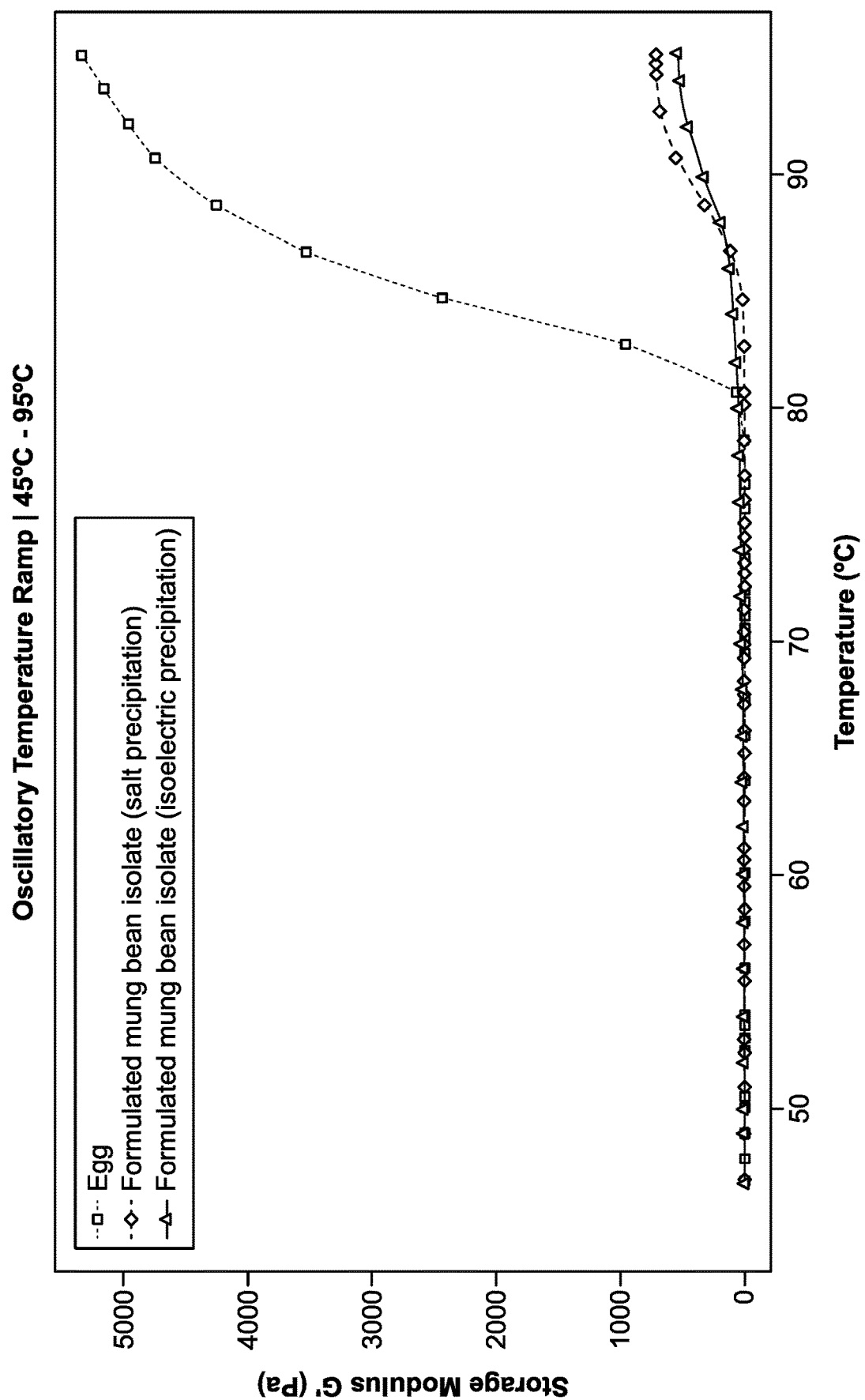

FIG. 22 graphically depicts an oscillatory temperature ramp comparing (♦) salt precipitated protein isolate; (Δ) isoelectric precipitation of protein isolate; to (□) a whole egg.

Figure 23:
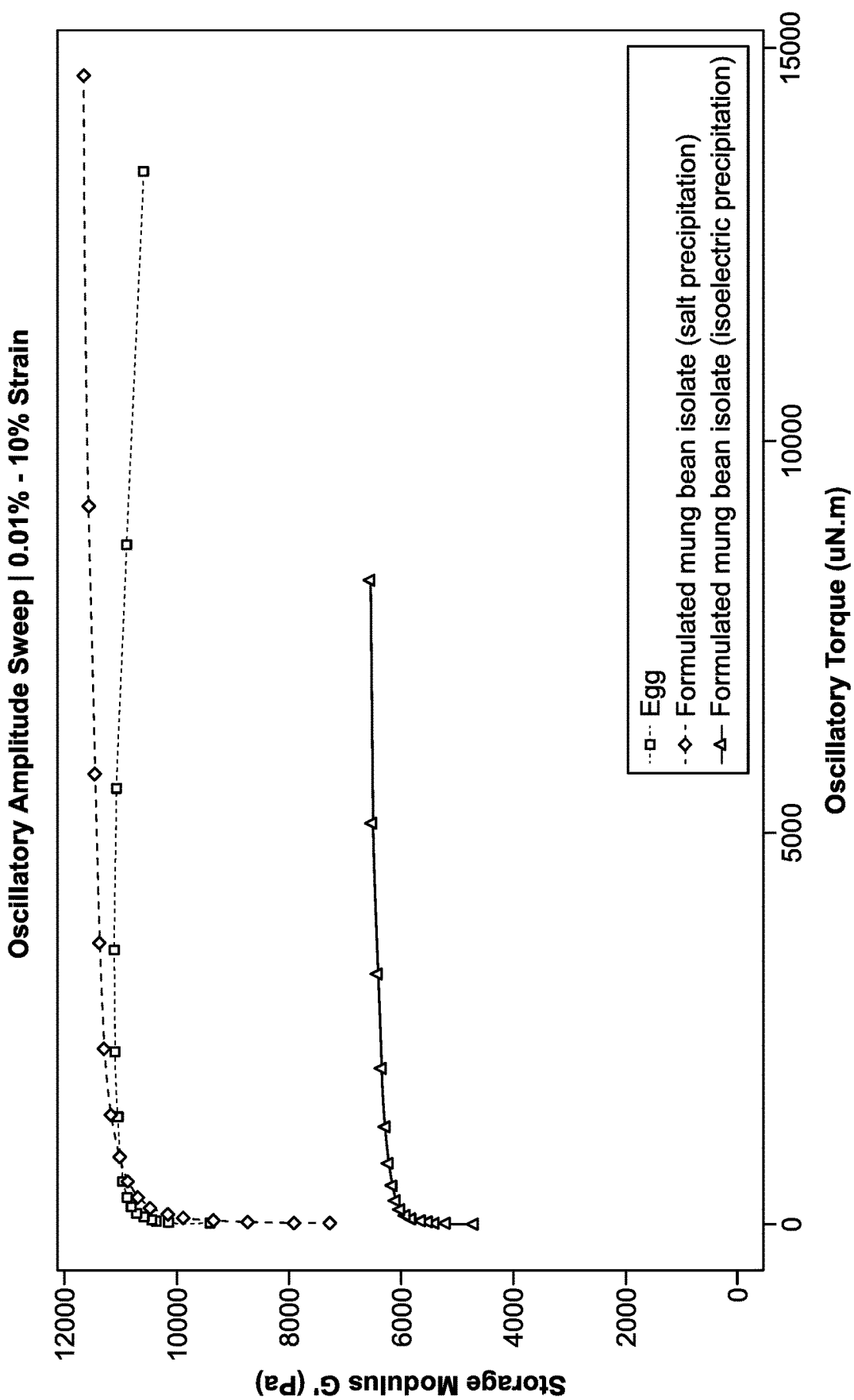

FIG. 23 graphically depicts an oscillatory amplitude sweep comparing (♦) salt precipitated protein isolate; (Δ) isoelectric precipitation of protein isolate; to (□) a whole egg.

Figure 24:
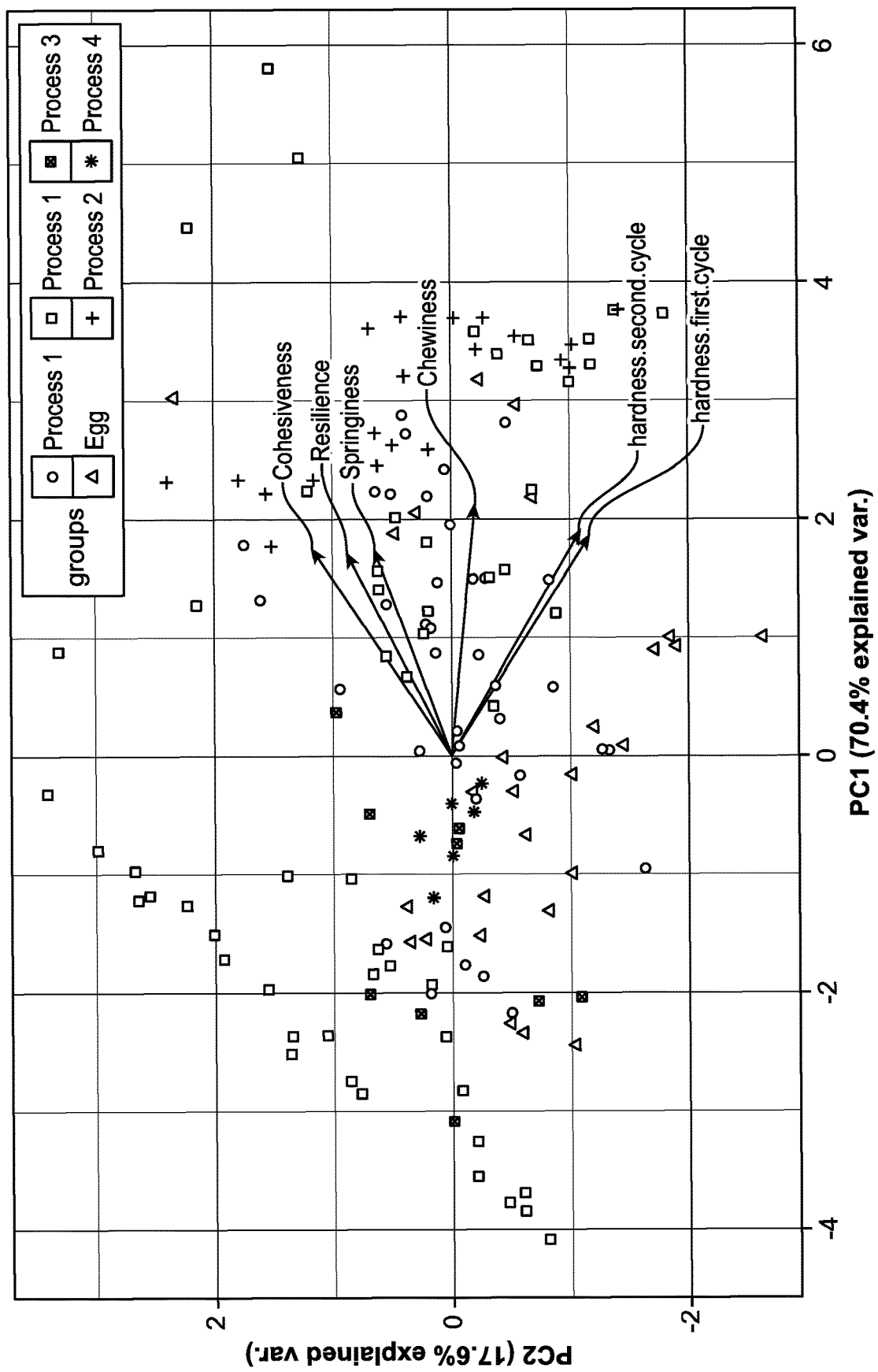

FIG. 24 compares the texture features of mung bean isolates formulated under different processes with that of various egg controls using a Principal Component Analysis 2-dimensional visualization.

Figure 25:
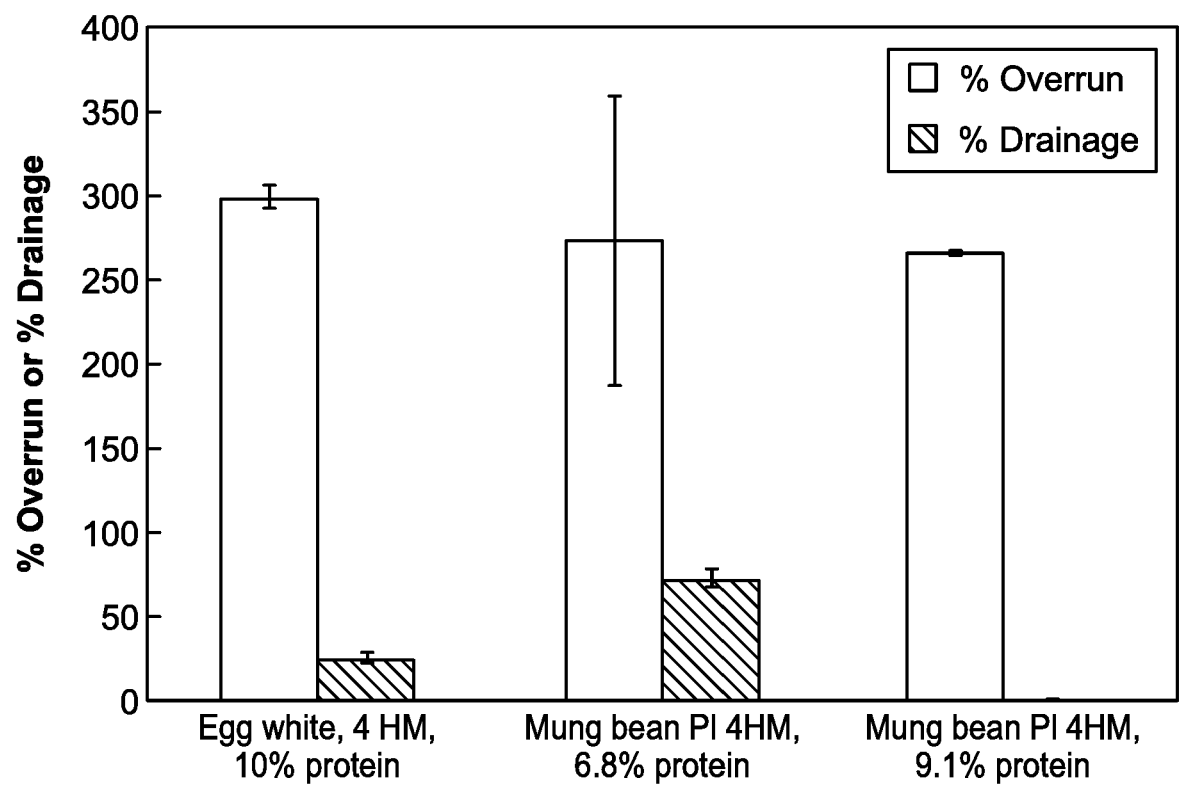

FIG. 25 depicts results from a foaming capacity test of samples with the specified purified mung bean protein concentrations.

Figure 26:
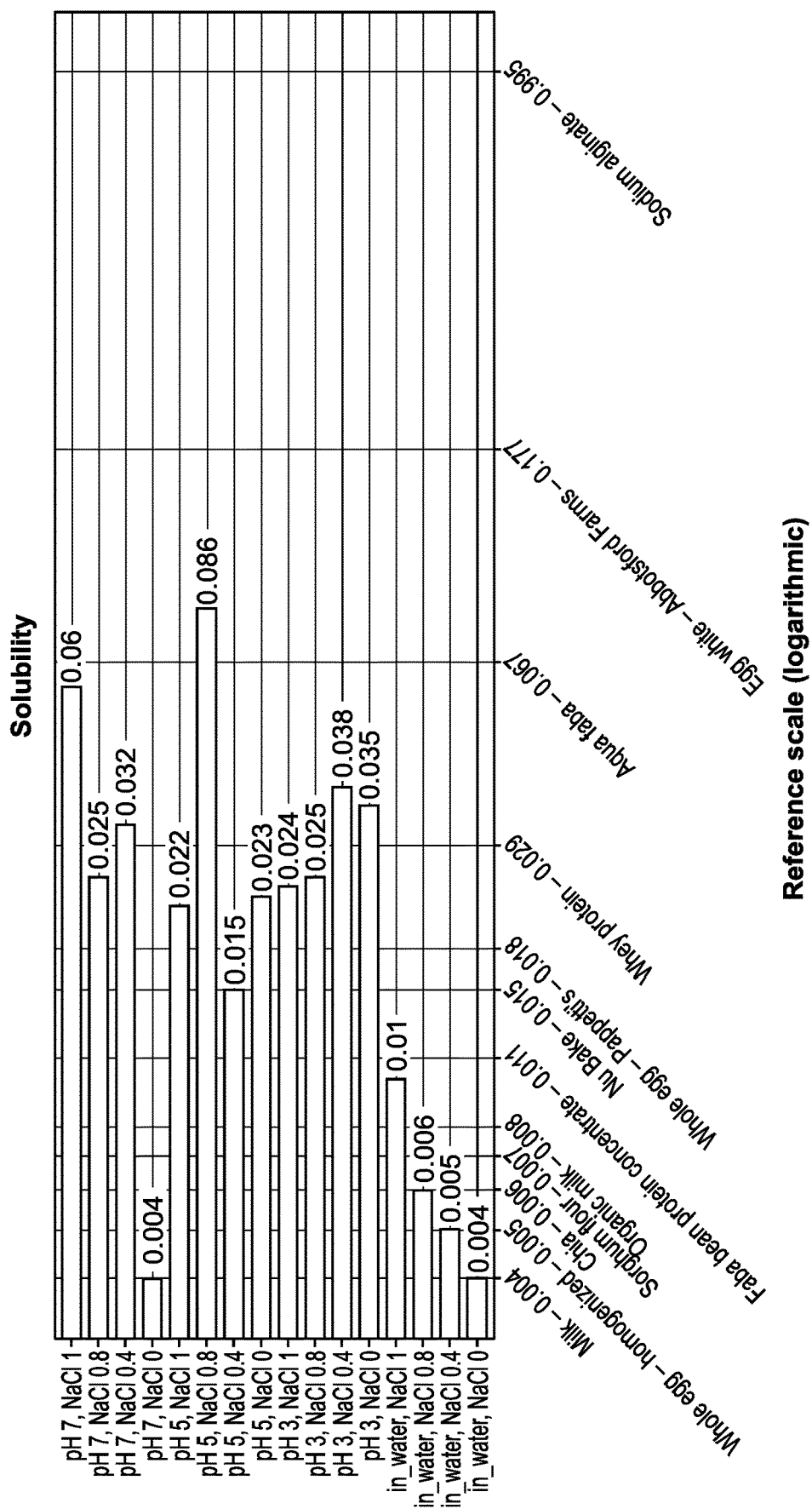

FIG. 26 graphically depicts the solubilities of various mung bean protein isolate formulations in comparison to several reference materials.

Figure 27:
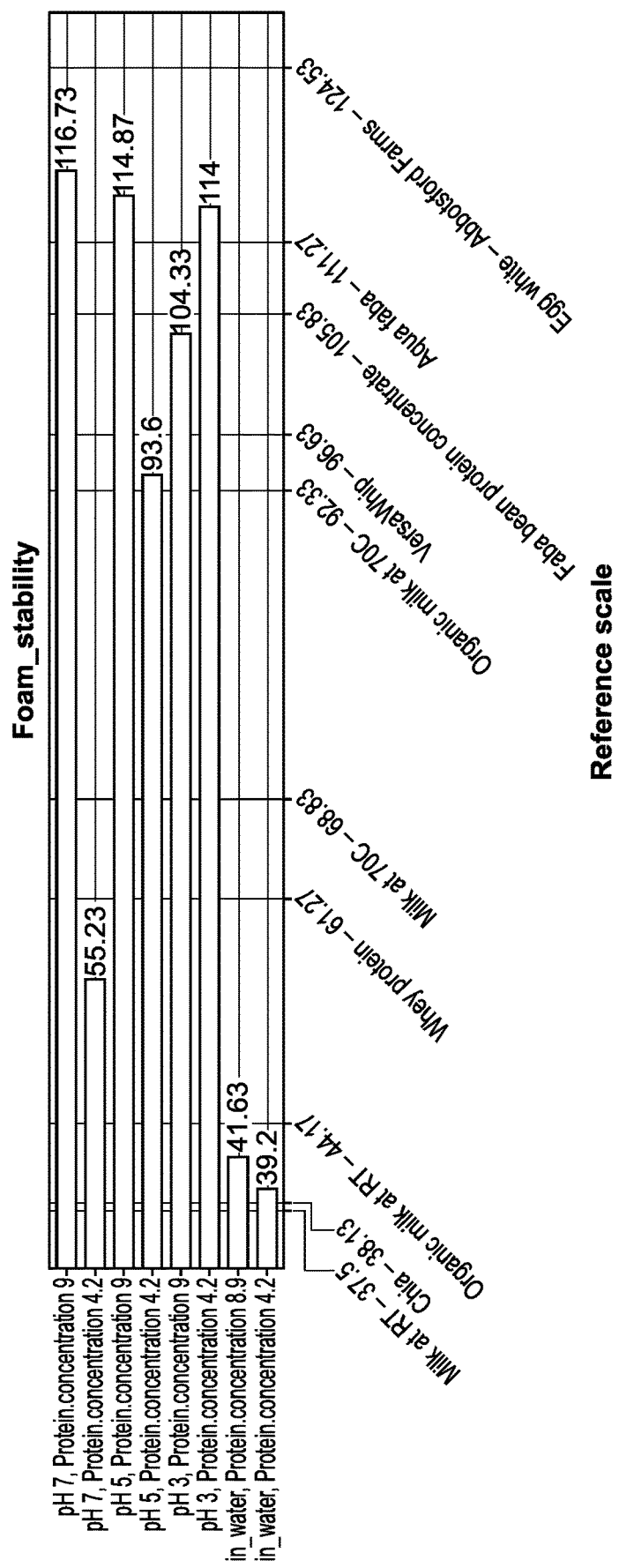

FIG. 27 graphically depicts the foam stability of various mung bean protein isolate formulations in comparison to several reference materials.

Figure 28:
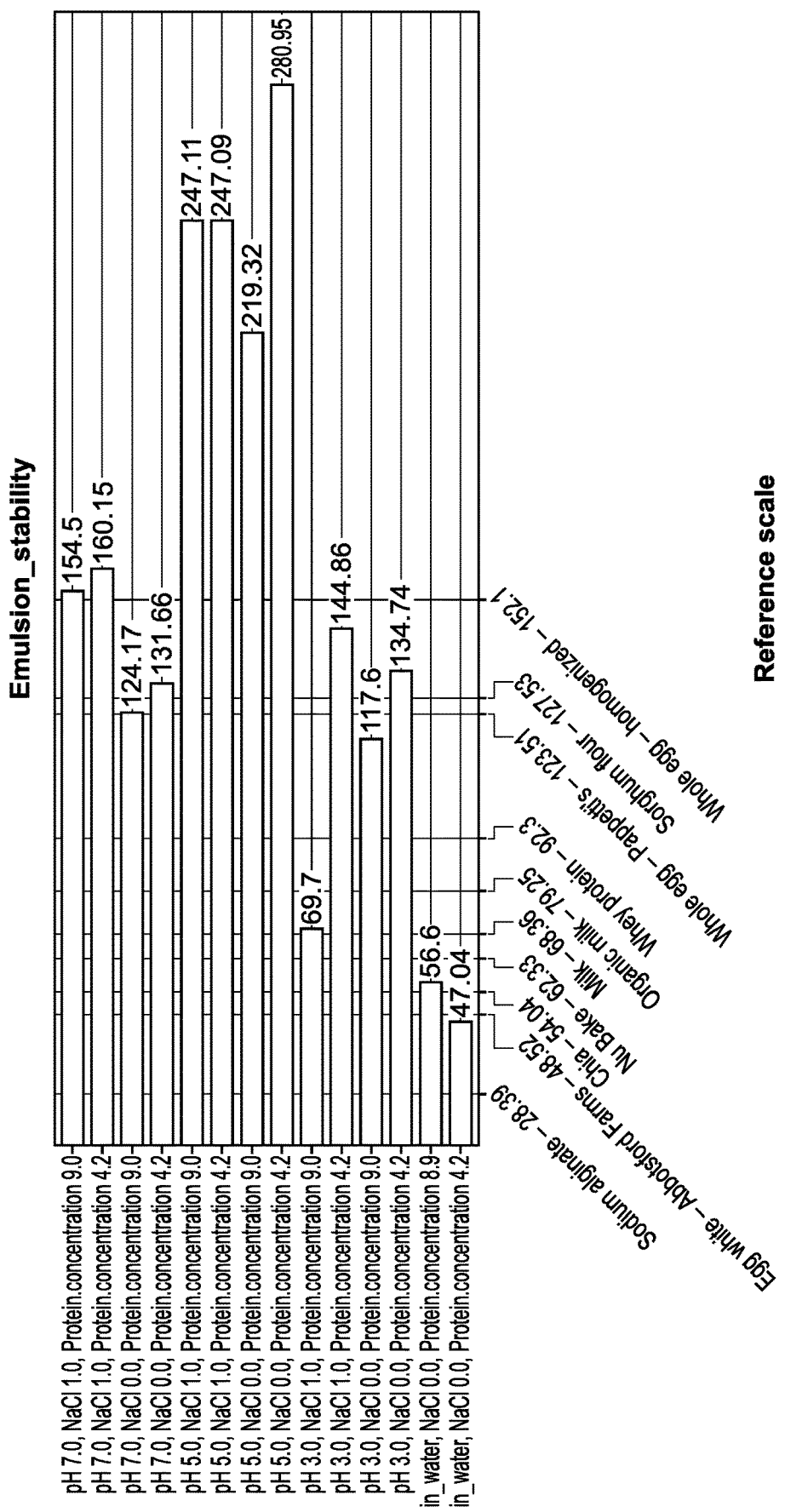

FIG. 28 graphically depicts the emulsion stability of various mung bean protein isolate formulations in comparison to several reference materials.

Figure 29:
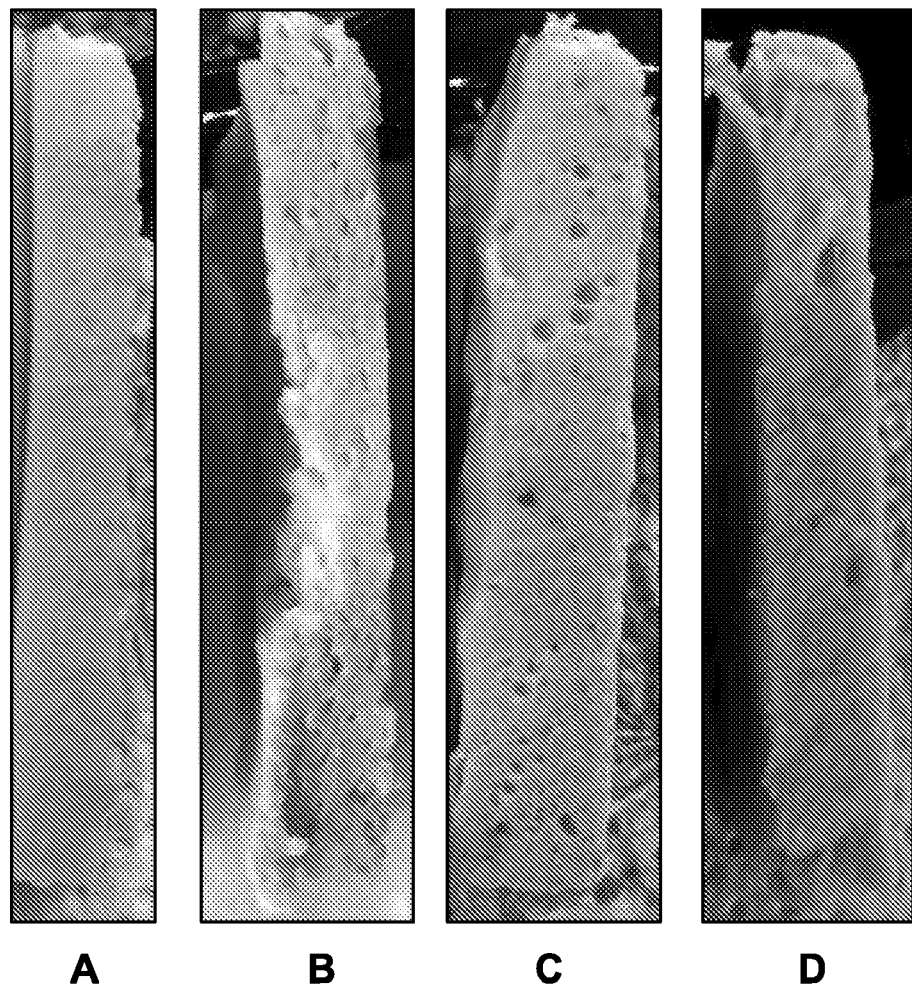

FIG. 29 visually depicts a cross section of an egg patty substitute from four liquid scramble formulations made with: (A) purified mung bean isolate; (B) purified mung bean isolate with iota-carrageenan & gum arabic; (C) purified mung bean isolate with konjac & xanthan gum; and (D) purified mung bean isolate with gellan.

Figure 30:
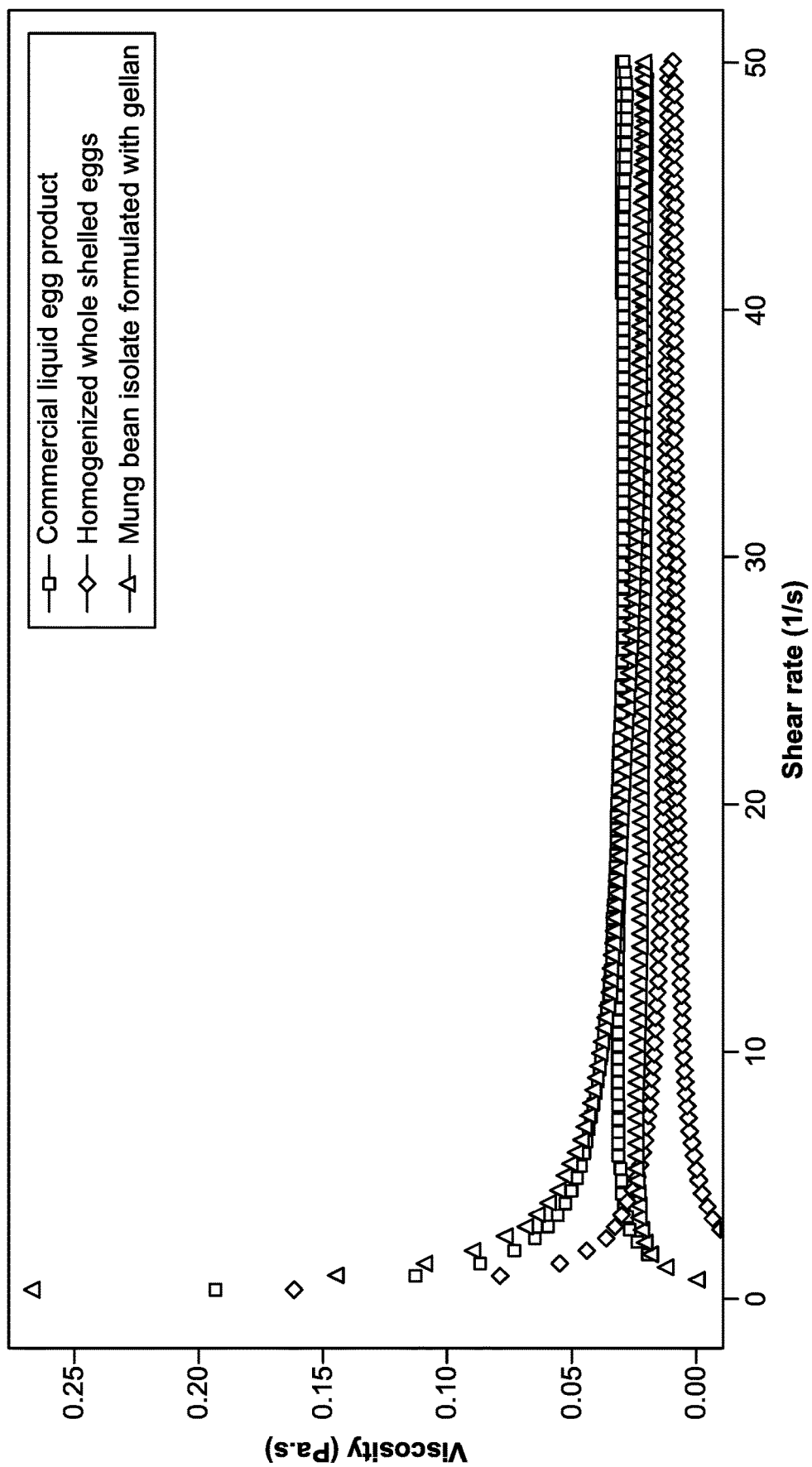

FIG. 30 shows a comparison of viscosity vs. shear rate/in (□) commercial liquid egg product; (◇) homogenized whole shelled eggs; and (▲) liquid scramble formulated with gellan.

Figure 31:
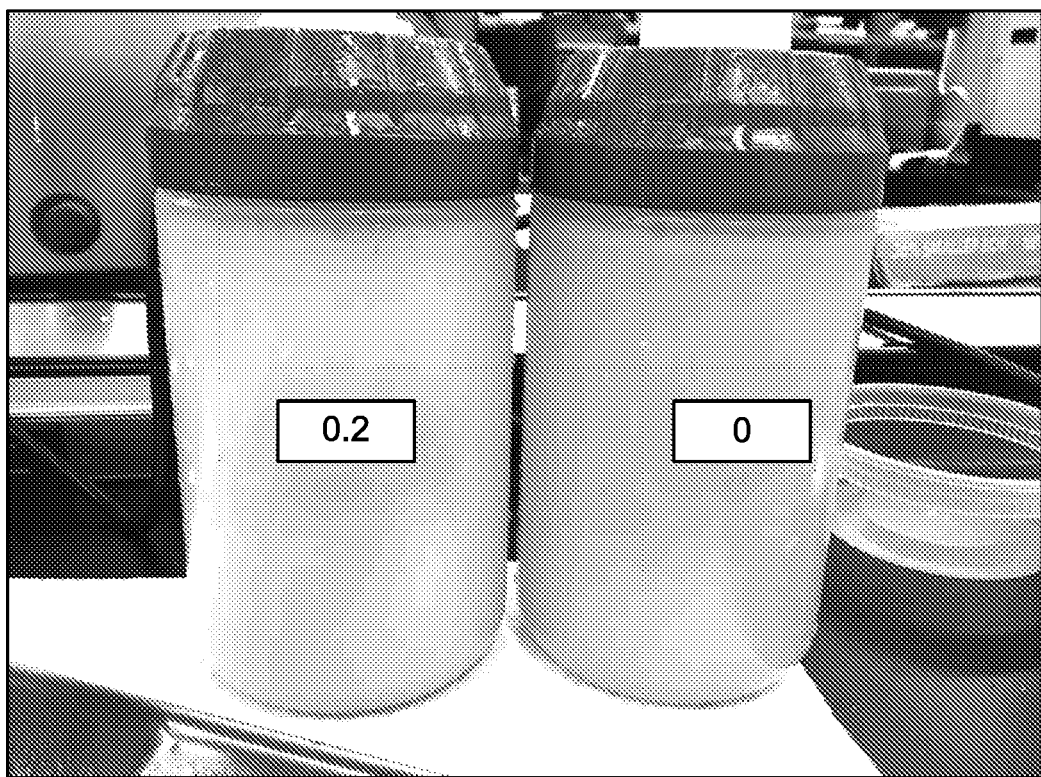

FIG. 31 visually depicts turbidity of extracts treated with and without transglutaminase.

Figure 32:
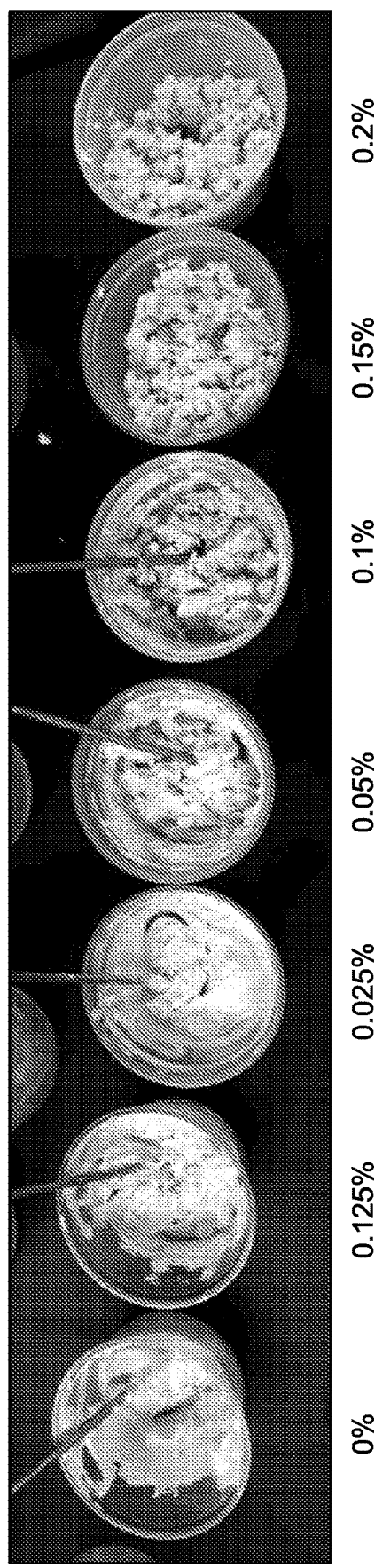

FIG. 32 visually depicts mungbean protein isolate reacted with various concentrations of transglutaminase. FIG. 16 visually depicts mung bean purified protein isolate in various formats.

Figure 33:
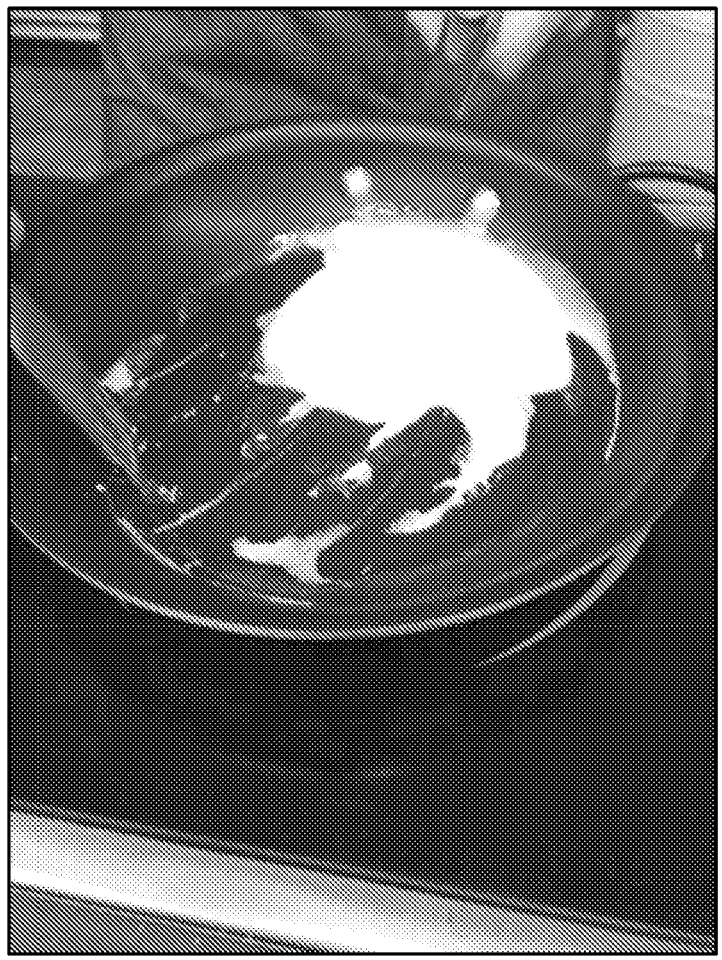

FIG. 33 visually depicts a scrambled egg analog, prepared with transglutaminase-reacted mungbean, during the cooking process.

Figure 34:

FIG. 34 visually depicts a scrambled egg analog with mungbean protein isolate and without pre-treatment with transglutaminase.

Figure 35:
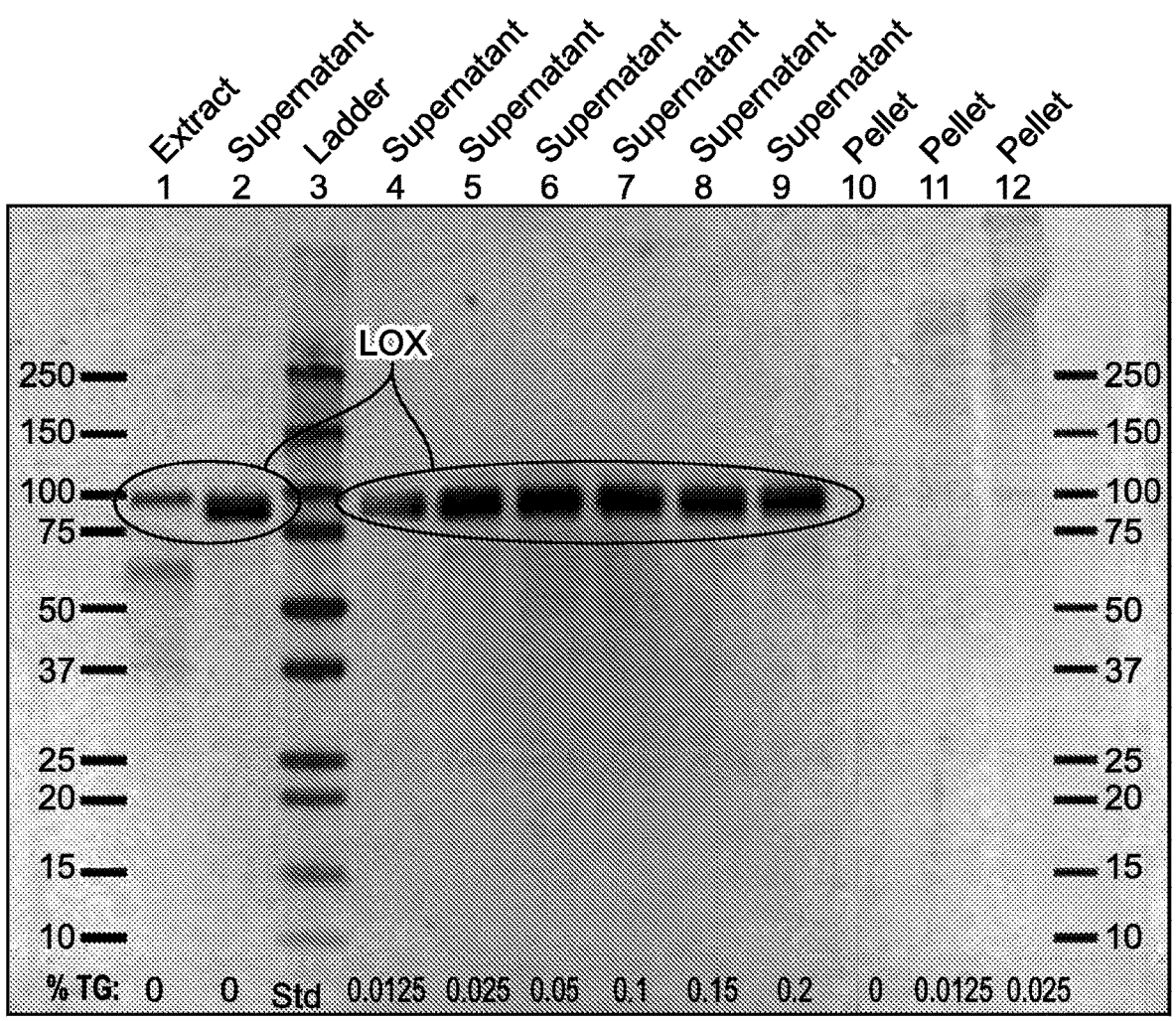

FIG. 35 depicts an image of a Western blot of supernatant and pellets prepared with varying levels of transglutaminase-treated mungbean post isoelectric precipitation.

Figure 36:
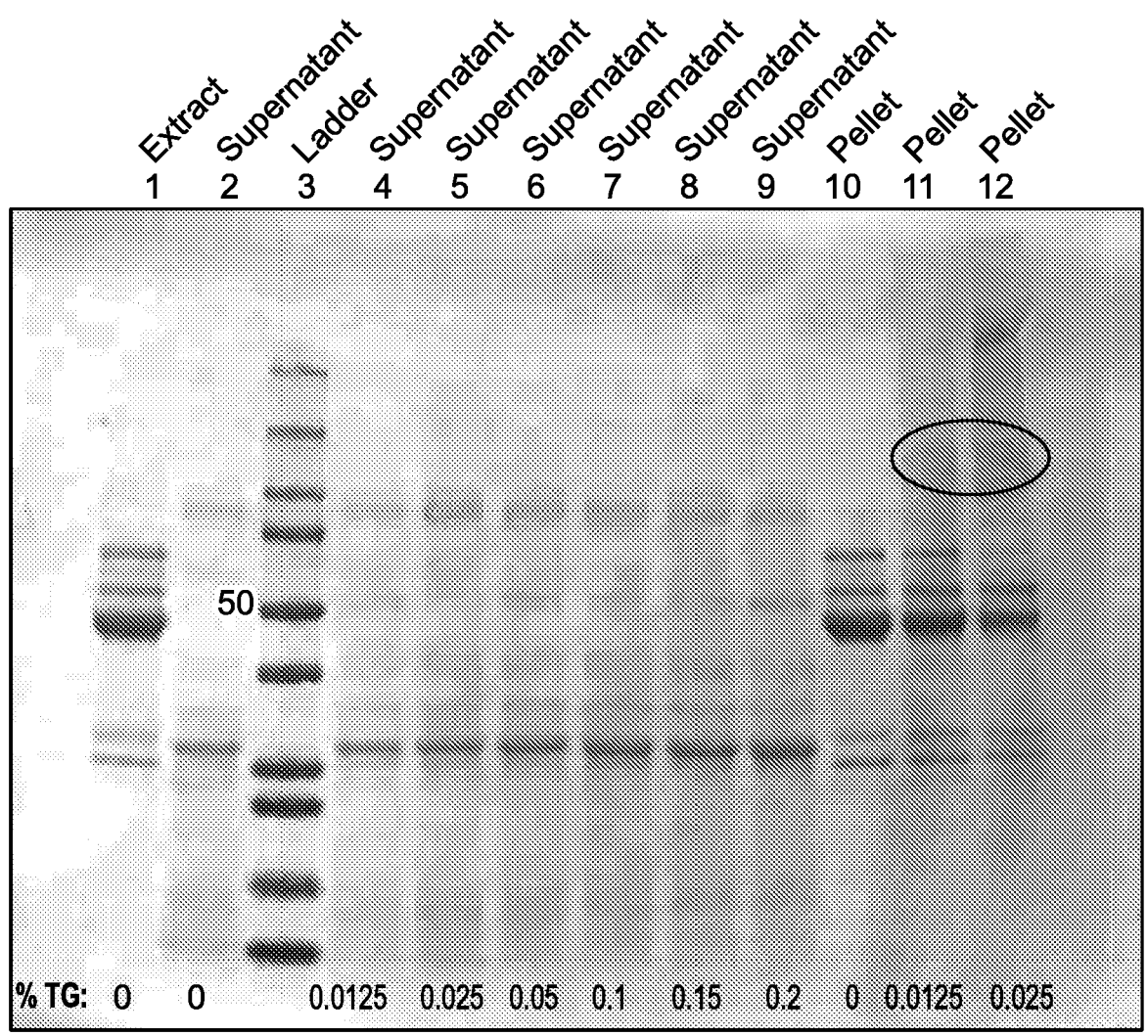

FIG. 36 depicts an image of a Ponceau red-stained SDS-PAGE membrane of supernatant and pellets prepared with varying levels of transglutaminase-treated mungbean post isoelectric precipitation.

Figure 37:
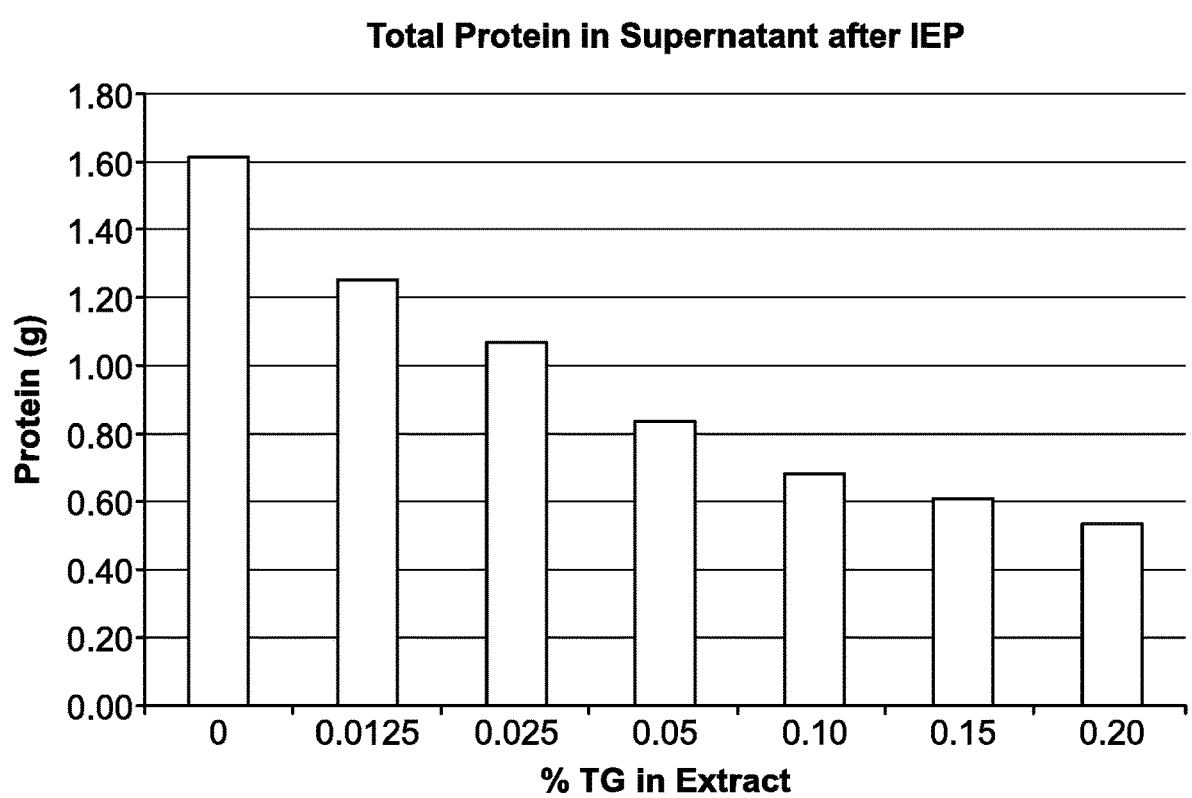

FIG. 37 graphically depicts total protein in supernatant in solutions prepared with varying levels of transglutaminase-reacted mungbean after isoelectric precipitation.

Figure 38:
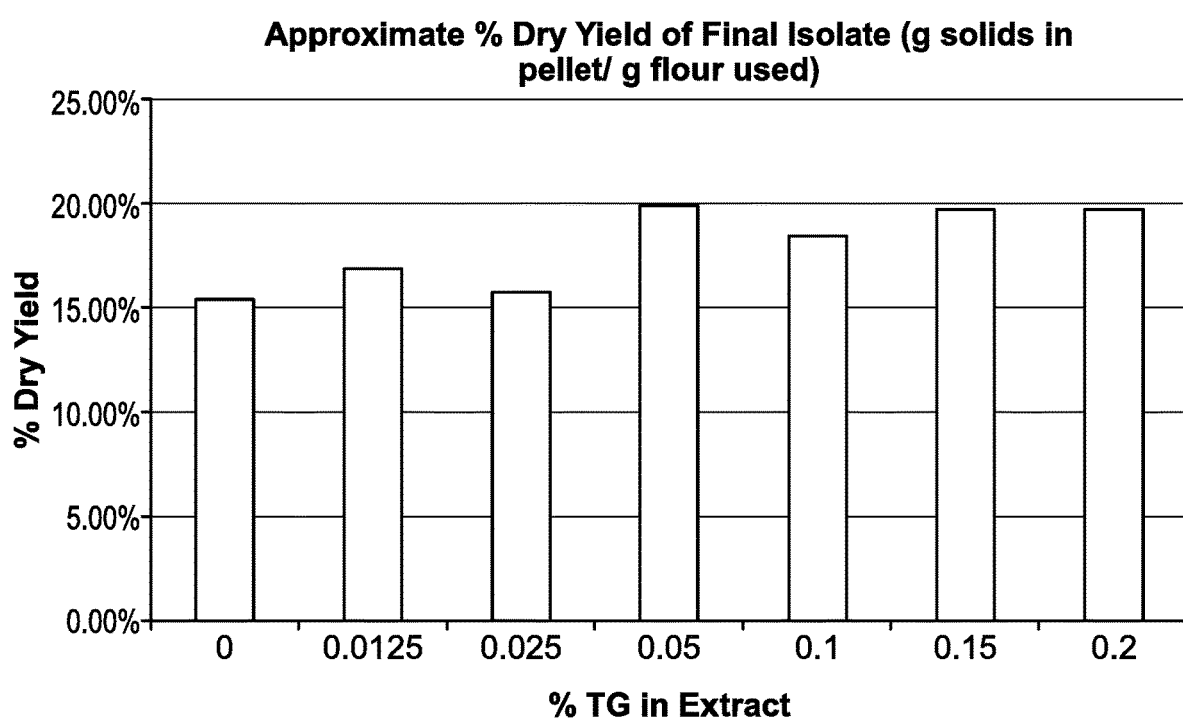

FIG. 38 graphically depicts approximate % dry yield of final protein isolates.

Figure 39:
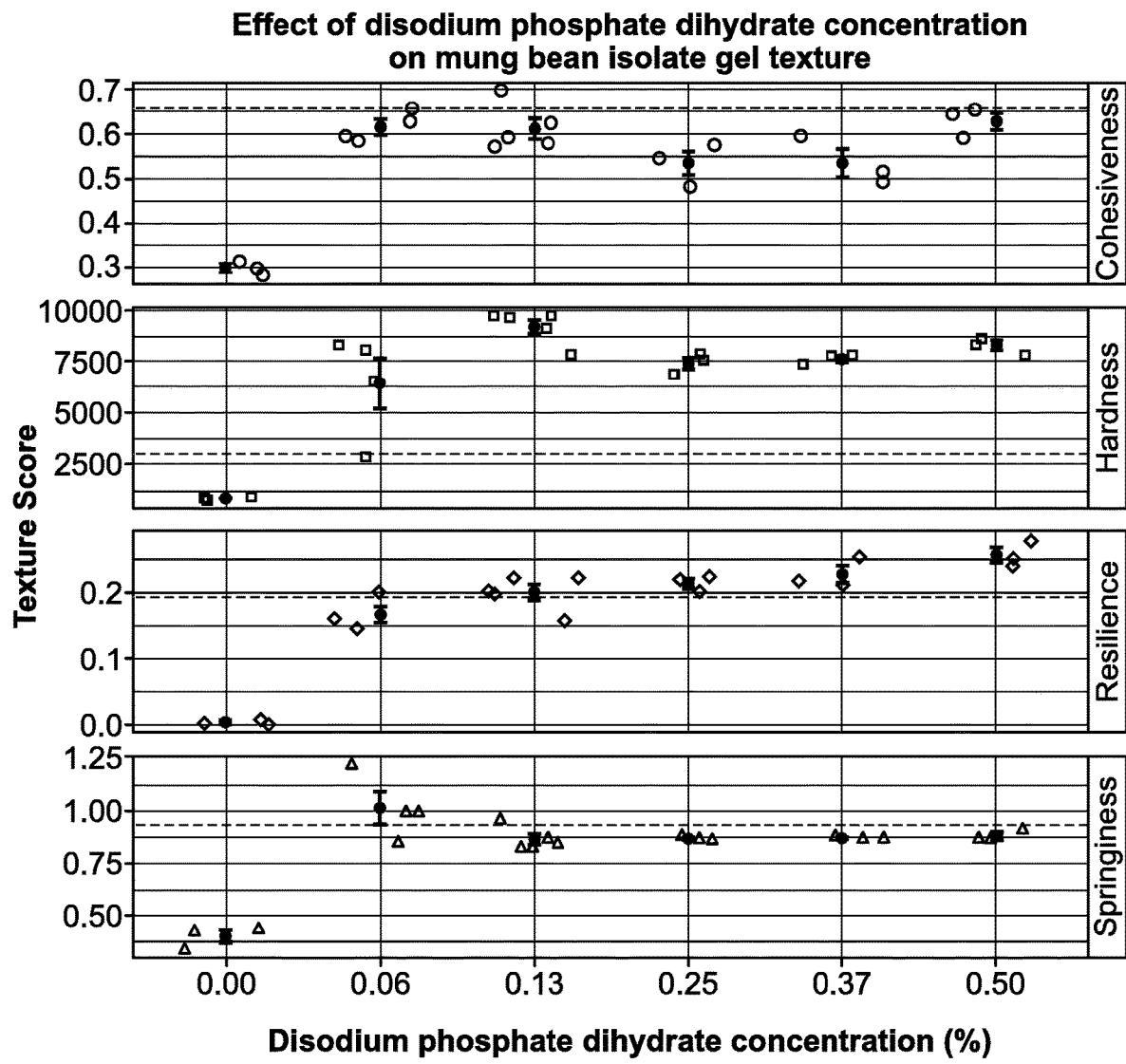

FIG. 39 graphically depicts the effect of disodium phosphate (DSP) dehydrate concentration on mung bean isolate gel texture.

Figure 40:
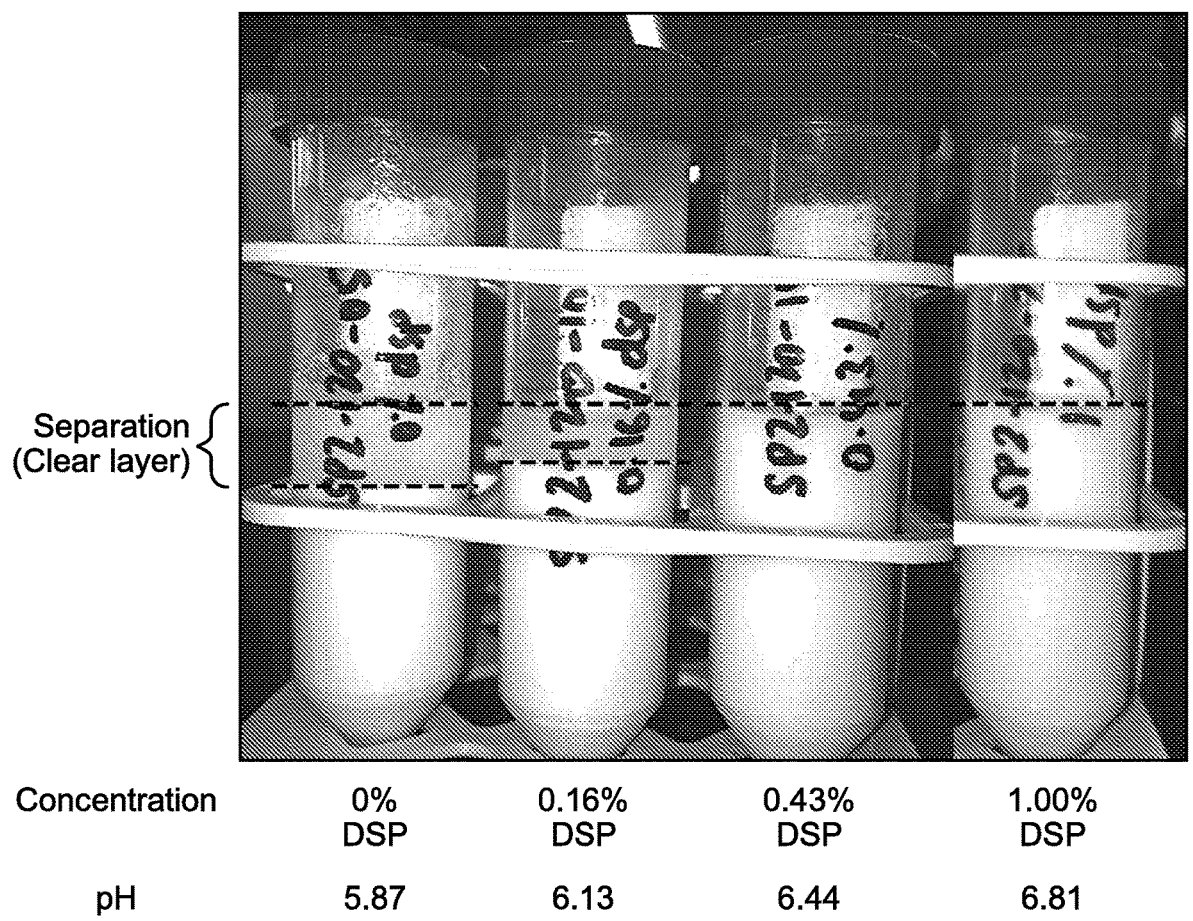

FIG. 40 depicts the effect of concentration of DSP on mung bean isolate dispersion stability.

Figure 41:
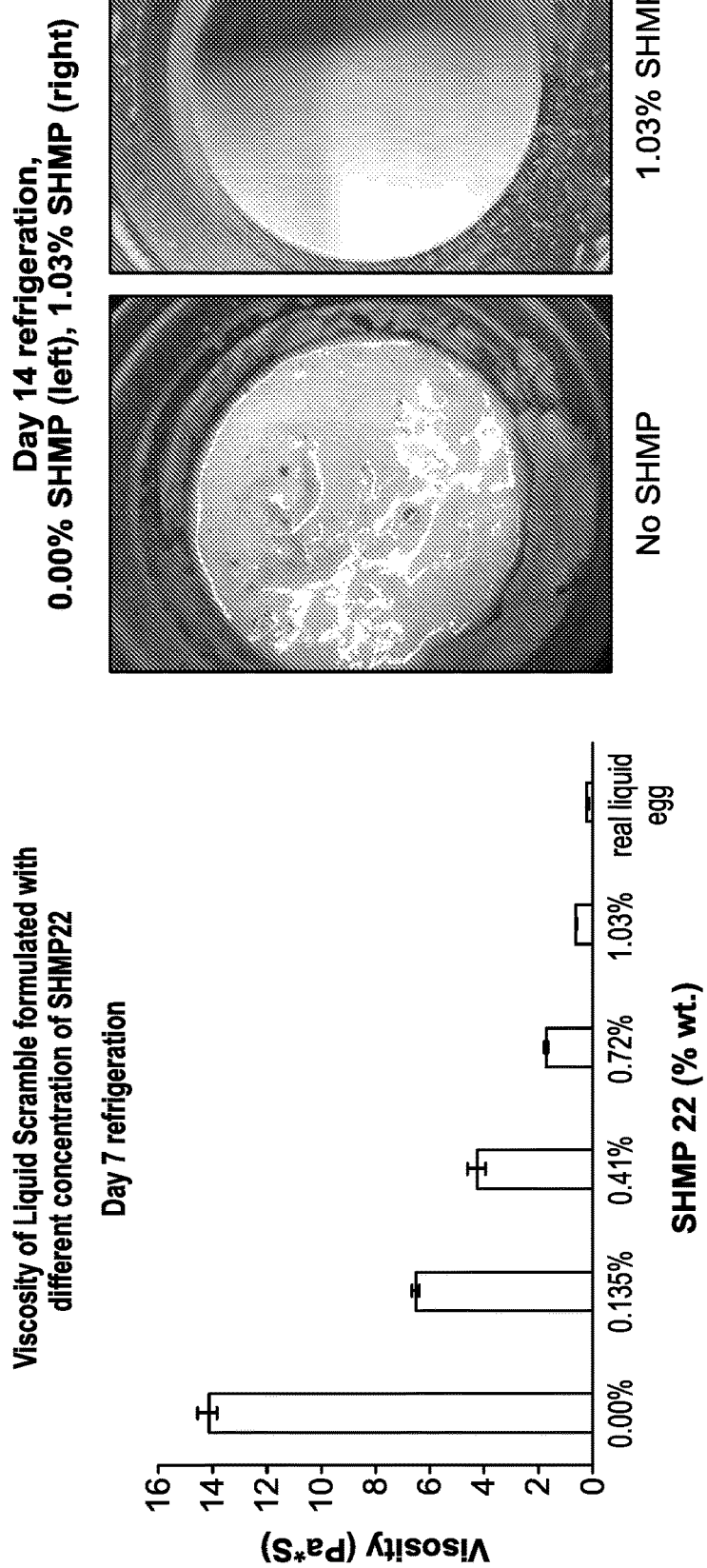

FIG. 41 depicts the dose response curve of long chain sodium hexametaphosphate in liquid egg analogue using mung bean protein isolate.

Figure 42:
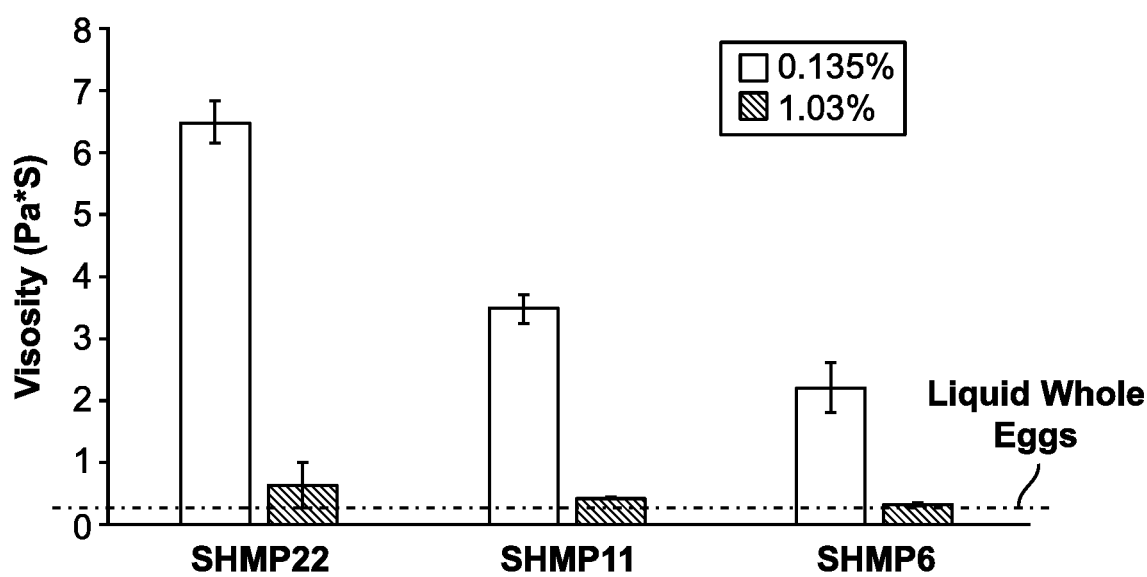

FIG. 42 depicts the effect of sodium hexametaphosphate chain length on viscosity of liquid egg analogue using mung bean protein isolate (dash line marks viscosity of commercial liquid whole eggs sample).

Figure 43:
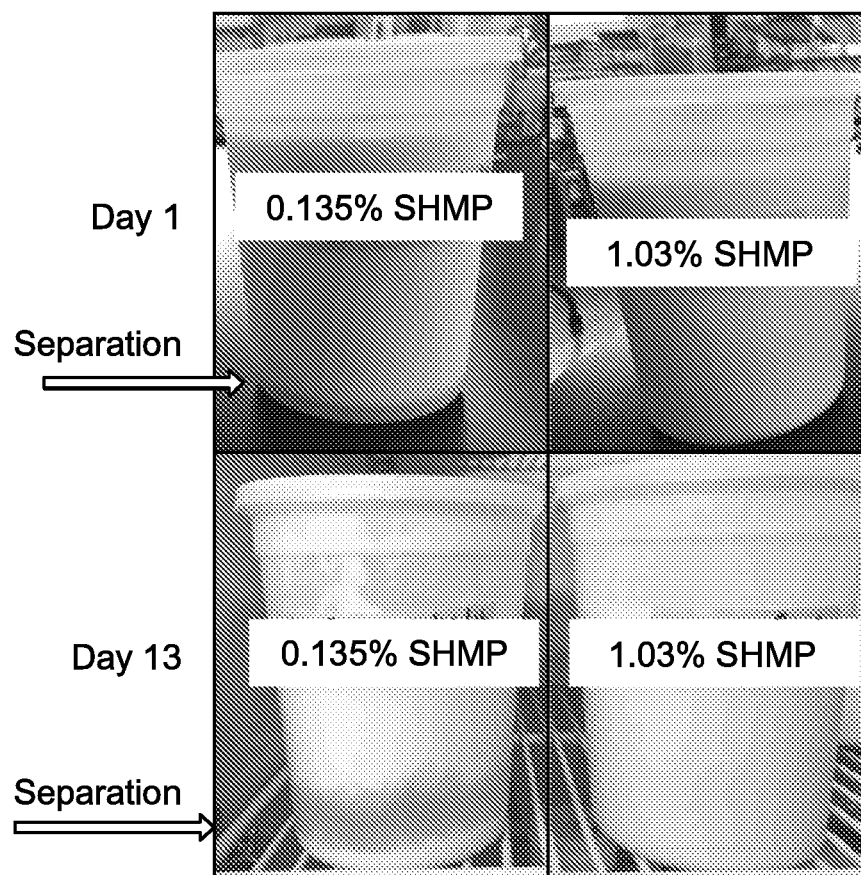

FIG. 43 depicts the effect of long chain SHMP concentration on emulsion stability of liquid egg analogue using mung bean protein isolate after 15 days of storage in a refrigerator.

Figure 44:
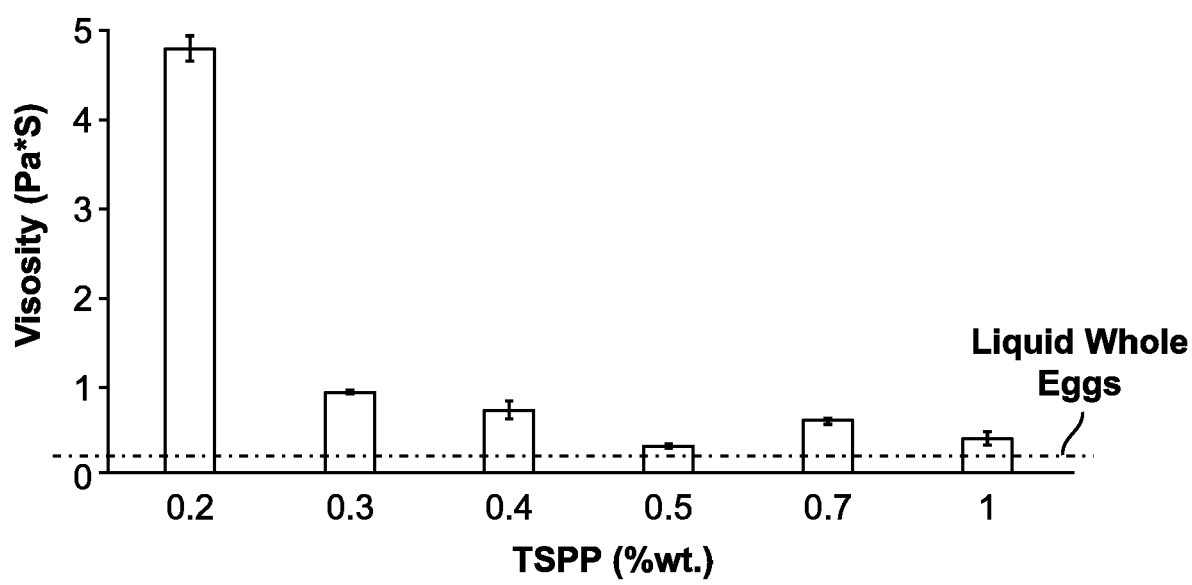

FIG. 44 depicts the dose response curve of tetrasodium pyrophosphate in liquid egg analogue using mung bean protein isolate (dash line marks viscosity of commercial liquid whole eggs sample).

Figure 45:
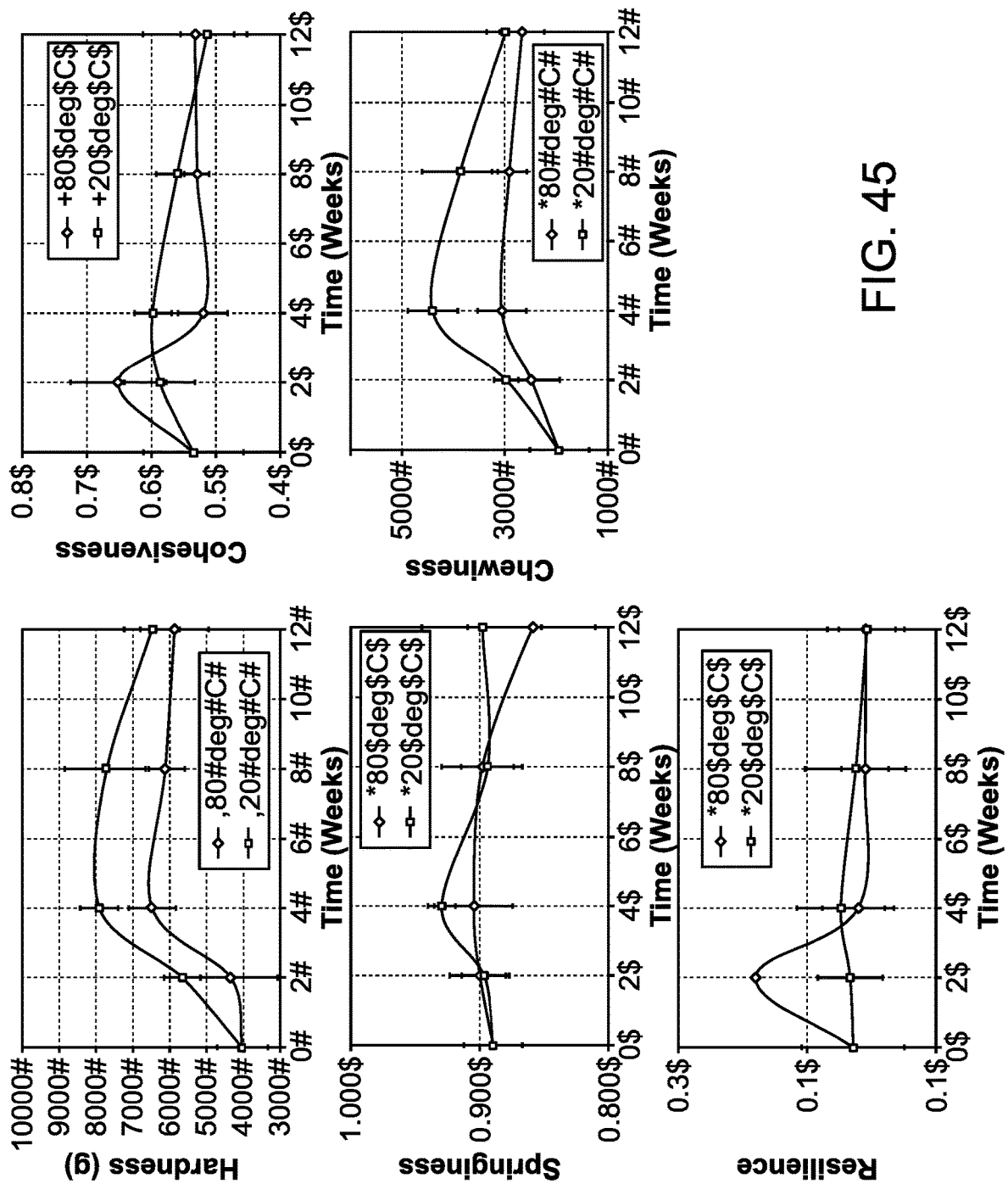

FIG. 45 graphically depicts the results of texture profile analysis (hardness, chewiness, springiness, resilience, and cohesiveness) of a mung bean patty prepared with a mung bean protein isolate composition provided herein.

Figure 46:
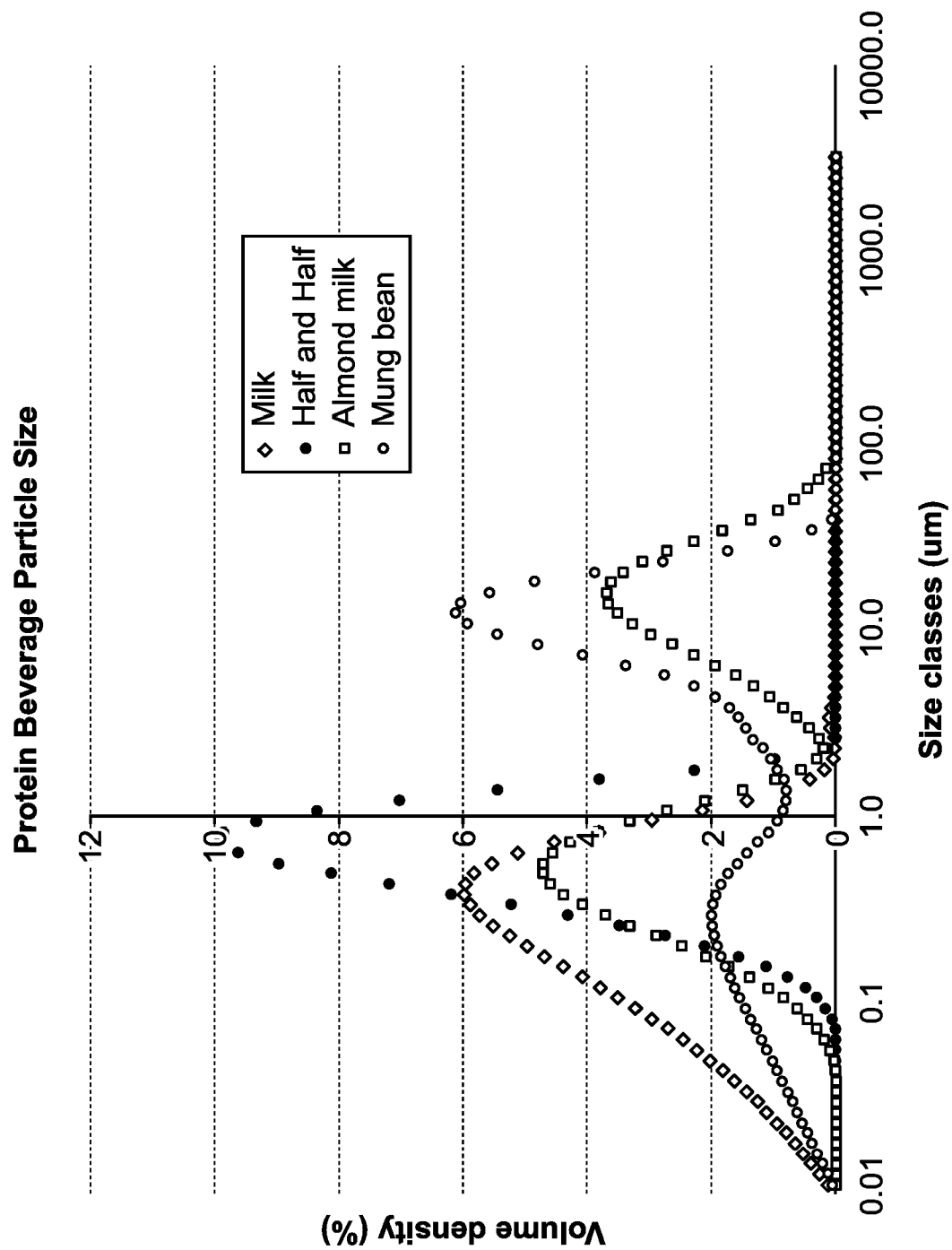

FIG. 46 graphically depicts the particle size of a mung bean protein beverage system, compared to almond milk, half and half and milk.

Figure 47:
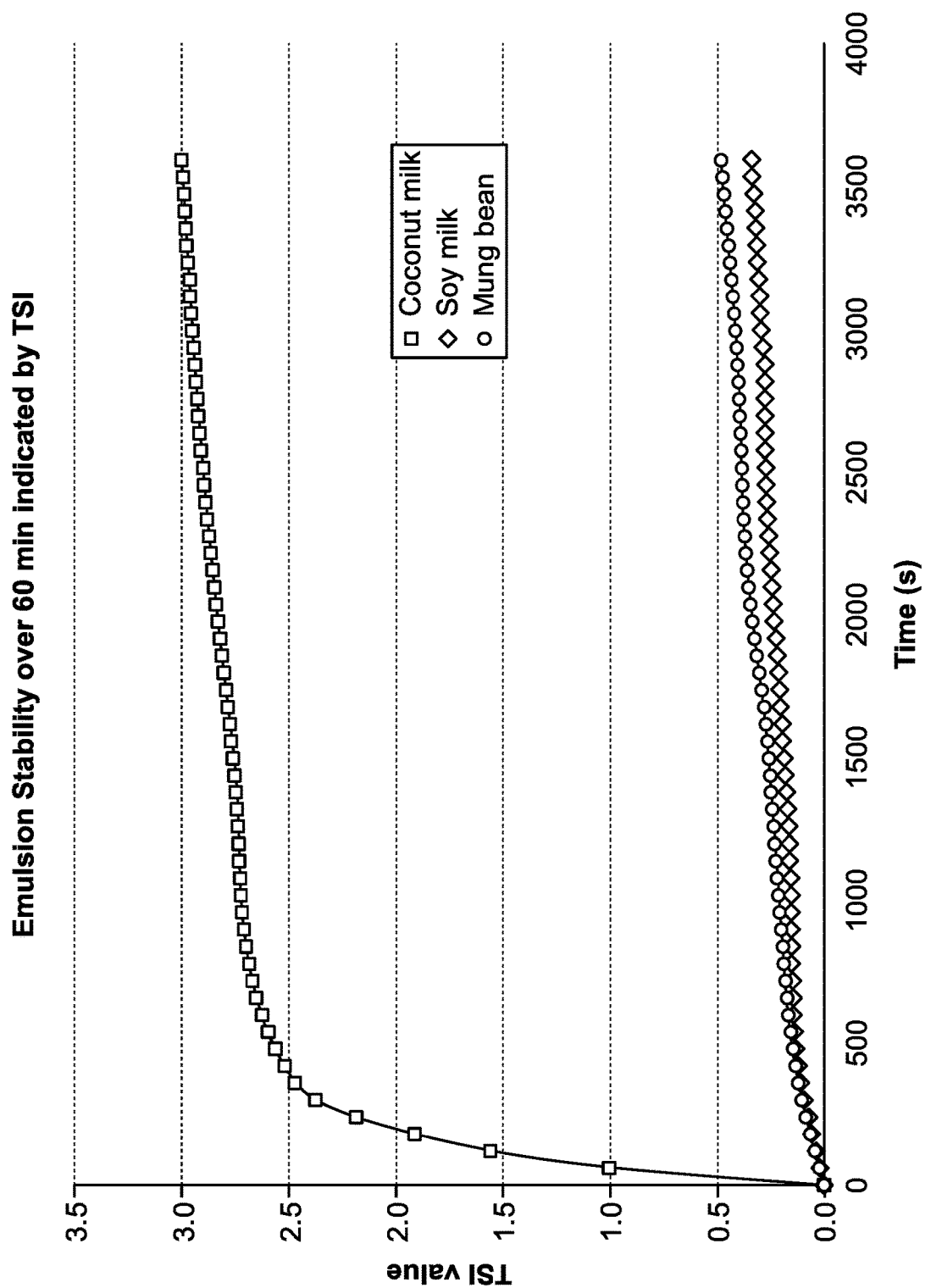

FIG. 47 graphically depicts the emulsion stability of a mung bean protein beverage system, compared to coconut milk and soy milk.

Figure 48:
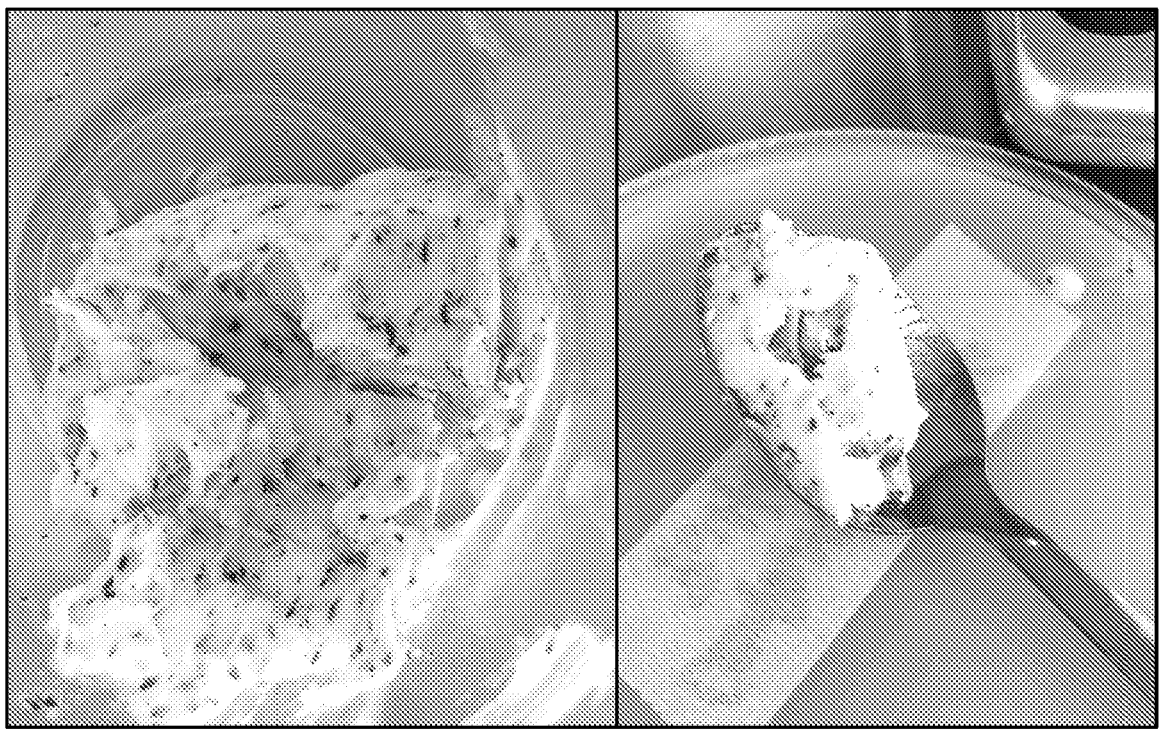

FIG. 48 visually depicts a mung-bean protein based butter system.

Figure 49:
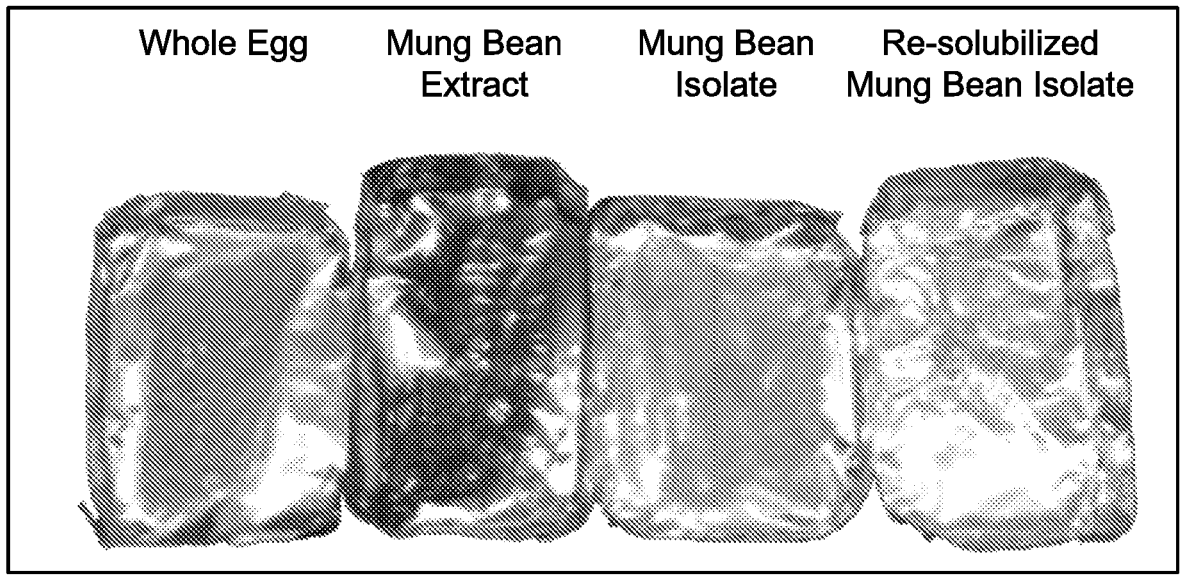

FIG. 49 visually depicts mung bean purified protein isolate in various formats.

Figure 50:
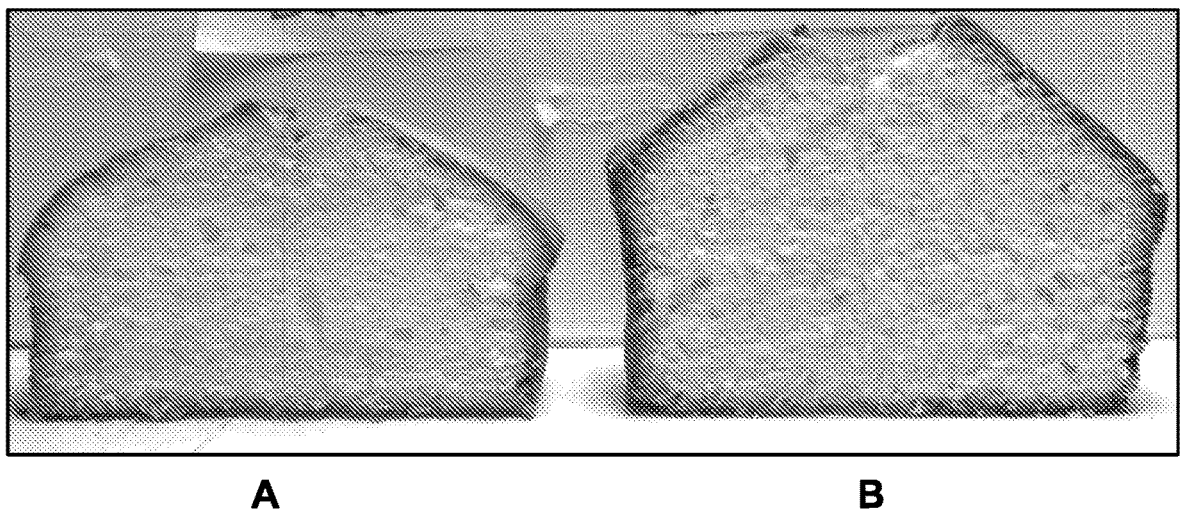

FIG. 50 visually depicts a cross section of a pound cake using (A) eggs and (B) protein extract from mung beans (19%).

Figure 51:
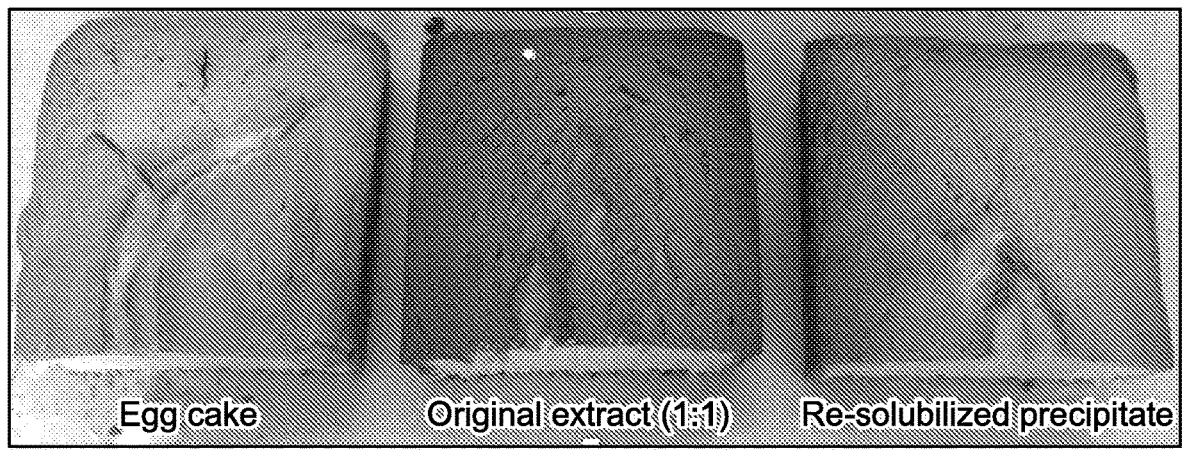

FIG. 51 visually depicts a top view of a pound cake made from eggs (left), protein extract (middle) and re-solubilized isolate (right).

Figure 52:
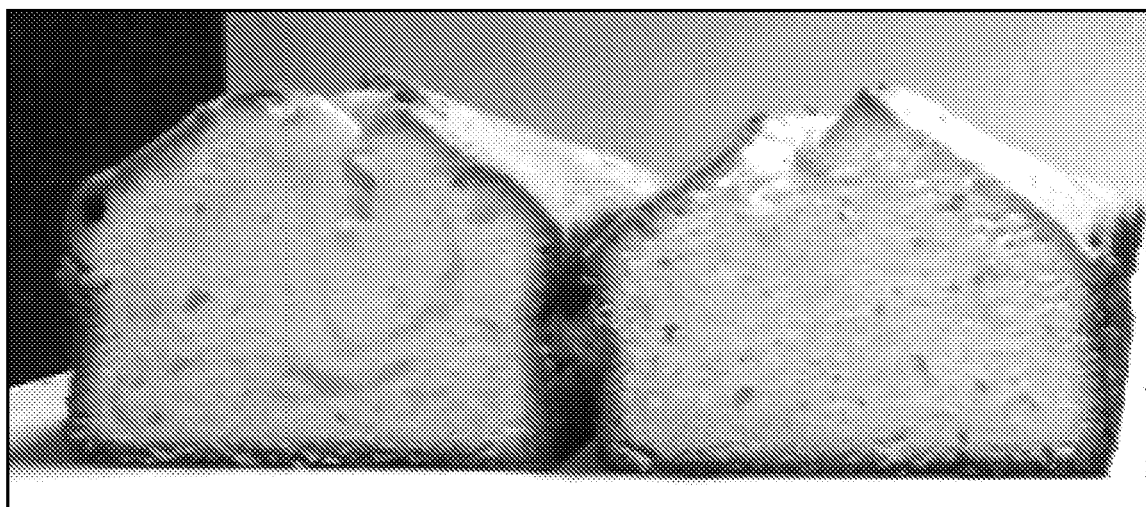

FIG. 52 visually depicts a cross section of a pound cake made using eggs (left) in comparison to a pound cake made using purified protein isolate (right).

Figure 53:
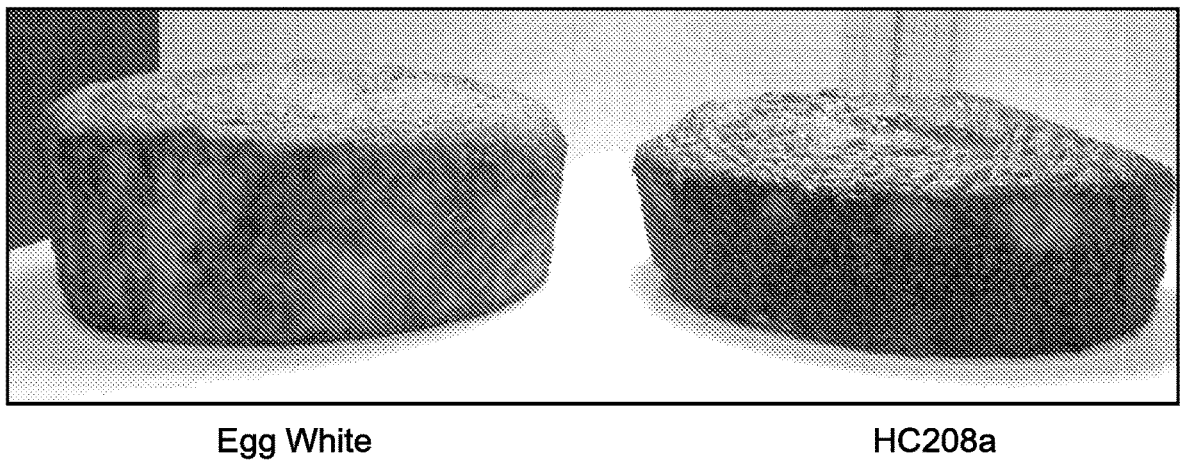

FIG. 53 visually depicts a side view of an angel food cake made using egg whites (left) in comparison to an angel food cake made using purified protein isolate (right).

Figure 54:
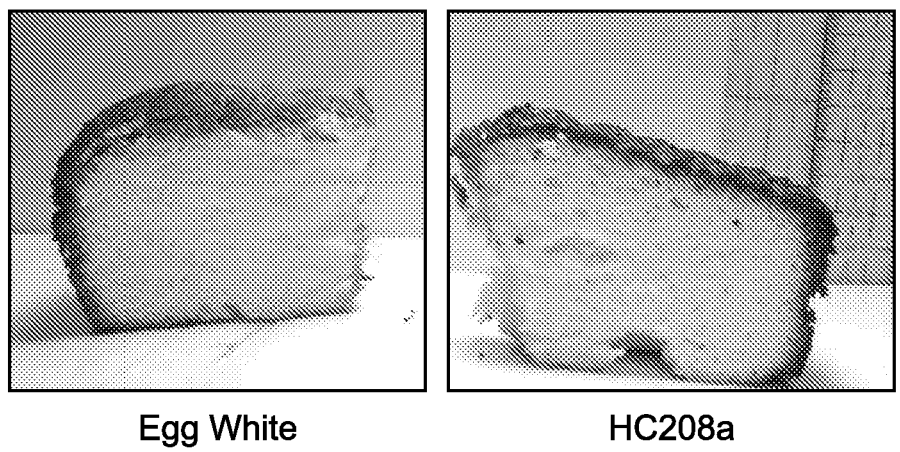

FIG. 54 visually depicts a cross section of a portion of an angel food cake in FIG. 53.

FIG. 55 graphically depicts texture profile analyses comparing mung bean protein meat analogue, commercial chicken nuggets/strips and commercial chicken nugget analogues.

Figure 56:
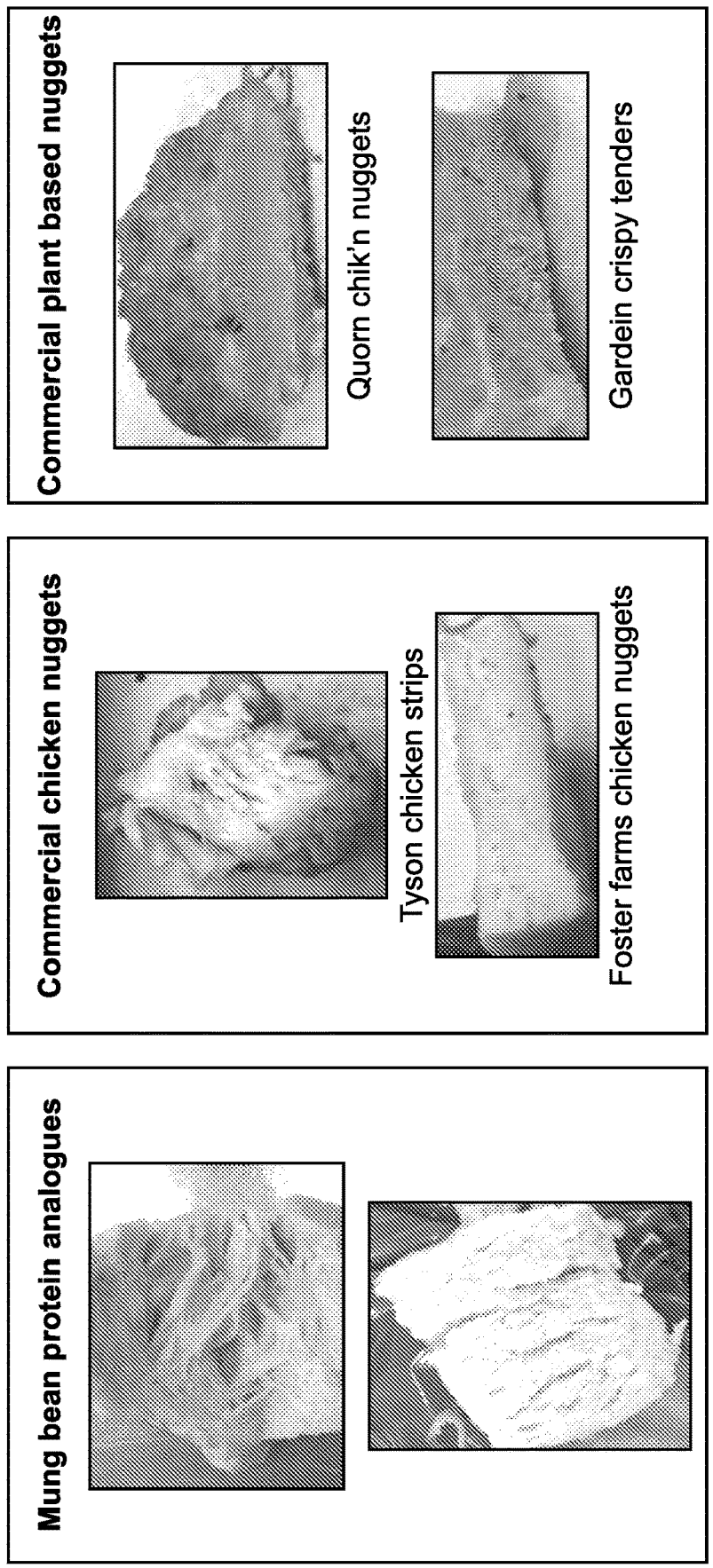

FIG. 56 visually depicts pictures of mung bean protein meat analogue, commercial chicken nuggets/strips and commercial chicken nugget analogues.

Figure 57:
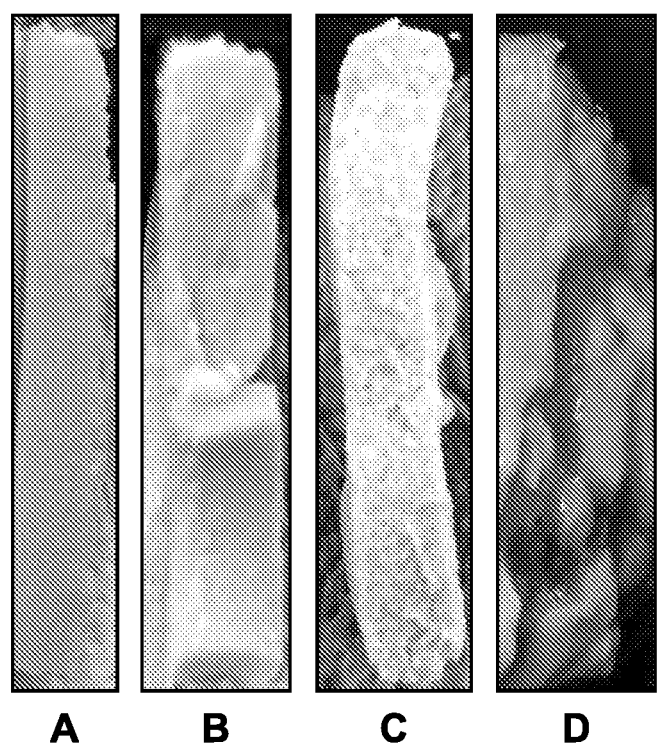

FIG. 57 visually depicts an egg patty substitute from four liquid scramble formulations (A) purified mung bean isolate via salt precipitation; (B) purified mung bean isolate via isoelectric precipitation; (C) purified mung bean & wheat protein isolates (50:50); and (D) purified mung bean & pea protein isolates (50:50).

Figure 58:
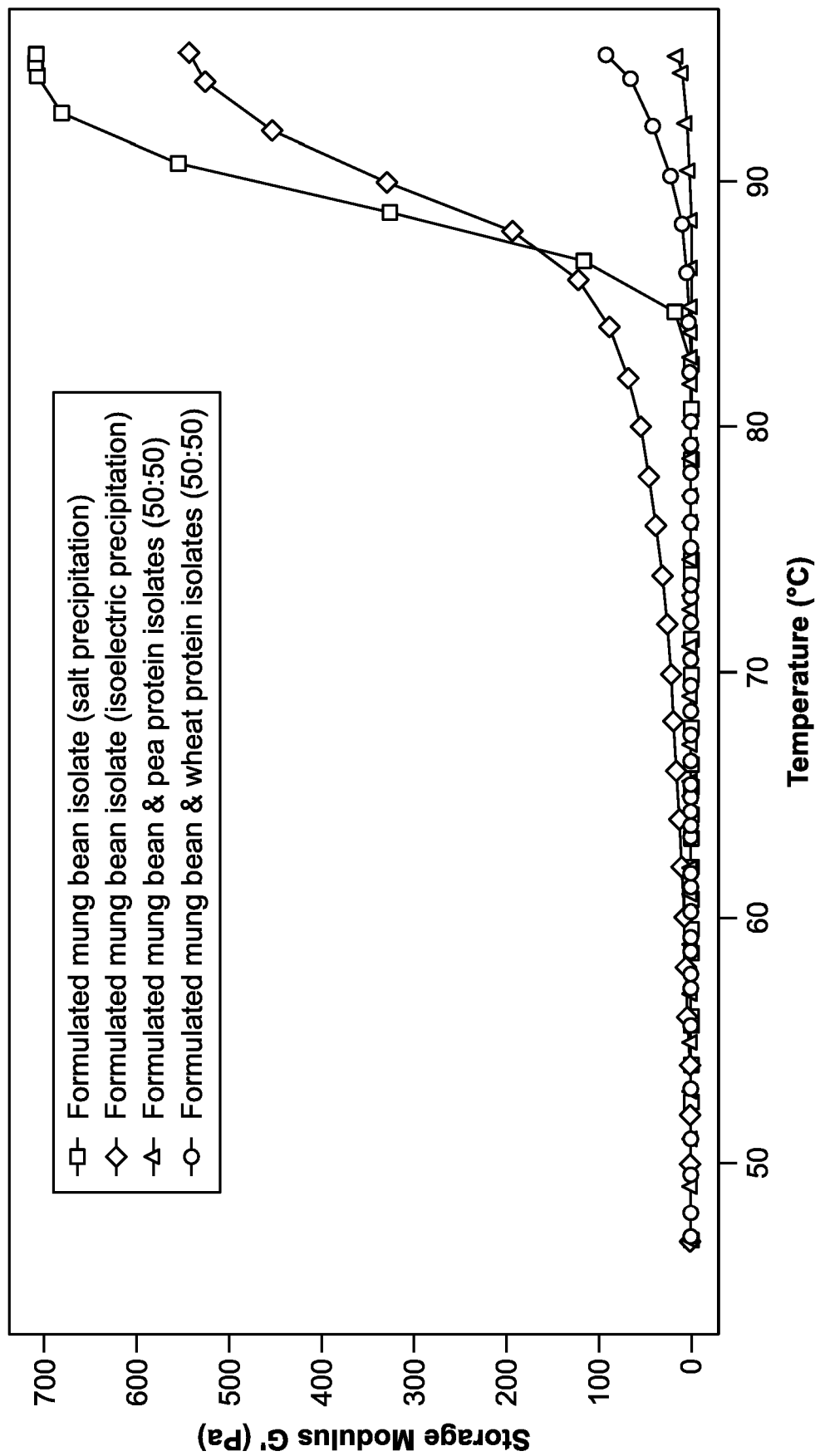

FIG. 58 graphically depicts an oscillatory temperature ramp comparing four liquid scramble formulations shown in FIG. 57.

Figure 59:
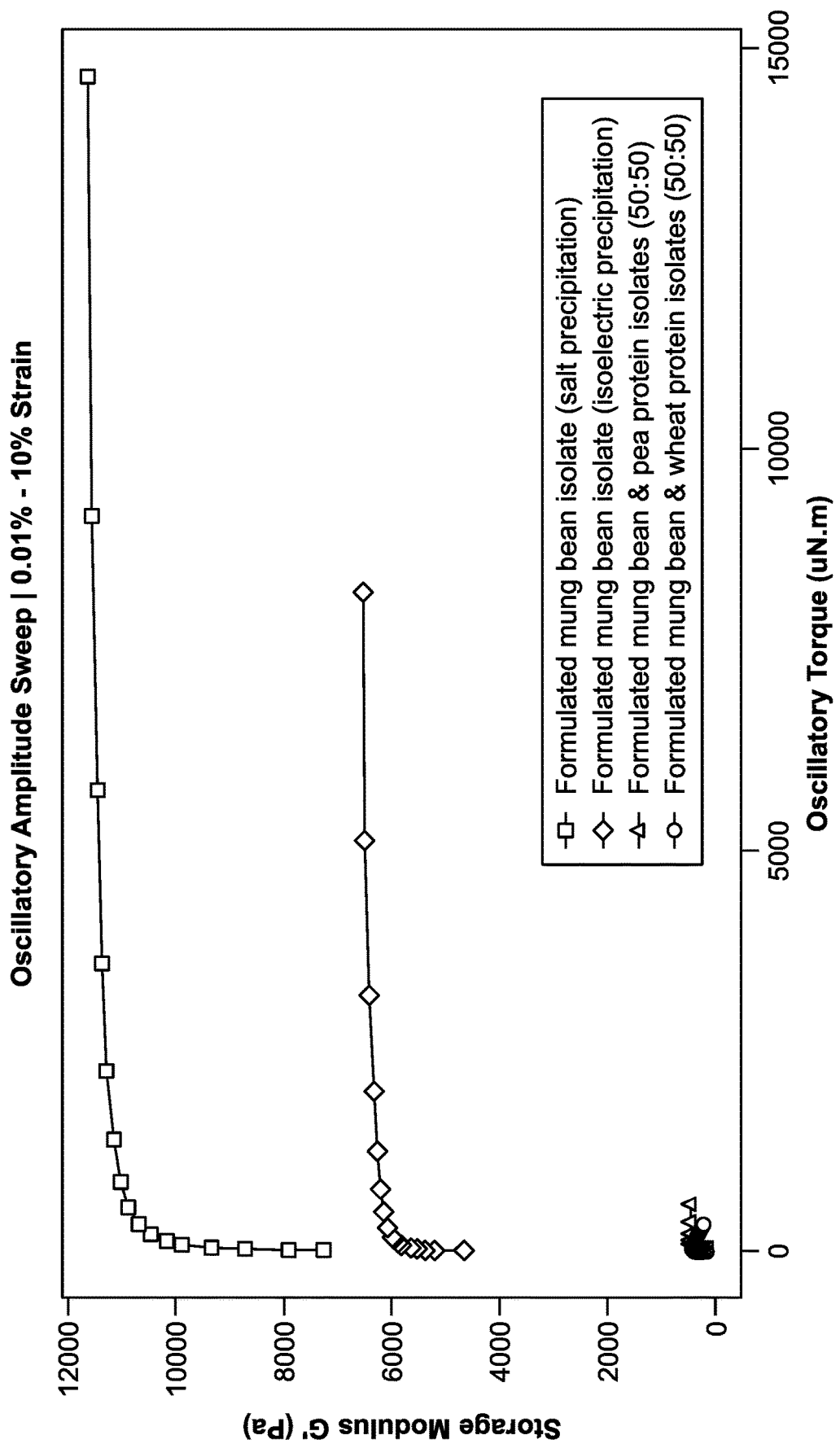

FIG. 59 graphically depicts an oscillatory amplitude sweep comparing four liquid scramble formulations shown in FIG. 57.

Figure 60:
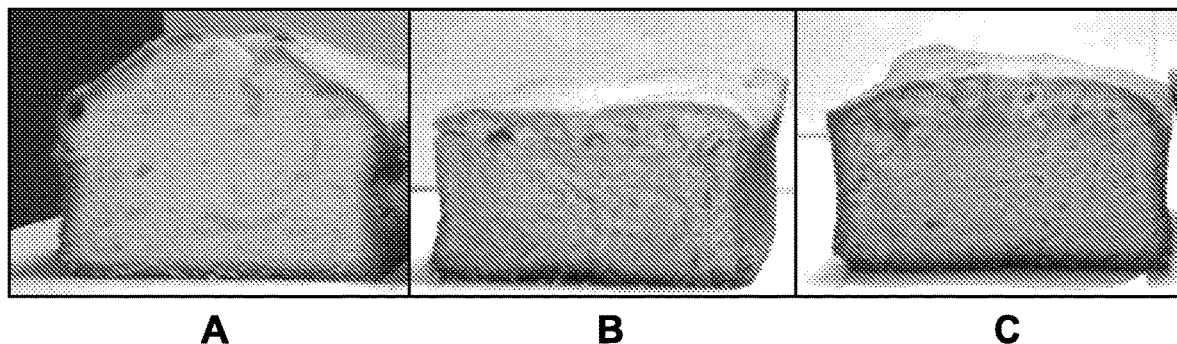

FIG. 60 visually depicts a cross section of a pound cake using (A) eggs; (B) purified golden lentils protein isolate and (C) purified toor dal protein isolate.

Figure 61:
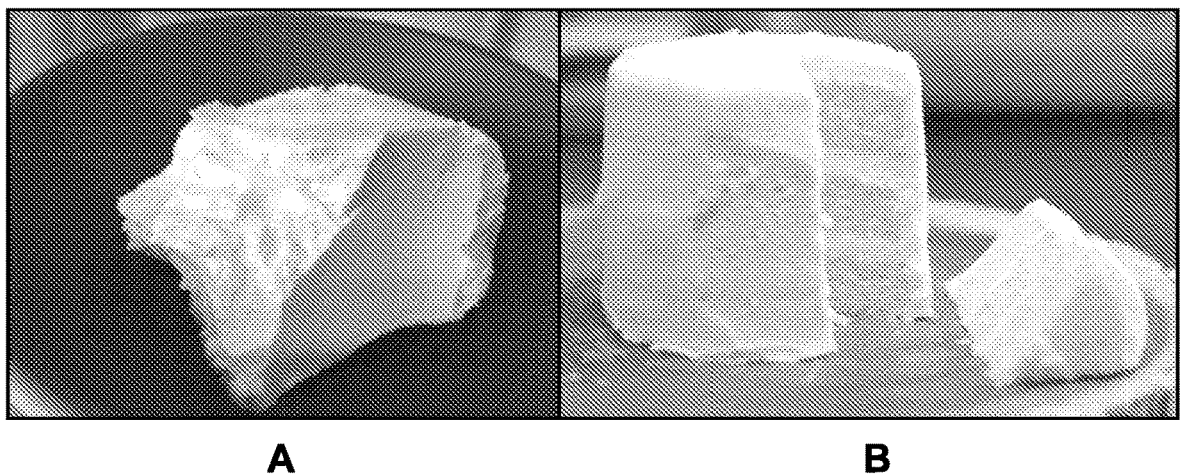

FIG. 61A visually depicts a mung bean protein isolate-based fat reduction shortening model.

FIG. 61B depicts a finished cake and frosting analog, both produced using a mung bean protein isolate-based fat reduction shortening model.

Figure 62:
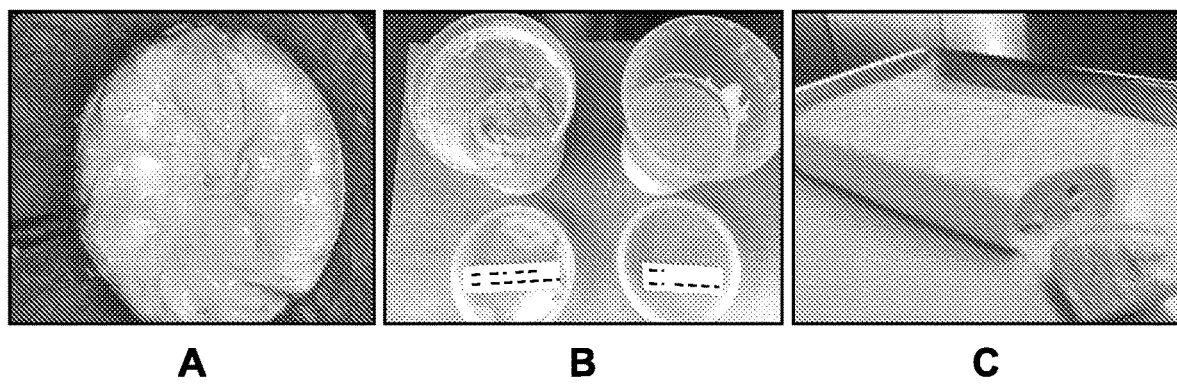

FIG. 62A depicts a non-finished, non-dairy analog in a Theromomix, just before the culturing step.

FIG. 62B depicts finished non-dairy analogs. The sample on the left has been allowed to culture without a finish step, while the sample on the right has been homogenized as a finished product for smooth consistency and the culturing process has been stopped at a pH of 5.

FIG. 62C depicts a finished, pressed non-dairy cream cheese analog.

Figure 63:
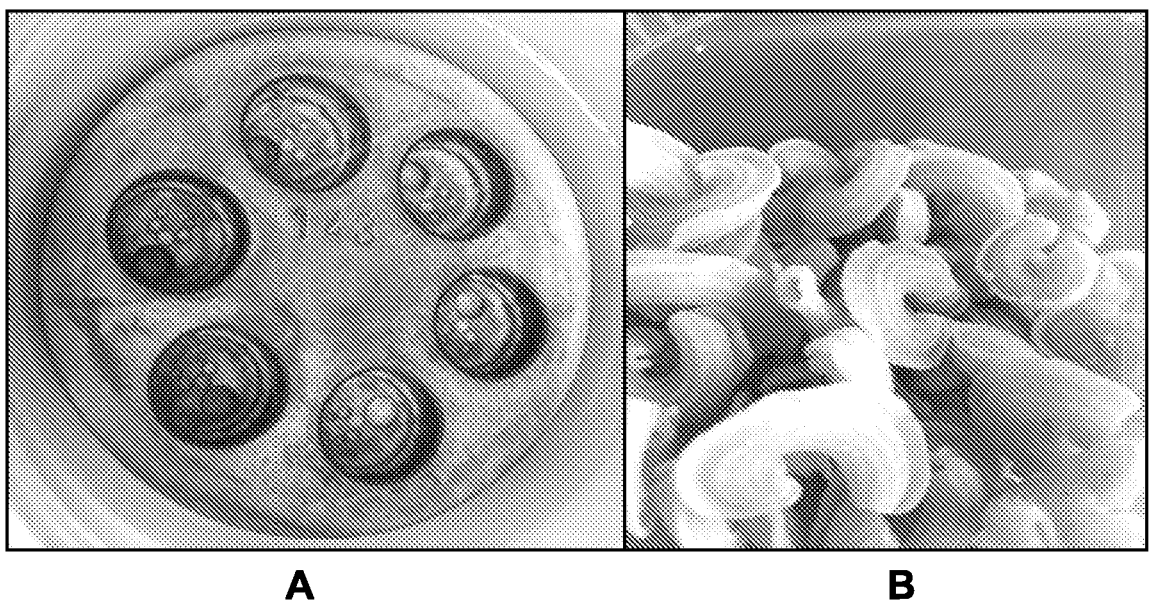

FIG. 63A depicts dye #143, used for extrusion of a mung-bean protein-based pasta analog.

FIG. 63B depicts finished a mung-bean protein-based pasta analog after being dried.

6. DETAILED DESCRIPTION OF THE EMBODIMENTS

6.1 Terminology

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value ±10%, ±5%, or ±1%. In certain embodiments, the term "about" indicates the designated value ±one standard deviation of that value.

The term "reduce" indicates a lessening or decrease of an indicated value relative to a reference value. In some embodiments, the term "reduce" (including "reduction") refers to a lessening or a decrease of an indicated value by about 5%, 10%, 15%, 20%, 25%, 30%, 35%, 40%, 45%, or 50% relative to a reference value. In some embodiments, the term "reduce" (including "reduction") refers to a lessening or a decrease of an indicated value by at least about 5%, 10%, 15%, 20%, 25%, 30%, 35%, 40%, 45%, or 50% relative to a reference value.

As used herein, the term "eggs" includes but is not limited to chicken eggs, other bird eggs (such as quail eggs, duck eggs, ostrich eggs, turkey eggs, bantam eggs, goose eggs), and fish eggs such as fish roe. Typical food application comparison is made with respect to chicken eggs.

As used herein, the term "enriched" refers to an increase in a percent amount of a molecule, for example, a protein, in one sample relative to the percent amount of the molecule in a reference sample. For example, an isolate enriched in a certain type of globulin protein relative to whole mung bean means that, the amount of the globulin protein in the isolate expressed as a percentage of the amount of total protein in the isolate, is higher than the amount of the globulin protein in a whole mung bean expressed as a percentage of the amount of total protein in the whole mung bean. In some embodiments, the enrichment is on a weight to weight basis. In some embodiments, the enrichment refers to an increase of about 5%, 10%, 15%, 20%, 25%, 30%, 35%, 40%, 45%, or 50% relative to the reference value or amount. In some embodiments, the enrichment refers to an increase of at least about 5%, 10%, 15%, 20%, 25%, 30%, 35%, 40%, 45%, or 50% relative to the reference value or amount.

As used herein, "plant source of the isolate" refers to a whole plant material such as whole mung bean, or from an intermediate material made from the plant, for example, a dehulled bean, a flour, a powder, a meal, ground grains, a cake (such as, for example, a defatted or de-oiled cake), or any other intermediate material suitable to the processing techniques disclosed herein to produce a purified protein isolate.

The term "transglutaminase" refers to an enzyme (R-glutamyl-peptide:amine glutamyl transferase) that catalyzes the acyl-transfer between γ-carboxyamide groups and various primary amines, classified as EC 2.3.2.13. It is used in the food industry to improve texture of some food products such as dairy, meat and cereal products. It can be isolated from a bacterial source, a fungus, a mold, a fish, a mammal and a plant.

The terms "majority" or "predominantly" with respect to a specified component, e.g., protein content refer to the component having at least 50% by weight of the referenced batch, process stream, food formulation or composition.

Unless indicated otherwise, percentage (%) of ingredients refer to total % by weight typically on a dry weight basis unless otherwise indicated.

The term "purified protein isolate", "protein isolate", "isolate", "precipitate", "protein extract", "isolated protein" or "isolated polypeptide" refers to a protein fraction, a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). One or more proteins or fractions may be partially removed or separated from residual source materials and/or non-solid protein materials and, therefore, are non-naturally occurring and are not normally found in nature. A polypeptide or protein may also be rendered substantially free of naturally associated components by isolation, using protein purification techniques known in the art and as described herein. A polypeptide that is chemically synthesized or synthesized in a cellular system different from the cell from which it naturally originates will be "isolated" from its naturally associated components. As thus defined, "isolated" does not necessarily require that the protein, polypeptide, peptide or oligopeptide so described has been physically removed from its native environment.

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, Methods Enzymol. 183:63-98 (1990) (incorporated by reference herein). For example, percent sequence identity between amino acid sequences can be determined using FASTA with its default parameters (a word size of 2 and the PAM250 scoring matrix), as provided in GCG Version 6.1, herein incorporated by reference.

6.2 Mung Bean Protein Isolate Compositions

Provided herein are one or more edible mung bean protein isolates comprising one or more desirable food qualities, including but not limited to, high protein content, high protein purity, reduced retention of small molecular weight nonprotein species (including mono and disaccharides), reduced retention of oils and lipids, superior structure building properties such as high gel strength and gel elasticity, superior sensory properties, and selective enrichment of highly functional 8S globulin/beta conglycinin proteins.

In preferred embodiments, the protein isolate provided herein is derived from mung bean. In some embodiments, the mung bean is *Vigna radiata*. In various aspects of the invention, the purified mung bean protein isolate described herein can be produced from any source of mung bean protein, including any varietal or cultivar of *V. radiata*. For example, the protein isolate can be prepared directly from whole plant material such as whole mung bean, or from an intermediate material made from the plant, for example, a dehulled bean, a flour, a powder, a meal, ground grains, a cake (such as, for example, a defatted or de-oiled cake), or any other intermediate material suitable to the processing techniques disclosed herein to produce a purified protein isolate. In some embodiments, the source of the plant protein may be a mixture of two or more intermediate materials. The examples of candidate intermediate materials provided herein are not intended to be limiting.

In preferred embodiments, provided herein are mung bean protein isolate compositions predominantly comprising a protein-based fraction. In preferred embodiments, the protein fraction is 50%-60%, 60%-70%, 70%-80%, 80%, 81%, 82%, 83%, 84%, 85%, 86%, 87%, 88%, 89%, 90%, 91%, 92%, 93%, 94%, 95%, 96%, 97%, 98%, 99% or even 100% of the mung bean isolate. In preferred embodiments, at least 60% by weight of the purified isolate is the protein fraction. In preferred embodiments, at least 65% by weight of the purified isolate is the protein fraction. In preferred embodiments, at least 70% by weight of the purified isolate is the protein fraction. In some embodiments, at least 75% by weight of the purified isolate is the protein fraction. In some embodiments, at least 80% by weight of the purified isolate is the protein fraction. In some embodiments, up to about 95% by weight of the purified isolate is the protein fraction.

Preferred embodiments include high purity protein isolates from mung bean that comprise at least 50% by weight of protein consisting of or comprising at least one globulin-type protein. While not wishing to be bound by a particular theory, it is believed that the globulin fraction provides the basis for functionality. Accordingly, the purified protein isolates are enriched in globulin protein relative to whole mung bean. In some embodiments, the globulin-like protein is mung bean 8S globulin/beta-conglycinin. In some embodiments, at least about 10%, 15%, 20%, 25%, 30%, 35%, 40%, 45%, 50%, 55%, 60%, 65%, 70%, 75%, 80%, 85%, or greater than 85% by weight of the protein fraction of the isolate consists of or comprises mung bean 8S globulin/beta-conglycinin. In other embodiments, about 60% to 80%, 65% to 85%, 70% to 90%, or 75% to 95% by weight of the protein fraction consists of or comprises mung bean 8S globulin/beta-conglycinin.

In some embodiments, purified protein isolate is concentrated between 100-200 g/L or higher.

In some embodiments, the mung bean isolate composition is reduced in the amount of 11S globulin relative to whole mung bean or mung bean flour. In some embodiments, the amount of 11S globulin is less than 10%, 8%, 8%, 7%, 6%, 5%, 4%, 3%, 2%, or 1% of the protein fraction of the isolate.

In some embodiments, proteins in the composition comprise nondenatured proteins. In other embodiments, proteins in the composition comprise denatured proteins.

In some embodiments, the mung bean protein isolate comprises about 1% to 10%, 2% to 9%, 3% to 8%, or 4% to 6% of carbohydrates (e.g., starch, polysaccharides, fiber) derived from the plant source of the isolate. In some embodiments, the mung bean protein isolate comprises less than about 10%, 9%, 8%, 7%, 6% or 5% of carbohydrates derived from the plant source of the isolate. In some embodiments, the mung bean protein isolate comprises about 9%, 8%, 7%, 6%, 5%, 4%, 3%, 2%, or about 1% of carbohydrates derived from the plant source of the isolate. In some embodiments, practice of the methods provided herein results in producing a mung bean protein isolate in which at least 10%, 20%, 30%, 40%, 50%, 60%, 70%, 80%, or 90% of the carbohydrate originally found in the mung bean protein source has been reduced.

In some embodiments, the mung bean protein isolate comprises about 1% to 10%, 2% to 9%, 3% to 8%, or 4% to 6% of ash derived from the plant source of the isolate. In some embodiments, the mung bean protein isolate comprises less than about 10%, 9%, 8%, 7%, 6% or 5% of ash derived from the plant source of the isolate. In some embodiments, the mung bean protein isolate comprises about 9%, 8%, 7%, 6%, 5%, 4%, 3%, 2%, or about 1% of ash derived from the plant source of the isolate. In some embodiments, practice of the methods provided herein results in producing a mung bean protein isolate in which at least 10%, 20%, 30%, 40%, 50%, 60%, 70%, 80%, or 90% of the ash originally found in the mung bean protein source has been reduced.

In some embodiments, the mung bean protein isolate comprises about 1% to 10%, 2% to 9%, 3% to 8%, or 4% to 6% of fats derived from the plant source of the isolate. In some embodiments, the mung bean protein isolate comprises less than about 10%, 9%, 8%, 7%, 6% or 5% of fats derived from the plant source of the isolate. In some embodiments, the mung bean protein isolate comprises about 9%, 8%, 7%, 6%, 5%, 4%, 3%, 2%, or about 1% of fats derived from the plant source of the isolate. In some embodiments, practice of the methods provided herein results in producing a mung bean protein isolate in which at least 10%, 20%, 30%, 40%, 50%, 60%, 70%, 80%, or 90% of the fats originally found in the mung bean protein source has been reduced.

In some embodiments, the mung bean protein isolate comprises about 1% to 10% of moisture derived from the plant source of the isolate. In some embodiments, the mung bean protein isolate comprises less than about 10%, 9%, 8%, 7%, 6% or 5% of moisture derived from the plant source of the isolate. In some embodiments, the mung bean protein isolate comprises about 9%, 8%, 7%, 6%, 5%, 4%, 3%, 2%, or about 1% of moisture derived from the plant source of the isolate.

In a particular embodiment, the mung bean protein isolate comprises less than 10% of carbohydrates, less than 8% of ash, less than 5% of fats, and less than 7% of moisture derived from the plant source of the isolate.

6.2.1 Mung Bean Proteins of the Isolate Compositions

Leguminous plants contain many types of proteins, two of which are globulins and albumins. Globulins and albumins are soluble proteins and make up the majority of the total proteins in mung bean. Globulins can be further classified as legumins, vicilins and convicilins. Amongst the 5,000 or so known *V. radiata* varietals, protein levels range from about 20-30%.

The globulin-type protein making up the majority by weight of the protein fraction of the isolates provided herein may all be of the same type of globulin-type protein, or it may comprise more than one type of globulin-type protein. For example, the globulin-type protein may include 7S globulin, 8S globulin, and/or 11S globulin. In some embodiments, the globulin-type protein is predominantly 8S globulin, meaning that a majority by weight of the globulin-type protein is 8S globulin. The globulin-type protein may also or alternatively include protein(s) homologous to 7S, 8S, and/or 11S globulin.

In some embodiments, the globulin-type protein of the mung bean protein isolates provided herein is a beta-conglycinin protein. In some embodiments, the beta-conglycinin protein is at least 50% identical to SEQ ID NO:1. In some embodiments, the beta-conglycinin protein is at least 60%, 65%, 70%, 75%, 80%, 85%, 90%, greater than 90%, or greater than 95% identical to SEQ ID NO:1.

In some embodiments, the mung bean protein isolate comprises a protein having sequence at least 75% identical to one or more globulin-type proteins from mung bean (e.g. 7S, 8S, 11S), wherein the protein is enriched in the isolate in relation to the amount of protein found in the plant source of the isolate. In some embodiments, the enriched protein has at least 50%, 60, 70%, 80%, 85%, 90%, 95%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or even higher identity to one or more globulin-type proteins from mung bean (e.g. 7S, 8S, 11S).

In some embodiments, the enriched mung bean protein isolate provided herein comprises at least one protein comprising an amino acid sequence having at least 50%, 60%, 70%, 80%, 90%, or 95% identity, or higher, to a sequence selected from the group of sequences corresponding to the following NCBI accession numbers: XP_014524354 (SEQ ID NO:1), NP_001304229 (SEQ ID NO:2), XP_014523938 (SEQ ID NO:3), NP_001304202 (SEQ ID NO:4), NP_001304231 (SEQ ID NO:5), XP_014523923 (SEQ ID NO:6), XP_014507363 (SEQ ID NO:7), XP_014492536 (SEQ ID NO:8), XP_014521758 (SEQ ID NO:9), XP_014515669 (SEQ ID NO:10), XP_014523936 (SEQ ID NO:11), and XP_014524353 (SEQ ID NO:12). In some embodiments, the mung bean protein isolate comprises at least two, three, four, five, six, seven, eight, nine, ten or more enriched proteins comprising an amino acid sequence having at least 50%, 60%, 70%, 80%, 90%, or 95% identity, or higher, to a sequence selected from the group of sequences corresponding to the following NCBI accession numbers: XP_014524354 (SEQ ID NO:1), NP_001304229 (SEQ ID NO:2), XP_014523938 (SEQ ID NO:3), NP_001304202 (SEQ ID NO:4), NP_001304231 (SEQ ID NO:5), XP_014523923 (SEQ ID NO:6), XP_014507363 (SEQ ID NO:7), XP_014492536 (SEQ ID NO:8), XP_014521758 (SEQ ID NO:9), XP_014515669 (SEQ ID NO:10), XP_014523936 (SEQ ID NO:11), and XP_014524353 (SEQ ID NO:12).

In, some embodiments, the mung bean protein isolate comprises a protein having at least 90% identity to SEQ ID NO:1. In some embodiments, the mung bean protein isolate comprises a protein having at least 90% identity to SEQ ID NO:1, in an amount that is at least 1% of the total protein of the isolate. In some embodiments, the amount the protein having at least 90% identity to SEQ ID NO:1 is at least 5, 10, 15, or 20% of the isolate. In some embodiments, the mung bean protein isolate is enriched for a protein having at least 90% identity to SEQ ID NO:1, in relation to the amount of the protein found in the plant source of the isolate. In some embodiments, the enriched protein is enriched by at least 5%, 10%, 15%, 20% or greater than 20%. In any of the preceding embodiments, the mung bean protein isolate can comprise a protein having at least 95% identity to SEQ ID NO: 1.

In, some embodiments, the mung bean protein isolate comprises a protein having at least 90% identity to SEQ ID NO:2. In some embodiments, the mung bean protein isolate comprises a protein having at least 90% identity to SEQ ID NO:2, in an amount that is at least 1% of the total protein of the isolate. In some embodiments, the amount the protein having at least 90% identity to SEQ ID NO:2 is at least 5, 10, 15, or 20% of the isolate. In some embodiments, the mung bean protein isolate is enriched for a protein having at least 90% identity to SEQ ID NO:2, in relation to the amount of the protein found in the plant source of the isolate. In some embodiments, the enriched protein is enriched by at least 5%, 10%, 15%, 20% or greater than 20%. In any of the preceding embodiments, the mung bean protein isolate can comprise a protein having at least 95% identity to SEQ ID NO: 2.

In, some embodiments, the mung bean protein isolate comprises a protein having at least 90% identity to SEQ ID NO:3. In some embodiments, the mung bean protein isolate comprises a protein having at least 90% identity to SEQ ID NO:3, in an amount that is at least 1% of the total protein of the isolate. In some embodiments, the amount the protein having at least 90% identity to SEQ ID NO:3 is at least 5, 10, 15, or 20% of the isolate. In some embodiments, the mung bean protein isolate is enriched for a protein having at least 90% identity to SEQ ID NO:3, in relation to the amount of the protein found in the plant source of the isolate. In some embodiments, the enriched protein is enriched by at least 5%, 10%, 15%, 20% or greater than 20%. In any of the preceding embodiments, the mung bean protein isolate can comprise a protein having at least 95% identity to SEQ ID NO: 3.

In, some embodiments, the mung bean protein isolate comprises a protein having at least 90% identity to SEQ ID NO:4. In some embodiments, the mung bean protein isolate comprises a protein having at least 90% identity to SEQ ID NO:4, in an amount that is at least 1% of the total protein of the isolate. In some embodiments, the amount the protein having at least 90% identity to SEQ ID NO:4 is at least 5, 10, 15, or 20% of the isolate. In some embodiments, the mung bean protein isolate is enriched for a protein having at least 90% identity to SEQ ID NO:4, in relation to the amount of the protein found in the plant source of the isolate. In some embodiments, the enriched protein is enriched by at least 5%, 10%, 15%, 20% or greater than 20%. In any of the preceding embodiments, the mung bean protein isolate can comprise a protein having at least 95% identity to SEQ ID NO: 4.

In, some embodiments, the mung bean protein isolate comprises a protein having at least 90% identity to SEQ ID NO:5. In some embodiments, the mung bean protein isolate comprises a protein having at least 90% identity to SEQ ID NO:5, in an amount that is at least 1% of the total protein of the isolate. In some embodiments, the amount the protein having at least 90% identity to SEQ ID NO:5 is at least 5, 10, 15, or 20% of the isolate. In some embodiments, the mung bean protein isolate is enriched for a protein having at least 90% identity to SEQ ID NO:5, in relation to the amount of the protein found in the plant source of the isolate. In some embodiments, the enriched protein is enriched by at least 5%, 10%, 15%, 20% or greater than 20%. In any of the preceding embodiments, the mung bean protein isolate can comprise a protein having at least 95% identity to SEQ ID NO: 5.

In, some embodiments, the mung bean protein isolate comprises a protein having at least 90% identity to SEQ ID NO:6. In some embodiments, the mung bean protein isolate comprises a protein having at least 90% identity to SEQ ID NO:6, in an amount that is at least 1% of the total protein of the isolate. In some embodiments, the amount the protein having at least 90% identity to SEQ ID NO:6 is at least 5, 10, 15, or 20% of the isolate. In some embodiments, the mung bean protein isolate is enriched for a protein having at least 90% identity to SEQ ID NO:6, in relation to the amount of the protein found in the plant source of the isolate. In some embodiments, the enriched protein is enriched by at least 5%, 10%, 15%, 20% or greater than 20%. In any of the preceding embodiments, the mung bean protein isolate can comprise a protein having at least 95% identity to SEQ ID NO: 6.

In, some embodiments, the mung bean protein isolate comprises a protein having at least 90% identity to SEQ ID NO:7. In some embodiments, the mung bean protein isolate comprises a protein having at least 90% identity to SEQ ID NO:7, in an amount that is at least 1% of the total protein of the isolate. In some embodiments, the amount the protein having at least 90% identity to SEQ ID NO:7 is at least 5, 10, 15, or 20% of the isolate. In some embodiments, the mung bean protein isolate is enriched for a protein having at least 90% identity to SEQ ID NO:7, in relation to the amount of the protein found in the plant source of the isolate. In some embodiments, the enriched protein is enriched by at least 5%, 10%, 15%, 20% or greater than 20%. In any of the preceding embodiments, the mung bean protein isolate can comprise a protein having at least 95% identity to SEQ ID NO: 7.

In, some embodiments, the mung bean protein isolate comprises a protein having at least 90% identity to SEQ ID NO:8. In some embodiments, the mung bean protein isolate comprises a protein having at least 90% identity to SEQ ID NO:8, in an amount that is at least 1% of the total protein of the isolate. In some embodiments, the amount the protein having at least 90% identity to SEQ ID NO:8 is at least 5, 10, 15, or 20% of the isolate. In some embodiments, the mung bean protein isolate is enriched for a protein having at least 90% identity to SEQ ID NO:8, in relation to the amount of the protein found in the plant source of the isolate. In some embodiments, the enriched protein is enriched by at least 5%, 10%, 15%, 20% or greater than 20%. In any of the preceding embodiments, the mung bean protein isolate can comprise a protein having at least 95% identity to SEQ ID NO: 8.

In, some embodiments, the mung bean protein isolate comprises a protein having at least 90% identity to SEQ ID NO:9. In some embodiments, the mung bean protein isolate comprises a protein having at least 90% identity to SEQ ID NO:9, in an amount that is at least 1% of the total protein of the isolate. In some embodiments, the amount the protein having at least 90% identity to SEQ ID NO:9 is at least 5, 10, 15, or 20% of the isolate. In some embodiments, the mung bean protein isolate is enriched for a protein having at least 90% identity to SEQ ID NO:9, in relation to the amount of the protein found in the plant source of the isolate. In some embodiments, the enriched protein is enriched by at least 5%, 10%, 15%, 20%, or greater than 20%. In any of the preceding embodiments, the mung bean protein isolate can comprise a protein having at least 95% identity to SEQ ID NO:9.

In, some embodiments, the mung bean protein isolate comprises a protein having at least 90% identity to SEQ ID NO:10. In some embodiments, the mung bean protein isolate comprises a protein having at least 90% identity to SEQ ID NO:10, in an amount that is at least 1% of the total protein of the isolate. In some embodiments, the amount the protein having at least 90% identity to SEQ ID NO:10 is at least 5, 10, 15, or 20% of the isolate. In some embodiments, the mung bean protein isolate is enriched for a protein having at least 90% identity to SEQ ID NO:10, in relation to the amount of the protein found in the plant source of the isolate. In some embodiments, the enriched protein is enriched by at least 5%, 10%, 15%, 20%, or greater than 20%. In any of the preceding embodiments, the mung bean protein isolate can comprise a protein having at least 95% identity to SEQ ID NO:10.

In, some embodiments, the mung bean protein isolate comprises a protein having at least 90% identity to SEQ ID NO:11. In some embodiments, the mung bean protein isolate comprises a protein having at least 90% identity to SEQ ID NO:11, in an amount that is at least 1% of the total protein of the isolate. In some embodiments, the amount the protein having at least 90% identity to SEQ ID NO:11 is at least 5, 10, 15, or 20% of the isolate. In some embodiments, the mung bean protein isolate is enriched for a protein having at least 90% identity to SEQ ID NO:11, in relation to the amount of the protein found in the plant source of the isolate. In some embodiments, the enriched protein is enriched by at least 5%, 10%, 15%, 20%, or greater than 20%. In any of the preceding embodiments, the mung bean protein isolate can comprise a protein having at least 95% identity to SEQ ID NO:11.

In, some embodiments, the mung bean protein isolate comprises a protein having at least 90% identity to SEQ ID NO:12. In some embodiments, the mung bean protein isolate comprises a protein having at least 90% identity to SEQ ID NO:12, in an amount that is at least 1% of the total protein of the isolate. In some embodiments, the amount the protein having at least 90% identity to SEQ ID NO:12 is at least 5, 10, 15, or 20% of the isolate. In some embodiments, the mung bean protein isolate is enriched for a protein having at least 90% identity to SEQ ID NO:12, in relation to the amount of the protein found in the plant source of the isolate. In some embodiments, the enriched protein is enriched by at least 5%, 10%, 15%, 20% or greater than 20%. In any of the preceding embodiments, the mung bean protein isolate can comprise a protein having at least 95% identity to SEQ ID NO:12.

According to other embodiments, purified protein isolates comprising a fragment of the above-described proteins are provided. These fragments preferably include at least 20 contiguous amino acids, more preferably at least 25, 30, 35, 40, 45, 50, 60, 70, 80, 90, 100 or even more contiguous amino acids.

6.2.2 Reduced Allergen Content

In some embodiments, the mung bean protein isolates provided herein have a reduced allergen content. In some embodiments, the reduced allergen content is relative to the allergen content of the plant source of the isolate. The mung bean protein isolate or a composition comprising the protein isolate may be animal-free, dairy-free, soy-free and gluten-free. Adverse immune responses such as hives or rash, swelling, wheezing, stomach pain, cramps, diarrhea, vomiting, dizziness and even anaphylaxis presented in subjects who are typically allergic to eggs may be averted. Further, the purified protein isolate or a composition comprising the protein isolate may not trigger allergic reactions in subjects based on milk, eggs, soy and wheat allergens. Accordingly, in some embodiments, the protein isolate is substantially free of allergens. In some embodiments, proteins such as Vig r 1, Vig r 2, Vig r 4, and Vig r 6 are also removed. In a particular embodiment, the mung bean protein isolate has a reduced (relative to the plant source of the isolate) or non-detectable amount of a protein comprising an amino acid sequence having at least 50%, 60%, 70%, 80%, 90%, or 95% identity, or higher, to pathogenesis-related protein (PR-10), corresponding to accession no. AAX19889.1 (SEQ ID NO:13).

6.2.3 Reduced Anti-Nutritional Factors

Dietary anti-nutritional factors are chemical substances that can adversely impact the digestibility of protein, bioavailability of amino acids and protein quality of foods (Gilani et al., 2012). In some embodiments, the mung bean protein isolates provided herein have reduced amount of anti-nutritional factors. In some embodiments, the reduced amount of anti-nutritional factors is relative to the allergen content of the plant source of the isolate. In some embodiments, the reduced anti-nutritional factor is selected from the group consisting of tannins, phytic acid, hemagglutinins (lectins), polyphenols, trypsin inhibitors, □-amylase inhibitors, lectins and protease inhibitors. In a particular embodiment, the mung bean protein isolate has a reduced (relative to the plant source of the isolate) or non-detectable amount of a protein comprising an amino acid sequence having at least 50%, 60%, 70%, 80%, 90%, or 95% identity, or higher, to a lectin protein corresponding to accession no. XP_014512565 (SEQ ID NO:14). In another particular embodiment, the mung bean protein isolate has a reduced (relative to the plant source of the isolate) or non-detectable amount of a protein comprising an amino acid sequence having at least 50%, 60%, 70%, 80%, 90%, or 95% identity, or higher, to a protease corresponding to accession no. XP_014505181 (SEQ ID NO:15).

6.2.4 Reduced Environmental Contaminants

Advantageously, the methods for producing mung bean protein isolates provided herein produce food-safe compositions that have one or more reduced environmental contaminants (relative to the plant source of the isolate). In preferred embodiments, environmental contaminants are either free from the mung bean protein isolates, below the level of detection of 0.1 ppm, or present at levels that pose no toxicological significance. In some embodiments, the reduced environmental contaminant is a pesticide residue. In some embodiments, the pesticide residue is selected from the group consisting of: chlorinated pesticides, including alachlor, aldrin, alpha-BHC, alpha-chlordane, beta-BHC, DDD, DDE, DDT, delta-BHC, dieldrin, endosulfan I, endosulfan II, endosulfan sulfate, endrin, endrin aldehyde, gamma-BHC, gamma-chlordane, heptachlor, heptachlor epoxide, methoxyclor, and permethrin; and organophosphate pesticides including azinophos methyl, carbophenothion, chlorfenvinphos, chlorpyrifos methyl, diazinon, dichlorvos, dursban, dyfonate, ethion, fenitrothion, malathion, methidathion, methyl parathion, parathion, phosalone, and pirimiphos methyl.

In other embodiments, the reduced environmental contaminant is selected from residues of dioxins and polychlorinated biphenyls (PCBs). In yet other embodiments, the reduced environmental contaminant is a mycotoxin. In some embodiments, the mycotoxin is selected from the group consisting of aflatoxin B1, B2, G1, G2, and ochratoxin A.

6.3 Methods of Producing Mung Bean Protein Isolates

Also provided herein are methods for producing a mung bean protein isolate having high functionality for a broad range of food applications. In some embodiments, the methods for producing the isolate comprise one or more steps selected from:

(a) Extracting one or more mung bean proteins from a mung bean protein source in an aqueous solution. In some embodiments, the extraction is performed at a pH between about 6.5-10.0.

(b) Purifying protein from the extract using at least one of two methods:

(i) precipitating protein from the extract at a pH near the isoelectric point of a globulin-rich fraction, for example a pH between about 5.0-6.0; and/or (ii) fractionating and concentrating protein from the extract using filtration such as microfiltration, ultrafiltration or ion-exchange chromatography.

(c) Recovering purified protein isolate.

In preferred embodiments, the methods provided herein produce mung bean protein isolates comprising one or more of the following features: a protein content of at least 60% by weight; a globulin-type protein content of at least 50% by weight of the protein content; a reduced oxidative enzyme activity relative to an otherwise unmodified source of the mung bean protein; and one or more modulated organoleptic properties that differ from the otherwise unmodified source of the mung bean protein.

In preferred embodiments, the mung bean protein isolate is produced using a series of mechanical processes, with the only chemicals used being pH adjusting agents, such as sodium hydroxide and citric acid, and ethylenediaminetetraacetic acid (EDTA) to prevent lipid oxidation activities that may affect the flavor of the isolate.

6.3.1 Dehulling and Milling

Although the mung bean protein isolates provided herein may be prepared from any suitable source of mung bean protein, where the starting material is whole plant material such as whole mung bean, a first step of the methods provided herein comprises dehulling the raw source material. In some such embodiments, raw mung beans may be de-hulled in one or more steps of pitting, soaking, and drying to remove the seed coat (husk) and pericarp (bran). The de-hulled mung beans are then milled to produce flour with a well-defined particle distribution size. In some embodiments, the particle distribution size is less than 1000, 900, 800, 700, 600, 500, 400, 300, 200 or 100 μm. In a particular embodiment, the particle distribution size is less than 300 μm to increase the rate and yield of protein during the extraction step. The types of mills employed may include one or a combination of a hammer, pin, knife, burr, and air classifying mills.

When feasible, air classification of the resultant flour may be deemed necessary to expedite the protein extraction process and enhance efficiency of the totality of the process. The method employed is to ensure the mung beans are milled to a particle size that is typically less than 45 μm, utilizing a fine-grinding mill, such as an air classifying mill. The resultant flour is then passed through an air classifier, which separates the flour into both a coarse and fine fraction. The act of passing the flour through the air classifier is intended to concentrate the majority of the available protein in the flour into a smaller portion of the total mass of the flour. Typical fine fraction (high-protein) yields may be 10-50%. The fine fraction tends to be of a particle size of less than 20 μm; however, this may be influenced by growing season and region of the original mung bean. The high-protein fraction typically contains 150-220% of the protein in the original sample. The resultant starch-rich byproduct stream also becomes value added, and of viable, saleable interest as well.

6.3.2 Extraction

In preferred embodiments, the methods comprise an extraction step. In some embodiments of the extraction step, an intermediate starting material, for example, mung bean flour, is mixed with aqueous solution to form a slurry. In some embodiments, the aqueous solution is water, for example soft water. The aqueous extraction may include creating an aqueous solution comprising one part of the source of the plant protein (e.g., flour) to about, for example, 3 to 15 parts aqueous extraction solution. In other embodiments, 5 to 10 volumes of aqueous extraction solution is used per one part of the source of the plant protein. Additional useful ratios of aqueous extraction solution to flour include 1:1, 2:1, 4:1, 6:1, 7:1, 8:1, 9:1, 10:1, 11:1, 12:1, 13:1, 14:1, 15:1 or alternatively 1:2, 1:3, 1:4, 1:5, 1:6, 1:7, 1:8, 1:9, 1:10, 1:11, 1:12, 1:13, 1:14, 1:15.

Preferably, the aqueous extraction is performed at a desired temperature, for example, about 2-10° C. in a chilled mix tank to form the slurry. In some embodiments, the mixing is performed under moderate to high shear. In some embodiments, a food-grade de-foaming agent (e.g., KFO 402 Polyglycol) is added to the slurry to reduce foaming during the mixing process. In other embodiments, a de-foaming agent is not utilized during extraction.

The pH of the slurry may be adjusted with a food-grade 50% sodium hydroxide solution to reach the desired extraction pH for solubilization of the target protein into the aqueous solution. In some embodiments, the extraction is performed at a pH between about 6.5-10.0. In other embodiments, the extraction is performed at neutral or near neutral pH. In some embodiments, the extraction is performed at a pH of about pH 5.5-pH 9, pH 6.0-pH 8.5 or more preferably pH 6.5-pH 8. In a particular embodiment, the extraction is performed at a pH of about 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In a particular embodiment, the extraction is performed at a pH of about 7.0.

Following extraction, the solubilized protein extract is separated from the slurry, for example, in a solid/liquid separation unit, consisting of a decanter and a disc-stack centrifuge. The extract is centrifuged at a low temperature, preferably between 3-10° C. The extract is collected and the pellet is resuspended, preferably in 3:1 water-to-flour. The pH is adjusted again and centrifuged. Both extracts are combined and filtered through using a Nylon mesh.

6.3.3 Charcoal Treatment

Optionally, the protein extract may be subjected to a carbon adsorption step to remove non-protein, off-flavor components, and additional fibrous solids from the protein extraction. This carbon adsorption step leads to a clarified protein extract. In one embodiment of a carbon adsorption step, the protein extract is then sent through a food-grade granular charcoal-filled annular basket column (<5% w/w charcoal-to-protein extract ratio) at 4 to 8° C. An illustrative carbon adsorption protocol is also provided in Example 1 below.

6.3.4 Acid Precipitation

In some embodiments, following extraction and optionally carbon adsorption, the clarified protein extract is acidified with a food-safe acidic solution to reach its isoelectric point under chilled conditions (e.g., 2 to 8° C.). Under this condition, the target protein precipitates and becomes separable from the aqueous solution. In some embodiments, the pH of the aqueous solution is adjusted to approximately the isoelectric point of at least one of the one or more globulin-type proteins in the protein-rich fraction, for example, mung bean 8S/beta conglycinin. In some embodiments, the pH is adjusted from an aqueous solution comprising the protein extract which has an initial pH of about 6.5-10.0 prior to the adjusting step. In some embodiments, the pH is adjusted to about 5.0 to 6.5. In some embodiments, the pH is adjusted to about 5.2-6.5, 5.3 to 6.5, 5.4 to 6.5, 5.5 to 6.5, or 5.6 to 6.5. In some embodiments, the pH is adjusted to about 5.2-6.0, 5.3 to 6.0, 5.4 to 6.0, 5.5 to 6.0, or 5.6 to 6.0. In certain embodiments, the pH is adjusted to about pH 5.4-5.8. In some embodiments, the pH is adjusted to about 5.2, 5.3, 5.4, 5.5, 5.6, 5.7, 5.8, 5.9, 6.0, 6.1, or 6.2.

In a preferred embodiment of the methods provided herein, the pH is adjusted, and precipitation of desired mung bean proteins is achieved, to a range of about pH 5.6 to pH 6.0. Without being bound by theory, it is believed that isoelectric precipitation at a range of about pH 5.6 to pH 6.0 yields a superior mung bean protein isolate, with respect to one or more qualities selected from protein yield, protein purity, reduced retention of small molecular weight non-protein species (including mono and disaccharides), reduced retention of oils and lipids, structure building properties such as high gel strength and gel elasticity, superior sensory properties, and selective enrichment of highly functional 8s globulin/beta conglycinin proteins. These unexpectedly superior features of mung bean protein isolates prepared by the methods provided herein are described, for example, in Examples 6 and 8. As demonstrated by the results described in Example 6, below, mung bean protein isolates that underwent acid precipitations at a pH range of about pH 5.6 to pH 6.0 demonstrated superior qualities with respect to protein recovery (in comparison to recovery of small molecules), gelation onset temperature, gel strength, gel elasticity, and sensory properties, in comparison to mung bean protein isolates that underwent acid precipitations at a pH below pH 5.6. Mung bean protein isolates that underwent acid precipitations at a pH range of about pH 5.2 to pH 5.8 also demonstrated substantially lower lipid retention when compared to mung bean protein isolates that underwent acid precipitations outside this range.

Suitable food-grade acids to induce protein precipitation include but are not limited to malic, lactic, hydrochloric acid, and citric acid. In a particular embodiment, the precipitation is performed with a 20% food-grade citric acid solution. In other embodiments, the precipitation is performed with a 40% food-grade citric acid solution.

In some embodiments, in addition to the pH adjustment, EDTA, for example, 2 mM of food-grade EDTA, may be added to the precipitation solution to inhibit lipid oxidation that may produce off-flavor compounds.

In alternative embodiments, the precipitation step comprises isoelectric precipitation at pH 5.6 combined with cryo-precipitation (at 1-4° C.), wherein the pH is adjusted to 5.4-5.8.

In another alternative embodiment, low ionic strength precipitation at high flow rates is combined with cryo-precipitation (at 1-4° C.). In some such embodiments, rapid dilution of the filtrate is performed in cold (1-4° C.) 0.3% NaCl at a ratio of 1 volume of supernatant to 3 volumes of cold 0.3% NaCl. Additional resuspension and homogenization steps ensure production of desired protein isolates.

In some embodiments, the precipitated protein slurry is then removed from the pH-adjusted aqueous solution and sent to a solid/liquid separation unit (for example, a one disc-stack centrifuge). In some embodiments of the methods, the separation occurs with the addition of 0.3% (w/w) food-grade sodium chloride, and a protein curd is recovered in the heavy phase. In preferred embodiments the protein curd is washed with 4 volumes of soft water under chilled conditions (2 to 8° C.), removing final residual impurities such as fibrous solids, salts, and carbohydrates.

6.3.5 Filtration

In some embodiments of the methods, filtration is used as an alternative, or an addition to, acid precipitation. Without being bound by theory, it is believed that while acid precipitation of the protein aids to remove small molecules, alternative methods such as ultra-filtration (UF) may be employed to avoid precipitation/protein aggregation events. Thus, in some embodiments, purifying the protein-rich fraction to obtain the mung bean protein isolate comprises performing a filtration, microfiltration or ultrafiltration procedure utilizing at least one selective membrane. An illustrative protocol is provided in Example 34 below.

6.3.6 Pasteurization

In some embodiments, the washed protein curd solution resulting from acid precipitation and separation is pasteurized in a high temperature/short time pasteurization step to kill any pathogenic bacteria that may be present in the solution. In a particular embodiment, pasteurization is performed at 74° C. for 20 to 23 seconds. In particular embodiments where a dry isolate is desired, the pasteurized solution is passed through a spray dryer to remove any residual water content. The typical spray drying conditions include an inlet temperature of 170° C. and an outlet temperature of 70° C. The final dried protein isolate powder typically has less than 5% moisture content. In some embodiments of the methods described herein, the pasteurization is omitted, to maintain broader functionality of the protein isolate.

6.3.7 Particular Embodiments of the Isolation Methods

An exemplary embodiment of the methods for producing a mung bean protein isolate provided herein is as follows:

1) Extraction with soft water at pH >6.5 in one or more stages. Extraction involves contacting mung bean flour with the aqueous solution in a ratio of 1:3-1:15 (flour:water) under moderate-to-high shear followed by solid-liquid separation step;

2) Optional treatment with activated carbon;

3) Isoelectric precipitation (pH 5.6 to pH 6.0) combined with cryo-precipitation method (at 1-4° C.) OR low ionic strength precipitation at very high flow rates combined with cryo-precipitation method (at 1-4° C.);

4) Followed by solid-liquid separation step.

Typically, the separation step includes washing with low concentration NaCl solution, 0.1% to 0.9% NaCl, preferably 0.3% to 0.5% NaCl.

As demonstrated in the Examples below, the methods provided herein increased the concentration of protein, and significantly reduced beany taste and flavor as well as the concentration of Maillard reactants in the resulting mung bean protein isolates.

6.3.8 Order of Steps and Additional Steps

It is to be understood that the steps of the method described above may be performed in alternative orders. For example, in some embodiments, subjecting the source of the plant protein to the fractionation process occurs before reducing the at least one impurity and before purifying the protein-rich fraction to obtain the purified protein isolate. In such embodiments, reducing the at least one impurity may occur either before or after purifying the protein-rich fraction to obtain the purified protein isolate. In some embodiments, reducing an impurity occurs before subjecting the source of the plant protein to the fractionation process and before purifying the protein-rich fraction to obtain the purified protein isolate, and subjecting the source of the plant protein to the fractionation process occurs before purifying the protein-rich fraction to obtain the purified protein isolate.

In some embodiments, the process includes additional steps, including one or more selected from: recovering the purified protein isolate (e.g., using centrifugation), washing the purified protein isolate, making a paste using the purified protein isolate, or making a powder using the purified protein isolate. In some embodiments, the purified protein isolate is rehydrated (e.g., to about 80% moisture content), and the pH of the rehydrated purified protein isolate is adjusted to a pH of about 6.0.

In other aspects, the compositions and methods provided herein reduce or remove a fraction comprising carbohydrate (e.g., starch) or a carbohydrate-rich protein isolate, post extraction, and provides opportunities to utilize these streams as product streams for multiple food applications including noodles and multiple bakery applications. Accordingly, also provided herein is a mung bean-derived carbo-

6.4 Scrambled Egg Analog Using Transglutaminase

In another aspect, provided herein is a plant-based scrambled egg analog comprising a mung bean protein isolate produced by the methods described herein, wherein the mung bean protein has been contacted with transglutaminase to provide advantageous textural, functional and organoleptic properties.

Food processing methods employing transglutaminases have been described in, for example, Japanese Patent 59059151, which discloses treating an emulsion containing proteins, oils or fats, and water with transglutaminase to produce gelatinous, crosslinked gel. Numerous patents disclose use of transglutaminase with milk or cheese such as U.S. Pat. No. 6,093,424 and other references disclose transglutaminase with pea protein isolates, for example, Chinese Patent 101703147A.

Even in view of these efforts, the need still exists for methods and compositions to produce an edible emulsion such as an egg substitute or a scrambled egg analog.

Thus, in some embodiments of the methods and compositions provided herein, transglutaminase is added to plant-based egg mimetic emulsions comprising mung bean protein isolate to achieve firmer and smoother gel textures upon heating of the emulsions.

In some embodiments, the transglutaminase is microencapsulated when utilized in the plant-based egg analogs provided herein. Microencapsulation of transglutaminase enzyme in plant-based egg mimetic emulsions maintains a stable emulsion by preventing contact of the protein substrate with the transglutaminase enzyme. Cross-linking reaction is initiated upon heating to melt the microencapsulating composition. Egg mimetic emulsions which include transglutaminase are inherently unstable in that the cross-linking reaction commences upon addition of the transglutaminase enzyme to the emulsion.

In addition to the preparation of plant-based egg analogs from mung bean protein isolates, this approach can be applied to other pulse relatives of the legume family which show similar functionality.

One advantage of transglutaminase is enhancing shelf-stable refrigerated or room temperature egg-mimetic emulsions which can be used to produce high-quality prepared food products exhibiting many of the characteristics of cooked or scrambled eggs or baked products, e.g. cakes and cookies, which normally contain eggs. Additional advantages include producing protein-rich ingredients with variable molecular weight and size creating a range of textures in finished food products. Accordingly, in various aspects, transglutaminase aids in functionality and texture of the final products.

In certain aspects of the invention, the method for producing egg substitute composition comprises contacting a legume protein with an amount of transglutaminase, preferably between 0.0001% to 0.1% to produce desired plant protein isolates. In some preferred embodiments, the method provides an amount of transglutaminase between 0.001% and 0.05%. In more preferred embodiments, the method provides an amount of transglutaminase between 0.001% and 0.0125%. In other embodiments, protein isolates produced outside of the preferred ranges produced scramble analog that were thicker or not readily homogenized into a formulation. Increased amount of transglutaminase to the protein does not appear to precipitate at pH 5.6 when the protein extract is treated with transglutaminase. Accordingly, the additional step of contacting the protein with the preferred amount of transglutaminase produced a desirable scramble analog.

Accordingly, in various aspects, provided herein is a mung-bean derived scramble analog comprising a protein isolate described herein, wherein the scramble analog comprises at least one or more of the following components: water, disodium phosphate and oil. In some embodiments, the scramble analog further comprises NaCl. In some embodiments, the scramble analog has been contacted with transglutaminase. In a particular embodiment, the scramble analog is comprise of the following formulation: Protein Solids: 11.3 g, Water: 81.79 g, Disodium phosphate: 0.4 g, Oil: 6.2 g, NaCl: 0.31 g (based on total weight of 100 g) wherein the protein solids are contacted with between 0.001% and 0.0125% of transglutaminase.

In additional embodiments, the methods and compositions lack lipoxygenase.

Accordingly, the present invention provides compositions for egg replacement, said composition comprising a plant-based protein isolate modified by transglutaminase; wherein said composition is essentially egg-free and, wherein said composition comprises one or more functional properties of a natural egg. Preferably, composition comprises emulsifying properties of a natural egg. More preferably, the composition provides plant-based protein isolate modified by 0.0001% to 0.0125% transglutaminase and exhibits reduced or even significantly reduced lipoxygenase activity or other enzymes which can oxidize lipids, as expressed on a volumetric basis relative to the whole plant extract. More preferably, the composition is essentially free of lipoxygenase or enzymes that can oxidize lipids. In further embodiments, the plant-based protein isolate is stably cross-linked.

In some aspects, the transglutaminase reduces or does not cross-link to lipoxygenase or enzymes that can oxidize lipids. Additional embodiments include encapsulating transglutaminase in microcapsules. The composition comprising the plant-based protein isolate is suitable for refrigeration or storage at room temperature and is shelf stable in emulsion. In further aspects, the transglutaminase is free, cross-linked and/or immobilized.

Additional aspects of the invention include a purified protein isolate comprising: a transglutaminase modified plant protein content of at least 60% by weight; a globulin-type protein content of at least 50% by weight of the plant protein; a reduced oxidative enzyme activity relative to an otherwise unmodified source of the plant protein; and one or more modulated organoleptic properties that differ from the otherwise unmodified source of the plant protein. Preferred embodiments include purified protein isolate modified by 0.0001% to 0.0125% transglutaminase.

In accordance with preferred methods of the invention, provided are methods for producing a purified protein isolate comprising: a. extracting one or more plant protein from a source in an aqueous solution at a pH between about 6.5-10.0; b. precipitating the plant protein at pH near its isoelectric point of a globulin-rich fraction or a pH between about 5.0-6.0; or fractionating and concentrating the plant protein using filtration, microfiltration or ultrafiltration or ion-exchange chromatography; c. recovering the purified protein isolate comprising a plant protein content of at least 60% by weight; a globulin-type protein content of at least 50% by weight of the plant protein; a reduced oxidative enzyme activity relative to an otherwise unmodified source of the plant protein; and one or more modulated organoleptic properties that differ from the otherwise unmodified source of the plant protein; and d. modifying the plant protein with transglutaminase in the extraction step a. or the recovery step b.

Preferred embodiments of the method to produce a purified protein isolate include step d. of modifying the plant protein with transglutaminase in the extraction step a. or the recovery step b. comprises 0.0001% to 0.0125% transglutaminase. Further embodiments provide compositions comprising purified protein isolate that is stably cross-linked and is essentially free of lipoxygenase or enzymes that can oxidize lipids. Additional embodiments include encapsulating and/or immobilizing the transglutaminase.

In accordance with preferred compositions of the invention, provided is an egg substitute composition comprising: plant protein solids, water, disodium phosphate, oil and salts such as NaCl, wherein said plant protein solid comprises a plant-based protein isolate modified by transglutaminase. Preferably, the plant-based protein isolate of the egg substitute composition is modified with 0.0001% to 0.0125% transglutaminase. The transglutaminase reduces or does not cross-link to lipoxygenase or enzymes that can oxidize lipids. In such embodiments, the egg substitute composition exhibits reduced or even significantly reduced lipoxygenase activity or other enzymes which can oxidize lipids. The transglutaminase cross-links proteins other than lipoxygenase and leaves the lipoxygenase free allowing it to stay in the supernatant in the isoelectric precipitation and centrifugation steps, away from the cross-linked protein. More preferably, the egg substitute composition is essentially free of lipoxygenase or enzymes that can oxidize lipids. Additional embodiments include contacting the plant-based protein isolate with transglutaminase that are encapsulated in microcapsules. The resulting egg substitute composition is suitable for refrigeration or storage at room temperature and is shelf stable in emulsion. Upon heating the emulsion, the egg substitute composition forms a gel, e.g., a scrambled egg analog. The egg substitute composition of the invention exhibits one or more organoleptic properties similar to a natural egg. The composition has modulated organoleptic properties such as increased or decreased fluffiness, airiness and mealy texture.

6.4.1 Cross-Linking to Prepare Egg-Like Textures

Figure 1:
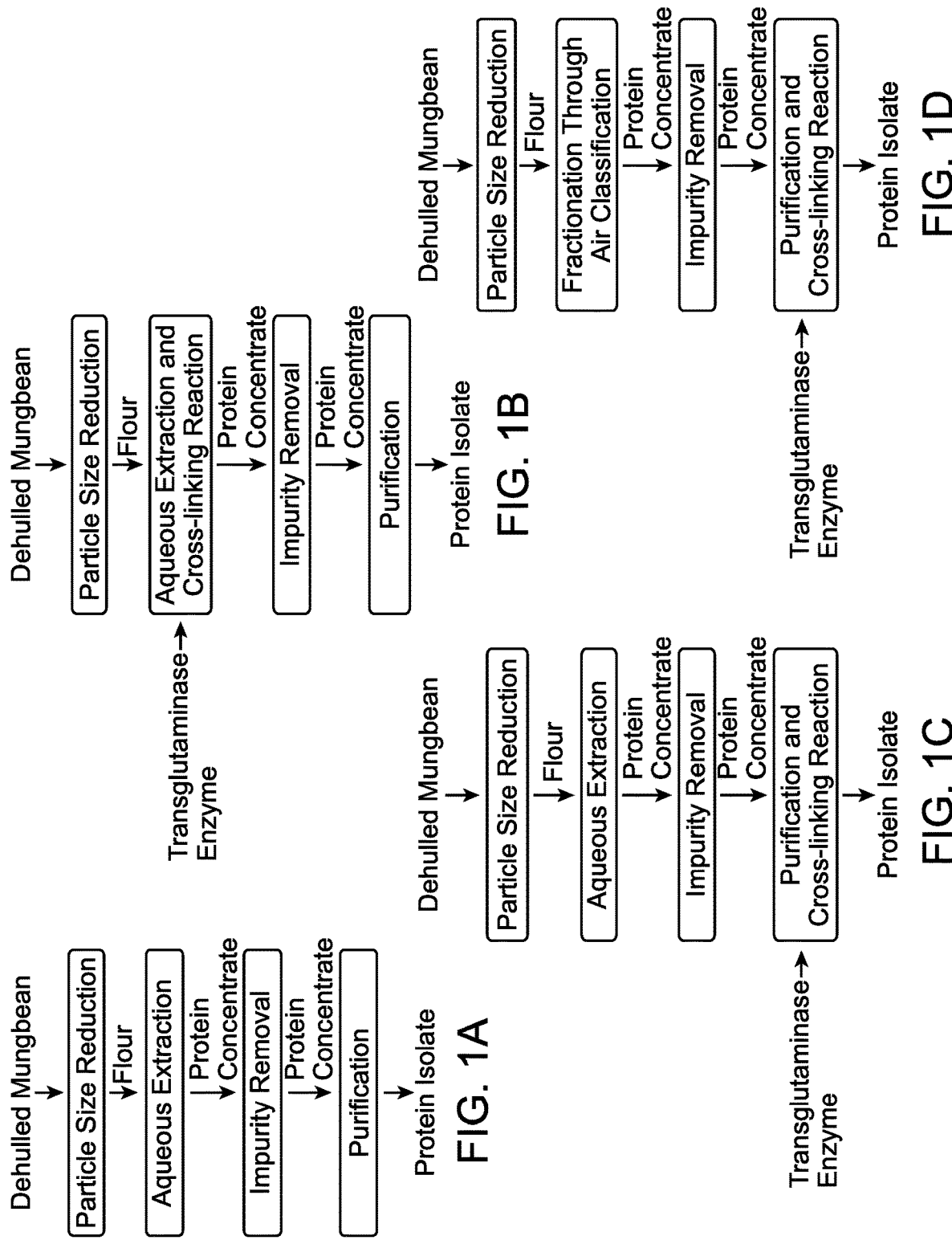
FIG. 1A depicts a general process diagram for mung bean protein isolation in accordance with the methods described herein.
FIG. 1B depicts a general process diagram for protein isolation using transglutaminase in the aqueous extraction step.
FIG. 1C depicts a general process diagram for protein isolation using transglutaminase in the purification step.
FIG. 1D depicts a general process diagram for dry-fractionation protein isolation using transglutaminase in the purification step.

Mung bean protein isolates suitable for producing egg-like textures can be prepared by adding a cross-linking step to the methods of preparing mung bean isolates provided herein. In one example, the cross-linking step can be added to the extraction step of the procedure, as depicted in FIG. 1B. For instance, a homogenous aqueous solution combining one part of mungbean flour with three to fifteen parts of water is prepared and pH adjusted to 6.5 to 8 with a suitable inorganic or organic acid or base. This mixture is centrifuged and the protein rich supernatant is decanted from the carbohydrate rich heavy phase. Transglutaminase powder is added to the protein rich solution at a concentration of 0.001 to 0.5% (w/w), heated to roughly 50° C. (optimum reaction temperature for transglutaminase) and incubated for 15 to 90 minutes. The reaction mixture is quickly heated to >70° C. for 1 to 5 minutes to inactivate the transglutaminase enzyme. The pH of the solution is adjusted to or near the isoelectric point of the globulin-rich component of the protein mixture (pH of about 5.4-5.8), rapidly cooled to less than 50° C. and centrifuged at >3,000×g. The supernatant is decanted, leaving a protein-rich powder, white to light tan in appearance, which can then further processed by commonly-available methods into a dried powder. The protein-rich powder can be incorporated into plant-based egg-mimetic emulsions which produce an egg-like texture upon heating, either in an oven, pan, skillet or hot water bath.

In another example, a homogenous aqueous solution combining one part of mungbean flour with three to fifteen parts of water is prepared and pH adjusted to 6.5 to 8 with a suitable inorganic or organic acid or base. The solution is centrifuged at >3000×g and the protein rich supernatant is separated from the carbohydrate rich heavy phase. Transglutaminase powder is added to the solution at a concentration of 0.001 to 0.5% (w/w), heated to roughly 50° C. (optimum reaction temperature for transglutaminase) and incubated for 15 to 90 minutes. After incubation, hydrogen peroxide solution is added to the solution to a final concentration of 0.01 to 0.1% (w/w). This oxidizes the cysteine residue on the transglutaminase, arresting activity. The solution is then brought to the PI point of the protein or protein fraction of interest (about 5.4-5.8 pH). The solution is then chilled and centrifuged. The supernatant is then decanted leaving a globulin rich heavy fraction. The globulin-rich fraction is diluted with water to a solids concentration of roughly 5-20% solids (w/w) and then spray dried. This is then mixed with water for spray drying. Sodium hydroxide is a process aid in this process. It has the added benefit of being an anti-microbial agent as well as a bleaching agent. After spray drying, all remnants of the oxidizing agent should have fully decayed.

In another example, mung bean extract is contacted with transglutaminase, but the process does not include a step to stop transglutaminase activity. A homogenous aqueous solution combining one part of mung bean flour with three to fifteen parts of water is prepared and pH adjusted to 6.5 to 8 with a suitable inorganic or organic acid or base. This is centrifuged at >3000×g and the protein rich supernatant is separated from the carbohydrate rich heavy phase. Transglutaminase powder is added to the solution at a concentration of 0.001 to 0.5% (w/w). The transglutaminase concentration would be chosen to create the desired texture for the finished product. The solution is heated to roughly 50° C. (optimum reaction temperature for transglutaminase) and incubated for 15 to 90 minutes. The solution is then brought to the PI point of the protein or protein fraction of interest (about 5.4-5.8 pH). The solution is then chilled and centrifuged. The supernatant is then decanted leaving a globulin rich heavy fraction. The resulting heavy fraction is quickly heated to >70° C. for 1 to 5 minutes to inactivate the transglutaminase enzyme. The heavy fraction is mixed with water and spray dried.

Mung bean protein isolates suitable for producing egg-like textures can also be prepared by performing cross-linking after acid precipitation of the protein, as depicted in FIG. 1C. In one example, a homogenous aqueous solution combining one part of mungbean flour with three to fifteen parts of water is prepared and pH adjusted to 6.5 to 8 with a suitable inorganic or organic acid or base. The solution is then centrifuged at >3,000×g. The protein-rich supernatant is decanted leaving a carbohydrate rich heavy phase. The pH of the protein rich solution is adjusted to or near the isoelectric point of the globulin-rich component of the protein mixture (pH of about 5.4-5.8), resulting in the precipitation of the globulin-rich protein. The solution is centrifuged at >3,000×g. The supernatant is decanted, leaving a globulin-rich protein fraction. This globulin-rich protein fraction is re-diluted in water to achieve a protein concentration of 5 to 25%. Transglutaminase powder is added to the solution at a concentration of 0.001 to 0.5% (w/w), heated to roughly 50° C. (optimum reaction temperature for transglutaminase) and incubated for 15 to 90 minutes. The reaction mixture is quickly heated to >70 C for 1 to 5 minutes to inactivate the transglutaminase enzyme. The mixture is then rapidly cooled to less than 50 C and centrifuged at >3,000×g. The supernatant is decanted, leaving a protein-rich powder, white to light tan in appearance, which can then further processed by commonly-available methods into a dried powder. The protein-rich powder can be incorporated into plant-based egg-mimetic emulsions which produce an egg-like texture upon heating, either in an oven, pan, skillet or hot water bath.

In another embodiment in which cross-linking is applied after acid precipitation of the protein, dry fractionation is used in place of aqueous extraction to produce the concentrate, as depicted in FIG. 1D. De-hulled mung beans are passed through successive mills, e.g. roller mill, followed by pin mill, to develop a flour with very fine particle size. The flour is then passed through a high-speed cyclone to separate larger from smaller particles. The protein-rich particles, roughly 55-60% protein, are then diluted in water to achieve a solution of roughly 5-25% solids. The pH of the solution is adjusted to or near the isoelectric point of the globulin-rich component of the protein mixture (pH of about 5.4-5.8), resulting in the precipitation of the globulin-rich protein. The solution is centrifuged at >3,000×g. The supernatant is decanted, leaving a globulin-rich protein fraction. This globulin-rich protein fraction is re-diluted in water to achieve a protein concentration of 5 to 25%. Transglutaminase powder is added to the solution at a concentration of 0.001 to 0.5% (w/w), heated to roughly 50° C. (optimum reaction temperature for transglutaminase) and incubated for 15 to 90 minutes. The reaction mixture is quickly heated to >70° C. for 1 to 5 minutes to inactivate the transglutaminase enzyme. The mixture is then rapidly cooled to less than 50° C. and centrifuged at >3,000×g. The supernatant is decanted, leaving a protein-rich powder, white to light tan in appearance, which can then further processed by commonly-available methods into a dried powder. The protein-rich powder can be incorporated into plant-based egg-mimetic emulsions which produce an egg-like texture upon heating, either in an oven, pan, skillet or hot water bath.

6.4.2 Cross-Linking with Immobilized Transglutaminase

As an alternative to using bulk, single-use transglutaminase enzyme, one may treat the process streams using transglutaminase enzyme immobilized on inert porous beads or polymer sheets, which may be used in either flat or spiral-wound configurations in a reactor. Typical immobilized enzyme supports for beads include silicon dioxide (perlite) or calcium alginate. The immobilized transglutaminase is prepared by contacting an aqueous solution of transglutaminase with the bead material and a cross-linking agent, such as glutaraldehyde which fixes the enzyme to the solid substrate. The enzyme-containing support is then dried and conditioned prior to use. The advantages of immobilized enzyme reactors include: 1) improved control of the enzymatic reaction exposure and temperature conditions leading to a more uniform outcome from batch-to-batch; and 2) improved economics enabled by reuse of the transglutaminase enzyme. The solid substrate reduces the potential and rate of denaturation of the transglutaminase enzyme.

6.4.3 Cross-Linking with Microencapsulated Transglutaminase

In some embodiments of the methods provided herein, a microencapsulated transglutaminase enzyme is used for preparing a plant-based liquid egg-like emulsion. For example, an emulsion containing a fat, water and emulsifier is prepared with the fat having a melting point between 50° C. and 80° C. Representative fats include stearic acid, palm and coconut shortening. Transglutaminase enzyme is then dispersed in the emulsion using a high shear mixer or homogenizer to achieve a flowable solution of rough 5-20% solids. The emulsion is then spray dried under typical conditions (150-175° C.), with short residence time. The transglutaminase enzyme-containing spray dried powder can then be incorporate into plant-based egg-mimetic emulsions as described herein.

6.5 Mung Bean Isolates with Modified Organoleptic Properties

Also provided herein is a process to produce an edible mung bean protein isolate from a source of a mung bean protein, the process comprising: subjecting the source of the mung bean protein to a fractionation process to obtain a protein-rich fraction, wherein at least 50% by weight of the protein-rich fraction comprises or consists of one or more globulin-type proteins; reducing at least one impurity, the at least one impurity associated with an off-odor or an off-flavor in the edible mung bean protein isolate; and purifying the protein-rich fraction to obtain the edible mung bean protein isolate. In some embodiments, at least 60% by weight of the edible mung bean protein isolate is plant protein. In some embodiments, an oxidative enzymatic activity of the edible protein isolate is lower than a corresponding oxidative enzymatic activity of the source of the plant protein. In some embodiments, an organoleptic property of the edible mung bean protein isolate differs from a corresponding organoleptic property of the source of the mung bean protein.

In certain aspects, the methods and compositions provide producing purified protein isolates having modulated organoleptic properties of one or more of the following characteristics: astringent, beany, bitter, burnt, buttery, nutty, sweet, sour, fruity, floral, woody, earthy, beany, spicy, metallic, sweet, musty, grassy, green, oily, vinegary, neutral and bland flavor or aromas. Preferably, the purified protein isolates exhibit modulated organoleptic properties such as a reduction or absence in one or more of the following: astringent, beany, bitter, burnt, buttery, nutty, sweet, sour, fruity, floral, woody, earthy, beany, spicy, metallic, sweet, musty, grassy, green, oily, vinegary neutral and bland flavor or aromas.

6.5.1 Methods for Modifying Organoleptic Properties

Preferably, the methods provided herein reduce or remove at least one impurity that may impart or is associated with an off-flavor or off-odor in the purified protein isolate. The one or more impurity may be a volatile or nonvolatile compound and may comprise, for example, lipoxygenase (EC 1.13.11.-), which is known to catalyze oxidation of fatty acids. As other examples, the at least one impurity may comprise a phenol, an alcohol, an aldehyde, a sulfide, a peroxide, or a terpene. Other biologically active proteins classified as albumins are also removed including lectins and protease inhibitors such as serine protease inhibitors and tryptic inhibitors.

In some embodiments, the at least one impurity may comprise one or more substrates for an oxidative enzymatic activity, for example one or more fatty acids. In some embodiments, the methods provided herein reduce or remove one or more fatty acids selected from: C14:0 (methyl myristate); C15:0 (methyl pentadecanoate); C16:0 (methyl palmitate; C16:1 methyl palmitoleate; C17:0 methyl heptadecanoate; C18:0 methyl stearate; C18:1 methyl oleate; C18:2 methyl linoleate; C18:3 methyl alpha linoleate; C20:0 methyl eicosanoate; and C22:0 methyl behenate. Without being bound by theory, it is believed that reducing or removing one or more fatty acids or other lipid substrates for oxidative enzymatic activity also reduces rancidity over time of the mung bean protein isolate. Further advantages may arise from increasing the ratio of protein to non-protein molecules in the isolate, enabling more consistent and homogenous performance and functionality in downstream food applications.

In some embodiments, reducing an impurity comprises reducing at least one enzyme that reacts with a lipid substrate. In such embodiments, reducing such impurity reduces at least one lipophilic off-flavor, lipophilic substrate, or a co-factor. In some embodiments, impurities are reduced by a solid absorption procedure using, for example, charcoal, a bentonite clay, or activated carbon.

In some embodiments, the purified mung bean protein isolate has a reduced oxidative enzymatic activity relative to the source of the mung bean protein. For example, the purified mung bean isolate can have about a 5%, 10%, 15%, 20%, or 25% reduction in oxidative enzymatic activity relative to the source of the mung bean protein. In some embodiments, the oxidative enzymatic activity is lipoxygenase activity. In some embodiments, the purified protein isolate has lower oxidation of lipids or residual lipids relative to the source of the plant protein due to reduced lipoxygenase activity.

In some embodiments, reduced lipoxygenase activity in the mung bean protein isolate is effected by contacting a mung bean protein extract or isolate with transglutaminase activity. Thus, also provided herein are mung bean protein isolates modified by transglutaminase, wherein the isolate exhibits reduced or even significantly reduced lipoxygenase activity (or other enzymes which can oxidize lipids) relative to the plant source of the isolate. For example, the mung bean protein isolates modified by transglutaminase can have at least about a 20%, 25%, 30%, 35%, 40%, 45%, 50%, 55%, 60%, 65%, 70%, or 75% reduction in lipoxygenase activity (or activity of an enzyme that can oxidize lipids) relative to the plant source of the isolate. In some embodiments, the amount of transglutaminase used to modify the mung bean protein isolates is between about 0.0001% to 0.0125%, as expressed on a volumetric basis to the amount of isolate or extract being modified.

In additional embodiments, reducing the at least one impurity comprises removing a fibrous solid, a salt, or a carbohydrate. Reducing such impurity comprises removing at least one compound that may impart or is associated with the off-flavor or off-odor. Such compounds may be removed, for example, using an activated charcoal, carbon, or clay. As another example, the at least one compound may be removed using a chelating agent (e.g., EDTA, citric acid, or a phosphate) to inhibit at least one enzyme that oxidizes a lipid or a residual lipid. In a particular example, EDTA may be used to bind co-factor for lipoxygenase, an enzyme that can oxidize residual lipid to compounds, e.g. hexanal, which are known to leave to off-flavors.

In some embodiments, separation of the protein from the residual source materials removes the undesirable organoleptic properties associated with proteins such as beany flavors or any of the unsuitable flavor profiles associated with compounds from Table 1, below.

The methods and compositions disclosed herein provide protein isolate characterized by its capacity to exhibit good organoleptic properties, for example by reducing undesired characteristics such as a "beany" aroma and taste. In preferred embodiments, components that are associated with off-flavors are removed or substantially reduced. Removal of undesired compounds may improve aroma, flavor or taste or a combination thereof. In some embodiments, methods for producing proteins isolates reduced in off-flavors involve one or more of the following methods:

1) isoelectric point (pH~5.6 to pH 6.0) precipitation to significantly reduce the level of lipoxygenase, which can oxidize any residual lipid to compounds, e.g. hexanal, which are known to leave to off-flavors;

2) use of a chelating agent, e.g. EDTA, to bind co-factor for lipoxygenase; and/or 3) use of immobilized activated charcoal after extraction to remove compounds which can contribute to off-flavors. In cases where lipid substrate is abundant, lipids may be collected in the supernatant and removed or reduced. The disclosed methods may provide improved functionality of a protein isolate through enrichment of a class of proteins and reduction of enzymes such as lipoxygenase, that catalyze oxidation primarily of unsaturated fatty acids or unsaturated fats. Accordingly, in some embodiments, methods for purifying a protein fraction or reducing a class of proteins to reduce off-flavors minimally affect the protein isolate composition's capacity to retain one or more desired functional properties.

Accordingly, in certain aspects, the methods and compositions disclosed herein modulate or improve the flavor profile of the protein isolate, which in turn modulates or improves the flavor profile of the food product comprising the protein isolate. In certain embodiments, the removal or reduction of certain non-protein fractions of the source of the plant protein, such as polysaccharides, especially those indigestible forms in legumes, may impart more desirable flavors. The removal or reduction of the non-protein fractions may result in the removal or reduction of undesirable small molecules, including cross-linked polyphenols, volatiles, and heavy metal ions. The disclosed methods and compositions may provide for the removal or reduction of target compounds including but not limited to cross-linked polyphenols, volatiles, heavy metal ions, p-coumaric acid (4-Hydroxycinnamic acid), ferulic acid (4-Hydroxy-3-methoxycinnamic acid) and 4-hydroxybenzoic acid (known polyphenols) in addition to various compounds that are attributed to undesired flavors or aroma. Accordingly, the methods and compositions may provide solubilized plant proteins characterized as having a neutral flavor and/or aroma. In yet other embodiments, the methods and compositions provide for modulation of flavors or aroma wherein a select compound is removed, reduced, or even incorporated.

Accordingly, one or more desired flavors or aroma may be removed, reduced, or added by modulating one or more small molecules that are attributed to certain flavors. One such method involves precipitation of protein to remove small molecules that are commonly associated with imparting undesirable flavors.

One way to characterize the aroma of a food product sample includes use of a GC SNFR Olfactory Port (PerkinElmer). Volatilized compounds from samples are injected into the GC column and the resulting compounds are separated and identified using mass spectrum. Table 1 provides an exemplary list of compounds and their effect on sensory properties. Additional compounds can be separated and identified to associate their sensory properties.

TABLE 1

| Compound Name | Sensory Properties |
|---|---|
| 1-heptanol | Green, solvent flavor |
| 1-Hexanol | Sharp, green, fruity |
| 1-pentanol | unpleasant aroma |
| 1-propene, 1-(methylthio) | herbicide |
| 11,4-pentadiene | hydrocarbon odor |
| 2-heptenal | natural nematocyte |
| 2-hexenal | leaf aldehyde |
| 2-Octenal, (E)- | nutty, cooked flour |
| 2-pentyl-furan | green, fruity |
| Benzaldehyde | almond |
| Benzyl Alcohol | floral |
| Butanedial | — |
| Diallyl disulphide | garlic-derived sulphur compound |
| Dodecanal | natural oil, citrus oil |
| nonanal | naturaloil/Culex attractant/perfume |
| Hstragole | natural oil: anise, tarragon, basil |
| Hexanal | etc. |
| Hydroperoxide, hexyl | fresh cut grass |
| Pentadecanal | — |
| pentanal | waxy |
| Sulfoxide, methyl phenethyl | valeraldehyde; flavoring |
| Tetradecanal | — |
| Trifluoroacetyl-a-terpineol | strong fatty oris odor |

Accordingly, in some embodiments, the method provides for the removal or reduction of one or more of these and/or other compounds. For example, as shown in Table 1, the presence of hexanal may result in a food product having an aroma resembling fresh cut grass. In some embodiments, such odor is removed or reduced. Similarly, the method provides for iterating, modifying or improving formulations by identifying certain compounds in the formulation, associating the one or more compounds to an olfactory sense and removing or reducing the compounds.

In some embodiments, the purified protein isolate has one or more organoleptic properties that differ from a corresponding organoleptic property of the source of the plant protein. Examples of organoleptic properties include, but are not limited to, astringent flavor or aroma, beany flavor or aroma, bitter flavor or aroma, burnt flavor or aroma, buttery flavor or aroma, nutty flavor or aroma, sweet flavor or aroma, sour flavor or aroma, fruity flavor or aroma, floral flavor or aroma, woody flavor or aroma, earthy flavor or aroma, beany flavor or aroma, spicy flavor or aroma, metallic flavor or aroma, sweet flavor or aroma, musty flavor or aroma, grassy flavor or aroma, green flavor or aroma, oily flavor or aroma, vinegary flavor or aroma, neutral flavor or aroma, or bland flavor or aroma. The source of the plant protein may have a flavor, an aroma, or a sensory impression (e.g., a beany flavor or smell) that makes the source of the plant protein undesirable or unsuitable for use in place of a reference food, such as, for example, an egg. Relative to the source of the plant protein, the purified protein isolate has a modified organoleptic property, and this modified organoleptic property may make the purified protein isolate more suitable for use in or as a substitute for the reference food. In other words, the purified protein isolate may have an organoleptic property that gives the purified protein isolate, or a composition incorporating the purified protein isolate, a flavor, aroma, or sensory impression that is similar or equivalent to the flavor, aroma, or sensory impression of the reference food. For example, the purified protein isolate may reduce or eliminate an organoleptic property of the source of the plant protein.

In some embodiments, an organoleptic property of the purified protein isolate may be similar or equivalent to the corresponding organoleptic property of an egg. In some embodiments, the purified protein isolate provides a flavor, an aroma, or a sensory impression that is similar or equivalent to the flavor, aroma, or sensory impression of a reference food product, such as, for example, an egg (liquid, scrambled, or in patty form), a cake (e.g., pound cake, yellow cake, or angel food cake), a cream cheese, a pasta, an emulsion, a confection, an ice cream, a custard, milk, a deli meat, chicken (e.g., chicken nuggets), or a coating.

6.6 Food Functionality of Mung Bean Protein Isolates

In certain aspects, the high purity mung bean protein isolates provided herein exhibit desirable functional characteristics such as emulsification, water binding, foaming and gelation properties as measured by standard methods in industry. In comparison to characteristics of an egg, such properties of purified protein isolates as measured are comparable to at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater. The methods provided herein produce high purity, preferably 50%, 60%, 70%, 80%, 90% or greater mung bean protein isolates that exhibit functional properties, e.g., emulsification and gelation consistent to a food product such as an egg. In preferred embodiments, the protein content is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater.

As demonstrated in the Examples below, a number of food applications were prepared incorporating purified mung bean protein isolates that exhibit one or more functional properties. The functional properties may include but are not limited to crumb density, structure/texture, elasticity/springiness, coagulation, binding, moisturizing, mouthfeel, leavening, aeration/foaming, creaminess, and emulsification of the food product such as an egg. Mouthfeel is a concept used in the testing and description of food products. Products made using exemplary protein isolates can be assessed for mouthfeel. In some embodiments products, e.g., baked goods, made using exemplary protein isolates have mouthfeel that is similar to products made with natural eggs. In some embodiments the mouthfeel of the products made using the exemplary protein isolates is superior to the mouthfeel of previously known or attempted egg substitutes, e.g., bananas, modified whey proteins, or Egg Beaters™.

Examples of properties which may be included in a measure of mouthfeel include: Cohesiveness: Degree to which the sample deforms before rupturing when biting with molars; Density: Compactness of cross section of the sample after biting completely through with the molars; Dryness: Degree to which the sample feels dry in the mouth; Fracturability: Force with which the sample crumbles, cracks or shatters. Fracturability encompasses crumbliness, crispiness, crunchiness and brittleness; Graininess: Degree to which a sample contains small grainy particles, may be seen as the opposite of smoothness; Gumminess: Energy required to disintegrate a semi-solid food to a state ready for swallowing; Hardness: Force required to deform the product to given distance, i.e., force to compress between molars, bite through with incisors, compress between tongue and palate; Heaviness: Weight of product perceived when first placed on tongue; Moisture absorption: Amount of saliva absorbed by product; Moisture release: Amount of wetness/juiciness released from sample; Mouthcoating: Type and degree of coating in the mouth after mastication (for example, fat/oil); Roughness: Degree of abrasiveness of product's surface perceived by the tongue; Slipperiness: Degree to which the product slides over the tongue; Smoothness: Absence of any particles, lumps, bumps, etc., in the product; Uniformity: Degree to which the sample is even throughout; homogeneity; Uniformity of Bite: Evenness of force through bite; Uniformity of Chew: Degree to which the chewing characteristics of the product are even throughout mastication; Viscosity: Force required to draw a liquid from a spoon over the tongue; and Wetness: Amount of moisture perceived on product's surface.

The purified protein isolate may also have one or more functional properties by itself or when incorporated into a composition. Such functional properties may include, but are not limited to, one or more of emulsification, water binding capacity, foaming, gelation, crumb density, structure forming, texture building, cohesion, adhesion, elasticity, springiness, solubility, viscosity, fat absorption, flavor binding, coagulation, leavening, aeration, creaminess, film forming property, sheen addition, shine addition, freeze stability, thaw stability, or color.

In some embodiments, at least one functional property of the purified protein isolate differs from the corresponding functional property of the source of the plant protein. In some embodiments, at least one functional property of the purified protein isolate is similar or equivalent to the corresponding functional property of a reference food product, such as, for example, an egg (liquid, scrambled, or in patty form), a cake (e.g., pound cake, yellow cake, or angel food cake), a cream cheese, a pasta, an emulsion, a confection, an ice cream, a custard, milk, a deli meat, chicken (e.g., chicken nuggets), or a coating.

In some embodiments, when the purified protein isolate is included in a food composition, the food composition has at least one functional property that is similar or equivalent to the corresponding functional property of a reference food product, such as, for example, an egg, liquid egg, scrambled egg, an egg patty, a cake (e.g., pound cake, yellow cake, or angel food cake), cream cheese, pasta, an emulsion, a confection, an ice cream, a custard, milk, a deli meat, chicken (e.g., chicken nuggets), or a coating.

In some embodiments, the purified protein isolate, either alone or when incorporated into a composition, is capable of forming a gel under heat or at room temperature.

6.6.1 Rheological Properties

Using a hybrid rheometer (TA Instruments Discovery HR-1) allows for measurements of viscoelastic behaviors of protein isolate preparations (e.g., gelation temperature, elasticity, viscosity) as functions of time and temperature. These types of physical measurements can correlate with product performance. In some embodiments, certain physical measurements of protein isolates and formulations containing protein isolates are used to predict optimal raw material sources (to the extent they demonstrate significant differences) and lead product development efforts.

As demonstrated in Example 6.3, mung bean protein isolates prepared from the isolation methods described herein that utilize a precipitation pH within a range of about 5.6 to 6.0 demonstrate superior structure building properties, including gelation temperature, gel strength and gel elasticity, without the addition of additional components such as alkali metal ions (e.g., NaCl, KCl), hydrocolloids, or other thickening or gelling agents. Accordingly, in another aspect, provided herein is a mung bean protein isolate having a gelation onset temperature below 90° C. In some embodiments, the gelation onset temperature of the mung bean protein isolate is below 89° C., 88° C., or 87° C. In another aspect, provided herein is a mung bean protein isolate having a gel strength of greater than 2% oscillation strain. In some embodiments, the gel strength of the mung bean protein isolate is greater than 3%, 4%, 5%, 6%, 7%, 8%, 9%, 10%, 11%, 12% oscillation strain. In another aspect, provided herein is a mung bean protein isolate having a gel elasticity of greater than 300 Pa. In some embodiments, the gel elasticity of the mung bean protein isolate is greater than 300, 500, 600, 700, 800, 900, 1000, 2000, 3000, 4000, 5000, 6000, 7000, 8000, or greater than 8000 Pa.

Also disclosed are the viscosities of egg and egg-free products formulated using mung bean protein isolates described herein over a wide range of experimental parameters, including Na2HPO4 concentration and moisture content. This method may be used to guide product development and quality control. FIG. 30 shows a comparison of viscosity vs. shear rate in (□) commercial liquid egg product; (◇) homogenized whole shelled eggs; and (Δ) liquid scramble formulated with gellan. The y axis, showing viscosity (Pa·s), is logarithmic due to the extreme range exhibited over the samples, which have viscosities as low as 0.03 Pa·s (egg) and as high as 0.27 Pa·s. 62% moisture, 0.5% Na2HPO4.

6.6.2 Moisture Content

Some embodiments provide purified protein isolates having a desired moisture content. In various embodiments, % moisture content is about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 80%, 85%, 90%, or even higher.

6.6.3 Particle Size

Pea protein isolates are commercially available in particle sizes ranging from 150 to 400 microns to fit a variety of applications. Smaller particles sizes are well-suited for beverages, nutrition bars and any application where a smooth mouth feel is desired. Larger particle sizes exhibit excellent water retention that reduce cooking loss, improves yield and provides a moist mouth feel. Medium-sized particle sizes are available for applications that require a bit of both attributes. Small, medium, and large-sized particle sizes have different applications and mouthfeel. Larger particle sizes are better suited for baking.

Mung bean protein concentrates are generally larger in particle size than other protein isolates. Still a fine powder, the larger particle size of protein concentrates makes them well-suited for water absorbing applications and for enhancing texture in baked goods and pastas. In certain embodiments, the purified protein isolate exhibits desired or excellent water retention that reduces cooking loss, improves yield and provides a moist mouthfeel.

In some embodiments, the particle size distribution is in a range of about 8.9-223.0 μm. In some embodiments, the particle size of the protein composition is less than or equal to 10 micrometers. More preferably, the particle size of the protein composition is less than or equal to 1 micrometer. In more preferred embodiments, the particle size of the protein compositions comprises less than or equal to 100 micrometers. In alternative embodiments, the particle size of the protein compositions is about 30 nm. In other embodiments, particle size of the protein compositions comprises 10-100 nm.

6.7 Food Applications of Mung Bean Isolates

In some embodiments, the mung bean protein isolate is used as a direct protein replacement of animal- or vegetablebased protein in a variety of conventional food and beverage products across multiple categories. In some embodiments, the use levels range from 3 to 90% w/w of the final product. Exemplary food categories and use levels in which the mung bean protein isolate provided herein finds use are summarized in Table 2. In some embodiments, the mung bean protein isolate is also used as a supplement to existing protein in food products.

TABLE 2

Exemplary Individual Proposed Food-Uses and Use Levels for Mung Bean Protein Isolate in Conventional Food and Beverage Products

| Food Category | Proposed Food-Uses | Exemplary Maximum Use Level of Mung Bean Protein Isolate (%) in Final Product |
| --- | --- | --- |
| Baked Goods and Baking Mixes | Cereal and granola bars | 10 |
| | Crackers | 5 |
| | Meal replacement/nutritional bars/energy bars | 30 |
| Beverages and Beverage Bases | Fermented beverages made from rice/barley/grains/legumes/tea | 8 |
| | Non-milk based instant protein powders | 90 (powder) |
| | Non-milk based nutritional beverages (RTD, and powdered types) including protein-enriched fruit smoothies | 20 (as consumed) |
| | Non-milk based weight control beverages, instant shakes, and protein drinks (RTD and powdered types) | 10 (as consumed) |
| Breakfast Cereals | Breakfast cereals (RTE) | 3 |
| Condiments and Relishes | Bean dips and spreads | 5 |
| | Seasoning sauces | 3 |
| Dairy Product Analogs | Non-dairy cheese | 5 |
| | Non-dairy cream cheese, spread, and dips | 5 |
| | Non-dairy cream or sour cream (liquid and powder) | 3 |
| | Non-dairy ice cream and frozen desserts | 3 |
| | Non-dairy milk | 3 |
| | Non-dairy coffee whiteners | 3 |
| | Non-dairy yogurt and non-dairy drinkable yogurts | 8 |
| | Whipped topping | 3 |
| Frozen Dairy Desserts and Mixes | Ice cream and other frozen dairy desserts | 3 |
| Fruit and Water Ices | Ice pops and sorbets | 3 |
| Gelatins, Puddings, and Fillings | Puddings and mousse | 3 |
| Grain Products and Pasta | Pasta | 4 |
| Milk Products | Milk-based instant protein powders | 90 (powder) |
| | Milk-based nutritional beverages (RTD and powdered types) | 5 (as consumed) |
| | Milk-based weight control beverages, instant milkshakes, protein drinks (RTD and powdered types), and milk-based smoothies | 3 (as consumed) |
| Plant Protein Products | Egg product analogs (meringue) | 5 |
| | Egg product analogs (quiche, frittata) | 8 |
| | Egg product analogs (scrambled eggs, omelet, hard boiled, liquid) | 20 |
| | Vegetarian food products and meat analogues | 20 |
| Snack Foods | Snack chips, popcorn, extruded snacks | 5 |

The purified mung bean protein isolates provided herein are suitable for various food applications and have been incorporated into, e.g., edible egg-free emulsion, egg analog, egg-free scrambled eggs, egg-free patty, egg-free pound cake, egg-free angel food cake, egg-free yellow cake, egg-free cream cheese, egg-free pasta dough, egg-free custard, egg-free ice cream, and dairy-free milk.

In various aspects, the compositions and methods incorporate one or more purified protein isolates in multiple food applications including liquid and patty scrambled egg substitute to a desired level of emulsification, water binding and gelation. In a preferred embodiment, a functional egg replacement product comprises purified protein isolate or extract (10-15%), and one or more of: oil (10%), hydrocolloid, preservative, and optionally flavors, water, lecithin, xanthan, sodium carbonate, black salt.

Accordingly, the methods and compositions enable ingredients to have desired functionalities from one or more purified protein isolates that are suitable as replacement ingredients in various food applications including but not limited to meat substitutes, egg substitutes, baked goods and fortified drinks.

In some embodiments, the purified protein isolate is incorporated in an egg substitute. In some such embodiments, the organoleptic property of the purified protein isolate (e.g., a flavor or an aroma) is similar or equivalent to a corresponding organoleptic property of an egg. The egg substitute may exhibit at least one functional property (e.g., emulsification, water binding capacity, foaming, gelation, crumb density, structure forming, texture building, cohesion, adhesion, elasticity, springiness, solubility, viscosity, fat absorption, flavor binding, coagulation, leavening, aeration, creaminess, film forming property, sheen addition, shine addition, freeze stability, thaw stability, or color) that is similar or equivalent to a corresponding functional property of an egg. In addition to the purified protein isolate, the egg substitute may include but are not limited to one or more of iota-carrageenan, gum arabic, konjac, xanthan gum, or gellan.

In some embodiments, the purified protein isolate is incorporated in an egg-free cake, such as a pound cake, a yellow cake, or an angel food cake. In some such embodiments, at least one organoleptic property (e.g., a flavor or an aroma) of the egg-free cake is similar or equivalent to a corresponding organoleptic property of a cake containing eggs. The egg-free cake may exhibit at least one functional property similar or equivalent to a corresponding functional property of a cake containing eggs. The at least one function property may be, for example, one or more of emulsification, water binding capacity, foaming, gelation, crumb density, structure forming, texture building, cohesion, adhesion, elasticity, springiness, solubility, viscosity, fat absorption, flavor binding, coagulation, leavening, aeration, creaminess, film forming property, sheen addition, shine addition, freeze stability, thaw stability, or color.

In some embodiments, the purified protein isolate is incorporated into an egg-free cake mix or an egg-free cake batter. In some such embodiments, the egg-free cake mix or batter has at least one organoleptic property (e.g., a flavor or aroma) of the egg-free cake batter is similar or equivalent to a corresponding organoleptic property of a cake mix or batter containing eggs. The egg-free cake mix or batter may exhibit at least one functional property similar or equivalent to a corresponding functional property of a cake batter containing eggs. The at least one functional property may be, for example, one or more of emulsification, water binding capacity, foaming, gelation, crumb density, structure forming, texture building, cohesion, adhesion, elasticity, springiness, solubility, viscosity, fat absorption, flavor binding, coagulation, leavening, aeration, creaminess, film forming property, sheen addition, shine addition, freeze stability, thaw stability, or color.

In some embodiments in which the purified protein isolate is included in an egg-free pound cake, a peak height of the egg-free pound cake is at least 90% of the peak height of a pound cake containing eggs. In some embodiments in which the purified protein isolate is included in an egg-free pound cake batter, a specific gravity of the egg-free pound cake batter is 0.95-0.99.

In some aspects, increased functionality is associated with the purified protein isolate in a food application. For instance, food products produced with the purified protein isolate may exhibit increased functionality in dome or crack, cake resilience, cake cohesiveness, cake springiness, cake peak height, specific gravity of batter, center doming, center crack, browning, mouthfeel, spring-back, off flavors or flavor.

In some embodiments, the purified protein isolate is included in a cream cheese, a pasta dough, a pasta, a milk, a custard, a frozen dessert (e.g., a frozen dessert comprising ice cream), a deli meat, or chicken (e.g., chicken nuggets).

In some embodiments, the purified protein isolate is incorporated in a food or beverage composition, such as, for example, an egg substitute, a cake (e.g., a pound cake, a yellow cake, or an angel food cake), a cake batter, a cake mix, a cream cheese, a pasta dough, a pasta, a custard, an ice cream, a milk, a deli meat, or a confection. The food or beverage composition may provide sensory impressions similar or equivalent to the texture and mouthfeel that replicates a reference food or beverage composition. In some embodiments, before being included in a food or beverage composition, the purified protein isolate is further processed in a manner that depends on a target application for the purified protein isolate. For example, the purified protein isolate may be diluted in a buffer to adjust the pH to a pH appropriate for the target application. As another example, the purified protein isolate may be concentrated for use in the target application. As yet another example, the purified protein isolate may be dried for use in the target application.

Various food applications incorporating high purity protein isolates from mung bean as the main functional ingredient were made including an egg-free emulsion (e.g. for an egg-free food product similar or equivalent to scrambled eggs), pound cake, yellow cake, angel food cake, a cream cheese, a pasta dough, a pasta, a custard, an ice cream, a milk, a deli meat, or a confection. Examples 8-12, 20, and 21 provide examples of the protein isolate incorporated into various food applications.

6.7.1 Vegan Patty

Various experiments provide evidence that mung bean protein isolate are suited for use as the sole gelling agent in a formulated vegan patty. In some embodiments, a hydrocolloid system comprised of iota-carrageenan and gum arabic enhances native gelling properties of mung bean isolate in a formulated patty. In other embodiments, a hydrocolloid system comprised of high-acyl and low-acyl gellan in a 1.5:1 ratio enhances native gelling properties of mung bean isolate in a formulated patty. In further embodiments, a hydrocolloid system comprised of konjac and xanthan gum enhances native gelling properties of mung bean isolate in a formulated patty.

6.7.2 Egg-Free Emulsion

In another aspect, provided herein is an edible egg-free emulsion comprising a mung bean protein isolate described herein. In some embodiments, the emulsion comprises one or more additional components selected from water, oil, fat, hydrocolloid, and starch. In some embodiments, at least or about 60-85% of the edible egg-free emulsion is water. In some embodiments, at least or about 10-20% of the edible egg-free emulsion is the protein isolate. In some embodiments, at least or about 5-15% of the edible egg-free emulsion is oil or fat. In some embodiments, at least or about 0.01-6% of the edible egg-free emulsion is the hydrocolloid fraction or starch. In some embodiments, the hydrocolloid fraction comprises high-acyl gellan gum, low-acyl gellan gum, iota-carrageenan, gum arabic, konjac, locust bean gum, guar gum, xanthan gum, or a combination of one or more gums thereof. In some embodiments, the emulsion further comprises one or more of: a flavoring, a coloring agent, an antimicrobial, a leavening agent, and salt.

In some embodiments, the emulsion further comprises phosphate. In some embodiments, the phosphate is selected from the group consisting of disodium phosphate (DSP), sodium hexamethaphosphate (SHMP), tetrasodium pyrophosphate (TSPP). In a particular embodiment, the emulsion comprises DSP. In another particular embodiment, the emulsion comprises DSP. In some embodiments, the amount of DSP in the emulsion is at least or about 0.01%, 0.02%, 0.03%, 0.04%, 0.05%, 0.06%, 0.07%, 0.08%, 0.09%, 0.1%, 0.11%, 0.12%, 0.13%, 0.14% or 0.15%; or greater than 0.15%. In another particular embodiment, the emulsion comprises SHMP. In some embodiments, the SHMP is a short chain SHMC, regular chain SHMP or a long chain SHMP. In some embodiments, the amount of SHMP in the emulsion is at least or about 0.4%, 0.5%, 0.6%, 0.7%, 0.8%, 0.9%, or 1%; or greater than 1%.

In a particular embodiment, provided herein is an edible egg-free emulsion having a pH of about 5.6 to 6.8. In some embodiments, the edible egg-free emulsion comprises water, a mung bean protein isolate described herein, an enzyme that modifies a structure of the protein isolate, and oil or fat. In some embodiments, the enzyme comprises a transglutaminase or proteolytic enzyme. In some embodiments, at least or about 70-85% of the edible egg-free emulsion is water. In some embodiments, at least or about 7-15% of the edible egg-free emulsion is the protein isolate. In some embodiments, at least or about 0.0005-0.0025% (5-25 parts per million) of the edible egg-free emulsion is the enzyme that modifies the structure of the protein isolate. In some embodiments, at least or about 5-15% of the edible egg-free emulsion is oil or fat.

Also provided herein is a patty made using any of the egg-free emulsions described above.

In some embodiments, a method provides an egg-free emulsion prepared using the protein isolate described herein, wherein the egg-free emulsion may be used to make for example an egg-free food product similar or equivalent to scrambled eggs, an omelet, or a quiche prepared using eggs. Accordingly, in some embodiments an egg-free emulsion comprises one or more of the exemplary protein isolates disclosed herein. The egg-free emulsion may further comprise for example a lipid, one or more carbohydrates, and optionally a protein-modifying enzyme, salt, flavorings, and/or colors. The proportions of these ingredients may be selected to modulate the texture, flavor, and/or color of the resulting egg-free food product. The resulting egg-free food product may provide sensory impressions similar or equivalent to the texture and mouthfeel that replicates an egg. Sensory quality parameters of a liquid scramble and patty are characterized as soft, compact gel with clean bite and moderate chewiness similar to eggs.

Some embodiments provide methods for preparing proteins as an egg substitute. For instance, by combining protein isolate prepared in Example 8 with 2% Na2HPO4 and bringing the ingredient to the following liquid composition: 21% total solids and 0.25% Na2HPO4, the protein is readily used as a plant-based egg substitute, a suitable replacement ingredient.

6.7.3 Baked Cakes

In another aspect, provided herein are one or more egg-free cake mixes, suitable for preparing one or more egg-free cake batters, from which one or more egg-free cakes can be made. In some embodiments, the egg-free cake mix comprises flour, sugar, and a mung bean protein isolate described herein. In some embodiments, the egg-free cake mix further comprises one or more additional components selected from: cream of tartar, disodium phosphate, baking soda, and a pH stabilizing agent. In some embodiments, the flour comprises cake flour.

Also provided herein is an egg-free cake batter comprising an egg-free cake mix described above, and water. In some embodiments, the egg-free cake batter is an egg-free pound cake batter, an egg-free angel food cake batter, or an egg-free yellow cake batter. In some embodiments, the egg-free cake batter has a specific gravity of 0.95-0.99.

Also provided herein is an egg-free cake made from an egg-free cake batters described above. In some embodiments, a peak height of the egg-free cake is at least 90% of a peak height of a pound cake containing eggs. In some embodiments, one or more characteristics of the egg-free cake is similar or equivalent to one or more corresponding characteristics of a cake containing eggs. In some embodiments, the one or more characteristics comprise resilience, cohesiveness, springiness, peak height, center doming, center crack, browning, mouthfeel, spring-back, or flavor. In some embodiments, the one or more characteristics comprise hardness, resilience, cohesiveness, springiness, or chewiness. In some embodiments, the one or more characteristics comprise a functional property or an organoleptic property. In some embodiments, the functional property comprises one or more of: emulsification, water binding capacity, foaming, gelation, crumb density, structure forming, texture building, cohesion, adhesion, elasticity, springiness, solubility, viscosity, fat absorption, flavor binding, coagulation, leavening, aeration, creaminess, film forming property, sheen addition, shine addition, freeze stability, thaw stability, or color.

In a particular embodiment, provided herein is an egg-free pound cake mix, comprising flour, sugar, and a mung bean protein isolate described herein. In some embodiments, the flour comprises cake flour. In some embodiments, the egg-free pound cake mix further comprises oil or fat. In some embodiments, the oil or fat comprises butter or shortening. In some embodiments, at least or about 25-31% of the egg-free pound cake batter is flour. In some embodiments, at least or about 25-31% of the egg-free pound cake batter is oil or fat. In some embodiments, at least or about 25-31% of the egg-free pound cake batter is sugar. In some embodiments, at least or about 6-12% of the egg-free pound cake batter is the protein isolate. In some embodiments, the batter further comprises disodium phosphate or baking soda.

Also provided herein is an egg-free pound cake batter comprising an egg-free pound cake mix described above, and further comprising water. In some embodiments, the egg-free pound cake batter comprises about four parts of the egg-free pound cake mix; and about one part water. In some embodiments, at least or about 20-25% of the egg-free pound cake batter is flour. In some embodiments, at least or about 20-25% of the egg-free pound cake batter is oil or fat. In some embodiments, at least or about 20-25% of the egg-free pound cake batter is sugar. In some embodiments, at least or about 5-8% of the egg-free pound cake batter is the protein isolate. In some embodiments, at least or about 18-20% of the egg-free pound cake batter is water.

In another particular embodiment, provided herein is an egg-free angel food cake mix comprising flour, sugar, and a mung bean protein isolate described herein. In some embodiments, at least or about 8-16% of the egg-free angel food cake mix is flour. In some embodiments, at least or about 29-42% of the egg-free angel food cake mix is sugar. In some embodiments, at least or about 7-10% of the egg-free angel food cake mix is the protein isolate. In some embodiments, the egg-free angel food cake mix further comprises cream of tartar, disodium phosphate, baking soda, or a pH stabilizing agent. In some embodiments, the flour comprises cake flour. Also provided herein is an egg-free angel food cake batter comprising an egg-free angel food cake mix described above, and water.

In another particular embodiment, provided herein is an egg-free yellow cake mix, comprising flour, sugar, and a mung bean protein isolate described herein. In some embodiments, at least or about 20-33% of the egg-free yellow cake mix is flour. In some embodiments, at least or about 19-39% of the egg-free yellow cake mix is sugar. In some embodiments, at least or about 4-7% of the egg-free yellow cake mix is the protein isolate. In some embodiments, the egg-free yellow cake mix further comprises one or more of baking powder, salt, dry milk, and shortening.

Also provided herein is an egg-free yellow cake batter comprising an egg-free yellow cake mix described above, and water.

Some embodiments provide methods to produce an egg-free pound cake using a protein isolate. For instance, a batter is created by mixing liquid solution comprising mung bean protein isolate with sugar, cake flour, and butter at 17° C. to 20° C. in 1:1:1:1 w/w ratio. The ingredients are blended together using single stage mixing on Hobart mixer for 6 minutes at 22° C. The batter is baked in pound cake pan for 45 minutes in 150° C. and cooled in pan for 2 hours at 22° C.

Sensory quality parameters of cakes made with the protein isolates are characterized as fluffy, soft, airy texture. The peak height was measured to be 90-110% of pound cake containing eggs. The specific gravity of cake batter with the purified mung bean protein isolate was 0.95-0.99 which was similar to that of cake batter with whole eggs of 0.95-0.96.

6.7.4 Cream Cheese Analog

In another aspect, provided herein is an egg-free cream cheese comprising a mung bean protein isolate described herein. In some embodiments, the egg-free cream cheese comprises one or more additional components selected from water, oil or fat, and hydrocolloid. In some embodiments, at least or about 75-85% of the egg-free cream cheese is water. In some embodiments, at least or about 10-15% of the egg-free cream cheese is the protein isolate. In some embodiments, at least or about 5-10% of the egg-free cream cheese is oil or fat. In some embodiments, at least or about 0.1-3% of the egg-free cream cheese is hydrocolloid. In some embodiments, the hydrocolloid comprises xanthan gum or a low-methoxy pectin and calcium chloride system. In some embodiments, the egg-free cream cheese further comprises a flavoring or salt. In some embodiments, one or more characteristics of the egg-free cream cheese is similar or equivalent to one or more corresponding characteristics of a cream cheese containing eggs. In some embodiments, the characteristic is a taste, a viscosity, a creaminess, a consistency, a smell, a spreadability, a color, a thermal stability, or a melting property. In some embodiments, the characteristic comprises a functional property or an organoleptic property. In some embodiments, the functional property comprises: emulsification, water binding capacity, foaming, gelation, crumb density, structure forming, texture building, cohesion, adhesion, elasticity, springiness, solubility, viscosity, fat absorption, flavor binding, coagulation, leavening, aeration, creaminess, film forming property, sheen addition, shine addition, freeze stability, thaw stability, or color. In some embodiments, the organoleptic property comprises a flavor or an odor.

Example 31 provides an exemplary cream cheese analog using a hydrocolloid system comprised of low-methoxy pectin with CaCl2 forms a continuous, soft gel with textural organoleptic properties reminiscent of cream cheese. Additional results provide a hydrocolloid system comprised of xanthan gum forms a continuous, soft gel with textural organoleptic properties reminiscent of cream cheese.

6.7.5 Egg-Free Pasta Dough

In another aspect, provided herein is an egg-free pasta dough comprising a mung bean protein isolate described herein. In some embodiments, the egg-free pasta dough comprises one or more additional components selected from flour, oil or fat, and water. In some embodiments, the flour comprises semolina flour. In some embodiments, the oil or fat comprises extra virgin oil. In some embodiments, the egg-free pasta dough further comprises salt. Also provided herein is an egg-free pasta made from an egg-free pasta dough described above. In some embodiments, the egg-free pasta is fresh. In some embodiments, the egg-free pasta is dried. In some embodiments, one or more characteristics of the egg-free pasta is similar or equivalent to one or more corresponding characteristics of a pasta containing eggs. In some embodiments, the one or more characteristics comprise chewiness, density, taste, cooking time, shelf life, cohesiveness, or stickiness. In some embodiments, the one or more characteristics comprise a functional property or an organoleptic property. In some embodiments, the functional property comprises: emulsification, water binding capacity, foaming, gelation, crumb density, structure forming, texture building, cohesion, adhesion, elasticity, springiness, solubility, viscosity, fat absorption, flavor binding, coagulation, leavening, aeration, creaminess, film forming property, sheen addition, shine addition, freeze stability, thaw stability, or color. In some embodiments, the organoleptic property comprises a flavor or an odor.

6.7.6 Plant-Based Milk

In another aspect, provided herein is a plant-based milk comprising a mung bean protein isolate described herein. In some embodiments, the plant-based milk comprises one or more additional components selected from water, oil or fat, and sugar. In some embodiments, at least or about 5% of the plant-based milk is the protein isolate. In some embodiments, at least or about 70% of the plant-based milk is water. In some embodiments, at least or about 2% of the plant-based milk is oil or fat. In some embodiments, the plant-based milk further comprises one or more of: disodium phosphate, soy lecithin, and trace minerals. In particular embodiments, the plant-based milk is lactose-free. In other particular embodiments, the plant-based milk does not comprise gums or stabilizers.

6.7.7 Egg-Free Custard

In another aspect, provided herein is an egg-free custard comprising a mung bean protein isolate described herein. In some embodiments, the egg-free custard comprises one or more additional components selected from cream and sugar. In some embodiments, at least or about 5% of the egg-free custard is the protein isolate. In some embodiments, at least or about 81% of the egg-free custard is cream. In some embodiments, at least or about 13% of the egg-free custard is sugar. In some embodiments, the egg-free custard further comprises one or more of: iota-carrageenan, kappa-carrageenan, vanilla, and salt. In some embodiments, the cream is heavy cream.

6.7.8 Egg-Free Ice Cream

In another aspect, provided herein is an egg-free ice cream comprising a mung bean protein isolate described herein. In some embodiments, the egg-free ice cream is a soft-serve ice cream or a regular ice cream. In some embodiments, the egg-free ice cream comprises one or more additional components selected from cream, milk, and sugar. In some embodiments, at least or about 5% of the egg-free ice cream is the protein isolate. In some embodiments, at least or about 41% of the egg-free ice cream is cream. In some embodiments, at least or about 40% of the egg-free ice cream is milk. In some embodiments, at least or about 13% of the egg-free ice cream is sugar. In some embodiments, the egg-free ice cream further comprises one or more of iota carrageenan, kappa carrageenan, vanilla, and salt. In some embodiments, the cream is heavy cream. In some embodiments, the milk is whole milk. In particular embodiments, the egg-free ice cream is lactose-free. In other particular embodiments, the egg-free ice cream does not comprise gums or stabilizers. In other embodiments, the egg-free ice provides a traditional mouthfeel and texture of an egg-based ice cream but melts at a slower rate relative to an egg-based ice cream.

6.7.9 Fat Reduction Shortening System (FRSS)

In another aspect, provided herein is fat reduction shortening system comprising a mung bean protein isolate described herein. In some embodiments, the FRSS comprises one or more additional components selected from water, oil or fat. In some embodiments, the FRSS further comprises sodium citrate. In further some embodiments, the FRSS further comprises citrus fiber. In some embodiments, at least or about 5% of the FRSS is the protein isolate. In preferred embodiments, the mung bean-based FRSS enables a reduction in fat content in a food application (e.g., a baking application) utilizing the FRSS, when compared to the same food application utilizing an animal and/or dairy based shortening. In some embodiments, the reduction in fat is at least 10%, 20%, 30% or 40% when compared to the same food application utilizing an animal and/or dairy based shortening.

In particular embodiments of the FRSS, the FRSS is prepared by an isolation process described herein, whereby the acid precipitation step is carried out at a pH of about 6.0. In some such embodiments, the resulting mung bean protein isolate is dried on a box dryer.

6.7.10 Meat Analogues

In another aspect, provided herein is a meat analogue comprising a mung bean protein isolate described herein. In some embodiments, the meat analogue comprises one or more additional components selected from water, oil, disodium phosphate, transglutaminase, starch and salt. In some embodiments, at least or about 10% of the meat analogue is the protein isolate. In some embodiments, preparation of the meat analogue comprises mixing the components of the meat analogue into an emulsion and pouring the emulsion into a casing that can be tied into a chubb. In some embodiments, chubs containing the meat analogue are incubated in a water bath at 50° C. for 2 hours. In further embodiments, the incubated chubbs are pressure cooked. In some embodiments, the pressure cooking occurs at 15 psi at about 121° C. for 30 min.

6.7.11 Food Applications: Co-Ingredients

6.7.11.1 Gums

Various gums useful for formulating one or more mung bean based food products described herein include, e.g., konjac, gum acacia, Versawhip, Guar+Xanthan, Q-extract, CMC 6000 (Carboxymethylcellulose), *Citri*-Fi 200 (citrus fiber), Apple fiber, Fenugreek fiber.

6.7.11.2 Phosphates

Various phosphates useful for formulating one or more mung bean based food products described herein include disodium phosphate (DSP), sodium hexamethaphosphate (SHMP), and tetrasodium pyrophosphate (TSPP). In a particular embodiment, the mung bean based food product comprises DSP. In some embodiments, the amount of DSP in the emulsion is at least or about 0.01%, 0.02%, 0.03%, 0.04%, 0.05%, 0.06%, 0.07%, 0.08%, 0.09%, 0.1%, 0.11%, 0.12%, 0.13%, 0.14% or 0.15%; or greater than 0.15%. In another particular embodiment, the mung bean based food product comprises SHMP. In some embodiments, the SHMP is a short chain SHMC, regular chain SHMP or a long chain SHMP. In some embodiments, the amount of SHMP in the emulsion is at least or about 0.4%, 0.5%, 0.6%, 0.7%, 0.8%, 0.9%, or 1%; or greater than 1%.

6.7.11.3 Starches

Starch is one of the most prevalent food ingredients, and has been shown to have useful emulsifying properties. Starch and starch granules are known to stabilize emulsions. Consequently, one or more starches are produced from plant compositions, such as, for example, arrowroot starch, cornstarch, tapioca starch, mung bean starch, potato starch, sweet potato starch, rice starch, sago starch, wheat starch. The hydrophobicity allows starch to be adsorbed at the oil-water interface, which prevents re-coalescence and hence droplet stability.

6.7.11.4 Preservatives

In certain embodiments, the methods and compositions comprise an effective amount of an added preservative in combination with the protein isolate.

Preservatives prevent food spoilage from bacteria, molds, fungi, or yeast (antimicrobials); slow or prevent changes in color, flavor, or texture and delay rancidity (antioxidants); maintain freshness. They include but are not limited to the following: ascorbic acid, citric acid, sodium benzoate, calcium propionate, sodium erythorbate, sodium nitrite, calcium sorbate, potassium sorbate, BHA, BHT, EDTA, tocopherols (Vitamin E) and antioxidants, which prevent fats and oils and the foods containing them from becoming rancid or developing an off-flavor. See Table 3.

TABLE 3

| Substance/class | Some foodstuffs in which they are used |
|---|---|
| Sorbic acid and sorbate compounds | Cheese, wines, dried fruit, fruit sauces, toppings |
| Benzoic acid, and benzoate | Pickled vegetables, low sugar jams and jellies, candied fruits, semipreserved fish products, sauces |
| Sulphur dioxide and sulphite compounds | Dried fruits, fruit preserves, potato products, wine |
| Natamycin | Surface treatment of cheese and sausage |
| Nitrite and nitrate compounds | Sausage, bacon, ham, foie gras, cheese, pickled herring |

6.8 Storage and Shelf Life of Compositions

In some embodiments, the protein isolate or compositions comprising the protein isolate may be stable in storage at room temperature for up to 1, 2, 3, 4, 5, 6, 7, 8, 9, or 10 weeks. In some embodiments, the protein isolate or compositions comprising the protein isolate may be stable for storage at room temperature for months, e.g. greater than 1, 2, 3, 4, 5, 6, 7, 8, 9, 10, 11, 12, or 13 months. In some embodiments, the protein isolate or compositions comprising the protein isolate may be stable for refrigerated or freezer storage for months, e.g. greater than 1, 2, 3, 4, 5, 6, 7, 8, 9, 10, 11, 12, or 13 months. In some embodiments, the protein isolate or compositions comprising the protein isolate may be stable for refrigerated or freezer storage for years, e.g. greater than 1, 2, 3, 4, 5, 6, 7, 8, 9, 10, 11, 12, or 13 years. In some embodiments, the protein isolate or compositions comprising the protein isolate may be stable for storage at room temperature for months, e.g. greater than 1, 2, 3, 4, 5, 6, 7, 8, 9, 10, 11, 12, or 13 months. In some embodiments, the protein isolate or compositions comprising the protein isolate may be stable for storage at room temperature for years, e.g. greater than 1, 2, 3, 4, 5, 6, 7, 8, 9, 10, 11, 12, or 13 years.

In some embodiments, storage as a dry material can increase the shelf-life of the protein isolate or a composition comprising the protein isolate. In some embodiments protein isolate or a composition comprising the protein isolate is stored as a dry material for later reconstitution with a liquid, e.g. water. In some embodiments, the purified protein isolate is in powdered form, which may be less expensive to ship, lowers risk for spoilage and increases shelf-life (due to greatly reduced water content and water activity).

In other embodiments the purified protein isolate or a composition comprising the protein isolate is reconstituted with a liquid, e.g. water, milk, or other liquid suitable for consumption. In one example, 36-45 grams of liquid can be added to 12-15 grams dry weight of the composition to produce a liquid scramble. The amount of liquid can be varied to suit a particular purpose for the reconstituted composition.

In additional embodiments, food composition comprising the purified protein isolate or a formulation thereof in an emulsion, under heat, under refrigeration or colder conditions or not ambient conditions.

7. EXAMPLES

7.1 Example 1: Particle Size Characterization

The efficiency of seed milling is reflected in the particle size distribution of the flours, and influences the composition of isolated materials and their functionality. Particle size of mung bean flours was characterized using Mastersizer AeroS (Malvern) and shown in Table 4. Materials used for isolation showed particle size distribution in a range of 8-220 μm.

TABLE 4

| Source name | Sample ID | Average Particle Size Distribution | | |
|---|---|---|---|---|
| | | Dx(10) (μm) | Dx(50) (μm) | Dx(90) (μm) |
| Mung Bean Batch 1 | 44 45 | 8.9 | 25.0 | 105.5 |
| Mung Bean Batch 2 | 43 46 | 12.3 | 41.5 | 206.0 |
| Mung Bean Batch 3 | 47 48 | 12.3 | 37.9 | 223.0 |

7.2 Example 2: Protein Isolate Purification Protocol

This example provides an exemplary protocol for preparing a mung bean protein isolate described herein.

A. Multistage Extraction.

Water is mixed with mung bean flour in a 5:1 tap water-to-flour ratio. The pH of the mixture is adjusted to pH 6.5-pH 8 with NaOH. The mixture is centrifuged at 6000×g for 15 minutes at 4° C. The extract is collected and the pellet is resuspended in 3:1 water-to-flour. The pH is adjusted to pH 6.5-pH 8 with NaOH, and centrifuged again at 6000×g for 15 minutes at 4° C. Both extracts are combined and filtered through 100 um Nylon mesh.

B. Charcoal Filtration or Off-Flavor Removal (Optional).

Charcoal specifications: ~500 um-1500 um particle size, 12×30 mesh size, acid washed. Charcoal preparation: 100 g of charcoal is mixed in 3 kg of water, poured through a filter, and the charcoal is collected. 1 g of charcoal is then added to 10 g of extract and incubated for ~15 min. The mixture is then centrifuged at 10000×g for 15 minutes, 4° C. The mixture can also be treated with a chelating agent, for example, 2 mM CaNa2 EDTA.

C. Acid Precipitations.

Isoelectric precipitation at pH 5.6+/−0.2 is combined with a cryo-precipitation method at 1-4° C. pH is brought down to pH 5.4-5.8 with 20% Citric Acid. Cool on ice for 1 h. Alternatively, low ionic strength precipitation can be performed at very high flow rates combined with cryo-precipitation method (at 1-4° C.). Rapid dilution of the filtrate is performed in cold (4° C.) 0.3% NaCl at a ratio of 1 volume of supernatant to 3 volumes of cold 0.3% NaCl. The filtrate is then centrifuged at 10,000×g for 15 minutes at 4° C.

D. Recovery.

The pellet is collected, resuspended and homogenized 1:4 (w/w) with 0.3% NaCl (4° C.). The pH is maintained at 5.6+/−0.1 with citric acid. The suspension is centrifuged at 10,000×g for 15 minutes at 4° C., and the final pellet is homogenized.

The final pellet is homogenized and the moisture content is recorded.

7.3 Example 3: Charcoal Treatment of Protein Extracts

This example provides an exemplary protocol for performing a carbon adsorption step to remove non-protein, off-flavor components (such as beany flavor) in the protein extraction process. Typical starting weights for input legume flour or material range from 1-12 kg, and typical yield is about 25% with a moisture content around 78%.

Charcoal specifications: ~500 um-1500 um particle size, 12×30 mesh size, acid washed.

Charcoal preparation: 100 g charcoal is mixed in 3 kg of water, poured through a filter and collected. This wash step is repeated for a total of 2 washes.

Preparation of extract: water is combined with flour in a 3:1 water-to-flour ratio, then centrifuged at 6000×g for 20 minutes at 4° C. Supernatant is collected and filtered through 100 um Nylon mesh.

Charcoal treatment: prepared charcoal is mixed with 1 L of extract and stirred for 15 minutes. The extract-charcoal mixture is then filtered through a 100 um filter to remove large charcoal particles, and centrifuged at 10,000×g for 15 minutes at 4° C. to remove remaining ash. 500 mM CaNa2EDTA is added to the extract to a final concentration of 2 mM CaNa2 EDTA, mixed, then incubated at 4° C. for 60 minutes. Rapid dilution of the filtrate is performed in cold (4° C.) 0.3% NaCl at a ratio of 1 volume of supernatant to 3 volumes of cold 0.3% NaCl. The filtrate is then centrifuged at 10,000×g for 15 minutes at 4° C., and the pellet collected.

The pellet is suspended and homogenized 1:4 (w/w) with 0.3% NaCl+0.7 mM CaNa2 EDTA (4° C.), and centrifuged at 10,000×g for 15 minutes at 4° C. The resulting pellet is washed 1:4 (w/w) with 0.3% NaCl (4° C.), then centrifuged at 10,000×g for 15 minutes at 4° C.

The final pellet is homogenized and the moisture content is recorded.

7.4 Example 4: Pilot Scale Protein Isolation Method

This example provides an exemplary protocol for pilot scale preparation of mung bean protein isolates. A general process block flow diagram is shown in FIG. 3. The process starts with a protein extraction stage, where milled mung bean flour is mixed with 5-10 volumes of soft water to form a slurry in a chilled mix tank (2-8° C.). The pH of the slurry is adjusted with a food-grade 50% NaOH solution to reach pH 7 for solublization of target protein into the aqueous solution. The slurry is then sent to a solid/liquid separation unit operation (typically a combination of one decanter and one disc-stack centrifuge), and the solubilized protein extract is separated from the fibrous starch fraction of the flour.

Optionally, the protein extract is pumped to pass through a food-grade charcoal filled annular basket column (at <5% charcoal to protein extract ratio, w/w) at 4° C. The primary function of this carbon adsorption step is to remove non-protein, off-flavor components (such as beany flavor) in the protein extraction. It also removes some fibrous solids and therefore leads to a clarified protein extract.

The clarified protein extract is acidified with a 20% food-grade citric acid solution to reach its isoelectric point (pH 5.6) under a Cryo condition (2° C.). Under this condition, the target protein precipitates and becomes separable from the aqueous solution. In addition to the pH adjustment, 2 mM of food-grade EDTA is added during this step to inhibit lipoxygenases activities that may incur off-flavor compounds generation. The precipitated protein slurry is then sent to a solid/liquid separation unit operation (typically one disc-stack centrifuge), and the protein curd is recovered in the heavy phase of the centrifuge step.

The protein curd is then washed with 4 volumes of soft water during the washing step under a Cryo condition (2° C.). Washing is regarded as a polishing step to remove impurities (e.g. fibrous solids, salts, carbohydrates) in the protein curd. In this step, 0.3% (w/w) food-grade sodium chloride is typically added to facilitate solid/liquid separation during centrifugation.

The washed protein curd solution is then pasteurized through a High Temperature/Short Time (HTST) pasteurization step. Similar to milk pasteurization, the primary function of this step is to kill any pathogenic bacteria that may be present in the washed protein curd solution. An exemplary HTST condition is 74° C. for 20-23 seconds.

The final step in the processing is spray drying, where the pasteurized protein solution is passed through a spray dryer to remove the water content. A typical spray drying condition has a dryer inlet temperature of 170° C., and a dryer outlet temperature of 72° C. The dried protein isolate powder typically has <5% moisture content.

7.5 Example 5: Ultrafiltration Studies

Ultrafiltration studies were conducted to evaluate the effectiveness in removing residual source materials, e.g., contaminating molecules including polysaccharides, from mung bean protein isolates. Ultrafiltration (UF) is a variety of membrane filtration in which forces like pressure or concentration gradients lead to a separation through a semi-permeable membrane. Suspended solids and solutes of high molecular weight are retained in the so-called retentate, while water and low molecular weight solutes pass through the membrane in the permeate (FIG. 4).

One experiment employed a 100 kDa MWCO membrane based upon the particle size determinations. Flow rates were much faster than previously observed even at low trans-membrane pressures, and ultimately the various fractions (~4× concentration). Permeate fractions were noticeably yellow in color and had a characteristic raw bean odor. About 750 ml of material was concentrated to 200 ml and then 260 ml of fresh 100 mM Na+/K+ phosphate buffer, pH 6.8 was added to wash or diafilter. Two permeate fractions were obtained, the primary and the permeate from the diafiltration step. Ultimately the retentate volume was concentrated to 200 ml and the membrane was rinsed to obtain residual protein.

Overall, the method successfully removed small molecules that are associated with unwanted odors in the protein isolate used for scrambled eggs, as judged by olfactory sensing, and also physically, by demonstrating that macro-molecular structures partition in the UF unit based on the particle size determination. Additional UF trials can determine whether or not microfluidized material containing sheared hydrocolloids can be subjected to UF directly. Accordingly, the method provides removal of small molecules that are associated with unwanted odors using ultrafiltration.

7.6 Example 6: Effect of Isoelectric Precipitation pH Value

7.6.1 Effect on Protein Yield, Purity and Small Molecule Retention

The effect of pH value during isoelectric precipitation was investigated to determine the effect on protein yield, purity and non-protein retention of the resulting mung bean protein isolate. Mung bean isolates were prepared as described in Example 2, with the exception that the isoelectric precipitation step was performed at either pH 4.9, pH 5.2, pH 5.6, or pH 6. Protein purity (mg/protein/mg dry weight) and protein yield (g/g flour) were determined, the results of which are depicted in FIGS. 5A and 5B, respectively. These results indicate that protein purity and protein yield were highest when isoelectric precipitation was performed at pH 5.6.

Size exclusion chromatography analysis was also performed on the isolates, the results of which are depicted in FIG. 6A and summarized in FIG. 6B. These results demonstrate that at the lower pH values (i.e., pH 4.9 and 5.2), more small molecules (e.g., carbohydrates such as mono and disaccharides) are recovered with proteins in the isolate, while at higher pH values (i.e., pH 5.6 and 6.0), a substantially higher percentage of proteins is recovered relative to small molecule recovery. Accordingly, precipitation of mung bean protein at a range of about pH 5.6 to about pH 6.0 provides better removal of small molecules that are associated with unwanted odors, enabling a higher percent recovery of protein in the resulting isolate.

7.6.2 Effect on Crude Lipids and Fatty Acid Retention

The effect of pH value during isoelectric precipitation was further investigated to determine the effect on oils and lipids retention of the resulting mung bean protein isolate. Mung bean isolates were prepared as follows. Mung bean flour was mixed in a 1:5 ratio with distilled water and mixed for 5 minutes using an overhead mixer. The pH of the solution was then adjusted to 7.0 using 10M NaOH while mixing was occurring. The solution was then centrifuged at 6,000 g for 10 minutes at 4° C. The supernatant was then decanted from the bottles and saved, while the pellets were discarded. The supernatant was split into 10 batches of equal weight. Each batch was mixed with the overhead mixer and pH adjusted using a 20% (w/w) citric acid solution to one of ten (10) desired pH values: pH 4.4, 4.6, 4.8, 5, 5.2, 5.4, 5.6, 5.8, 6, and 6.2. Once the desired pH was reached in each batch, the solution was allowed to stir for another minute to allow the pH to stabilize. Each batch was then moved to the centrifuge and set to spin at 10,000 g for 15 minutes at 4° C. The supernatants were then discarded and the pellets were collected for quantitation of: (1) total protein recovery; (2) crude lipids; and (3) fatty acid analysis.

Crude lipid extraction was performed via pressurized fluid extraction using a Dionex ASE 350 system. Samples were mixed in an about 1:1 ratio (w:w) using diatomaceous earth. Samples were extracted at 100° C. for 5 minutes using Petroleum Ether (BD Analytical). The extracts were evaporated and the residue weights were recorded as % crude lipids. About 100 mg of each crude extract was diluted to 10 mL using Methyl tert-Butyl Ether (BD Analytical). 500 µL of each extract was transferred to amber HPLC vials. Free Fatty Acids were derivatized by adding 250 µL of Trimethylsulfonium hydroxide solution (TCI Organics, 0.2 M in Methanol). Vials were heated at 100° C. for 10 minutes, cooled, and transferred to a GC for analysis. FAMEs were identified using Free Fatty Acid Mixture 74× purchased from NuChek Prep. Samples were separated on an Agilent 7890B GC-FID system using a FAMEWAX Column (30 m×0.25 mm×0.25 Restek).

As shown in FIG. 7, total protein recovery was highest when mung bean protein was acid precipitated at pH 5.4 to 5.6, consistent with earlier observations. The y-axis represents grams of protein recovered from 100.7 grams of extract comprising the protein.

As shown in FIG. 8, mung bean protein isolate that underwent acid precipitation at pH 5.4 to 5.6 also retained the least amount of crude lipid among the range of precipitation pHs tested. As shown in FIG. 8A, the total amounts of crude lipid appear to be enriched, relative to the amount of crude lipid in the pre-precipitation extract (far left), when the isolate underwent precipitation at pH 4.4, 4.6, 4.8 and 5.0, 6.0, and 6.2.

FIGS. 9A and 9B depict the amounts of specific fatty acids (FAMES) in each of the mung bean protein isolates precipitated from pH 4.4 to 6.2. The specific fatty acids measured are (from left to right): C14:0 (methyl myristate); C15:0 (methyl pentadecanoate); C16:0 (methyl palmitate; C16:1 methyl palmitoleate; C17:0 methyl heptadecanoate; C18:0 methyl stearate; C18:1 methyl oleate; C18:2 methyl linoleate; C18:3 methyl alpha linoleate; C20:0 methyl eicosanoate; and C22:0 methyl behenate. FIG. 9A provides a view of the amounts of each of these fatty acids recovered for isolates precipitated at each of the above pH values, while FIG. 9B provides a closer view of the amounts of the minor lipid types. For each specific fatty acid measured, mung bean protein isolate that underwent acid precipitation at pH 5.4 to 5.6 also retained the least amount of FAMES.

7.6.3 Effect on Gelation

The effect of pH value during isoelectric precipitation was further investigated to determine the effect on structure building properties, in particular, the ability to form a gels from the resulting mung bean protein isolate.

Gelation of mung bean protein isolates precipitated at pH 4.4, 5.0, 5.6 and 6.0, respectively, was characterized with dynamic oscillatory rheology. A rheometer (MCR502, Anton Paar) equipped with a flat parallel plate geometry (40 mm diameter) was used to monitor each isolate's viscoelastic properties as a result of increasing temperature. For each precipitation pH value, samples of isolate were prepared at 13.3% protein concentration. About 1.5 mL of sample was loaded onto the lower plate of the rheometer and was trimmed according to standard procedures. A solvent trap was loaded with 2 mL of distilled $H_2O$ to prevent evaporation of water within the sample as a result of the increase in temperature during the measurement.

The storage (G') and loss (G") modulus were continuously recorded during a temperature ramp from 30 to 95° C. at a heating rate of 5° C./min under small deformation conditions (0.1% strain) at a constant angular frequency of 10 rad/s followed by a 5 minute hold at 95° C. After this hold, the temperature of the material was reduced to 50° C. and an amplitude sweep test from 0.01 to 100% strain was carried out at a constant frequency of 10 rad/s in order to characterize the gelled material's linear viscoelastic region. Each sample was run in triplicate.

Rheology data was analyzed to extract certain features that are pertinent to characterizing the behavior of gels produced by the isolate under the conditions defined above.

Onset gelation temperature was extracted from the raw data and interpreted as the inflection point of the phase angle versus temperature over the range examined. Upon gelation events the phase angle decreases markedly as a function of temperature and can be used as a precise measure of the temperature at which the material underwent a distinct transition in its internal structure. As shown in FIG. 10, gelation onset temperature was substantially lower for isolates that were precipitated at pH 5.6 (87.4° C.) to pH 6.0 (85.4° C.) compared to isolates that were precipitated at pH 4.4 to 5.0 (both 90.7° C.).

Gel strength was also extracted from the raw data and defined as the oscillation strain (%) at which the storage modulus exceeded the linear viscoelastic range as a function of oscillation strain. As shown in FIG. 11, gel strength was substantially higher for isolates that were precipitated at pH 5.6 (7.00%) and pH 6.0 (11.83%) compared to isolates that were precipitated at pH 4.4 and 5.0 (both below 1.40%). In particular, the magnitude of increase in gel strength when isolates were precipitated at pH 5.6 to 6.0 was about five- to nine-fold, representing an unexpectedly superior gel strength, when compared to isolates that were precipitated at pH 4.4 to 5.0.

Gel elasticity was likewise extracted from the raw data of the storage modulus versus oscillation strain, and was defined as the stress (Pa) at which the storage modulus exceeded the linear viscoelastic range as a function of oscillation strain. As shown in FIG. 12 gel elasticity was substantially higher for isolates that were precipitated at pH 5.6 (1145.08 Pa) to pH 6.0 (8209.94 Pa) compared to isolates that were precipitated at pH 4.4 (194.40 Pa) to pH 5.0. (207 Pa) In particular, the magnitude of increase in gel elasticity when isolates were precipitated at pH 5.6 to 6.0 was about five- to forty-fold, representing an unexpectedly superior gel elasticity when compared to isolates that were precipitated at pH 4.4 to 5.0.

7.6.4 Effect on Sensory Properties

The effect of pH value during isoelectric precipitation was further investigated to determine the effect on sensory properties of egg-like patties prepared from isolates precipitated at pH 5.2 and 5.6, respectively. The patty formulation comprising protein isolate precipitated at pH 5.2 included: water (78%); protein isolate (14.72%); oil (6.2%); DSP (0.42%); emulsifier (0.4%); salt (0.31%) and enzyme (0.002%). The patty formulation comprising protein isolate precipitated at pH 5.6 included: water (79%); protein isolate (14.02%); oil (6.2%); DSP (0.42%); emulsifier (0.4%); salt (0.31%) and enzyme (0.002%). For each sample, mung bean protein isolate was blended with water, oil, disodium phosphate, emulsifier and salt in the formula to make a homogenous mixture under medium to high shear mixing. The mix was then heated to temperatures to 50° C., followed by addition of enzyme. This material was then filled into silicone molds to form patties. The silicone molds were maintained at 55° C. for 23 min followed by transfer to impingement oven and cooking at 250° F. for 10 min. The silicone molds were cooled and unmolded which resulted in round patties.

Patty formulations prepared with mung bean protein isolates that were precipitated at pH 5.2 did not fully "cook", that is, the patty did not form a firm gel, while patty formulations prepared with isolate precipitated at pH 5.6 did form intact pattys. This result limited the ability to conduct a direct sensory comparison of the two pattys. Nevertheless, ten subjects sampled the products and provided sensory comments that are summarized in Table 5 below. Almost all subjects perceived patties made with the isolate precipitated at pH 5.2 different than at 5.6. The most commonly used attribute to describe the patty made with the isolate precipitated at pH 5.2 was "sour."

TABLE 5

| Patty made with isolate precipitated at pH 5.2 | Patty made with isolate precipitated at pH 5.6 |
|---|---|
| Sour (6) | Beany (4) |
| Bitter (2) | Neutral (1) |
| Off-flavored (1) | Normal (1) |
| More flavor (1) | |
| Creamy (1) | |

Moreover, texture profile analysis (TPA) was performed on a patty made from each isolate. Instrumental texture profile parameters were recorded using a Brookfield Texture Analyzer equipped with a 38 mm probe. Samples were submitted to two uniaxial compression cycles at a test speed of 1 mm/s, initially triggered by a 5 g load. Target compression distance was set to 7 mm, corresponding to 70% deformation. Hardness, cohesiveness, springiness, and resilience were determined, the results of which are provided in FIG. 13. The sample made with the isolate precipitated at pH 5.2 was less firm, cohesive, springy and resilient than the sample made with the isolate precipitated at pH 5.6.

7.6.5 Conclusion

In sum, mung bean protein isolates that underwent acid precipitations at a pH range of about pH 5.6 to pH 6.0 demonstrated superior qualities with respect to protein recovery (in comparison to recovery of small molecules), gelation onset temperature, gel strength, gel elasticity, and sensory properties, in comparison to mung bean protein isolates that underwent acid precipitations at a pH below pH 5.6. Mung bean protein isolates that underwent acid precipitations at a pH range of about pH 5.2 to pH 5.8 also demonstrated substantially lower lipid retention when compared to mung bean protein isolates that underwent acid precipitations outside this range.

7.7 Example 7: Low Yielding Alternative Process

An alternative process, yielded very low protein amounts. Before precipitation, extracts were heated at 65° C. for 2 hours, followed by centrifugation at 10,000×g 1 hour, 25° C. Pellets were discarded and supernatants were collected and precipitated by low ionic strength precipitation at very high flow rates combined with cryo-precipitation method.

7.8 Example 8: Protein Composition of Mung Bean Protein Isolates

Biochemical analyses of mung bean protein isolates prepared in accordance with Example 2 were undertaken to determine their compositional make-up, as well as any compositional changes, for example, protein enrichment, throughout the isolation process. Four (4) non-consecutive batches of the mung bean protein isolate.

Table 6 provides a proximate analysis of protein, carbohydrate, fat, moisture and ash content in mung bean protein isolate prepared in accordance with the methods described herein, compared to the starting material, de-hulled mung bean.

TABLE 6

| Sample | Protein (%) | Carbohydrates (%) | Fats (%) | Moisture (%) | Ash (%) |
|---|---|---|---|---|---|
| De-hulled mung bean | 26.6 | 60.9 | 1.73 | 9.04 | 2.53 |
| Mung bean protein isolate | 80.7 | 6.52 | 3.36 | 4.78 | 7.52 |

Mung bean proteins comprise largely (~90%) globulins, represented by 8S, 11S and 7S globulins. 8S globulin, which typically represents ~90% of the total globulins in mung bean, is a heterotrimeric protein having a molecular weight of ~150 kDa, with each monomer having a molecular weight of ~49 kDa. 11S globulin, which typically represents <10% of the total globulins in mung bean, has a molecular weight of ~64 kDa. 7S globulin, which typically represents <5% of the total globulins in mung bean, has a molecular weight of ~44-45 kDa. In order to examine changes in protein distribution throughout the protein isolation process, size exclusion chromatography (SEC) analyses was conducted on samples obtained through progressive stages of the isolation process.

FIGS. 14A and 14B provides a comparison of the protein molecular weight distributions from (A) samples obtained immediately after protein extraction from mung bean flour but prior to isoelectric precipitation (IEP), and (B) samples obtained after IEP and washing. IEP and washing of the extracts results in enrichment of total protein from 62.4% (+/−5.34%) to 70% (+/−11.7%), a reduction of non-protein species from 37.55% (+/−5.35%) to 30% (+/−11.7%). There also appears to be an increase in the amount of 8S protein (as a % of total non-agglomerated proteins), and a reduction in the amount of 11S protein (as a % of total non-agglomerated proteins).

An assessment of the protein profiles in supernatant and pellet fractions obtained from the IEP step and washing step, respectively, was performed to confirm the enrichment of 8S globulin and reduction of 11S globulin throughout the isolation process. FIGS. 14C and 14D show that IEP results in retention of the majority of 8S globulin in the precipitate (pellet) fraction, with very little 8S present in the supernatant; while the majority of 11S globulin is retained in the supernatant, with very little present in the precipitate. FIGS. 14E and 14F show that the wash step following IEP further enhances the 8S globulin population in the precipitate, leaving behind very little in the supernatant, while 11S globulin is barely detectable in the precipitate but makes up a substantial portion of the proteins in the supernatant. A substantial portion of total protein in the SEC analysis appeared as a very high molecular weight agglomerate, the identity of which was unclear, and could represent agglomerates of 8S and/or 11S globulins. However, the pattern of distribution of molecular weight species corresponding to 8S and 11S throughout the isolation process strongly suggest that 8S globulin is being enriched while 11S globulin is being reduced by the isolation process.

To determine at the level of protein identity whether 8S globulin was being enriched by the isolation process, the identity of proteins from extracts and isolates was investigated by two-dimensional-liquid chromatography-tandem mass spectrometry (2D-LC-MS/MS). Raw MS/MS spectra were searched against the *Vigna radiata* genome and a decoy sequence database. Spectrum counting was used to calculate the relative amount of each protein in reference to the total protein amount. Table 7 provides the predicted identities and representative amounts (expressed as % mean value) of proteins whose abundance was >1% of total protein in the sample. Values are provided for sample taken through just the extraction process ("Extract") and sample taken all the way through the isolation process, including IEP ("Isolate"). The percent increase of protein abundance in the isolate relative to the extract is expressed as "% enrichment."

TABLE 7

| NCBI accesion number | Protein ID | Protein Coverage | Extract | | Isolate | | Enrichment factor | % Enrichment |
| --- | --- | --- | --- | --- | --- | --- | --- | --- |
| | | | % Mean value | % SDV | % Mean value | % SDV | | |
| XP_014524354 (SEQ ID NO: 1) | PREDICTED: beta-conglycinin, beta chain-like | 70% | 10.59 | 0.44 | 11.58 | 0.28 | 1.09 | 9.38 |
| NP_001304229 (SEQ ID NO: 2) | beta-conglycinin, beta chain-like precursor | 72% | 10.48 | 0.44 | 11.30 | 0.25 | 1.08 | 7.76 |
| XP_014523938 (SEQ ID NO: 3) | PREDICTED: beta-conglycinin, beta chain-like isoform X2 | 70% | 9.30 | 0.35 | 10.69 | 0.94 | 1.15 | 14.93 |
| NP_001304202 (SEQ ID NO: 4) | beta-conglycinin, beta chain-like precursor | 81% | 8.17 | 0.36 | 9.54 | 0.99 | 1.17 | 16.74 |
| NP_001304231 (SEQ ID NO: 5) | beta-conglycinin, beta chain-like precursor | 74% | 7.28 | 0.47 | 7.57 | 1.41 | 1.04 | 4.03 |
| XP_014523923 (SEQ ID NO: 6) | PREDICTED: beta-conglycinin, beta chain-like | 57% | 6.48 | 0.21 | 7.92 | 1.10 | 1.22 | 22.34 |
| XP_014507363 (SEQ ID NO: 7) | PREDICTED: beta-conglycinin, beta chain-like | 54% | 6.26 | 0.19 | 7.82 | 0.99 | 1.25 | 24.79 |
| XP_014492536 (SEQ ID NO: 8) | PREDICTED: beta-conglycinin, beta chain-like | 85% | 5.91 | 0.23 | 5.77 | 0.75 | 0.98 | −2.36 |
| XP_014521758 (SEQ ID NO: 9) | PREDICTED: glycinin G4-like | 81% | 4.63 | 0.45 | 5.56 | 0.70 | 1.20 | 20.27 |
| XP_014515669 (SEQ ID NO: 10) | PREDICTED: beta-conglycinin, beta chain-like | 55% | 3.83 | 0.22 | 4.00 | 0.95 | 1.04 | 4.34 |
| XP_014523936 (SEQ ID NO: 11) | PREDICTED: beta-conglycinin, alpha' chain-like | 65% | 2.43 | 0.40 | 3.06 | 0.57 | 1.26 | 26.10 |
| XP_014524353 (SEQ ID NO: 12) | PREDICTED: beta-conglycinin, beta chain-like, partial | 66% | 1.86 | 0.25 | 2.47 | 0.58 | 1.33 | 32.62 |

FIG. 15 provides an amino acid sequence alignment of the above sequences (SEQ ID Nos:1-12) in both tabular and graphical form. The alignment indicates that SEQ ID Nos: 2-9 and 12 are at least within 50% identity to SEQ ID NO. 1, which is predicted to be a beta-conglycinin protein. These results demonstrate that isoelectric precipitation of mung bean extracts enriches for beta-conglycinins (up to 30%) relative to total proteins in mung bean isolate compositions.

7.9 Example 9: Protein Isolate Analyses

Four (4) non-consecutive batches of the mung bean protein isolate (prepared in accordance with Example 2) were analyzed to verify that the isolation process produces a consistent product. The results of the batch analyses are provided in Table 8. The results show that the isolation process produces a consistent product.

TABLE 8

Results of Analyses of 4 Non-Consecutive Batches of Mung Bean Protein Isolate

| | | Lot No. | | | |
|---|---|---|---|---|---|
| Parameter | Specification | Batch 1 (122.1) | Batch 2 (123.1) | Batch 3 (124.1) | Batch 4 (133.1) |
| Proximate analysis | | | | | |
| Moisture (%) | <7% | 4.2 | 3.4 | 4.3 | 3.1 |
| Protein (%) | >80% | 82.3 | 83.9 | 85.2 | 82.8 |
| Fat (%) | 3 to 5 | 4.2 | 4.0 | 3.7 | 4.4 |
| Ash (%) | <8% | 6.8 | 6.1 | 6.0 | 6.8 |
| Carbohydrate (%) | <10 | 7.0 | 5.4 | 4.5 | 5.4 |
| Microbiological | | | | | |
| Aerobic plate count (CFU/g) | <100,000 | 24,000 | 31,000 | 42,000 | 55,000 |
| *Listeria* spp. | Negative | Negative | Negative | Negative | Negative |
| *Salmonella* spp. | Negative | Negative | Negative | Negative | Negative |
| *Escherichia coli* | Negative | Negative | Negative | Negative | Negative |
| Heavy metals | | | | | |
| Arsenic (ppm) | ≤0.05 | <0.05 | <0.05 | <0.05 | <0.05 |
| Cadmium (ppm) | ≤0.05 | <0.05 | <0.05 | <0.05 | <0.05 |
| Lead (ppm) | ≤0.05 | <0.05 | <0.05 | <0.05 | <0.05 |
| Mercury (ppm) | ≤0.025 | <0.025 | <0.025 | <0.025 | <0.025 |

CFU = colony-forming units

7.10 Example 10: Amino Acid Profile

Analysis on the amino acid composition of 4 representative batches of the mung bean protein isolate described in Example 9 were performed, the results of which are provided in Table 9 below. The results indicate that the amino acid profile of the protein isolate is consistent from batch to batch, and the mung bean protein isolate contains a balanced amino acid profile.

TABLE 9

Amino Acid Composition of 4 Batches of the Mung Bean Protein Isolate

| | Lot No. (% wt of total protein) | | | |
|---|---|---|---|---|
| Amino Acid | Batch 1 (122.1) | Batch 2 (123.1) | Batch 3 (124.1) | Batch 4 (133.1) |
| Aspartic acid + asparagine | 12.41 | 12.44 | 12.33 | 12.18 |
| Threonine | 2.82 | 2.77 | 2.89 | 2.75 |
| Serine | 5.35 | 5.30 | 5.32 | 5.24 |
| Glutamic acid + glutamine | 18.69 | 18.60 | 18.08 | 18.15 |
| Glycine | 3.39 | 3.34 | 3.43 | 3.30 |
| Alanine | 3.97 | 3.94 | 4.04 | 3.89 |
| Valine | 5.51 | 5.49 | 5.49 | 5.39 |
| Methionine | 1.33 | 1.25 | 1.32 | 1.26 |
| Isoleucine | 4.86 | 4.86 | 4.89 | 4.81 |
| Leucine | 8.60 | 8.59 | 8.65 | 8.49 |
| Tyrosine | 3.24 | 3.23 | 3.33 | 3.19 |
| Phenylalanine | 6.83 | 7.01 | 6.92 | 6.84 |
| Lysine | 7.03 | 7.09 | 7.09 | 7.07 |
| Histidine | 2.87 | 2.86 | 2.90 | 2.85 |
| Arginine | 7.39 | 7.51 | 7.43 | 8.85 |
| Proline | 4.43 | 4.44 | 4.49 | 4.39 |
| Hydroxyproline | 0.04 | 0.03 | 0.03 | 0.03 |
| Cysteine | 0.33 | 0.32 | 0.38 | 0.33 |
| Tryptophan | 0.94 | 0.91 | 0.99 | 0.96 |

7.11 Example 11: Vitamins, Minerals, Carbohydrates, and Lipids

Analyses for vitamins, minerals, carbohydrates, and lipids on 3 non-sequential batches of the protein isolate (prepared in accordance with Example 2) were conducted, the results of which are provided in Table 10 below.

TABLE 10

Analyses for Vitamin, Mineral, Carbohydrate and Lipid Content of the Mung Bean Protein Isolate and Mung Bean Flour

| | Lot No. Lot Numbers | | |
|---|---|---|---|
| Parameter | IIIMNB75.3 | VMGB105.25 | VIPS109.21 |
| Vitamins | | | |
| Vitamin A (IU/100 g) | | | |
| Beta-carotene | <200 | <200 | <200 |
| Retinol | <200 | <200 | <200 |
| Vitamin C (mg/100 g) | | | |
| Ascorbic acid | <0.1 | <0.1 | <0.1 |
| Vitamin D (IU/100 g) | | | |
| D2 (ergocalciferol) | N/A | N/A | N/A |
| D3 (cholcalciferol) | <200 | <200 | <200 |
| Vitamin B5 (mg/100 g) | | | |
| Calcium pantothenate | 0.62 | 0.93 | 0.34 |
| Vitamin B6 (mg/100 g) | | | |
| Pyridoxine HCl | 0.09 | 0.07 | 0.05 |
| Vitamin B12 (µg/100 g) | | | |
| Cyanocobalamin | 10.10 | <2 | <2 |
| Vitamin K1 (µg/100 g) | | | |
| Phytonadione | 39.22 | 37.13 | 40.24 |
| Vitamin K2 (µg/100 g) | | | |
| MK-4 | <20 | <20 | <20 |
| MK-7 | <50 | <50 | <50 |
| Tocopherols (mg/100 g) | | | |
| Beta- | 0.006 | 0.01 | 0.007 |
| D-alpha- | 1.11 | 2.4 | 2.5 |
| Delta- | 0.02 | 0.04 | 0.09 |
| Gamma- | 0.78 | 2.0 | 1.49 |
| Thiamin (mg/100 g) | 0.13 | 0.12 | 0.10 |
| Riboflavin (mg/100 g) | 0.13 | 0.09 | 0.06 |
| Niacin (mg/100 g) | 0.90 | 0.13 | 0.47 |
| Folic acid (µg/100 g) | 3.55 | 4.78 | 7.59 |
| Biotin (µg/100 g) | <2 | <2 | <2 |
| Minerals | | | |
| Calcium (mg/100 g) | 116 | 44.27 | 22.20 |
| Iron (mg/100 g) | 10.68 | 8.27 | 7.81 |
| Sodium (mg/100 g) | 2,348 | 979 | 1,364 |
| Potassium (mg/100 g) | 828 | 886 | 392 |
| Magnesium (mg/100 g) | 108 | 143 | 114 |
| Phosphorus (mg/100 g) | 570 | 545 | 494 |
| Zinc (µg/100 g) | 3,210 | 1,584 | 897 |
| Copper (mg/100 g) | 1.97 | 1.68 | 1.39 |
| Molybdenum (µg/100 g) | 3.85 | 2.53 | 170 |
| Selenium (µg/100 g) | 0.78 | 0.41 | 23.26 |
| Lipids | | | |
| Fat (%) | 3.08 | 3.36 | 3.36 |
| Saturated | 1.42 | 1.60 | 1.38 |
| Monounsaturated | 0.318 | 0.255 | 0.212 |
| Polyunsaturated | 1.29 | 1.35 | 1.51 |
| Trans | 0.05 | 0.15 | 0.26 |
| Carbohydrates | | | |
| Starch | Absent | Absent | Absent |
| Dietary fiber (g/100 g) | <0.5 | <0.5 | <0.5 |

N/A = not available

7.12 Example 12: Environmental Contaminants

7.12.1 Pesticide Residues

Considering that the mung bean protein isolate is derived from a natural source, analyses for a number of chlorinated and organophosphate pesticide residues on 3 non-consecutive batches of the protein isolate were conducted. Chlorinated pesticides tested for included alachlor, aldrin, alpha-BHC, alpha-chlordane, beta-BHC, DDD, DDE, DDT, delta-BHC, dieldrin, endosulfan I, endosulfan II, endosulfan sulfate, endrin, endrin aldehyde, gamma-BHC, gamma-chlordane, heptachlor, heptachlor epoxide, methoxyclor, and permethrin. Organophosphate pesticides tested for included azinophos methyl, carbophenothion, chlorfenvinphos, chlorpyrifos methyl, diazinon, dichlorvos, dursban, dyfonate, ethion, fenitrothion, malathion, methidathion, methyl parathion, parathion, phosalone, and pirimiphos methyl. The results of the batch analyses are provided in Table 11, and indicate that the level of chlorinated and organophosphate pesticide residues for the mung bean protein isolate (prepared in accordance with Example 2) is below the level of detection of 0.1 ppm.

TABLE 11

Analyses for Residual Chlorinated and Organophosphate Pesticides in Representative Batches of the Mung Bean Protein Isolate and Mung Bean Flour

| | | Manufacturing Lot No. Lot Numbers | | |
|---|---|---|---|---|
| Parameter | Specification | IIIMNB75.3 | VMGB105.25 | VIPS109.21 |
| Chlorinated (ppm) | ≤0.1 | <0.1 | <0.1 | <0.1 |
| Phosphates (ppm) | ≤0.1 | <0.1 | <0.1 | <0.1 |

7.12.2 Dioxins and Polychlorinated Biphenyls

In addition to pesticide residues, 3 non-consecutive batches of the mung bean protein isolate (prepared in accordance with Example 2) were also analyzed for residues of dioxins and polychlorinated biphenyls (PCBs). The results of the analyses are provided in Table 12. These compounds were determined to be either absent from the tested materials or present at levels that were of no toxicological significance.

TABLE 12

Analyses for Residual Dioxin[a] and Polychlorinated Biphenyls[b] in Representative Batches of the Mung Bean Protein Isolate and Mung Bean Flour

| Parameter | Level of Detection | Lot No. Lot Numbers | | |
|---|---|---|---|---|
| | | IIIMNB75.3 | VMGB105.25 | VIPS109.21 |
| Dioxins* | <1 ppt | 2.2 | 2.4 | 0.55 |
| Total PCB | <0.5 ppb | 0.315 | 0.977 | 0.002 |
| Monochloro | <0.5 ppb | ND | ND | ND |
| Dichloro | <0.5 ppb | 0.311 | 0.967 | ND |
| Trichloro | <0.5 ppb | ND | ND | ND |
| Tetrachloro | <0.5 ppb | ND | ND | ND |
| Pentachloro | <0.5 ppb | 0.0037 | 0.0103 | 0.0021 |
| Hexachloro | <0.5 ppb | ND | ND | ND |
| Heptachloro | <0.5 ppb | ND | ND | ND |
| Octachloro | <0.5 ppb | ND | ND | ND |
| Nonachloro | <0.5 ppb | ND | ND | ND |
| Decachloro | <0.5 ppb | ND | ND | ND |

ND = not detected;
PCB = polychlorinated biphenyls;
ppb = parts per billion;
ppt = parts per trillion.
[a]Environmental Protection Agency (EPA) Method 1613B [high resolution gas chromatography/high resolution mass spectrometry (HRGC/HRMS)].
[b]Environmental Protection Agency (EPA) Method 1668A (HRGC/HRMS).

7.12.3 Mycotoxins

Non-sequential batches of the mung bean protein isolate (prepared in accordance with Example 2) were analyzed for the presence of mycotoxins, including aflatoxin B1, B2, G1, G2, and ochratoxin A, by liquid chromatography-mass spectrometry (LC-MS). The results of the analyses provided in Table 13 indicate that the protein isolate is devoid of any residual mycotoxins.

TABLE 13

Analyses for Residual Mycotoxins in Representative Batches of the Mung Bean Protein Isolate and Mung Bean Flour

| Parameter | Lot No. Lot Numbers | | |
|---|---|---|---|
| | IIIMNB75.3 | VMGB105.25 | VIPS109.21 |
| Aflatoxin B1[a] | <5 ppb | <5 ppb | <5 ppb |
| Aflatoxin B2[a] | <5 ppb | <5 ppb | <5 ppb |
| Aflatoxin G1[a] | <5 ppb | <5 ppb | <5 ppb |
| Aflatoxin G2[a] | <5 ppb | <5 ppb | <5 ppb |
| Ochratoxin A[b] | <7 ppb | <7 ppb | <7 ppb |

[a]Limit of detection = 5 to 10 ppb
[b]Limit of detection = 10 ppb

7.13 Example 13: Anti-Nutritional Factors

Dietary anti-nutritional factors are chemical substances that can adversely impact the digestibility of protein, bioavailability of amino acids and protein quality of foods (Gilani et al., 2012). The anti-nutritional factors reported in mung bean are tannins, phytic acid, hemagglutinins (lectins), polyphenols, trypsin inhibitors, □-amylase inhibitors, and protease inhibitors (Dahiya et al., 2015), which have been reported to be partially or completely removed or degraded during certain processing steps such as dehulling, germination, soaking, and heating (Mubarak, 2005).

The presence of protein-based anti-nutritional factors in representative batches of the mung bean protein isolate (prepared in accordance with Example 2) and mung bean flour was analyzed using a 2-dimensional nano liquid chromatography-mass spectrometry/mass spectrometry (LC-MS/MS) method combined with a proteomic analysis. The results provided in Table 14 indicated that the protein isolation process resulted in a decrease in relative abundance of lectin and protease inhibitor proteins as compared to the mung bean flour samples. Following proteomic analyses no matches to known □-amylase inhibitors were identified. In a separate analysis, the level of lectins in 3 representative batches of each the protein isolate and mung bean flour was analyzed, and the results showed low levels of lectins (<0.05 mg/g) in these samples.

TABLE 14

Relative Abundance of Protein-Based Anti-Nutritional Factors in Representative Batches of the Mung Bean Protein Isolate and the Mung Bean Flour

| Anti-Nutritional Factor | Protein Isolate (%) | | | | | Flour (%) | | | | |
|---|---|---|---|---|---|---|---|---|---|---|
| | 15-686.0317-119.1 | 15-686-0319-120.1 | 15-686.0324-121.1 | 15686.0331-122.1 | 15-686.0402-123.1 | 15-686.0317-MNB-16-0001 | 15-686-0319-MNB-15-0012 | 15-686.0324-MNB-15-0020 | 15686.0331-MNB-16-0001 | 15-686.0402-MNB-16-001 |
| Lectin[a] | ND | 0.001 | 0.024 | ND | ND | ND | 0.001 | 0.032 | ND | ND |
| Protease inhibitor[b] | 0.0075 | 0.00775 | 0.0082 | 0.01 | 0.01 | 0.015 | 0.0228 | 0.03375 | 0.027 | 0.0172 |

ND = not detected
[a]Average of protein accession no. XP_014512565 and XP_014514843.
[b]Average of protein accession no. XP_014505181, XP_014501457, XP_014516943, XP_014517066, XP_014521704, and XP_014522196.

In addition to protein-based anti-nutritional factors (i.e., protease inhibitors, alpha-amylase inhibitors, and lectins), levels of non-protein-based anti-nutritional factors (i.e., polyphenols and phytic acid) were also measured in several representative batches of the mung bean protein and mung bean flour. Generally, low levels of total polyphenols were identified in the protein isolate (98 to 203 mg gallic acid equivalent (GAE)/100 g), as compared to the levels in the mung bean flour (117 to 344 mg GAE/100 g). Levels of phytic acid ranged from 759 to 918 mg/100 g in the protein isolate, as compared to a phytic acid range of 685 to 716 mg/100 g in the mung bean flour.

7.14 Example 14: Allergenicity

A comparative protein analysis was conducted of 5 putative protein allergens associated with mung bean according to the AllergenOnline database (http://www.allergenonline.org/) with a union set of 1,867 proteins identified across 5 batches of mung bean flour and their corresponding protein isolates (FARRP, 2016). In total, 18 sequences in the flours and protein isolates matched 4 of the putative mung bean allergens. The matches had >50% sequence identity calculated over full-length alignments, with E-values lower than 1e-7. The putative allergens were seed albumin (CAA50008.1, 4 hits), pathogenesis-related protein-10 (PR-10) (AAX19889.1, 2 hits), 8S globulin beta-isoform precursor (ABG02262.1, 12 hits), and 8s globulin alpha-isoform precursor (ABW23574.1, 12 hits). The relative abundance of putative allergen matches in representative batches of the protein isolate and the mung bean flour are shown in Table 15. The protein isolation process substantially removes or reduces the levels of the PR-10 protein allergen to those that are negligible to none. More specifically, PR-10 protein allergens were detected at levels of 0.002 to 0.003% in the mung bean flour, and when levels of these allergens were measured in the protein isolate, trace levels (0.001%) were detected in one batch (Lot No. 15-686-0319-120.1), while no PR-10 protein allergens were detected in the other 4 batches. The protein isolation process did not seem to change the relative abundance of the putative albumin and globulin allergens to a significant degree as compared to the mung bean flours, and the differences noted are likely within experimental error.

A similar analysis was performed for the union set of 1,083 proteins identified in spray-dried protein isolate (finished product; Lot No. 123.1), and uncooked, and cooked samples prepared from the spray-dried protein isolate (Table 16). More specifically, the spray-dried sample was resuspended in 100 mM Hepes pH 8.6 and diluted in 10 mM sodium phosphide (NaP) pH 8.0 buffer to 0.5 mg/mL. Next, to prepare the uncooked sample, the spray-dried material was solubilized in water to make a 12% w/w protein solution and diluted in 10 mM NaP pH 8 buffer to 0.5 mg/mL. The cooked sample was prepared in a similar manner with an additional cooking step (250° F. for 10 min) prior to addition of NaP buffer. No pathogenesis-related protein 10 (AAX19889.1) matches were detected. As shown in Table 16 below, the protein isolation process and cooking do not significantly alter the relative abundance of putative allergens (all changes were within 3% of the initial value for each sample). However, during the protein isolation process, levels of putative 8S globulin isoform precursor and alpha subunit, both of which are major protein storage sources and function proteins in mung bean seeds, were slightly enriched or depleted.

TABLE 16

Relative Abundance of Putative Allergen Matches in Spray-Dried, Uncooked, and Cooked Mung Bean Protein Isolate Samples

| Protein Type | Lot No. 123.1 | | |
|---|---|---|---|
| | Spray-Dried (%) | Uncooked (%) | Cooked (%) |
| 8S globulin[a] | 8.160 | 8.026 | 8.157 |
| Albumin[b] | 0.351 | 0.482 | 0.382 |

[a]Average of protein accession no. XP_014524354, XP_014523938, NP_001304202, XP_014523923, XP_014507363, NP_001304231, XP_014492536, XP_014523936, XP_014524353, and XP_014523928.

[b]Protein accession no. XP_014513134

TABLE 15

Relative Abundance of Putative Allergen Matches in Representative Batches of the Mung Bean Protein Isolate and Mung Bean Flour

| | Lot No. | | | | | | | | | |
|---|---|---|---|---|---|---|---|---|---|---|
| | Protein Isolate (%) | | | | | Flour (%) | | | | |
| Protein Type | 15-686.0317-119.1 | 15-686-0319-120.1 | 15-686.0324-121.1 | 15686.0331-122.1 | 15-686.0402-123.1 | 15-686.0317-MNB-16-0001 | 15-686-0319-MNB-16-15-0012 | 15-686.0324-MNB-15-0020 | 15686.0331-MNB-16-0001 | 15-686.0402-MNB-16-001 |
| Albumin[a] | 0.153 | 0.159 | 0.242 | 0.071 | 0.166 | 0.262 | 0.367 | 0.258 | 0.437 | 0.263 |
| 8S globulin[b] | 7.021 | 6.496 | 6.354 | 6.755 | 6.693 | 6.048 | 6.294 | 5.861 | 6.037 | 6.093 |
| PR-10[c] | ND | 0.001 | ND | ND | ND | 0.002 | 0.003 | ND | 0.002 | 0.002 |

ND = not detected

[a]Average of protein accession no. XP_014524354, NP_001304229, XP_014523938, XP_014523928, XP_014523936, XP_014524353, XP_014515669, NP_001304202, XP_014523923, XP_014507363, XP_014492536, and NP_001304231.

[b]Average of protein accession no. XP_014513134, NP_001304082, XP_014511316, and XP_014512898.

[c]Average of protein accession no. XP_014506982 and XP_014508691.

7.15 Example 15: Mung Bean Protein Isolate Stability

A 24-month stability study is currently underway, wherein 4 non-consecutive batches of the mung bean protein isolate (prepared in accordance with Example 2) are stored at room temperature in airtight containers. The composition of the protein isolate (i.e., moisture, protein, oil, ash, and carbohydrates) is measured at various time points throughout the study period (i.e., 4, 6, 9, 12, 18, and 24 months). The interim results of the stability study are presented in Table 17 below. The moisture, protein content, oil content, ash, and carbohydrates of the mung bean protein isolate does not significantly change from the established product specifications, suggesting that the protein isolate is stable when stored up to 6 months. The values for the oil/lipid content of the protein isolate are presented below, and these values do not significantly change following storage up to 6 months.

TABLE 17

Interim Results of Stability Testing of Mung Bean Protein Isolate when Stored at Room Temperature

| | Lot No. | | | | | | | |
|---|---|---|---|---|---|---|---|---|
| | Batch 1 (122.1) | | Batch 2 (123.1) | | Batch 3 (124.1) | | Batch 4 (133.1) | |
| Parameter | Week 1 | Week 26 | Week 1 | Week 25 | Week 1 | Week 19 | Week 1 | Week 15 |
| Moisture (%) | 4.78 | 5.39 | 4.66 | 5.40 | 5.14 | 5.34 | 4.76 | 5.16 |
| Protein (%) | 84.7 | 86.9 | 86.7 | 86.3 | 86.8 | 86.6 | 85.5 | 85.1 |
| Oil (%) | 0.84 | 0.64 | 0.65 | 0.62 | 0.70 | 0.34 | 0.70 | 0.55 |
| Ash (%) | 7.16 | 5.98 | 6.33 | 5.99 | 6.14 | 6.08 | 6.73 | 8.91 |
| Carbohydrate (%) | 6.52 | 5.79 | 5.66 | 6.39 | 5.72 | 6.24 | 6.71 | 4.68 |

7.16 Example 16: Protein Digestibility and Corrected Amino Acid Score for the Mung Bean Protein Isolate The PDCAAS rating, which was proposed by the Food and Agriculture Organization of the United Nations (FAO) in 1989, was adopted by the FDA in 1993 as "the preferred best" method to evaluate protein quality (FAO/WHO, 1991; U.S. FDA, 1993). This method is based on the principle that the nutritive value of a protein depends upon its capacity to provide nitrogen and amino acids in adequate amounts to meet human (essential) amino acid requirements. While the quality of some proteins can be assessed directly using amino acid score values, others cannot because of poor digestibility and/or bioavailability. Consequently, both amino acid composition and digestibility measurements are considered necessary to accurately predict the protein quality of foods for human diets (FAO/WHO, 1991). In practice, the PDCAAS relates the content of the first limiting essential amino acid of the test protein to the content of the same amino acid in a reference pattern of essential amino acids (i.e., amino acid score), correcting for fecal digestibility, which is often measured using a rat balance assay (FAO/WHO, 1991).

The PDCAAS for the mung bean protein isolate (prepared in accordance with Example 2) is calculated using the following formula, where the reference pattern of essential amino acids is based on amino acid requirements of 2- to 5-year-old pre-school aged children, which was determined by the FAO/WHO/UNU in 1985 (see Table 18).

$$PDCAAS(\%) = \frac{\text{mg of limiting amino acid in 1 g of test protein}}{\text{mg of same amino acid in 1 g of reference protein}} \times \text{fecal digestibility} \times 100\%$$

TABLE 18

Calculation of Amino Acid Scores for the Mung Bean Protein Isolate

| Essential Amino Acid | Total Amino Acid Content* (mg/g protein) | FAO Reference Requirements for Amino Acids** (mg/g crude protein) | Calculated Amino Acid Scores Using FAO Reference Requirements |
|---|---|---|---|
| Histidine | 28.7 | 19 | 1.51 |
| Isoleucine | 48.6 | 28 | 1.73 |
| Leucine | 85.8 | 66 | 1.30 |
| Lysine | 70.7 | 58 | 1.22 |
| Methionine Cysteine | 16.3 | 25 | 0.65 |
| Tyrosine Phenylalanine | 101.5 | 63 | 1.61 |
| Threonine | 28.1 | 34 | 0.83 |
| Tryptophan | 9.5 | 11 | 0.86 |
| Valine | 54.7 | 35 | 1.56 |

FAO = Food and Agriculture Organization of the United Nations
*The values for each amino acid is the mean of 4 batch data.
**Reference requirements for amino acids as determined by the FAO for 2- to 5-year-old pre-school aged children (FAO/WHO/UNU, 1985).

As presented in Table 18, the limiting amino acids in the protein isolate are the sulfur-containing amino acids, methionine and cysteine having the lowest amino acid score of 0.65. Taking the amino acid score of 0.65 into account and based on a true fecal digestibility of 84% reported for mung beans (Khan et al., 1979), the % PDCAAS for the mung bean protein isolate is calculated as 0.55 (i.e., 0.65×84%). In vivo fecal digestibility studies were conducted in rats using two batches of mung bean protein isolate. Digestibility of each isolate was assessed both on a diet of uncooked isolate and on isolate which had been prepared and cooked though a heating process. Test groups consisted of four male albino rats that were each fed a 15 g/day diet consisting of roughly 10% protein formulated with other vitamins, minerals and calories necessary for rat survival. Test groups were fed this diet for nine consecutive days, with fecal collection taking place during days 5-9. Fecal material was then analyzed for protein concentration, by way of nitrogen content, using the Kjeldahl method to assess the True Digestibility (TD) of the protein source. As seen in Table 19, the in vivo PDCAAS values are in agreement with in vitro values mentioned above, and are not affected by the cooking process. The average measured True Digestibility score of 96.4 for the mung bean protein isolate compares favorably with the measured True Digestibility score of 97.1 for the casein control.

TABLE 19

Fecal Digestibility of Cooked and Uncooked Mung Bead Protein Isolate in Rats

| | Lot No. | | | |
|---|---|---|---|---|
| | Batch 1 (124.1) | | Batch 2 (143.1) | |
| Parameter | Uncooked | Cooked (ML_16) | Uncooked | Cooked (ML_14) |
| True Digestibility | 95.696 | 97.321 | 97.004 | 94.754 |
| Amino Acid Score | 0.592 | 0.561 | 0.580 | 0.532 |
| PDCAAS | 56.65 | 54.60 | 56.26 | 50.41 |

7.17 Example 17: Thermal Characterization of Isolates from Mung Bean and Other Plant Sources Denaturation of mung bean protein isolate (prepared in accordance with Example 2) was determined by differential scanning calorimetry (DSC) as an indicator of thermal stability. Solids state differential scanning calorimeter (Q20, TA Instruments) was used to determine denaturation temperature. Temperature of endothermic peak can be associated with protein denaturation. Isolates from various plant sources were created by cryo-precipitation at low ionic strength. Isolate solutions adjusted by dilution with distilled water to 13% solids were used for DSC analysis. After equilibration at 40° C. the sample, enclosed in a hermetic aluminum pan, and an empty reference pan were heated from 40° C. to 120° C. with an increment of 3° C./min. Isolates from Mung bean, similarly to whole egg, showed significantly lower thermal stability (70° C.-78° C.) than materials from other plant sources (84° C.-101° C.). Denaturation temperatures of protein isolates are shown in FIG. 16 and summarized in Table 20 below.

TABLE 20

| | | DSC Denaturation Temp (° C.) | |
|---|---|---|---|
| Isolate ID | Source Name | Peak #1 | Peak #2 |
| 39.2 | Red Lentil | 87.93 | |
| 156.2 | Hutterite Soup | 101.14 | |
| 158.2 | Green Black Eye Pea | 84.19 | |
| 162.2 | Lina Cisco's Bird Egg | 84.71 | 96.38 |
| 165.2 | October | 84.68 | 95.69 |
| 168.2 | Creamy White Eye Pea | 84.88 | |
| 171.2 | Tiger Eye | 86.09 | 96.03 |
| 208a.43 | Mung Bean | 71.90 | |
| 213.37 | Mung Bean | 70.83 | 78.04 |
| | Whole Egg | 80.67 | |

Solid-state Differential Scanning calorimetry was used to study the unfolding thermodynamics of protein isolate purified from different mung bean sources. Proteins were isolated by low ionic strength precipitation at very high flow rates combined with cryo-precipitation method. Temperature scanning ranged from 40° C. to 100° C. at a rate of 4° C. per min. Melting temperatures vary from 77° C. to 85° C. as shown in FIG. 17.

Solid-state Differential Scanning calorimetry was used to study the unfolding thermodynamics of protein prepared by isoelectric precipitation at pH.5.6. Isolates before pasteurization (62.1), isolate after pasteurization (62.2), spray dried isolate (62.3) were solubilized at different percent solids and compared. Melting temperatures and heat absorbed by the material (enthalpy) are shown in FIGS. 18A and 18B respectively. Temperature scanning ranged from 40° C. to 100° C. at a rate of 5° C. per min. Spray Dried isolate denaturation temperature is higher (shifted up of 2° C. to 5° C.) and energy absorbed for denaturation is the same for all isolates and increases with % solids.

7.18 Example 18: Gelation: Water Binding Capacity and Structure Building Properties Table 21 shows the water binding capacity used to assess the ability of a plant isolate sample to retain liquid (water) after heat-induced gelation, following disruption via centrifugation. The higher the % WBC, the higher the amount of water retained. Plant isolates were normalized to 13% solids with distilled water, heated at 65° C., and 85° C. for 60 min and centrifuged at 4700 rpm for 15 min. The % WBC was calculated from the weight of serum released by the gel during centrifugation.

TABLE 21

| | | Water Binding Capacity % | |
|---|---|---|---|
| Isolate ID | Source name | 65 C. | 85 C. |
| 39.2 | Red Lentil | 37.30 | |
| 156.2 | Hutterite Soup | 45.50 | 65.28 |
| 158.2 | Green Black-Eyed Pea | 49.11 | 92.79 |
| 165.2 | October | 43.87 | 63.26 |
| 168.2 | Creamy White-Eyed Pea | 52.49 | 86.84 |
| 171.2 | Tiger Eye | 41.37 | 69.86 |
| 208a.43 | Mung Bean Batch 1 | 86.68 | 98.97 |
| 213.37 | Mung Bean Batch 2 | 69.50 | 97.87 |

FIG. 19 shows heat induced mung bean isolate gels show at both temperatures (65° C. and 85° C.) higher water binding capacity, than isolate gels from other plant sources, which indicates stronger gel network and increased functionality of mung bean isolates.

The strength of gel structure was determined after heat induced gelation at 65° C. for 10-90 min. After cooling down the samples were vigorously agitated by Vortex. Structure of heat induced gels from isolates from mung bean and other plant sources was visually evaluated and categorized based on following criteria and shown in Table 22:

TABLE 22

| Source ID | Source name | Structure category after heating at 65 C. for 10-90 min | | | | | | | | |
|---|---|---|---|---|---|---|---|---|---|---|
| | | 10 | 20 | 30 | 40 | 50 | 60 | 70 | 80 | 90 |
| 38 | Black Calypso | 0 | 0 | 0 | 0 | 0 | 0 | 0 | 1 | 1 |
| 82 | Yellow Split Pea | 0 | 0 | 0 | 0 | 0 | 0 | 0 | 0 | 0 |
| 104 | Vallarta Beans | 0 | 0 | 0 | 0 | 1 | 1 | 1 | 1 | 1 |
| 120 | Swedish Brown Beans | 0 | 0 | 0 | 0 | 0 | 0 | 0 | 0 | 0 |
| 185 | Anasazi Beans | 0 | 0 | 0 | 0 | 0 | 0 | 0 | 0 | 0 |
| 243 | Mung Bean Batch 1 | 0 | 0 | 0 | 1 | 3 | 4 | 4 | 4 | 5 |
| 208a | Mung Bean Batch 2 | 0 | 1 | 2 | 4 | 4 | 5 | 5 | 5 | 5 |

These results demonstrate that mung bean protein isolates show higher gelation and gel network building properties upon heating relative to other tested plant isolates.

7.19 Example 19: Rheological Characterization of Mung Bean Isolates and Other Plant Sources Using Dynamic Oscillatory Rheology Gelation of high purity protein isolates of mung bean, other plant sources and food applications of interest were characterized with dynamic oscillatory rheology. A discovery hybrid rheometer (TA Instruments) equipped with a parallel plate geometry (40 mm diameter) was used to monitor the material's storage (G') and loss (G") modulus during a temperature ramp from 45° C. to 95° C. under small deformation conditions (0.5% strain) at a constant angular frequency of 10 rad/s. The gelation temperature was recorded as the temperature where G' undergoes the highest relative increase. Following every oscillatory temperature ramp, the temperature of the material was reduced to 50° C. and an amplitude sweep test from 0.01% to 10% strain was carried out in order to record the gelled material's linear viscoelastic region.

FIG. 20 shows the gelation temperature of isolates from various mung bean sources: HCF-213, HCF-234, and HCF-208a have gelation temperatures comparable to that of a whole egg.

FIG. 21 visually depicts gelled mung bean isolates obtained from a single source but precipitated under different conditions in comparison to egg. While the formulated mung bean isolates do not gel at the same temperature as homogenized whole shelled eggs (see FIG. 22), they exhibit a viscoelastic profile similar to that of whole egg in the amplitude sweep, especially the isolate obtained by salt precipitation (see FIG. 23).

7.20 Example 20: Texture Characterization of Gelled Mung Bean Isolates Using Texture Profile Analysis (TPA)

Instrumental texture profile parameters were recorded using a Brookfield Texture Analyzer equipped with a 38 mm probe. Samples were submitted to two uniaxial compression cycles at a test speed of 1 mm/s, initially triggered by a 5 g load. Target compression distance was set to 7 mm, corresponding to 70% deformation. Hardness, cohesiveness, springiness, chewiness and resilience were determined and compared to food applications of interest. FIG. 24 compares the texture features of mung bean isolates formulated under different processes with that of various egg controls using a Principal Component Analysis 2-dimensional visualization. The texture of several purified protein isolates formulated using different Processes 1-4 (i.e. JP1-69, JP1-70, JP1-71) were shown to be comparable to that of an egg control in terms of hardness, cohesiveness, springiness, chewiness and resilience. Formulations were varied in the components used in protein modifying enzymes, hydrocolloid and salt levels. Purification parameters varied in pH, salt, acid, temperature and time.

7.21 Example 21: Foaming Capacity Test

A foaming capacity test was performed on mung bean isolates (prepared in accordance with Example 2) by measuring the % overrun after making a foam of protein solution (at a specified concentration) using a Cuisinart handheld mixer at speed 4 at room temperature for 4-6 min taking care that the samples are not over whipped. The % overrun was measured as a ratio of foam volume to volume of initial liquid. The foam was then held stationary for 30 min and % drainage was measured. % drainage, an indicator of foam stability, was measured as ratio of foam volume after 30 min to initial foam volume. Higher % drainage suggests low foam stability. FIG. 25 shows the results of % overrun and % drainage with 2 mung bean protein isolates in comparison to an egg white control.

7.22 Example 22: Characterization of Solubility of Isolates from Mung Bean

Solubility of mung bean isolates (prepared in accordance with Example 2) was measured using the technique of nephelometry. Nephelometry measures the amount of light scattered within a liquid sample, and quantifies the turbidity with high sensitivity. A NEPHELOstar Plus plate reader (BMG Labtech) was used to perform solubility measurements in a 96 well plate based format. The NEPHELOstar uses a polarized helium-neon laser at 632.8 nm. The nephelometer settings that were used include a beam focus of 2.5 mm and intensity of 10%. Orbital averaging was used, with a diameter of 3 mm. The measurement time per well was 0.26 s with a positioning delay (settling time) of 0.1 s. Before measurement each plate was subject to 10 s of double-orbital shaking at 500 rpm to homogenize the sample solutions within the wells. Solubility measurements were performed at room temperature. Clear, flat bottom 96 Well Greiner Microplates were used. Solubility of the mung bean isolate was studied under various solvent conditions, including at pH 3, 5, and 7 as well as in the presence of 0, 0.4, 0.8, and 1 wt % NaCl. Citrate and disodium phosphate buffers were used to control the pH of the aqueous fractions. A concentration gradient of isolate ranging from 0-8.9 wt % protein was used to determine the protein solubility at all 12 solvent conditions (3 pHs×4 NaCl concentrations). Each measurement was run in triplicate to ensure reproducibility.

Solubility was determined by performing a linear fit of the data of Relative Nephelometer Units (RNUs) versus protein concentration. Two lines were fit and the linear regression was optimized to obtain two lines of best fit for the increase in RNU that occurs as protein concentration increases. The solubility value was determined to be the protein concentration at which these two lines intersected one another. Data provided in FIG. 26 corresponds to these values of solubility. In nearly all the conditions tested, aqueous solutions comprising mung bean protein isolate showed superior solubility when compared to milk, homogenized whole egg, chia, sorghum flour, and organic milk.

7.23 Example 23: Characterization of Foam Stability of Isolates from Mung Bean Foam stability measurements were performed on a Dynamic Foam Analyzer (DFA100) instrument from Kruss. Three measurement modes were used to collect the maximal amount of information on foam stability: foam and liquid level height (measured via light scattering), structure (measured via image analysis of time lapse images of foam), and liquid content (measured via conductivity measured along a string of electrodes placed at different heights throughout the sample). Advance software was used for data analysis. The following instrument settings were used: air flow rate of 0.2 L/min, with light illumination of 40% for height measurements and light illumination of 75% for structure measurements. 45 mL of aqueous protein solution was used and twice that volume (90 mL) of air was mechanically purged through the liquid. Air was passed through a 16-40 um sintered glass frit in the DFA100. The stability of the foam was evaluated over a time period of 10 minutes, which began immediately after the purging of air through the sample. A data sampling interval of 6 frames per minute (fpm), resulting in 60 images that were analyzed for bubble structure. The camera was positioned at a height of 55 mm above the bottom of the measurement vessel.

Aqueous protein samples were prepared under various solvent conditions, including at pH 3, 5, and 7 and protein concentrations of 4.2 and 8.9 wt % protein. Citrate and disodium phosphate buffers were used to control the pH of the aqueous fractions. Each sample was run in triplicate.

The stability of the foam was calculated as the foam index. It is a measure of the maximum foam height and the decay of the foam height over time. The total height of the foam and solution was integrated in time from the end of the air purge until the end of the experiment (10 minutes). This integration incorporates the effects of both the maximum foaming capacity (as described by the maximum height) and the stability (determined by the loss in height of the foam and solution). A high foam index indicates a well-performing material for foaming. Data in FIG. 27 reports the foam quality of Mung Bean Isolates and several reference materials.

7.24 Example 24: Characterization of Emulsion Stability of Isolates From Mung Bean Emulsion stability measurements were performed on oil in water emulsions containing Mung bean protein isolate in order to study the emulsification properties of the isolates. First, aqueous solutions of isolate under various solvent conditions were prepared. Final protein concentrations in the emulsions were 4.2 and 8.9 wt % protein, and aqueous fractions were prepared at pH 3, 5, and 7 as well as in the absence and presence of NaCl (1 wt %). Citrate and disodium phosphate buffers were used to control the pH of the aqueous fractions. Aqueous solutions were mixed by vortexing at high speed for about 10 seconds. Canola oil was added at a mass ratio of/3 of the total volume via serological pipette and vortexed at high speed for 10 seconds. The total volume (about 15 mL) was homogenized at 5000 rpm using a 20 mm saw tooth probe with a Pro Scientific PRO25D homogenizer for 4 minutes. The emulsion was then distributed into 4 mL glass vials using a positive displacement pipette, dispensing 3 mL of sample per glass vial. Each sample was run in triplicate. Directly prior to measurement the sample was homogenized for 4 min at 5000 rpm using a 7 mm diameter saw tooth prive with the Pro Scientific PRO25D homogenizer.

A Formulaction Turbiscan Lab instrument was used to study emulsion stability. This instrument uses light scattering to characterize phase separation within an emulsion. Raw data collected by the instrument includes values of transmittance and backscattering as a function of the height of the sample and time. Each sample was measured over a period of 10 minutes, with the backscattering of incident light on the sample measured at an interval of 25 s.

Backscattering data from Turbiscan measurements was processed in order to evaluate overall emulsion stability as a function of time. Backscattering (BS) at the final time point of 10 minutes was examined after subtracting a baseline of backscattering measured at time point 0 minutes (Equation 1). This change in backscattering (ΔBS) at 10 minutes over the entire height of the sample was used to extract an index of emulsion stability, referred to as the Stability index (SI) (Equation 2, FIG. 28). The stability index is essentially the area under the curve of ΔBS versus height, and is defined by the equations shown below.

$$\Delta BS_{h,t} = BS_{h,t} - BS_{h,0} \tag{1}$$

$$SI = \frac{\sum_{h=0}^{H} |\Delta BS_{h,t} - \Delta BS_{h,t-1}|}{H} + SI_{t-1} \tag{2}$$

The higher the stability index, the less stable the emulsion. Lower stability indices indicate higher emulsion stability.

7.25 Example 25: Liquid Egg Substitute

FIG. 29 (A-D) visually depicts four liquid egg substitute formulations comprising mung bean protein isolate.
A—Mung bean isolate
B—Mung bean isolate with iota-carrageenan & gum arabic
C—Mung bean isolate with konjac & xanthan gum
D—Mung bean isolate with gellan FIG. 30 shows a comparison of viscosity v. shear rate in a liquid scramble formulation. Egg-like patty formulations with mung bean protein isolates and gellan exhibit similar viscosity profiles as regular eggs. Their Newtonian behavior makes them pourable and eligible to be used as a liquid scramble egg substitute product.

A representative formulation of an egg-like patty includes: water (75-85%); mung bean protein isolate (10-15%); oil (5-10%); hydrocolloid (0.1-3%) (which includes either one of the following combinations: (1) high-acyl & low-acyl gellan gum; (2) iota-carrageenan & gum arabic; (3) konjac & xanthan gum); starches (0.1-6%); flavors (1-2%); and salt (<1%). The emulsion mixture is at pH 5.6-6.8.

High purity isolates from mung bean are rehydrated to 80% moisture content and adjusted to pH 6.0 with 1M NaOH. Emulsion of plant protein isolate, oil, hydrocolloid, salt and other ingredients were prepared using a Pro Scientific shear mixer operated at 5000 rpm for 4 min at room temperature. Emulsion is deposited in round molds (3 in diameter), and the amount deposited per mold is 50 g. Convection oven set at 220° F. for 55 min.

7.26 Example 26: Preparation of a Scramble Product Using Transglutaminase

Preparation and use of a mung bean protein concentrate or isolate was pre-reacted with transglutaminase during processing. Transglutaminase was added to an aqueous intermediate process stream comprising a mung bean protein, incubated at a defined temperature for a defined period of time followed by inactivation of the enzyme by heat applied for a short period of time, or by addition of oxidizing agent, such as hydrogen peroxide. The transglutaminase enzyme was applied at multiple points in the process of preparing a protein concentrate or isolate. The result of this process is a purified, stable cross-linked, highly functional mung bean protein-rich product which can be used in refrigerated or room temperature shelf-stable liquid plant-based food product emulsions.

After contacting the protein with the transglutaminase powder, it was noted that 0.2% transglutaminase treated extract was more turbid than 0% transglutaminase, indicative of protein aggregation in the transglutaminase treated extract. FIG. 31 shows the extracts after 15 minute 50° C. incubation, but before isoelectric precipitation. It was evident that all extracts treated with transglutaminase were more turbid as more transglutaminase was added, again indicative of protein aggregation in the transglutaminase treated extract. It was also noted that after the cooling portion of the process, the higher transglutaminase extracts started forming curds.

Additional tests were performed to determine how different amounts of transglutaminase powder added to 900 g extract would affect the final isolate in a scramble formula. FIG. 32 shows the varying amounts of transglutaminase powder (as percentage of extract weight). Increased amounts of transglutaminase appeared to result in rubbery pellets or curds.

Incorporating preferred embodiments of protein reacted with the transglutaminase in a scramble analog resulted in characteristics that were fluffier, more airy and/or less mealy. See FIG. 33, which depicts the improved scramble formulation with 0.0125% transglutaminase shown during the cooking process; and FIG. 34, which compares the desired scramble that was characteristically fluffier, more airy and less mealy, to a scramble made without transglutaminase.

7.27 Example 27: Analysis of Transglutaminase-Reacted Mung Bean Protein

To determine whether and to what extent transglutaminase may be cross-linking lipoxygenase to the protein globulins of interest in the prepared mung bean isolates, isolates were prepared as depicted in FIG. 1B, that is, reacted with varying amounts of transglutaminase prior to isoelectric precipitation. Supernatants and pellets (containing a globulin rich heavy fraction) were collected post precipitation, run on SDS PAGE and the amounts of lipoxygenase per sample were determined by Western Blotting.

FIG. 35 depicts a Western blot stained for lipoxygenase, all lanes containing about 5 ug protein samples from supernatant (lanes 4-9) or pellet (lanes 10-12), whereby the samples have been reacted with varying amounts of transglutaminase as follows:

Lane Key (all Supernatants and Pellets are Post-IEP):

| | |
|---|---|
| 1. | Extract |
| 2. | 0% TG Supernatant |
| 3. | Ladder |
| 4. | 0.0125% TG Supernatant |
| 5. | 0.025% TG Supernatant |
| 6. | 0.05% TG Supernatant |
| 7. | 0.1% TG Supernatant |
| 8. | 0.15% TG Supernatant |
| 9. | 0.2% Supernatant |
| 10. | 0% TG Pellet |
| 11. | 0.0125% TG Pellet |
| 12. | 0.025% TG Pellet |

As evident in lanes 10-12, no lipoxygenase was carried over to the globulin-rich pellets, while lanes 2 and 4-9 show that lipoxygenase clearly remained in the supernatant. Without being bound by theory, while it was anticipated that the transglutaminase might cross-link lipoxygenase to the desired proteins, this result implies that the transglutaminase is either not cross-linking lipoxygenase or not cross linking to the protein globulin of interest, which was unexpected.

To determine whether any high molecular weight protein complexes are formed in pellets treated with transglutaminase, the membrane was Ponceau red stained. As shown in FIG. 36, there appears to be a high molecular weight protein of about 100-150 kda (shown in oval). In addition, the amount of 50 Kda globulin band in these pellets is decreased in comparison to 0% transglutaminase. This could indicate a complex formed by the globulins linking together. Additional tests are contemplated to discern the complex further.

To determine the effect of transglutaminase treatment on the yield of protein resulting from the isolation procedure, protein amounts were assessed in both supernatant and pellets from samples reacted with varying amounts of transglutaminase. As shown in FIG. 37, protein concentration of the supernatants decreased with increasing amounts of transglutaminase. As shown in FIG. 38, the % dry yield of final protein isolates (g solids in pellet/g flour used) increased after 0.05% transglutaminase in extract. Together, these results suggest that more protein is retained in the globulin-rich pellet fraction, and total protein yield is increased, with increasing amounts of transglutaminase treatment during the isolation process.

Together, these results suggest that more protein is retained in the globulin-rich pellet fraction, and total protein yield is increased, with increasing amounts of transglutaminase treatment during the isolation process.

7.28 Example 28: Effect of Phosphates on Mung-Bean Derived Egg Analogue Compositions Phosphates are commonly used as buffering and emulsifying salts in dairy and meat protein systems. The type of phosphate salt and their concentration used in protein systems have been shown to influence textural and functional properties of proteins. This example illustrates the influence of three types of phosphates ((1) disodium phosphate; (2) sodium hexametaphosphate; and (3) tetrasodium pyrophosphate), and their concentration on functionality of mung bean protein isolate in egg patty analogue and in liquid egg analogue products.

7.28.1 Influence of Concentration of Disodium Phosphate on Textural Properties of Egg Patty Analogue Made Using Mung Bean Protein Isolate Egg patty analogue was prepared using mung bean protein isolate with varying levels of disodium phosphate, water, canola oil, enzyme as described in Table 23. All ingredients were blended to make a homogenous mix. This mix was heated to 40-55° C. and poured into circular silicone molds holding 50 g in each cavity. The molds were incubated at 40-50° C. for 20-60 minutes after which they were baked at 250-275° F. for 45-60 min in a convection oven to make patties. After baking, patties were cooled to room temperature, demolded and used for texture profile analysis.

Texture profile analyses of mung bean protein patty was conducted using a Brookfield Texture Analyzer equipped with a 38 mm diameter cylindrical probe. Mung bean patty samples were cut into cylinders with 2.54 cm diameter and height of 1 cm. Samples were analyzed using two uniaxial compression cycles triggered at a 5 g load. Target compression distance was set to 0.7 cm, corresponding to 70% deformation performed at a rate of 1 mm/s. Hardness, cohesiveness, springiness, and resilience of mung bean protein patty were determined and compared to that of commercial egg patty product.

TABLE 23

| Ingredient | % in product |
| --- | --- |
| Mung bean protein isolate | 11-16.00 |
| Disodium phosphate | [0.00-0.06-0.13-0.25-0.37-0.50] |
| Water | 75-79.00 |
| Oil | 6-8 |
| Enzyme | 0.001-0.002 |
| Emulsifier | 0.2-0.7 |

Adding disodium phosphate to the formulation between 0.01-0.5% improved overall organoleptic properties of mung bean patty and closely mimicked egg patty texture (FIG. 39). In absence of DSP (at 0%) mung bean patty had significantly lower hardness, cohesiveness, springiness and resilience compared to an egg patty. Upon addition of DSP there was an increase in hardness, cohesiveness, springiness and resilience of the mung bean patty that were comparable to that of egg patty. There was no significant change in texture parameters between 0.06 and 0.5% and was independent of DSP dose in this concentration range. These results suggest that DSP influences functionality of mung bean protein isolate in an egg patty analogue formulation providing improved textural performance. Mung bean patty using disodium phosphate dose of as low as 0.06% can help achieve egg patty type texture in formulation.

7.28.2 Influence of Concentration of Disodium Phosphate on Mung Bean Protein Isolate Dispersability Mung bean isolate dispersion was prepared using the formulation shown in Table 24. First, disodium phosphate was mixed with distilled water and vortexed until completely soluble. Mung bean protein isolate was then added to the solution and homogenized using Pro Scientific Inc. homogenizer for 3-5 mins at 6000-7000 rpm. The samples were left standing in a refrigerator (~4° C.) for 24 h after which pictures were recorded and pH measurements were carried out.

TABLE 24

Mung bean protein isolate dispersion with DSP

| Ingredients | Concentration (%) |
| --- | --- |
| Water | 82-84 |
| Mung bean isolate | 17-18 |
| Disodium phosphate | 0-1 |

Increase in DSP concentration improved dispersion stability of mung bean protein isolate in water. Sample with no DSP (0% DSP) qualitatively showed maximum separation on standing over 24 hours (FIG. 40) where the mung protein isolate settled towards the bottom of the tube forming a relatively clear top layer of liquid. At concentrations of 0.43% and 1% DSP there was no separation observed after 24 hours of standing. In addition, pH of mung bean protein isolate dispersion increased with increasing concentration of DSP. These results suggest that addition of disodium phosphate increases dispersability and dispersion stability of mung bean protein isolate. pH changes along with change in ionic strength of the mixture may be the mechanism driving dispersion stability.

7.28.3 Influence of Concentration and Chain Length of Sodium Hexametaphosphate on Viscosity and Emulsion Stability of Liquid Egg Analogue Made Using Mung Bean Protein Isolate

TABLE 25

Phosphates tested

| Phosphates tested | pH (1%; DI water) | Abbreviation |
| --- | --- | --- |
| Sodium Hexametaphosphate Long Chain FCC, crushed | 6 | SHMP22 |
| Sodium Hexametaphosphate Regular Chain FCC, powder | 7 | SHMP11 |
| Sodium hexametaphosphate Short Chain, powder | 8.3 | SHMP6 |

Liquid egg analogue was prepared using the formulation shown in Table 26. All ingredients were blended to make a uniform and homogenous mixture. The mix was held at 50-55° C. for 10-20 min followed by pasteurization at 70-75° C. for 5-15 min. The final mix coming out of the pasteurizer was bottled and stored under refrigeration until further testing.

Viscosity was measured on these samples using a shear rheometer (Discovery HR-1, TA Instruments) at 4° C. across varying shear rates of 0.1 $s^{-1}$ to 50 $s^{-1}$. Emulsion stability was measured qualitatively through visual assessment of separation in emulsion.

TABLE 26

Formulation for liquid egg analogue using mung bean protein isolate

| Ingredient | Percentage |
| --- | --- |
| Water | 75-80% |
| Mung bean protein Isolate | 10-15% |
| Oil | 5-8% |
| Emulsifier | 0-0.8% |
| Gum | 0-0.5% |
| Salt | 0-0.5% |
| Phosphate salt (above table) | 0.134% to 1.03% |
| Enzyme | 0.0001-0.0005% |
| Total | 100% |

Addition of long chain sodium hexametaphosphate greatly decreased the viscosity of liquid egg analogue formulation using mung bean protein isolate (FIG. 41). With increase in concentration of SHMP22 in formulation between 0.1 and 1.1% there was a decrease in the viscosity of formulation. Formulation at 1.03% of SHMP22 had viscosity (0.62±0.01 Pa-s) closer to that of liquid whole eggs at 0.14±0.02 (Pa-s) compared to the formulation with no SHMP that was an order of magnitude more viscous (4.1±0.35 Pa-s).

Short chain sodium heaxametaphosphate had a larger impact on viscosity of mung bean protein liquid egg analogue compared to long chain sodium hexametaphosphate. At 1.03%, SHMP6 in formulation further reduced viscosity than SHMP 22 and SHMP11, and was more comparable to that of liquid whole eggs (FIG. 42). Additionally, for a given type of sodium hexametaphosphate chain length the formulation viscosity was lower at a higher concentration of SHMP (between 0.1-1.1%).

Higher concentration of SHMP22 made a more stable emulsion when tested over 13 days of refrigerated storage (FIG. 43). Formulation prepared at 1.03% SHMP22 did not separate over 13 days of refrigerated storage. However, formulation with SHMP22 at 0.135% was less stable and showed separation after 13 days of storage.

7.28.4 Influence of Concentration Tetrasodium Pyrophosphate (TSPP) on Viscosity of Liquid Egg Analogue Using Mung Bean Protein Isolate Addition of TSPP greatly decreased the viscosity of liquid egg analogue formulation using mung bean protein isolate similar to the manner in which sodium hexametaphosphate reduced viscosity (FIG. 44). With increase in concentration of TSPP in formulation between 0.2 and 1% there was a decrease in viscosity.

7.29 Example 29: Mung Bean Patty Stability 7.29.1 Moisture and pH

The stability of mung bean patties under frozen storage conditions (−20 and −80° C.) was evaluated over 12 weeks. The mung bean patties were prepared from 15.5% spray-dried mung bean protein isolate (Lot No. 122.1), water, salt, fat and minor food additives (<3% of product). The ingredients were blended and precooked at 121.1° C. for 10 minutes, and bagged in polyethylene bags and stored in freezer over the course of the study. Changes in pH and moisture were measured at 0, 2, 4, 8, and 12 weeks. At each time point, frozen patties were thawed in a convection oven at 121.1° C. for 20 to 24 minutes until an internal temperature of 74° C. The pH was measured using a standard pH meter, and the moisture content of patties was measured gravimetrically using a loss-on-drying analyzer. Overall, the pH and moisture did not change significantly throughout the study period, suggesting that mung bean patties are stable over 12 weeks of storage at −20 and −80° C. (Table 27).

TABLE 27

Results of Stability Testing of Mung Bean Patties when Stored for 12 Weeks under Frozen Conditions (−20 and −80° C.)

| Time Point | pH −80° C. | pH −20° C. | Moisture −80° C. | Moisture −20° C. |
|---|---|---|---|---|
| Day 0 | 8.07 | 8.07 | 68.43 ± 0.77 | 68.43 ± 0.77 |
| Week 2 | 8.37 | 8.30 | 67.76 ± 1.66 | 64.09 ± 1.88 |
| Week 4 | 8.13 | 8.18 | 62.95 ± 0.95 | 66.15 ± 0.78 |
| Week 8 | 8.38 | 8.05 | 66.63 ± 0.33 | 67.39 ± 0.10 |
| Week 12 | 8.23 | 8.10 | 68.02 ± 2.14 | 68.57 ± 1.32 |

7.29.2 Texture Profile

The texture profile (hardness, chewiness, springiness, resilience, and cohesiveness) of the mung bean patty prepared as described above in Section 6.29.1 was evaluated at day 0, and weeks 2, 4, 8, and 12. The storage conditions (−20 and −80° C.) were similar to what was previously indicated in Section 6.29.1. Texture profile analysis was performed on a Brookfield CT3 analyzer using a cylindrical probe (38 mm diameter) set for 70% deformation, trigger load of 5.0 g, and test speed of 1 mm/s. The results of the analysis are provided in FIG. 45. Overall, the hardness, chewiness, and cohesiveness of the mung bean patty increased in the first 4 weeks of the study, and were not significantly different between weeks 8 and 12. Although these properties were changed throughout the first half of the study, there were no significant differences reported by sensory panel members.

7.30 Example 30: Sensory Results of Other Plant Protein Isolates Prepared Using Acid Precipitation Method A soy bean protein isolate prepared using the acid precipitation method described above was used to prepare an egg-like scramble product. The resulting product had a pretty bad odor and flavor, and the emulsion was slimy. The product appeared very similar to a waffle batter, did not move fluidly, and was sludgy upon attempts to mix it. The texture of finished product was poor, and most formulations did not even cook all the way through. The cooked product had a very silken like top, and the interior separated a bit as it cooked causing a mealy interior texture.

A fava bean protein isolate prepared using the acid precipitation method described above was used to prepare an egg-like scramble product. The resulting product had did not initially have any odor, but as mixing began the emulsions were built a very strong "sour cheese" odor became apparent. This odor carried through to the taste of the product. The product was very yellow in color, and cooked up to a mass of small curd like textures. The product did not form one solid unit, and seemed to be broken after cooking.

A garbanzo bean protein isolate prepared using the acid precipitation method described above was used to prepare an egg-like scramble product. The resulting product did not perform well, and was among the worst performing protein isolates during this experiment. 6 out of 8 pucks exploded due to the large amount of moisture in the protein. As it came to room temperature, the protein was shedding water in the container, essentially breaking the protein. The flavor was similar to the bitterness in hummus, or tahini, which was very unpleasant in large amounts. Texture was also poor, especially the ones that exploded.

7.31 Example 31: Cream Cheese Analog

A representative cream cheese analog formulation includes:
Water (75-85%)
Protein isolate (10-15%)
Oil (5-10%)
Hydrocolloid (0.1-3%) which includes either 1) a low-methoxy pectin and calcium chloride system; 2) xanthan gum
Flavors (1-2%)
Salt (<1%)

Emulsion of plant protein isolate, oil, hydrocolloid, salt and other ingredients were prepared using a Pro Scientific shear mixer operated at 5000 rpm for 4 min at room temperature. Emulsion is deposited in round molds (3 in diameter). Amount deposited per mold is 50 g. Convection oven set at 220° F. for 55 min.

7.32 Example 32: Alternative Yogurt System

A representative alternative yogurt formulation includes: water, mung bean protein isolate, sugar, oil, and a bacterial culture.

The following tests were done on a magic bean yogurt prototype and benchmarked against Dannon's All Natural Plain Yogurt and Lucerne's Greek Plain Yogurt.

7.32.1 Rheological Properties of Gel Systems

The rheological properties of the prototypes were measured using the rheometer DHR-1 where 1 ml of sample undergo an oscillatory amplitude sweep from 0.03-500 Pa with a constant frequency of 1 Hz at 10° C. with a cone-in-plate geometry. The storage modulus and loss modulus were measured which can help identify the viscoelastic properties of the gel. Plateau value of G' in the LVE-region describes the rigidity of the sample at rest while the plateau value G" is a measure for the viscosity of the unsheared sample. Yield stress was also derived from the intersection of the storage modulus and loss modulus functions, indicating where the material transform from a viscoelastic solid to a viscoelastic liquid.

TABLE 28

| | G' Storage Modulus (Rigidity) | G" Loss Modulus (Viscosity) | Yield Stress (Pa) |
|---|---|---|---|
| Lucerne | 1404.15 | 310.67 | 172.19 |
| Dannon | 448.39 | 125.02 | 46.11 |
| Magic Bean | 239.59 | 61.54 | 27.30 |

The results above suggest that the yogurt prototype made with mung bean protein isolate exhibits a texture that is much more similar to a Dannon yogurt. It has a smooth and creamy texture compared to the Lucerne Greek yogurt, which has a more hardened gel-like texture. The prototype was made only using coconut oil, protein and water. The addition of stabilizers and gums can potentially bring the product closer to the other end of the texture spectrum.

7.32.2 Texture Analysis of Emulsion Gels

Texture profile analysis was performed on these 3 samples using the Brookfield TA instrument. TPA is a test where the sample was compressed twice in the cycle. Cylindrical probe TA-11 (25.4 mm D, 35 mm L) was used to compress samples of 16 ml in a 6-well plate well. The test speed was set-up as 1 mm/s and targeted a compression of 10 mm. Three compressions were done on 3 sample replicates to obtain the following data (Table 29).

| Yogurt | Gel Hardness (g) |
|---|---|
| Mung Bean | 18 |
| Dannon | 36 |
| Lucerne | 166 |

The results above suggest that the prototype made with mung bean protein isolate has a mouthfeel and texture much more similar to Dannon, by a 2-fold difference.

7.33 Example 33: Mung Bean-Derived Protein Beverage System

A representative protein beverage system formulation includes: water, mung bean protein isolate, sugar and oil.

Particle size analysis was performed on a mung bean-derived protein beverage prototype and benchmarked against Organic Valley's Whole fat milk and Half&Half, 365 Everyday Value's almond milk. Emulsion stability was also benchmarked against Silk's coconut milk and 365 Everyday Value's soy milk.

7.33.1 Particle Size of Fat Droplets

The particle size distribution of fat droplets was measured using the Mastersizer 3000. The instrument utilized laser diffraction to measure the angular variation in intensity of the scattered light diffracted by the dispersed particles. The angular scattering intensity data is then analyzed to calculate the size of the particles that created the scattering pattern using the Mie theory of light scattering.

The emulsion sample was first diluted in distilled water and added to the chamber until the laser obscuration limit was in range for the measurement.

The data in Table 30 below and in FIG. 46 show the average size class of the particles in the beverage product. The plots are generated from averaging three distributions obtained from three measurements. As shown in FIG. 46, two peaks were observed for the dairy alternative beverage product while only one peak was seen for the dairy beverages.

TABLE 30

| Beverage | First peak size (μm) | Second peak size (μm) |
|---|---|---|
| Milk | 0.38 | / |
| Half & Half | 0.81 | / |
| Almond Milk | 0.55 | 15.41 |
| Mung Bean | 0.30 | 11.94 |

7.33.2 Emulsion Stability of a Liquid Emulsion System

Emulsion stability was measured by detecting the change of backscattering and transmission when the light source goes through the emulsion sample over time. An emulsion sample of 3 ml was transferred to a glass vial and was scanned every 1 min for 60 min under room temperature.

Turbiscan Stability Index (TSI) was used to reflect the emulsion stability of the emulsion samples studied. It is calculated as the cumulative delta-backscattering difference relative to the first scan. The larger the value of TSI, the larger the difference between the backscattering detected, which indicates a less stable sample.

TABLE 31

| Beverage Type | TSI value at 60 min |
|---|---|
| Coconut milk | 3.01 |
| Soy milk | 0.34 |
| Mung Bean | 0.48 |

The TSI value enables a comparison between samples under the same protocol. As indicated by the data shown in Table 31 and FIG. 47, the prototype made with mung bean protein isolate exhibits similar stability behavior compared to a soy milk beverage. It has a 6-fold lower TSI value than coconut milk, indicating that a mung bean protein-based beverage can have better shelf stability than a coconut milk beverage.

7.34 Example 34: Mung Bean Protein-Derived Butter System

A representative mung-bean based butter system includes: disodium phosphate, water, mung bean protein isolate, a bacterial culture and oil. A prototype non-dairy mung-bean based butter system is depicted in FIG. 48.

7.35 Example 35: Pound Cake

FIG. 49 provides a visual depiction during various stages of the isolation of protein from mung bean extract, where the concentration of Maillard reactants and beany flavor is significantly reduced. Application of mung bean isolate in baked goods results in better product appearance (lighter color) and sensory properties (reduced bitter and beany flavour). FIG. 50 provides a cross section of a pound cake of a moong dal protein extract 19% in comparison to that of a pound cake made with eggs. FIG. 51 provides a top view of the dome of the pound cake where the egg-based cake (left) and the re-solubilized precipitate (right) have similar dome and cracking as opposed to the original protein extract (center).

A representative pound cake formulation using protein extract includes: Cake flour (25%), Butter (25%), Sugar (25%), Protein extract at 34% total solids and 19% protein.

Cake batter was prepared using a single stage mixing process on a Hobart N90 mixer at low speed with a flat paddle. Flour, sugar and butter were added to the mixer. Mung bean extract was prepared by mixing mung bean flour with water in 1:1 (w/w) ratio and centrifuged at 6000×g for 30 min at room temperature. Protein extract was added in a stream and mixed at low speed for a minute. Mixing proceeded for 5 more min at medium speed. The batter was poured into 21 oz rectangular aluminium pans and baked at 300° F. for 45 min. Comparison of a mung bean extract pound cake and egg-based pound cake as shown in FIG. 49 is shown in Table 32 below.

TABLE 32

| Properties | MUNG BEAN EXTRACT POUND CAKE | EGG POUND CAKE |
|---|---|---|
| Specific gravity | 0.92 ± 0.04 | 0.91 ± 0.01 |
| Peak height (in) | 2.89 ± 0.07 | 2.40 0.01 |

A representative pound cake formulation using protein isolate includes: Cake flour (25%), Butter (25%), Sugar (25%), Protein isolate solids containing (>80% protein) (5-6.25%) Disodium phosphate or baking soda, and water.

Table 33 provides the results comparing the functional properties of a representative pound cake made with purified mung bean protein isolate to an egg-based pound cake.

TABLE 33

| Properties | Mung bean protein isolate 208 n pound cake | Egg pound cake |
|---|---|---|
| Cake resilience | 0.15 ± 0.01 | 0.12 ± 0.01 |
| Cake cohesiveness | 0.37 ± 0.01 | 0.35 ± 0.02 |
| Cake springiness | 7.18 ± 0.17 | 6.84 ± 0.17 |
| Cake peak height (inch) | 2.424 | 2.151 |
| Specific gravity of batter | 0.95 | 0.97 |
| Center doming | + | ++ |
| Center crack | ++ | ++ |
| Browning | ++ | ++ |
| Mouthfeel | Moist, clean finish, no residual sweetness | Moist, clean finish, no residual sweetness |
| Spring-back | High | Medium |
| Off flavors | None | None |
| Flavor | Strong buttery, medium sweetness, brown rounded flavor | Strong buttery and dairy notes, medium sweetness, low brown notes, rounded flavor |

Cake batter was prepared using a single stage mixing process on a Hobart N90 mixer at low speed with a flat paddle. Add flour, sugar and butter to Hobart N50 mixer. Mix protein isolate and water. Add protein isolate in a stream and mix at low speed for a minute. Continue mixing for 5 more min at medium speed. Pour batter in 10 oz rectangular aluminum pans. Bake at 300° F. for 45 min. A representative pound cake made with the purified protein isolate is shown in FIG. 52.

7.36 Example 36: Angel Food Cake

A representative angel cake formulation using purified mung bean protein isolate includes: Cake flour (15.2%), Cream of tartar (0.6%), Sugar (42%) Salt (0.2%), Protein isolate solids (7.56-10.5%), Disodium phosphate (pH stabilizing agent) (0-0.21%), Added Water (31-34.23).

Protein was solubilized with added water and disodium phosphate. Protein isolate, added water, disodium phosphate and cream of tartar were mixed on medium speed on a Hobart N50 mixer with a balloon whisk. Sugar was then added slowly and whisking continued. Sugar and flour were added while mixing at slow speed on the Hobart mixer. 140 g of batter was filled in 4"×5" tube pan and baked at 350° F. for 17 min. Results are shown in FIG. 53 and FIG. 54.

Table 34 provides the results comparing the functional properties of a representative angel food cake made with the mung bean proteins isolate to an egg-white angel food cake.

TABLE 34

| Properties | Egg white angel food cake | Mung bean isolate (208a) angel food cake |
|---|---|---|
| % solids in egg/replacer | 20 | 18.5 |
| Hardness (g) | 319 ± 65 | 820 ± 223 |
| Resilience | 0.31 ± 0.04 | 0.24 ± 0.02 |
| Cohesiveness | 0.7 ± 0.04 | 0.61 ± 0.02 |
| Springiness (mm) | 7.52 ± 1.68 | 9.58 ± 0.7 |
| Chewiness index (g) | 190 ± 31 | 406112 |

7.37 Example 37: Pasta Dough

A representative pasta dough formulation using purified protein isolate includes: 100 g mung bean protein isolate pulse blended with ½ cup Semolina flour, ½ teaspoon salt, and 35 mL extra virgin olive oil, then mixed with 30 mL of water. The resulting pasta exhibited an ability to retain structure and maintain a desirable al dente texture for longer periods of time during cooking. In addition, the resulting pasta dough retained structure during retorting, suggestions use in canned applications, including pasta-based soups. Resulting pasta had a smooth texture and white appearance.

7.38 Example 38: Meat Analogue

Mung bean protein isolate was utilized to prepare an egg-free emulsion that was made into: (i) an egg analog for use as a patty in breakfast sandwiches and as a scramble; and (ii) a meat analogue for use as deli meat or chicken nuggets.

For use as an egg analog, the protein isolate was utilized with and without (a) buffering salts; (b) heating between temperatures of 20° C. and 95° C.; and (c) low shear to high shear homogenization. When the isolate is blended with transglutaminase enzyme at 25-55° C., followed by incubation for 0-60 min at 25-55° C. and finally oven baked at 121-200° C. for 5-15 min, the isolate produces various types of textures that resemble cooked eggs. The textures of egg-free patty produced using the above process includes firm, clean cut, cohesive, elastic textures similar to well cooked scrambled eggs prepared on a high heat pan. The textures of the egg-free scramble were soft, springy, airy, elastic, creamy, cohesive, and resilient, similar to low to medium cooked scrambled eggs.

Representative Formulation:
a. 80% water;
b. 11.8% protein isolate comprising about 85% plant protein
c. 0.43% disodium phosphate
c. 0.0010% (10 ppm) transglutaminase
d. 6.2% canola oil;
e. 1.15% egg type and dairy type flavors
f. 0.15% natural yellow color
g. 0.3% salt wherein the mixture is at a pH around 6.5

Protein isolate powder and all remaining dry were mixed with water and oil at low shear for 8 min in a thermally jacketed mixer (Thermomix) (setting 2 will provide RPM range). This mix was heated while continuing to be mixed until the temperature reached 83° C. The mix was then cooled to 50° C., and 10 ppm transglutaminase enzyme was added and mixed for another 30 s. Mixing was followed by incubation of emulsion at 50° C. for 60 min in round shaped silicone molds (3 in diameter). Post incubation, the samples were baked in an impingement oven at 121 C for 10 min. The resultant round patties had mild egg and dairy flavors and neutral plant flavor. The patty texture was soft, springy, airy, elastic, creamy, cohesive, and resilient, similar to an egg patty.

Alternately, the same formulation of emulsion mix after enzyme addition when poured into casings, tied at the ends to make tube-shaped chubbs, and incubated in a water bath at 50° C. for 2 hours, made strong gels. The chubbs were untied and the gel was sliced into round patties and oven baked at 121° C. for 10 min. The resultant round patties had mild egg and dairy flavors and neutral plant flavor. The patty texture was soft, springy, airy, elastic, creamy, cohesive, and resilient, similar to an egg patty.

7.39 Example 39: Meat Analogue

Mung bean protein isolate was utilized to prepare an egg-free emulsion that was made into a meat analogue. The protein isolate was utilized with and without (a) buffering salts; (b) heating between temperatures of 50° C. and 95° C. and (c) low to medium shear homogenization. When blended with transglutaminase enzyme at 25-55° C., followed by incubation for 60-120 min at 25-55° C., and finally pressure cooked at 15-29 psi for 20-60 min, the cooked product had a deli meat like texture.

Representative Formulation:
a. 80% water;
b. 13% protein isolate comprising about 85% plant protein
c. 0.43% disodium phosphate
c. 0.0010% (10 ppm) transglutaminase
d. 6.2% canola oil;
g. 0.3% salt wherein the mixture is at a pH around 6.5

Protein isolate powder and all remaining dry were mixed with water and oil at low shear for 8 min in a thermally jacketed mixer (Thermomix) (setting 2). This mix was heated while continuing to be mixed until the temperature reached 83° C. The mix was then cooled to 50° C. and 10 ppm transglutaminase enzyme was added and mixed for another 30 s. The emulsion mix was poured into casings, tied at the ends to make tube-shaped chubbs and were incubated in a water bath at 50 C for 2 hours. Post incubation the samples were pressure cooked at 15 psi at about 121° C. for 30 min. The chubbs were cooled to room temperature, untied and resulting gel had a texture similar to chicken nuggets. The gel texture was soft, medium chewy, fibrous, springy, elastic, cohesive, and resilient, similar to chicken nuggets.

7.40 Example 40: Comparative Analysis of Meat Analogues

Meat analogue was prepared using mung bean protein isolate following the formulation shown in Table 35. Mung bean protein isolate was blended with water, oil, disodium phosphate, salt and starch in the formula to make a homogenous mixture under medium to high shear mixing. The mix was then heated to temperatures between 25-95° C., followed by addition of enzyme. This material was then filled into casings to form cylindrical chubbs. The chubbs were maintained at 40-55° C. for 60-120 min followed by extrusion and cooking under pressure of 8-15 psig for 30-120 min. The chubbs were cooled and sliced into nuggets.

TABLE 35

| Ingredient | Range (%) |
| --- | --- |
| Water | 65-80 |
| Mung bean protein isolate | 20-40 |
| Oil | 2-8 |
| Disodium phosphate | 0.1-0.8 |
| Salt | 0.1-0.5 |
| Enzyme | 0.001-0.002 |
| Starch | 0-0.5 |

Meat analogue samples were analyzed for their textural properties. Brookfield Conn.3 texture analyzer was used to carry out texture profile analyses. 25.4 mm cylindrical probe was used for this analyses. Mung bean nugget samples were cut into cylinders with 2.54 cm diameter and height of 1 cm. Samples were analyzed using two uniaxial compression cycles triggered at 5 g load. Target compression distance was set to 0.7 cm, corresponding to 70% deformation performed at a rate of 1 mm/s.

Samples that underwent heated before enzyme treatment were termed as 'Preheat trials' and samples that were not heated before enzyme treatment were termed as 'No heat trial'.

'Preheat' and 'no heat' trials using mung bean protein isolate made meat analogues that showed comparable textural properties of hardness, cohesiveness, chewiness and resilience to that of commercial chicken nuggets and commercial meat analogues made using soy protein isolate and pea protein isolates (FIG. 55). Mung bean protein meat analogue outperformed some of the commercial meat analogues in texture as recorded by texture profile analyses. The gel texture was soft, medium chewy, fibrous, springy, elastic, cohesive, and resilient similar to chicken nuggets. Additionally, the visual fibrous appearance similar to muscle fibers of chicken was also observed in the mung bean protein meat analogues (FIG. 56).

7.41 Example 41: Food Applications Made with Other Protein Isolates

Other protein isolates did not function as well as mung bean in varied food product applications. See FIG. 57, which visually depicts an egg patty substitute from four liquid scramble formulations: (A) purified mung bean isolate via salt precipitation; (B) purified mung bean isolate via isoelectric precipitation; (C) purified mung bean & wheat protein isolates (50:50); and (D) purified mung bean & pea protein isolates (50:50). As demonstrated in (C) and (D), when mung bean protein isolates are combined with other proteins such as wheat or pea, functionality is lost. This is demonstrated by extremely low storage modulus after amplitude sweep testing compared to formulations made with mung bean protein isolates only. See FIGS. 61-63.

7.42 Example 42: Processes and Compositions for Fat Reduction Shortening System (FRSS)

Also provided herein is a representative shortening model system with the ability to reduce necessary fats utilized in common baking applications. By utilizing particular mung bean protein isolates provided herein, the system has the ability to allow fat reduction in model systems, up to and >40%, with minimal to zero negative return to texture, moisture and structure, compared to equal amounts to equivalent incumbent bakery shortening.

7.42.1 Representative Mung Bean Protein Isolation Process for FRSS Applications Step 1:
800 kg of de-hulled, milled Mung bean flour (100 mesh screen size) was extracted with 4000 L RO water (1 part of flour to 5 parts of water ratio), the pH of the extraction slurry was around pH 6.7. In order to solubilize the protein in flour, pH of the extraction was adjusted to pH 7 by addition of NaOH. The temperature of the extraction was at around 15° C.

Step 2:
The extraction slurry was fed to a pilot scale decanter centrifuge (Alfa Laval Foodec 360) at ~2100 L/hr feed rate, 3272 rpm bowl speed to separate the protein extract in liquid phase from the fibre and starch rich solid phase.

Step 3:
The liquid phase from the decanter was then sent to a high speed bowl centrifuge (Alfa Laval Clara 80) to separate the fine particles present in the liquid. This was run at 1695 L/h feed and 8142 rpm centrifuge speed. A fraction of the fine particles was removed after the high speed bowl centrifuge separation.

Step 4:
The clarified liquid extract from step 3 was pH adjusted to pH 6.0 by addition of citric acid, and the protein of interest precipitates out at the target pH. The precipitation tank was chilled to 10° C. with an external heat exchanger.

Step 5:
The precipitated protein slurry from step 4 was sent to the high speed bowl centrifuge (Alfa Laval Clara 80) at a feed rate of 350-500 L/hr and the protein is recovery in the solid discharge section of the centrifuge at ~17% total solid (TS). The purity of the protein recovered is between 83-87% (by dry mass, Kjeldahl method was used to quantify the nitrogen content in the sample).

Step 6:
The recovery slurry (17% TS) was spray dried on a pilot scale box dryer, two inlet air temperature conditions were used (180 and 210° C.), and the slurry was fed to the dryer at 45-55 kg/hr feed rate, the spray dried powder (pale yellow color) was collected with a moisture content <5%.

7.42.2 Representative FRSS Formulation

A representative Fat Reduction Shortening System (FRSS) formulation comprising mung bean protein isolate (prepared in accordance with the above process) includes: Water (34.55%), Refined Coconut Oil (44.4%), Expeller pressed Canola Oil (14.8%), Mung Bean Isolate (4.93%), Sodium Citrate (0.98%), Citrus Fiber from Orange (0.29%).

Protein was solubilized with Sodium Citrate and municipal water using a Vorwerk Thermomix. Mung Bean Isolate was combined with Sodium Citrate and water, applying heat and specific sheer to create a stable emulsion mixture. Additional water, a portion of the finish weight of oil and Citrus Fiber are combined and added to the protein mixture using heat and sheer for a specific time. The final mixture is cooled to a range of (40-50° C.) and transferred to a clean Thermomix vessel for further processing.

The mixture is turned at moderate vortex for the duration of oil emulsification (10 minutes). Both remaining oils are tempered and combined. Oil is streamed in a consistent flow for the duration of the total weight of the remaining oil. Sheer is gradually increased as oil and protein mixture are combined to maintain consistency throughout the final product. The final product is placed in a vacuum bag and is compressed to consolidate the FRSS mass. The finished bagged product is refrigerated for no less then 12 hours to solidify the final texture.

FIG. 61A depicts a finished mung bean isolate shortening model, ready to be applied to baking applications.

7.42.3 Baking Applications Utilizing Mung-Bean Derived FRSS

The FRSS was applied to numerous baking applications in amounts equal to amounts typically used for the incumbent, fractured palm oil shortening, in an attempt to demonstrate the viability of the protein driven system in a 1-to-1 comparison. A pilot formulation of a sponge cake (which does not include eggs and dairy) was compared to a known commercial sponge cake using shortening, eggs and dairy (butter and milk).

A representative white sponge cake formulation utilizing the purified mung bean isolate described above includes: Sugar (42.401%), All Purpose Flour (23.77%), Cake Flour (22.63%), Ventura, palm shortening (8.401%), Double acting Baking Powder (1.087%), Salt (0.988%), Natural Flavoring (0.287%), Sodium Bicarb (0.247%), Citric Acid (0.099%), Vanilla (0.049%). Additional water is used to complete the cake model.

In combination, a represented cake frosting model formulation using FRSS based on purified mung bean isolate includes: Confectioners' Sugar 10× (71.88%), FRSS (23.89%), Municipal Water (3.17%), Salt (1.06%).

The frosting analog was compared to commercially known frosting made with hydrogenated palm oil.

Cake mix was prepared by plating sugar and FRSS in combination with vanilla and natural flavors. Dry ingredients are combined and sifted (#16) then added to the plated shortening/sugar mixture. The entire batch combines for 10 minutes or until well incorporated and final sifted (#16) for consistency of materials. The cake batter is prepared with additional municipal water and a Hobart stand mixer with paddle attachment. Water and mix are combined on a low speed for 30 seconds. The bowl and paddle are scraped down and the mix is then turned on a medium speed for 1 minute to fully emulsify the mixture and incorporate air into the system. The mixture is poured into a 9"×9" pan and baked at 350 degrees for 18-24 minutes. Finished cake is allowed to cool on a rack until ambient temperature.

The frosting analog is prepared by combining ½ total confectioner's sugar and the total FRSS at a low speed, using the Hobart mixer and a paddle attachment until incorporated. The bowl and paddle are scrapped down and the other ½ of the sugar is introduced in small amounts to blend thoroughly. Water and Salt are added and the mix is blended to a smooth consistency.

FIG. 61B depicts the finished cake and frosting analog.

7.42.4 Other Applications: Mung-Bean Derived Non-Dairy Cream Cheese Analog

A sample non-dairy cream cheese analog was produced utilizing the water binding and emulsification properties of the mung bean protein isolate described above. By manipulating with heat and sheer as well as conditioning with calcium and ultimately culturing, a texture and flavor of traditional dairy cream cheese can be achieved.

A representative formulation using purified mung bean protein isolate includes: Municipal water (65.01%), Expeller pressed Canola Oil (27.95%), Purified Mung Bean Protein Isolate (9.75-11.25%), Sugar (1.5-5%), Calcium Chloride (1.30%), Salt (0.65%), Lactic Acid (0.26%)

Using a Vorwerk Thermomix, protein was solubilized with water, sugar and salt. Heat and medium sheer is applied for 30 minutes. The final temperature will exceed 85 C. The mixture is allowed to run at medium sheer for an additional 7-10 minutes to cool slightly (50-60 C) and keep consistency.

Increasing Thermomix speed to medium high, 75% of the canola oil is streamed into the mixture. The calcium chloride, diluted in 25 g of the remaining oil is added and allowed to sheer for 5 minutes. After calcium is fully incorporated the remaining oil is streamed in a consistent flow for the duration of the total weight of the remaining oil.

Once the base is homogenized, it is transferred to an ice bath and chilled to (40° C.). Using the Thermomix, heated to 40° C., the chilled mixture is sheered at medium speed to keep the mixture smooth and set the appropriate temperature for culturing. Diluting culture pellets-CH (0.022-0.25%) with 5 g of municipal water prepares the culture for the mixture. When the culture is introduced, the batch is allowed to turn for 5 minutes to fully incorporate the culture. The finished mixture is transferred to a 1 qt. container and placed in a sous vide water bath (40° C.) after a PH value is taken.

A final mix pH is necessary as a starting point for the analog in the water bath. The product is "cultured" for a period of time no less than 3 hours or until the pH value has dropped to 4.6-5.1.

The final cultured blend is sheered in a Thermomix at 85° C. for 7 minutes on a medium speed to make the product smooth and homogenized and set the culturing process. The final mix is pressed into a mold for shape and final texture.

FIG. 62A depicts a non-finished, non-dairy analog in a Theromomix, just before the culturing step. FIG. 62B depicts finished non-dairy analogs. The sample on the left has been allowed to culture without a finish step, while the sample on the right has been homogenized as a finished product for smooth consistency and the culturing process has been stopped at a pH of 5. FIG. 62C depicts a finished, pressed non-dairy cream cheese analog.

7.42.5 Other Applications: Mung-Bean Derived Pasta Dough and Pasta

A sample pasta dough was produced utilizing the binding and structure building capabilities of purified mung bean isolate described above. The pasta analog is gluten free, relying on the structure building ability of the protein isolate to mimic traditional wheat flour texture.

A representative formulation using the above mung bean protein isolate includes: Mung Bean Flour-raw (41%), Purified Mung Bean Isolate (9%), Long Grain White Rice Flour (30%), Corn Flour (20%). Additional municipal water (32.5% of total weight of formula) is used to complete the dough. Water amounts will vary +/−2% based on ambient conditions (humidity).

Using a Roma Pama pasta extruder, dry ingredients and purified mung bean isolate (spray dried) are added to the RP hopper and blended for a minimum of 2 minutes to fully incorporate. Once ingredients are blended, municipal water is streamed into the mix and RP begins to form the dough. The blend will have the consistency of wet sand. The pasta dough turns in the RP hopper for 9-11 minutes until the dough is optimally conditioned.

Using #143 pasta dye for the RP, dough is extruded in a smooth and continuous motion until the hopper is empty. As dough is extruded, it is collected in perforated drying baskets and placed into a drying rack. Extruded pasta needs a minimum of 2 hours to cure and set the pasta.

FIG. 63A shows dye #143, used for extrusion of the pasta analog. FIG. 63B depicts shows the finished pasta analog after being dried All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. An egg substitute comprising:
   (a) transglutaminase modified mung bean protein composition, wherein the mung bean protein composition comprises a mung bean protein content of at least 60% by weight, wherein the mung bean protein content comprises at least 50% by weight of globulin protein, wherein the globulin protein comprises 8S and 11S globulin;
   (b) wherein said mung bean protein composition exhibits a gel strength of greater than 2% oscillation strain.

2. The egg substitute of claim 1, wherein the egg substitute is an egg-free emulsion, egg analog, egg-free scramble, or an egg-free patty.

3. The egg substitute of claim 1, wherein the egg substitute comprises transglutaminase in an amount of at least or about 0.0005 up to about 0.0025% (5-25 parts per million).

4. The egg substitute of claim 1, wherein the egg substitute comprises at least one additional ingredient selected from the group consisting of a hydrocolloid, a gum, and a phosphate.

5. The egg substitute of claim 1, wherein the egg substitute is an egg-free emulsion comprising at least or about 60-85% water, at least or about 10-20% of the mung bean protein composition, and at least or about 5-15% oil or fat.

6. The egg substitute of claim 1, wherein the egg substitute further comprises a phosphate selected from the group consisting of disodium phosphate, sodium hexametaphosphate and tetrasodium pyrophosphate.

7. The egg substitute of claim 1, wherein the modulated organoleptic properties comprise a reduction or absence in one or more of the following properties: astringent, beany, bitter, burnt, buttery, nutty, sweet, sour, fruity, floral, woody, earthy, beany, spicy, metallic, sweet, musty, grassy, green, oily, vinegary neutral and bland flavor or aromas.

8. The egg substitute of claim 1, wherein the mung bean protein composition exhibits a gel elasticity of greater than 300 Pa.

9. The egg substitute of claim 1, wherein the mung bean protein composition comprises up to about 95% by weight mung bean protein.

10. The egg substitute of claim 9, wherein the mung bean protein comprises at least 60% by weight of globulin protein.

11. The egg substitute of claim 10, wherein the globulin protein comprises 8S globulin/beta conglycinin.

12. The egg substitute of claim 11, wherein the globulin protein comprises a protein having at least 50% identity to SEQ ID NO. 1.

13. The egg substitute of claim 1, wherein the globulin protein is enriched in the mung bean protein composition in relation to the amount of globulin protein found in the plant source of the mung bean protein.

14. The egg substitute of claim 13, wherein the enrichment is at least 5%, 10%, 15%, 20% or greater than 20%, in relation to the amount of globulin protein found in the plant source of the mung bean protein.

15. The egg substitute of claim 1, wherein one or more compounds selected from the group consisting of allergens, anti-nutritional factors, and environmental contaminants is reduced in the mung bean protein composition in relation to the amount of the one or more compounds found in the plant source of the mung bean protein composition.

16. The egg substitute of claim 1, wherein the egg substitute has reduced rancidity relative to an egg substitute prepared from unmodified mung bean protein composition.

17. The egg substitute of claim 1, wherein the mung bean protein composition is spray dried.

18. The egg substitute of claim 1, wherein the transglutaminase modified mung bean protein composition has a gelation temperature below 90° C.

19. The egg substitute of claim 1, wherein the egg substitute comprises transglutaminase in an amount of at least or about 0.0005% up to about 0.0125% (5-125 parts per million).

20. The egg substitute of claim 1, wherein the egg substitute comprises transglutaminase in an amount of at least or about 0.0005% up to about 0.5%.

21. An egg substitute comprising:
   (a) a transglutaminase modified mung bean protein composition, wherein the mung bean protein composition comprises a mung bean protein content of at least 60% by weight, wherein the mung bean protein content comprises at least 50% by weight of globulin protein, wherein the globulin protein comprises 8S and 11S globulin;
   (b) wherein said mung bean protein composition exhibits a gel strength of greater than 2% oscillation strain; and
   (c) wherein said mung bean protein composition is spray dried.

22. The egg substitute of claim 21, wherein the transglutaminase modified mung bean protein composition has a gelation temperature below 90° C.

23. The egg substitute of claim 21, wherein the egg substitute comprises transglutaminase in an amount of at least or about 0.0005% up to about 0.0125% (5-125 parts per million).

24. The egg substitute of claim 21, wherein the egg substitute comprises transglutaminase in an amount of at least or about 0.0005% up to about 0.5%.

25. An egg substitute comprising:
   (a) a transglutaminase modified mung bean protein composition, wherein the mung bean protein composition comprises a mung bean protein isolate comprising a mung bean protein content of at least 60% by weight, wherein the mung bean protein content comprises at least 50% by weight of globulin protein, and wherein the globulin protein comprises 8S and 11S globulin, and wherein the mung bean isolate precipitates at a pH greater than 5.0 and wherein said mung bean isolate exhibits a gel strength of greater than 2% oscillation strain.

26. The egg substitute of claim 25, wherein the egg substitute comprises transglutaminase in an amount of at least or about 0.0005% up to about 0.0125% (5-125 parts per million).

27. The egg substitute of claim 25, wherein the egg substitute comprises transglutaminase in an amount of at least or about 0.0005% up to about 0.5%.

* * * * *